(12) United States Patent
Küppers-Munther et al.

(10) Patent No.: US 10,294,457 B2
(45) Date of Patent: May 21, 2019

(54) MATURATION OF HEPATOCYTE-LIKE CELLS DERIVED FROM HUMAN PLURIPOTENT STEM CELLS

(71) Applicant: Takara Bio Europe AB, Göteborg (SE)

(72) Inventors: Barbara Küppers-Munther, Göteborg (SE); Josefina Edsbagge, Torslanda (SE)

(73) Assignee: Takara Bio Europe AB, Gothenburg (SE)

( * ) Notice: Subject to any disclaimer, the term of this patent is extended or adjusted under 35 U.S.C. 154(b) by 0 days.

(21) Appl. No.: 14/648,365

(22) PCT Filed: Nov. 28, 2013

(86) PCT No.: PCT/EP2013/075017
§ 371 (c)(1),
(2) Date: May 29, 2015

(87) PCT Pub. No.: WO2014/083132
PCT Pub. Date: Jun. 5, 2014

(65) Prior Publication Data
US 2015/0307839 A1    Oct. 29, 2015

Related U.S. Application Data

(60) Provisional application No. 61/731,266, filed on Nov. 29, 2012, provisional application No. 61/731,281, filed on Nov. 29, 2012.

(30) Foreign Application Priority Data

Nov. 29, 2012   (DK) ................... 2012 70740
Nov. 29, 2012   (DK) ................... 2012 70741

(51) Int. Cl.
C12N 5/071      (2010.01)

(52) U.S. Cl.
CPC .......... *C12N 5/067* (2013.01); *C12N 2501/06* (2013.01); *C12N 2501/385* (2013.01); *C12N 2501/405* (2013.01); *C12N 2501/415* (2013.01); *C12N 2501/727* (2013.01); *C12N 2501/999* (2013.01); *C12N 2506/02* (2013.01); *C12N 2506/03* (2013.01); *C12N 2506/45* (2013.01); *C12N 2533/52* (2013.01); *C12N 2533/54* (2013.01)

(58) Field of Classification Search
CPC .... C12N 5/067; C12N 5/0671; C12N 5/0672; C12N 5/0606; C12N 2506/03; C12N 2506/02; C12N 2501/385; C12N 5/0607
See application file for complete search history.

(56) References Cited

U.S. PATENT DOCUMENTS

| 8,148,151 B2 | 4/2012 | Zhao et al. |
| 2005/0054092 A1 | 3/2005 | Xu et al. |
| 2006/0003446 A1 | 1/2006 | Keller et al. |
| 2007/0196514 A1* | 8/2007 | Li ............ A61K 31/404 424/722 |
| 2007/0254359 A1 | 11/2007 | Rezania et al. |
| 2009/0053182 A1* | 2/2009 | Ichim .......... A61K 35/545 424/93.7 |
| 2010/0143313 A1 | 6/2010 | Yarmush et al. |
| 2010/0166713 A1* | 7/2010 | Dalton ............ C12N 5/0603 424/93.7 |
| 2010/0173414 A1 | 7/2010 | Turovets et al. |
| 2012/0143316 A1 | 6/2012 | Seguin et al. |

FOREIGN PATENT DOCUMENTS

| EP | 2436775 A1 | 4/2012 |
| JP | H11511472 A | 10/1999 |
| WO | 2003046141 A2 | 6/2003 |
| WO | 2003055992 A2 | 7/2003 |

(Continued)

OTHER PUBLICATIONS

Falasca, L et al. The effect of retinoic acid on the re-establishment of differentiated hepatocyte phenotype in primary culture. Cell Tissue Res. 1998. 293: 337-347.*
Si-Tayeb, K et al. Highly efficient generation of human hepatocyte-like cells from induced pluripotent stem cells. Hepatology. 2010. 51(1): 297-305.*
Moghe, PV et al. Cuture matrix configuration and composition in the maintenance of hepatocyte polarity and function. Biomaterials. 1996. 17: 373-385.*
Ohmura, T et al. 9-cis retinoic acid is a direct hepatocyte mitogen in rats. Life Sciences. 1996. 58(11): PL 211-216.*
Huang, J et al. Retinoic acid signalling induces the differentiation of mouse fetal liver-derived hepatic progenitor cells. Liver International. 2009. 29(10): 1569-1581. (Year: 2009).*
International Search Report and Written Opinion for Application PCT/EP2013/075017 dated Apr. 25, 2014.

(Continued)

*Primary Examiner* — Renee Claytor
*Assistant Examiner* — Susan E. Fernandez
(74) *Attorney, Agent, or Firm* — Fox Rothschild LLP

(57) ABSTRACT

The present invention relates to directed differentiation and maturation of hepatocyte-like cells. In particular, the present invention relates to exposure of hepatocyte-like cells to an activator of a retinoic acid responsive receptor, such as retinoic acid (RA), optionally in combination with an inhibitor of GSK-3 (Glycogen synthase kinase 3) or activator of Wnt signalling and/or with the overlay of the cells with one or more components characteristic of the mammalian extracellular matrix (matrix overlay). The present invention also relates to exposure of hepatocyte-like cells to an activator of a retinoic acid responsive receptor, such as retinoic acid (RA), optionally in combination with an inhibitor of a cycline dependent kinase (CDK) and/or with the overlay of the cells with one or more components characteristic of the mammalian extracellular matrix (matrix overlay). The hepatocyte-like cells obtained in accordance with the present invention show a phenotype which is more similar to that of primary hepatocytes than previously shown.

22 Claims, 77 Drawing Sheets

(56) References Cited

FOREIGN PATENT DOCUMENTS

| WO | 2004099394 A2 | 11/2004 | |
|---|---|---|---|
| WO | 2005017131 A2 | 2/2005 | |
| WO | 2006117212 A2 | 11/2006 | |
| WO | 2007042225 A2 | 4/2007 | |
| WO | 2007050043 A2 | 5/2007 | |
| WO | 2007140968 A1 | 12/2007 | |
| WO | 2008094597 A2 | 8/2008 | |
| WO | 2009013254 A1 | 1/2009 | |
| WO | 2009027654 A1 | 3/2009 | |
| WO | 2010065679 A1 | 6/2010 | |
| WO | 2010088735 A1 | 8/2010 | |
| WO | 2011050476 A1 | 5/2011 | |
| WO | 2011060342 A2 | 5/2011 | |
| WO | 2011116930 A1 | 9/2011 | |
| WO | WO 2011116930 A1 * | 9/2011 | ............ C12N 5/067 |

OTHER PUBLICATIONS

Behbahan et al., "New approaches in the differentiation of human embryonic stem cells and induced pluripotent stem cells toward hepatocytes," Stem Cell Reviews, Sep. 2011, vol. 7, No. 3, pp. 748-759.
Cai et al., "Retinoic acid represses CYP7A1 expression in human hepatocytes and HepG2 cells by FXR/RXR-dependent and independent mechanisms," Journal of Lipid Research, Aug. 2010, vol. 51, No. 8, pp. 2265-2274.
Huang et al., "Retinoic acid signalling induces the differentiation of mouse fetal liver-derived hepatic progenitor cells," Liver International: Official Journal of the International Association for the Study of the Liver, Nov. 2009, vol. 29, No. 10, pp. 1569-1581.
Ishii et al., "Effects of extracellular matrixes and growth factors on the hepatic differentiation of human embryonic stem cells," American Journal of Physiology, Gastrointestinal and Liver Physiology, Aug. 2008, vol. 295, No. 2, pp. G313-G321.
Touboul et al., "Generation of functional hepatocytes from human embryonic stem cells under chemically defined conditions that recapitulate liver development," Hepatology (Baltimore, MD), May 2010, vol. 51, No. 5, pp. 1527-1765.
Yu et al., "Hepatocyte-like cells differentiated from human induced pluripotent stem cells: relevance to cellular therapies," Stem Cell Research, Nov. 2012, vol. 9, No. 3, pp. 196-207.
Zhang et al., "Generation characterization and potential therapeutic applications of mature and functional hepatocytes from stem cells," Journal of Cellular Physiology Feb. 2013, Jun. 27, 2012, vol. 228, No. 2, pp. 298-305.
Zhao et al., "Promotion of the efficient metabolic maturation of human pluripotent stem cell-derived hepatocytes by correcting specification defects," Cell Research, Oct. 16, 2012, vol. 23, No. 1, pp. 157-161.
International Search Report and Written Opinion for Application PCT/EP2013/075018 dated Feb. 3, 2014.
Allenby et al., "Retinoic acid receptors and retinoid X receptors: Interactions with endogenous retinoic acids," Proc. Natl. Acad. Sci. USA (Jan. 1993); 90:30-34.
Brolen et al., "Hepatocyte-like cells derived from human embryonic stem cells specifically via definitive endoderm and progenitor stage," Journal of Biotechnology (2010); 145:284-294.
Kim et al., "Epigenetic signatures and temporal expression of lineage-specific genes in hESCs during differentiation to hepatocytes in vitro," Human Molecular Genetics, Feb. 1, 2011, vol. 20, No. 3, pp. 401-412.
Kim et al., Differentiation of Mouse Embryonic Stem Cells into Endoderm without Embryoid Body Formation,: PLOS One, Jan. 1, 2010, vol. 5, No. 11, p. e14146.
Pennarossa et al., "Brief demethylation step allows the conversion of adult human skin fibroblasts into insulin-secreting cells," Proceedings of the National Academy of Sciences, May 21, 2013, vol. 110, No. 22, pp. 8948-8953.
Banerjee, "DNA methylthansferase inhibition induces mouse embryonic stem cell differentiation into endothelial cels," Experimentation Cell Research, Jan. 15, 2010, vol. 312, No. 2, pp. 172-180.
Wang et al., "Generating cells of the gastrointestinal system: current approaches and applications for the differentiation of human pluripotent stem cells," Journal of Molecular Medicine, Springer, Berlin, DE, Jun. 20, 2012, vol. 90, No. 7, pp. 763-771.
Jiang et al., "Histone H3K27me3 demethylases KDM6A and KDM6B modulate definitive endoderm differentiation from human ESCs by regulating WNT signaling pathway," Cell Research, Aug. 21, 2012, vol. 23, No. 1, pp. 122-130.
Chen et al., "Rapid Generation of Mature Hepatocyte-Like Cells from Human Induced Pluripotent Stem Cells by an Efficient Three-Step Protocol," Hepatology (Apr. 2012); 55(4):1193-1203.
Heyman et al., "9-Cis Retinoic Acid is a High ffinity Ligand for the Retinoid X Receptor," Cell (Jan. 24, 1992); 68A:397-406.
Heins et al., "Derivation, Characterization, and Differentiation of Human Embryonic Stem Cells," Stem Cells (2004); 22:367-376.
Hay et al., "Efficient Differentiation of Hepatocytes from Human Embryonic Stem Cells Exhibiting Markers Recapitulating Liver Development in Vivo," Stem Cells (2008); 26:894-902.
Hay et al., "Direct Differentiation of Human Embryonic Stem Cells to Hepatocyte-Like Cells Exhibiting Functional Activities," Cloning and Stem Cells (2007); 9(1):51-62.
Idres et al., "Activation of Retinoic Acid Receptor-dependent Transcription by All-trans-retinoic Acid and Metabolites and Isomers," The Journal of Biological Chemistry (Aug. 30, 2002); 277(35):31491-31498.
Klimanskaya et al., "Human embryonic stem cell lines derived from single blastomeres," Nature (Nov. 23, 2006); 444:481-485.
Magee et al., "Retinoic Acid Mediates Down-regulation of the α-Fetoprotein Gene through Decreased Expression of Hepatocyte Nuclear Factors," The Journal of Biological Chemistry (Nov. 6, 1998); 273(45):30024-30032.
Martin et al., "Human embryonic stem cells express an immuogenic nonhuman sialic acid," Nature Medicine (Feb. 2005); 11(2):228-232.
Mercader et al., "Human Embryo Culture," Essential Stem Cell Methods, Chapter 16, Academic Press, 1st Edition (2009) (19 pages).
Mfopou et al., "Noggin, Retinoids, and Fibroblast Growth Factor Regulate Hepatic or Pancreatic Fate of Human Embryonic Stem Cells," Gastroenterology (2010); 138:2233-2245.
Page et al., "Gene Expression Profiling of Extracellular Matrix as an Effector of Human Hepatocyte Phenotype in Primary Cell Culture," Toxicol Sci (Jun. 2007); 97(2):384-397.
Qian et al., "Identification of Retinoic Acid-Responsive Elements on the HNF1α and HNF4α Genes," Biochemical and Biophysical Research Communications (2000); 276:837-842.
Levy et al., "Long-term culture and expansion of primary human hepatocytes," Nature Biotechnology (Dec. 2015); 33(12):1264-1271.
Song et al., "Efficient generation of hepatocyte-like cells from human induced pluripotent stem cells," Cell Research (2009); 19(11):1233-1242.
Zhou et al., "Generation of Induced Pluripotent Stem Cells Using Recombinant Proteins," Cell Stem Cell (May 8, 2009); 4(5):381-384.
Yu et al., "Induced Pluripotent Stem Cell Derivation," Essentials of Stem Cell Biology, Chapter 37, Academic Press, 2nd Edition (2009).
Wang et al., "Lineage Restriction of Human Hepatic Stem Cells to Mature Fates is Made Efficient by Tissue-Specific Biomatrix Scaffolds," Hepatology (Jan. 2011); 53(1):293-305.
Turner et al., "Human Hepatic Stem Cell and Maturational Liver Lineage Biology," Hepatology (Mar. 2011); 53(3):1035-1045.
Thomson et al., "Embryonic Stem Cell Lines Derived from Human Blastocysts," Science (Nov. 6, 1998); 282:1145-1147.
Takahashi et al., "Induction of Pluripotent Stem Cells from Adult Human Fibroblasts by Defined Factors," Cell (Nov. 30, 2007); 131(5):861-872.
Sullivan et al., "Generation of Functional Human Hepatic Endoderm from Human iPS cells," Hepatology (Jan. 2010); 51(1):329-335.

(56) References Cited

OTHER PUBLICATIONS

Hatzis et al., "Regulatory Mechanisms Controlling Human Hepatocyte Nuclear Factor 4α Gene Expression," Molecular and Cellular Biology (Nov. 2001): 21(21):7320-7330.
Funakoshi et al., "Comparison of Hepatic-like Cell Production from Human Embryonic Stem Cells and Adult Liver Progenitor Cells: CAR Transduction Activates a Battery of Detoxification Genes," Stem Cell Rev and Rep (2011); 7:518-531.
Dunn et al., "Long-Term in Vitro Function of Adult Hepatocytes in a Collagen Sandwich Configuration," Biotechnol. Prog. (1991); 7:237-245.
Chung et al., "Human Embryonic Stem Cell Lines Generated without Embryo Destruction," Cell Stem Cell (Feb. 2008); 2:113.
Duan et al., "Differentiation and Characterization of Metabolically Functioning Hepatocytes from Human Embryonic Stem Cells," Stem Cells (2010); 28:674-686.
Moreno Manzano et al., "Human renal mesangial cells are a target for the anti-inflammatory action of 9-cis retinoic acid," British Journal of Pharmacology (2000); 131:1673-1683.

\* cited by examiner

Figure 1:
Fig. 1A)
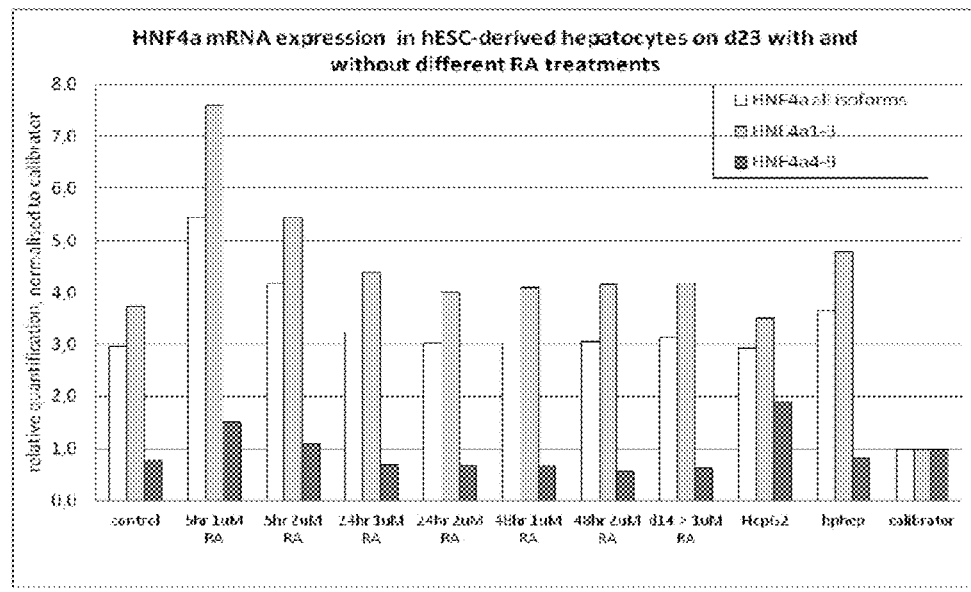
Fig. 1B)
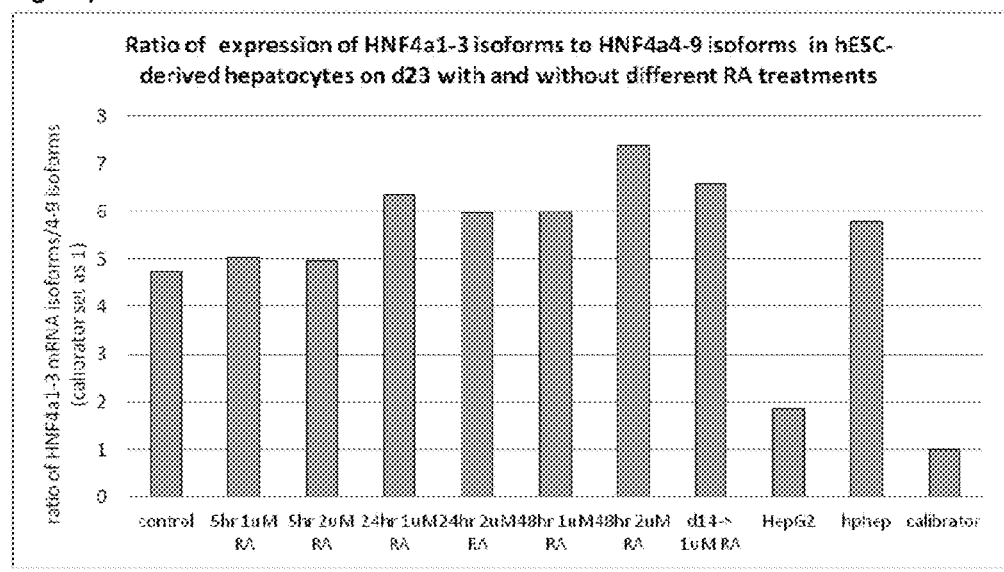

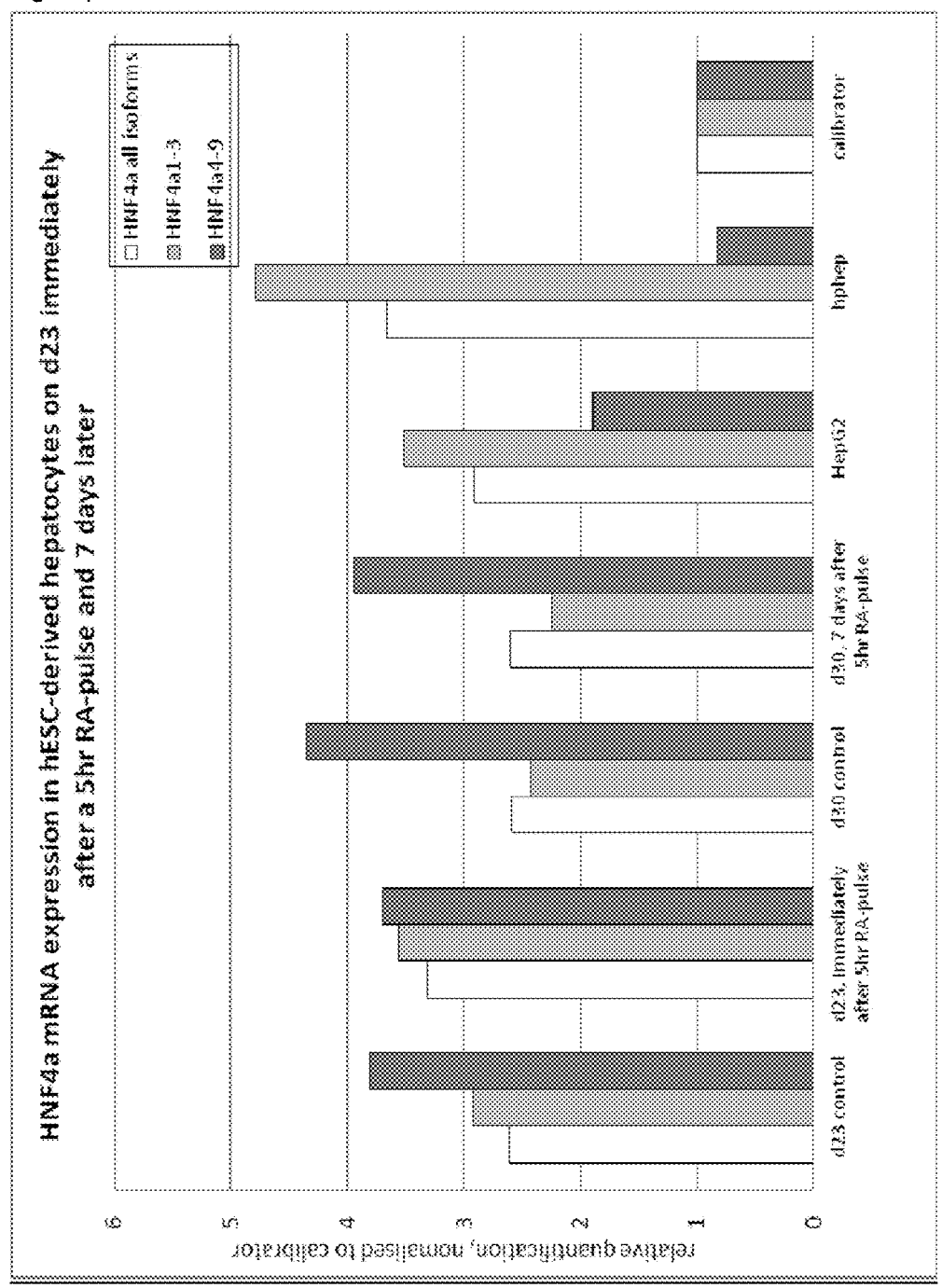

Fig. 2D)
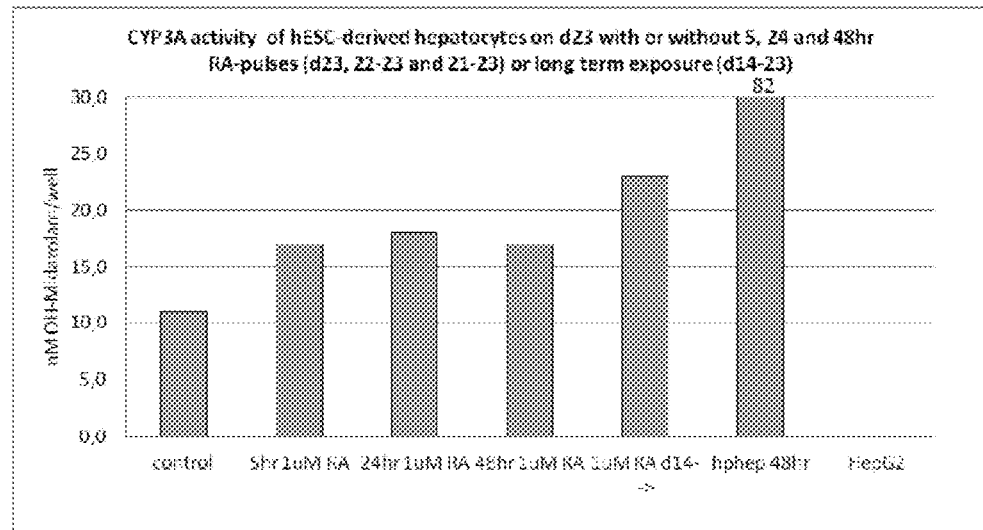
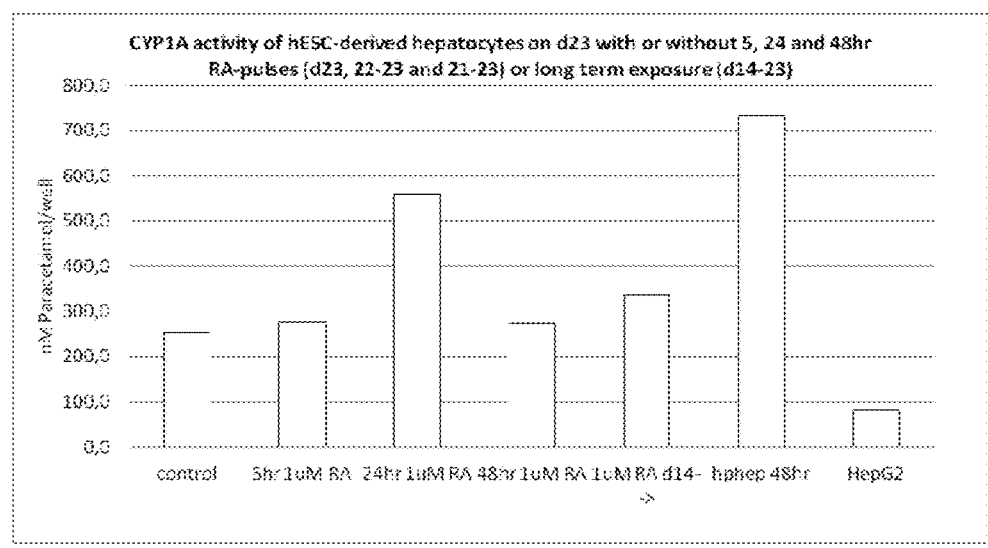

Figure 3:
Fig. 3A)
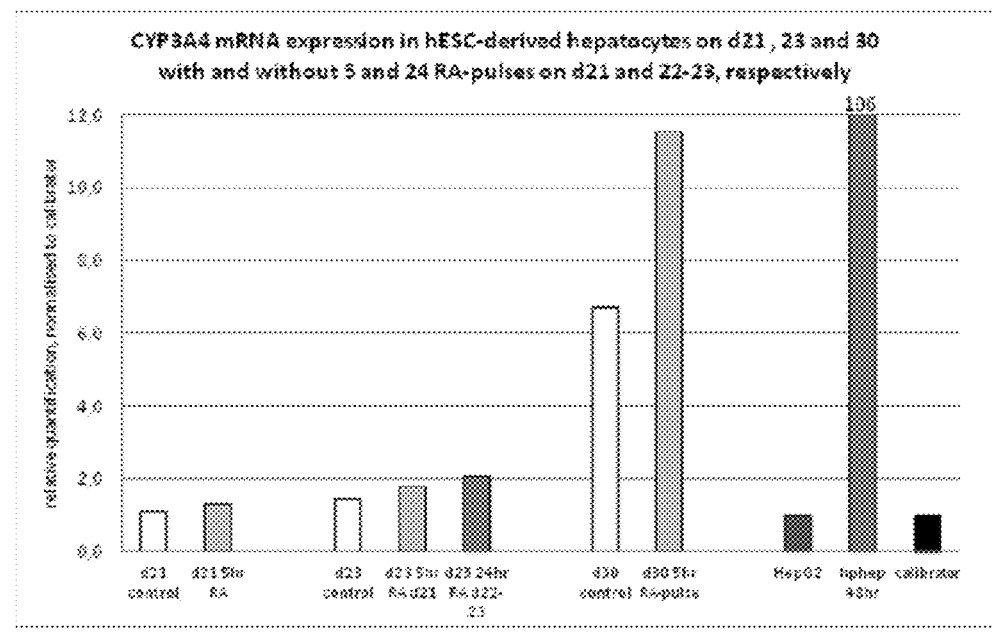
Fig. 3B)
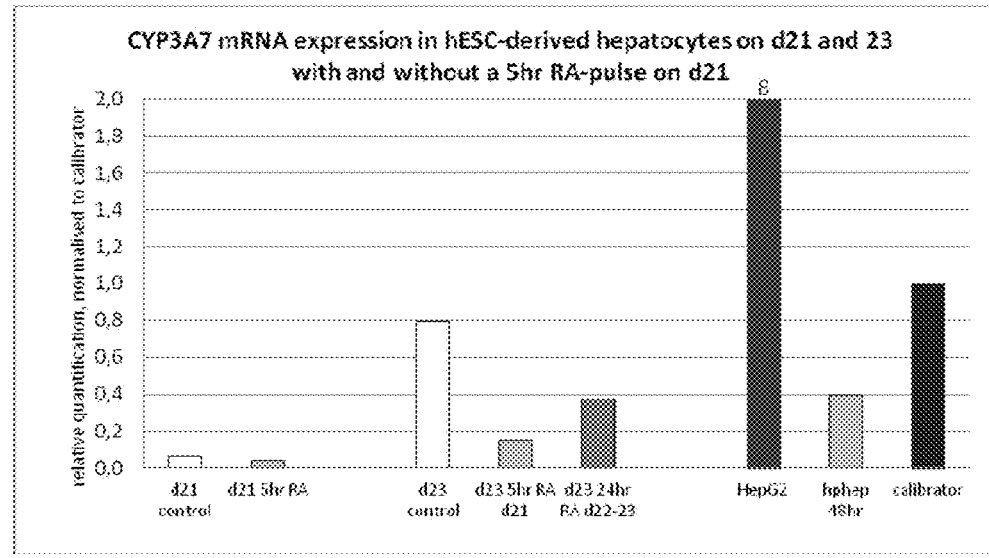

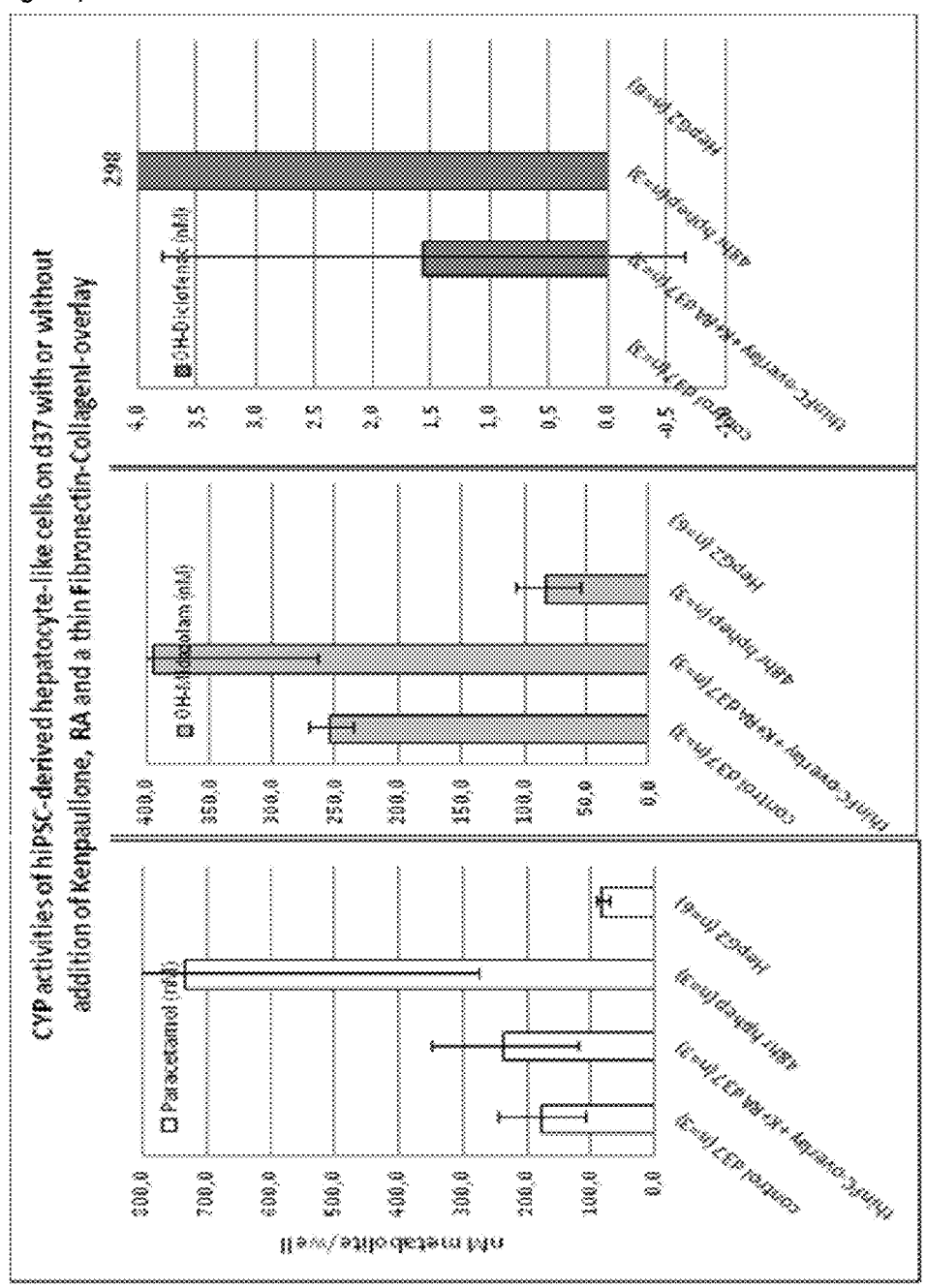

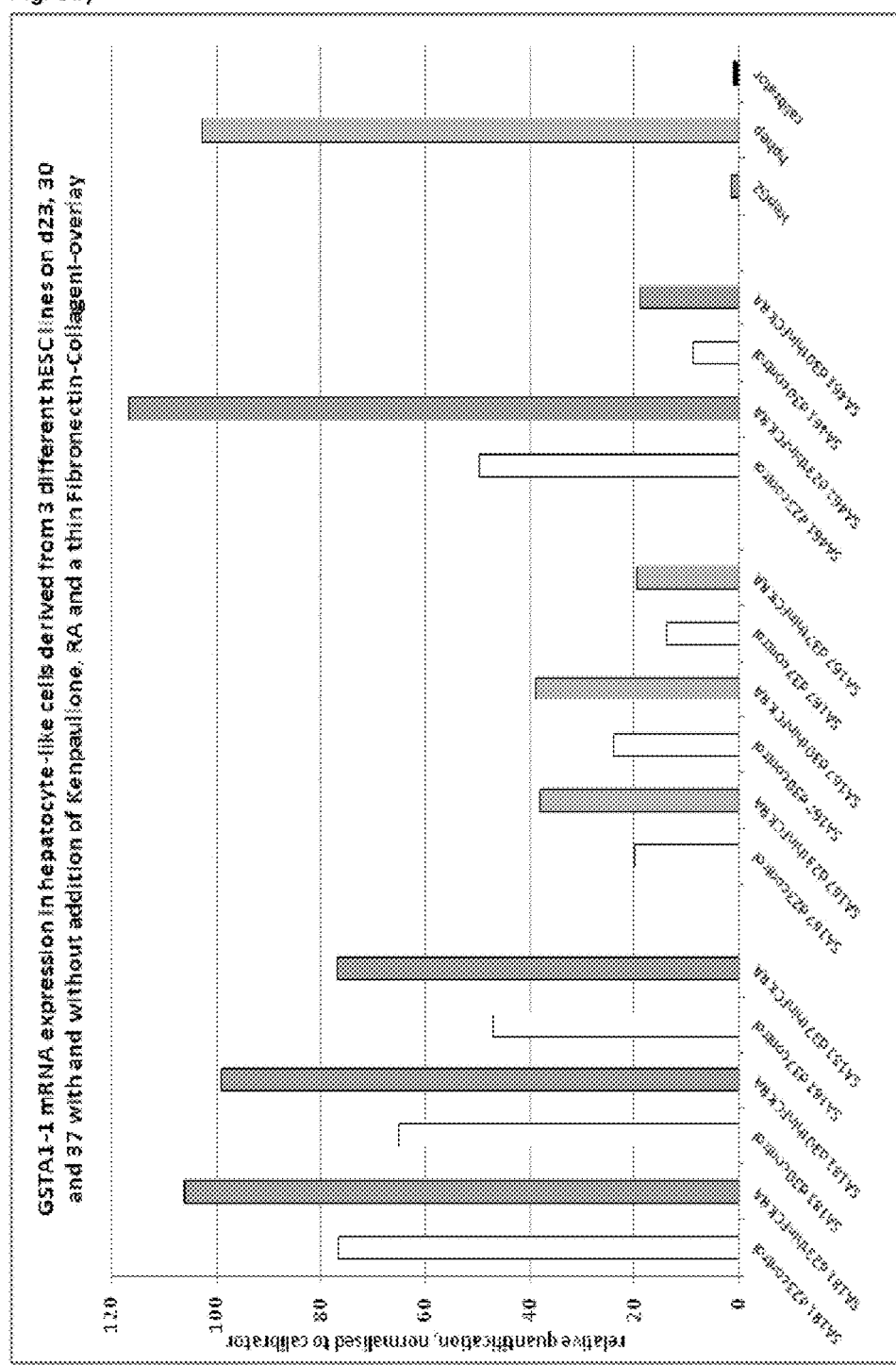

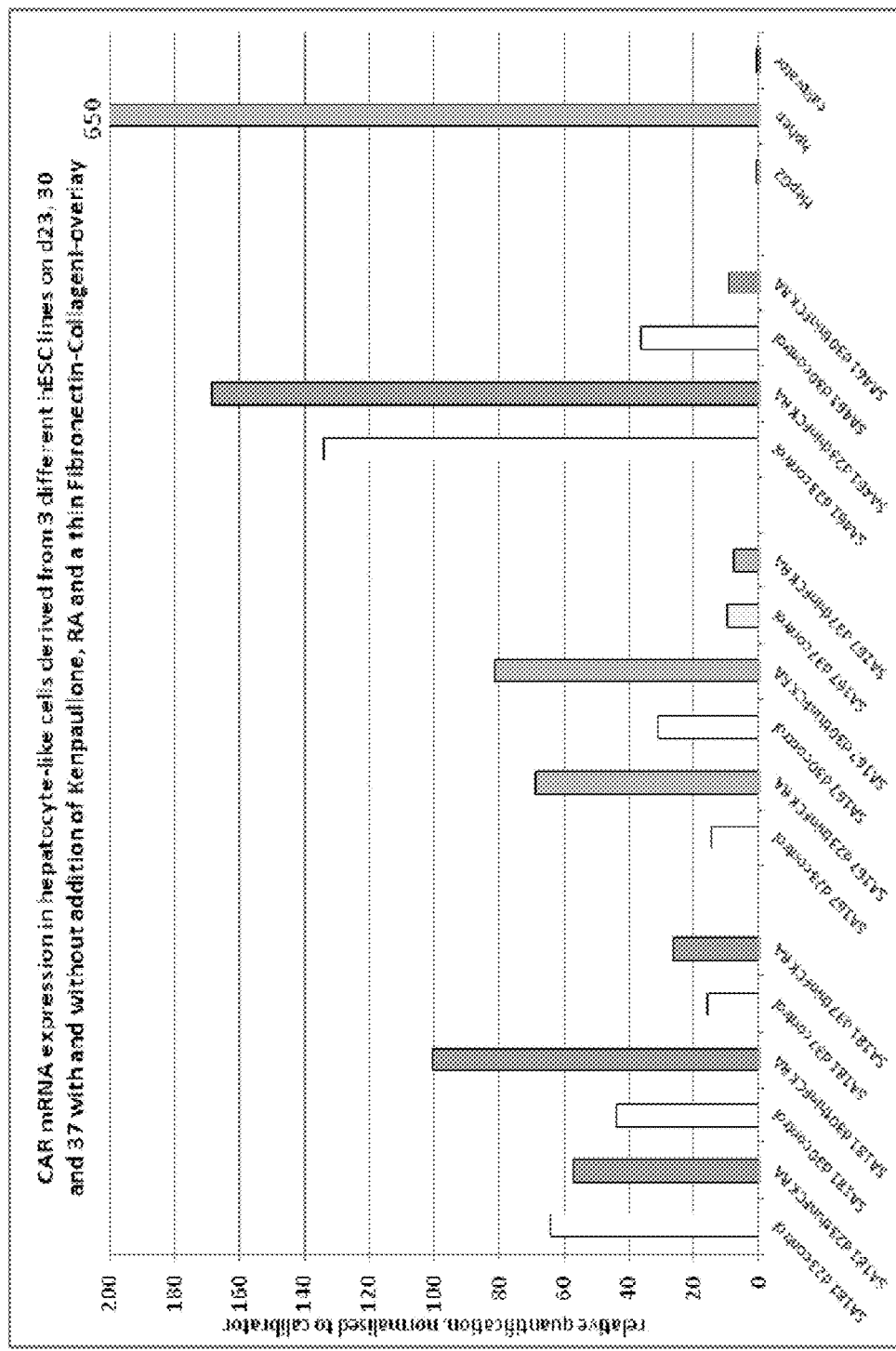

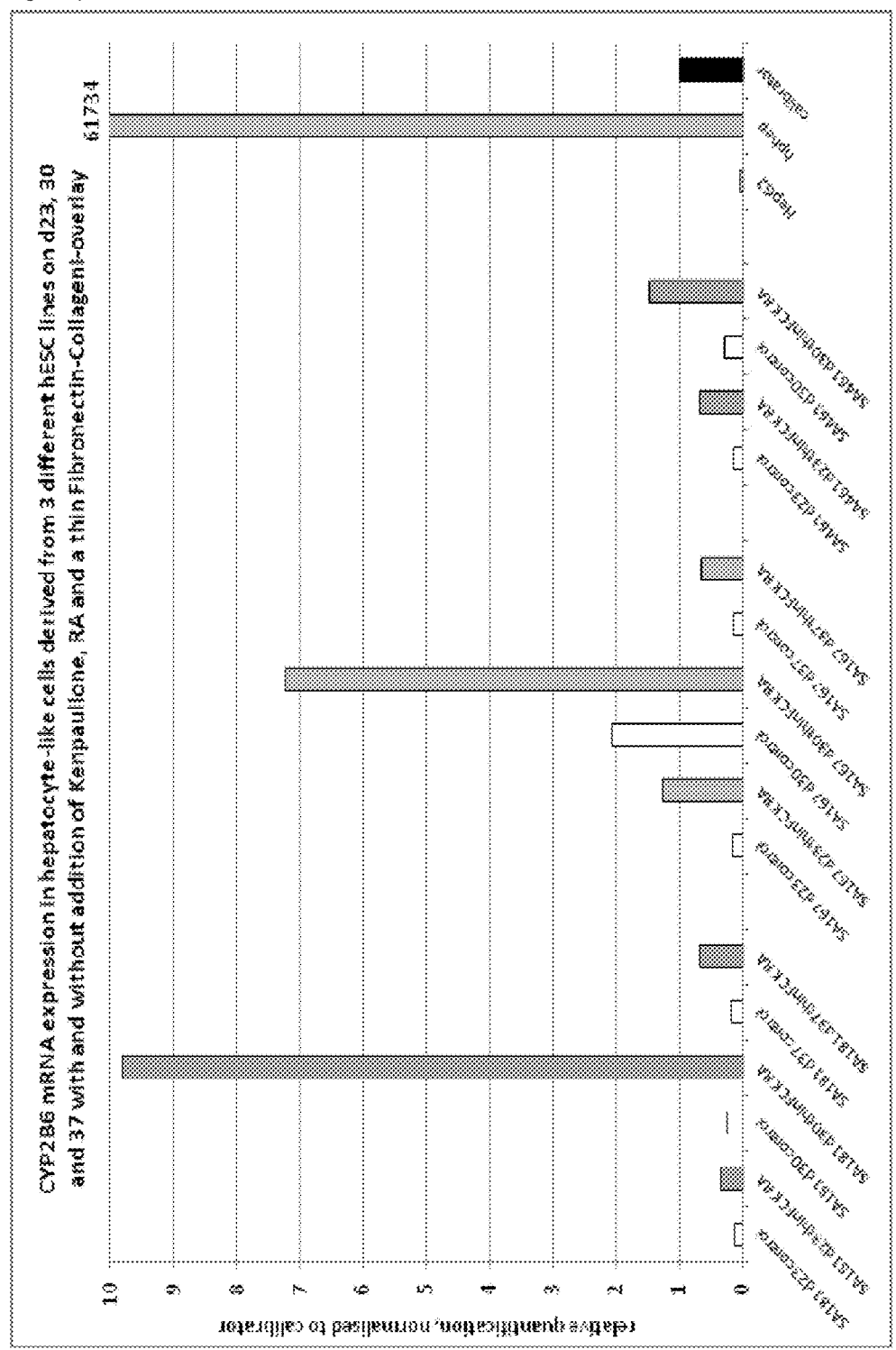

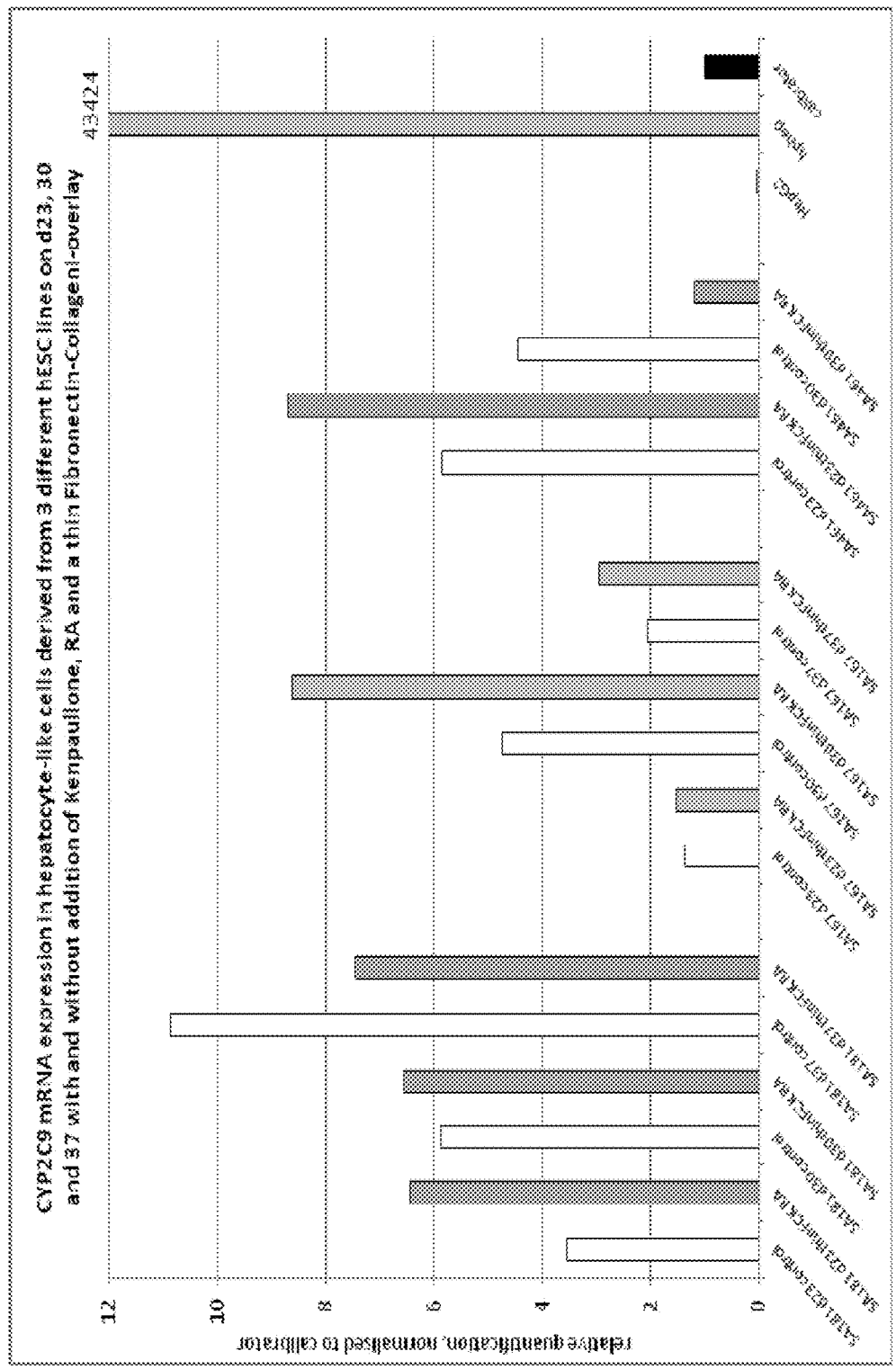

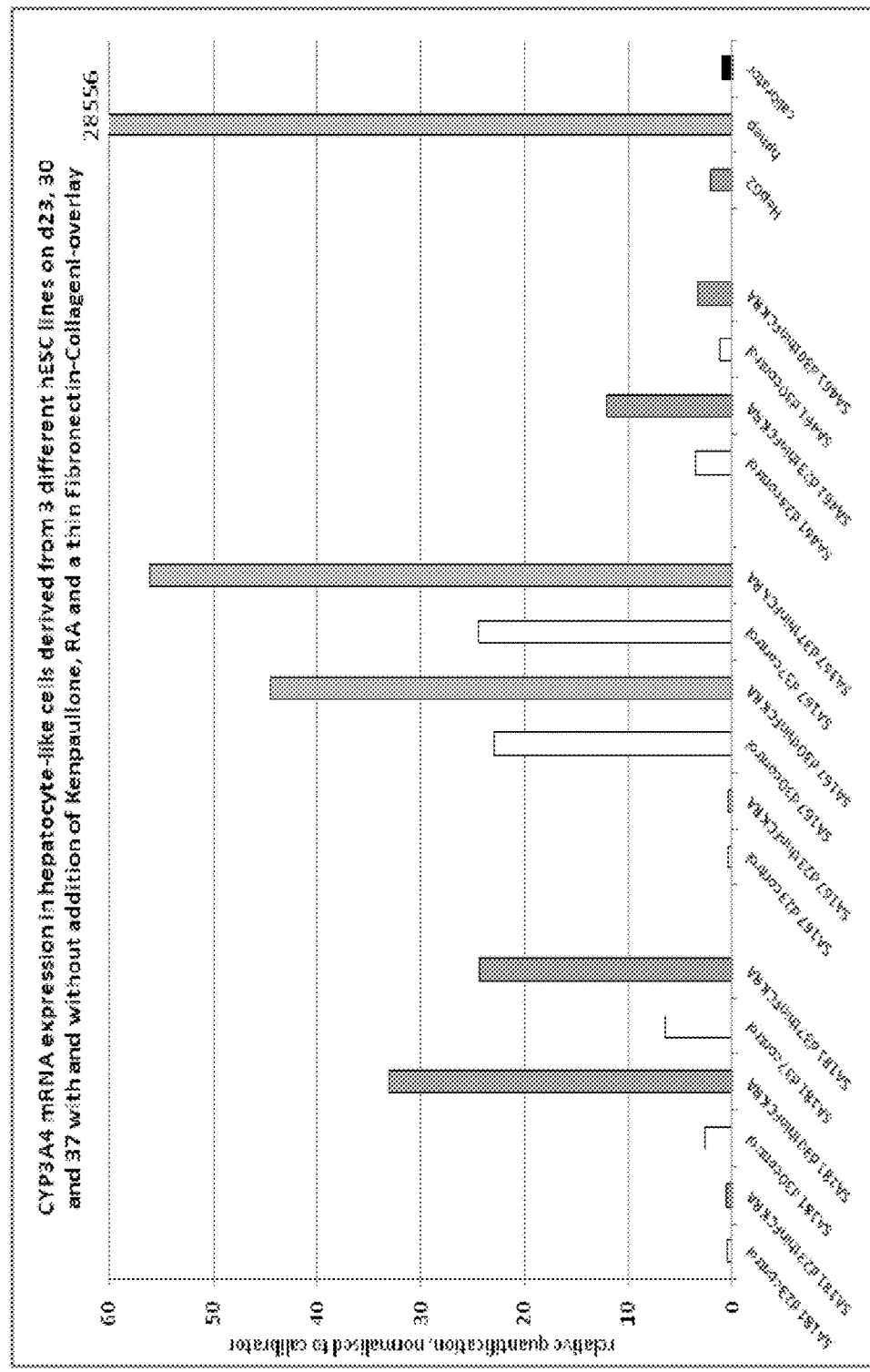

Fig. 6C)
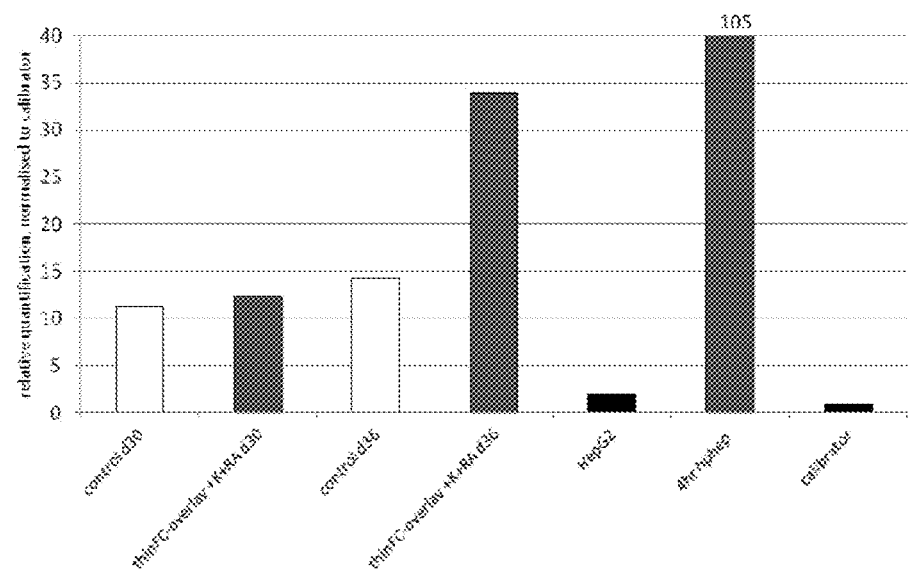
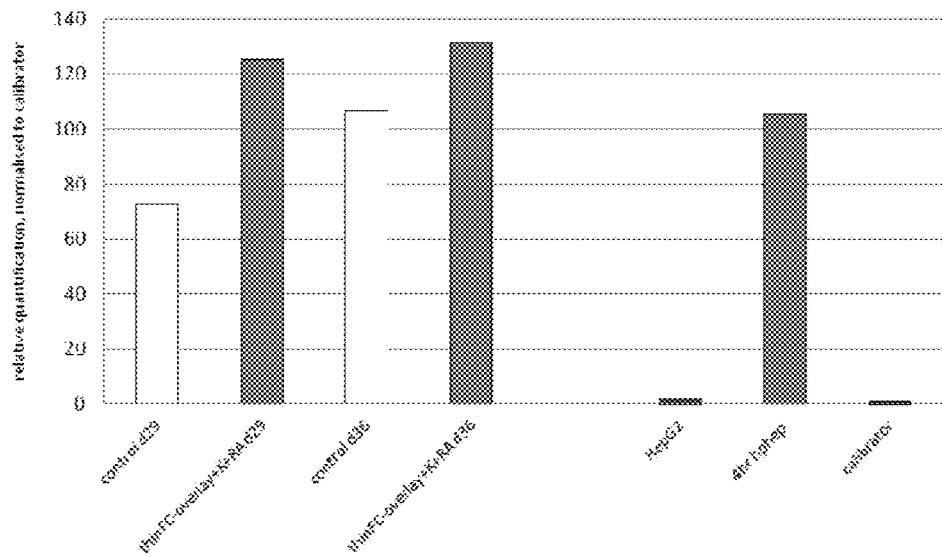

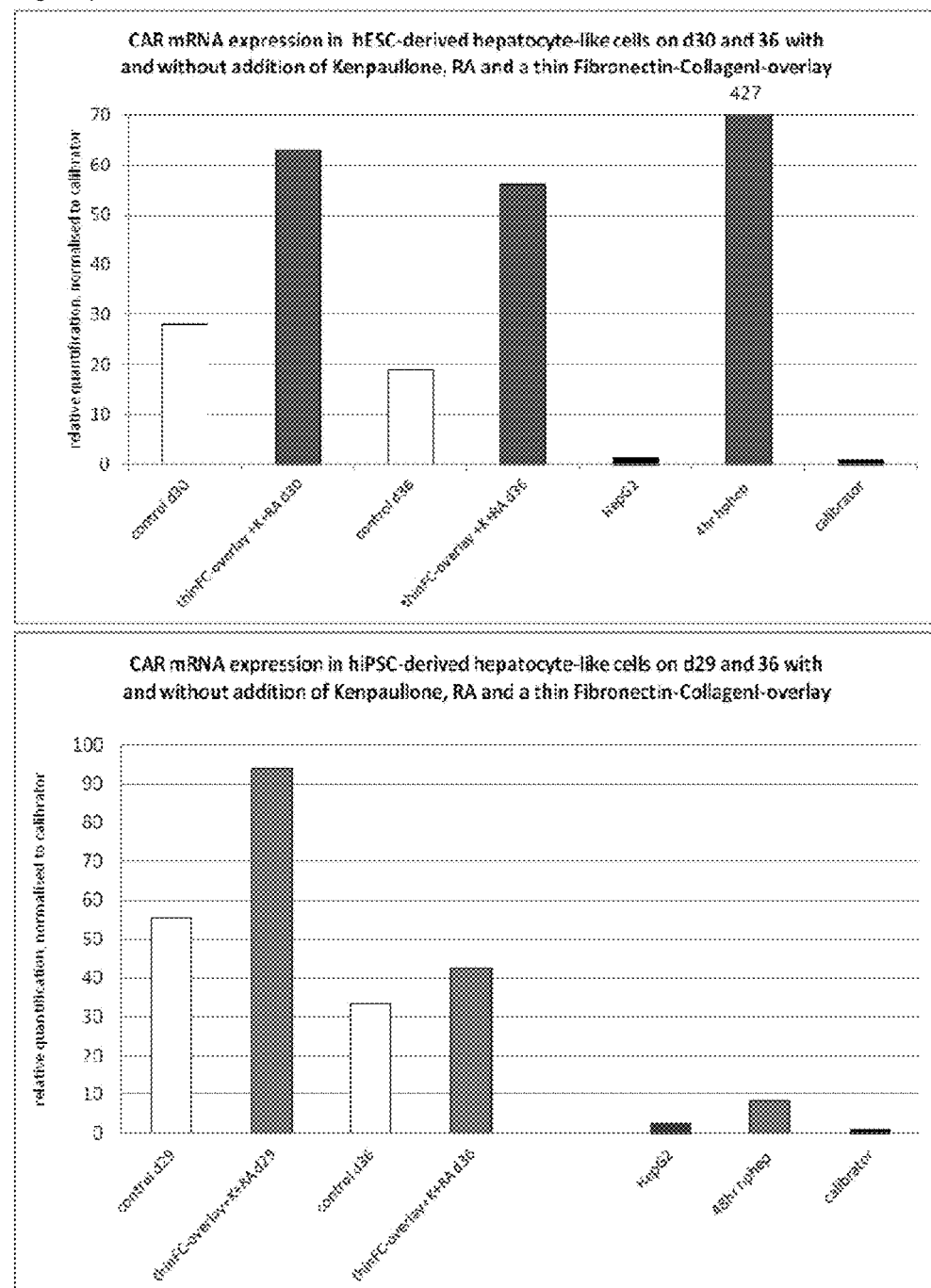

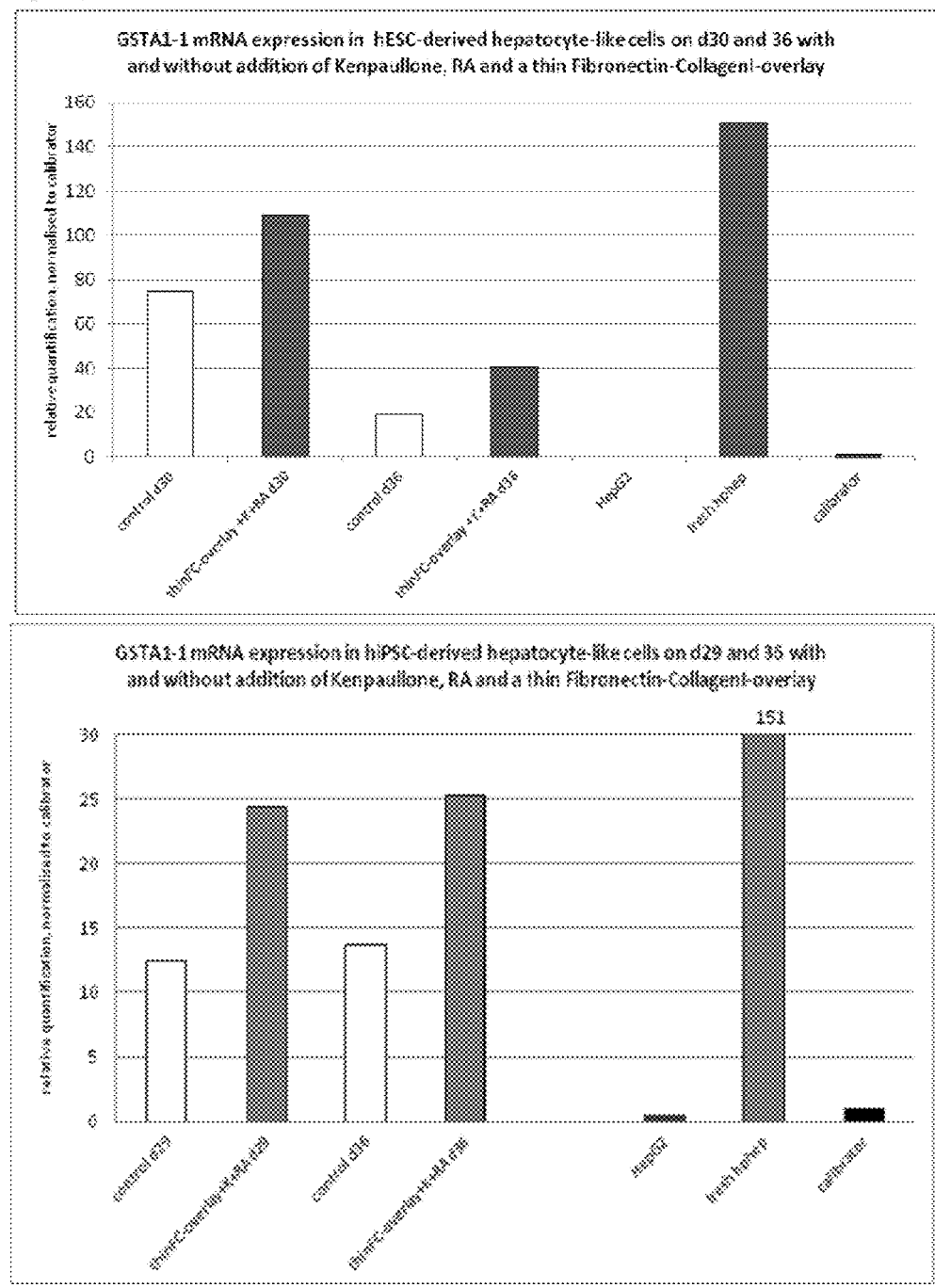

Figure 7:
Fig. 7A) The morphology of hESC-derived hepatocyte-like cells on d28 with and without the addition of a thin Fibronectin-Collagen I-overlay

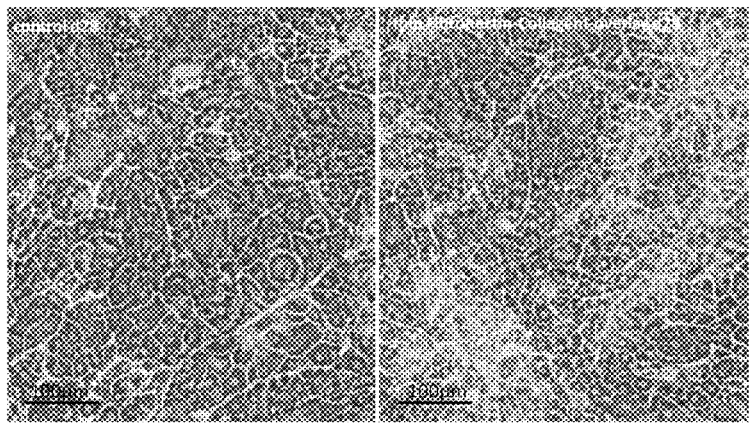

Fig. 7B) The morphology of hESC-derived hepatocyte-like cells on d35 with and without the addition of a thin Fibronectin-Collagen I-overlay.

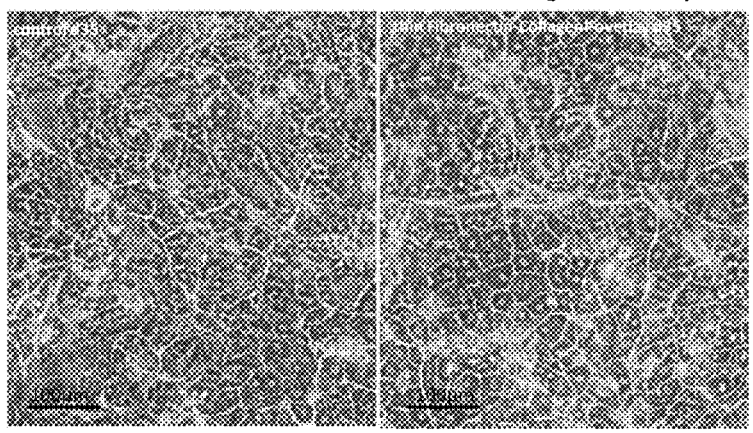

Fig. 7C) The morphology of hESC-derived hepatocyte-like cells on d43 with and without the addition of a thin Fibronectin-Collagen I-overlay.

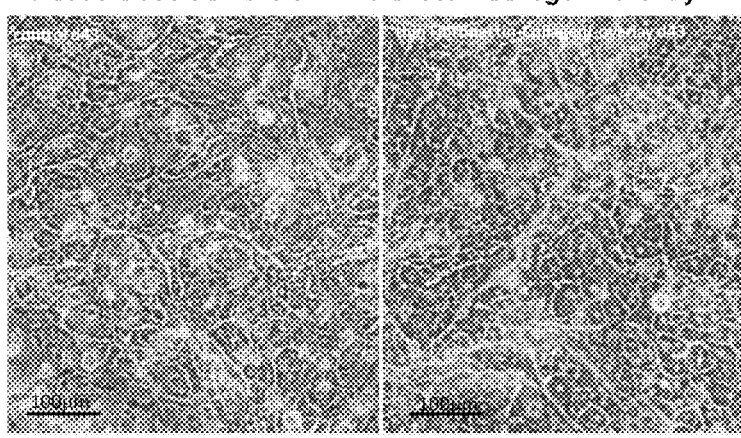

Figure 8:
Fig. 8A) The morphology of hESC-derived hepatocyte-like cells on d30 with and without the addition of Kenpaullone, RA and a thin Fibronectin-Collagen I-overlay.
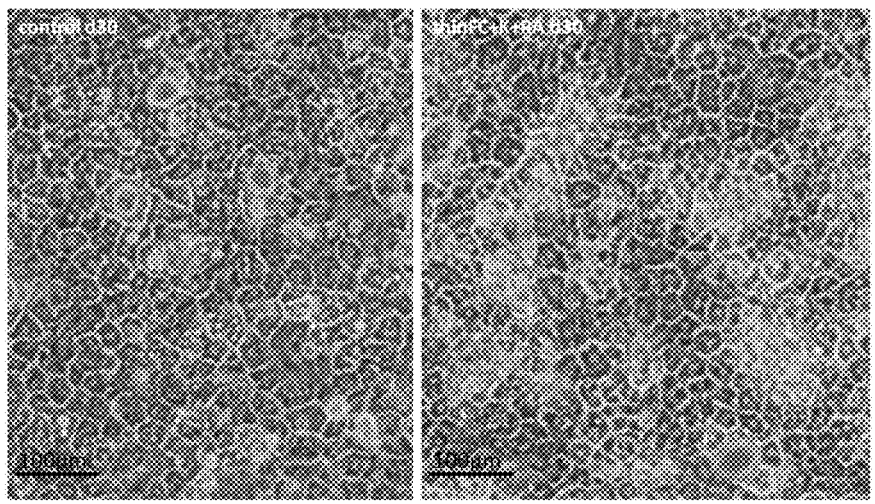
Fig. 8B) The morphology of hESC-derived hepatocyte-like cells on d35 with and without the addition of Kenpaullone, RA and a thin Fibronectin-Collagen I-overlay.
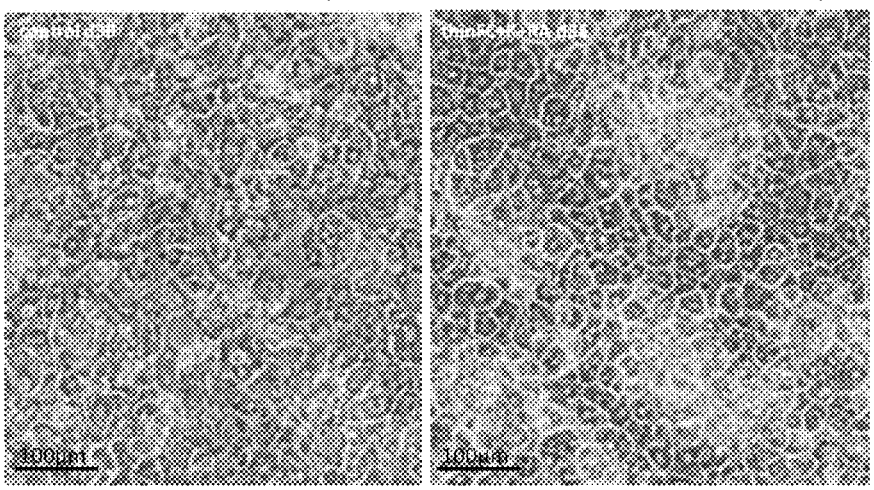

Fig. 8C) The morphology of hiPSC-derived hepatocyte-like cells on d28 with and without the addition of Kenpaullone, RA and a thin Fibronectin-Collagen I-overlay.
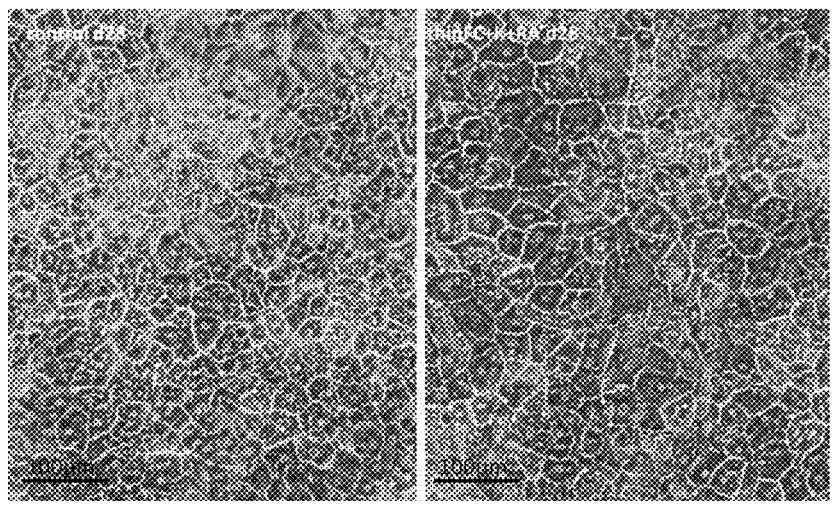
Fig. 8D) The morphology of hiPSC-derived hepatocyte-like cells on d36 with and without the addition of Kenpaullone, RA and a thin Fibronectin-Collagen I-overlay.
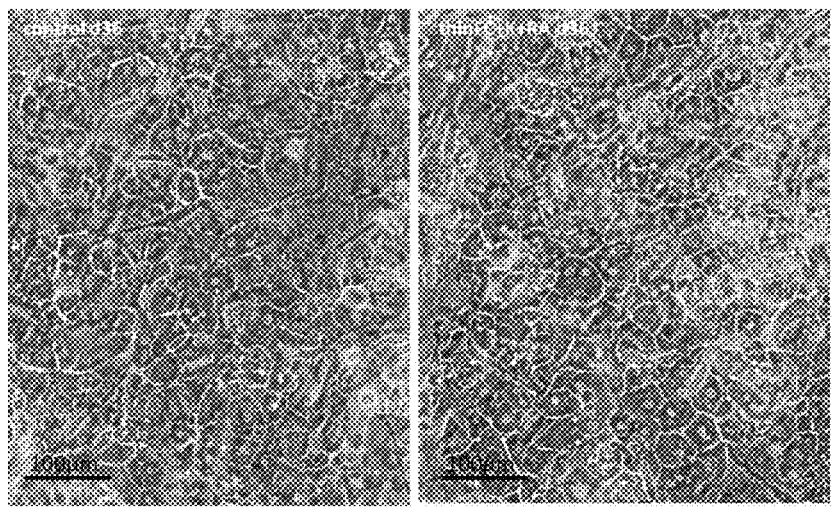

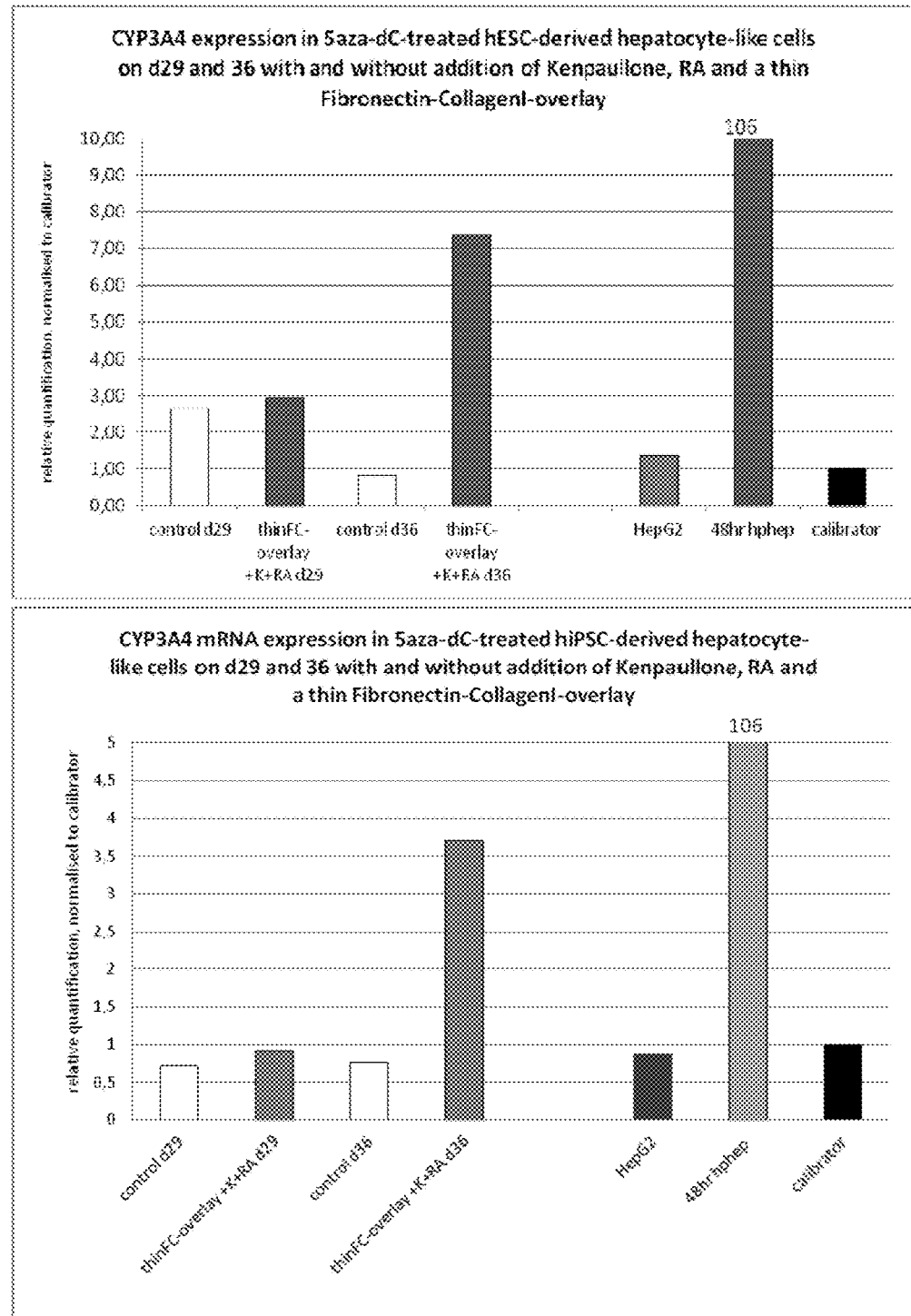

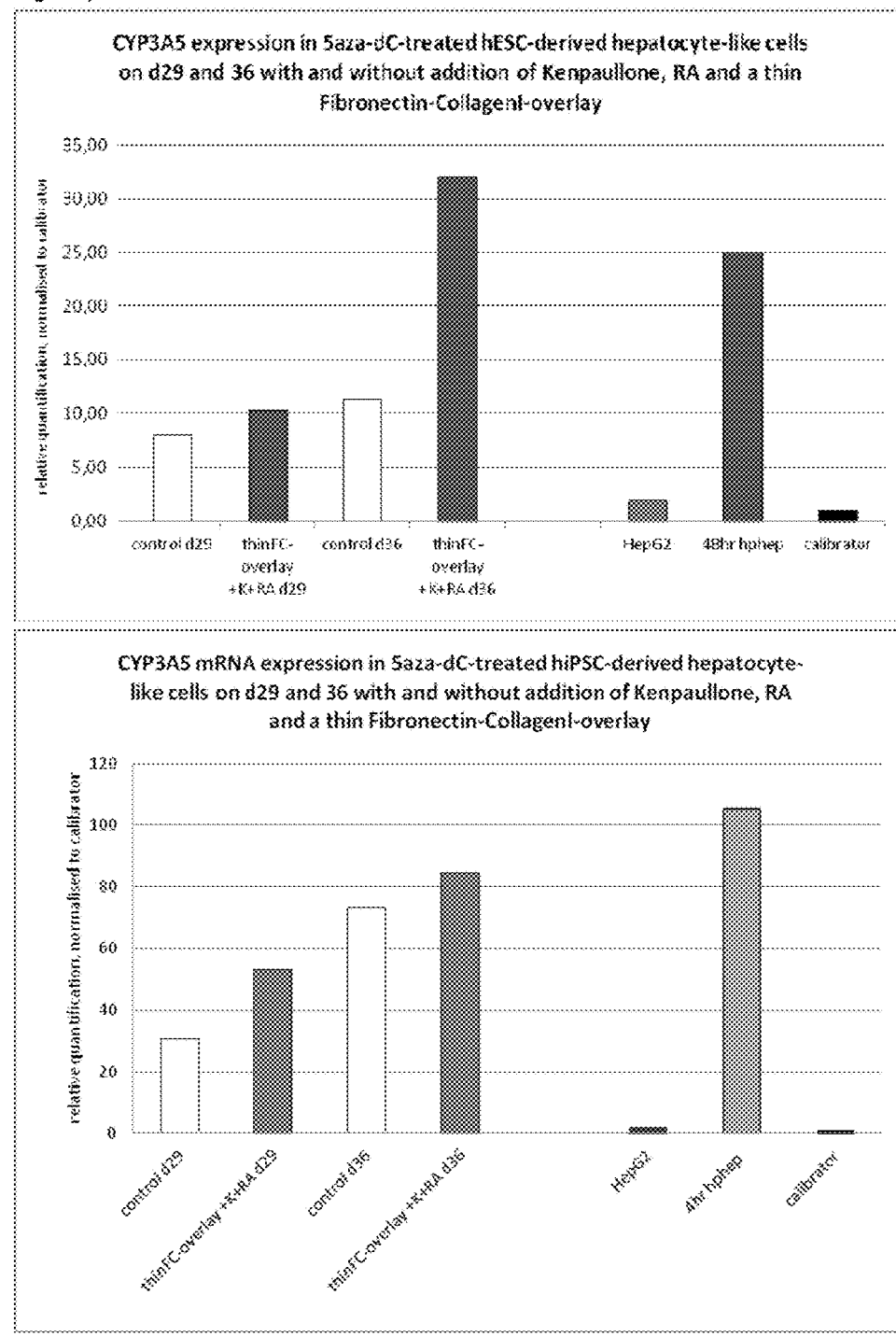

Fig. 9F)
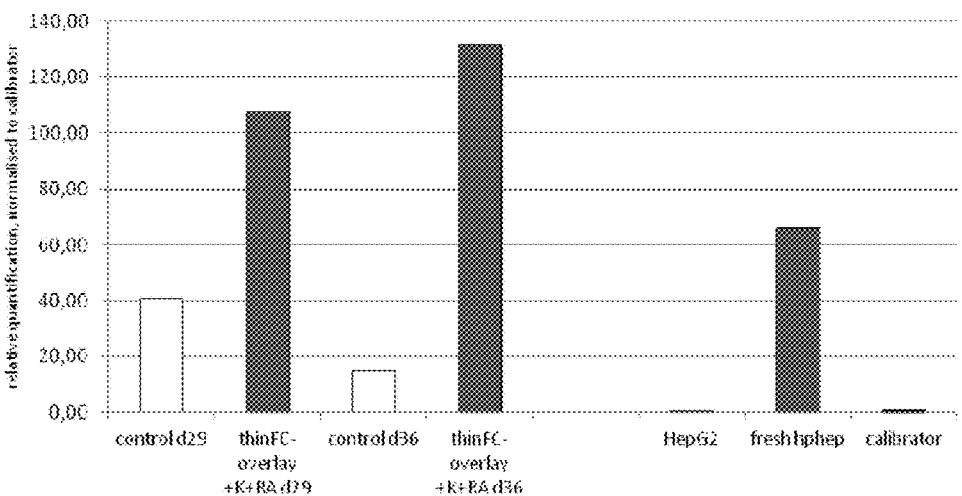
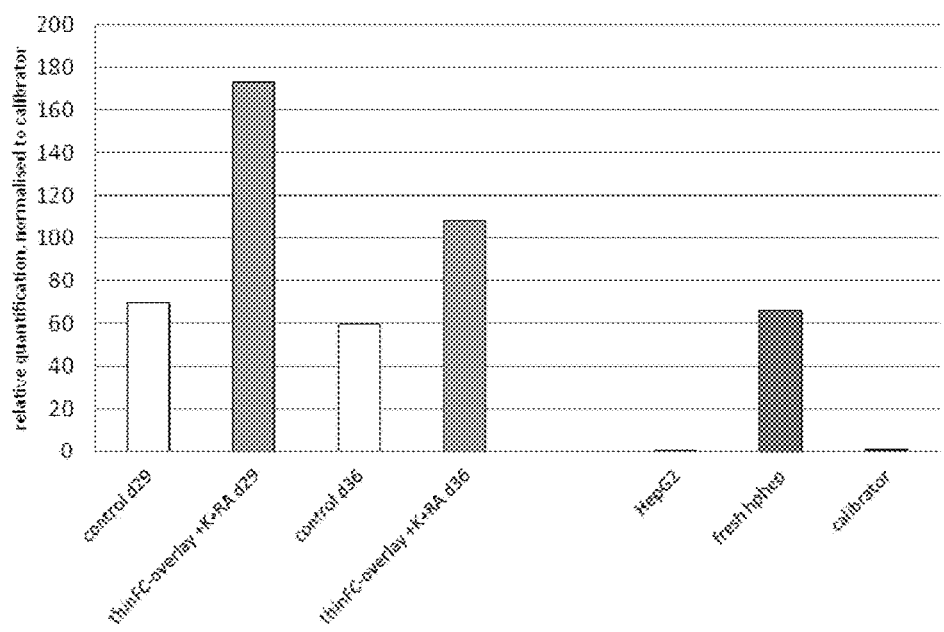

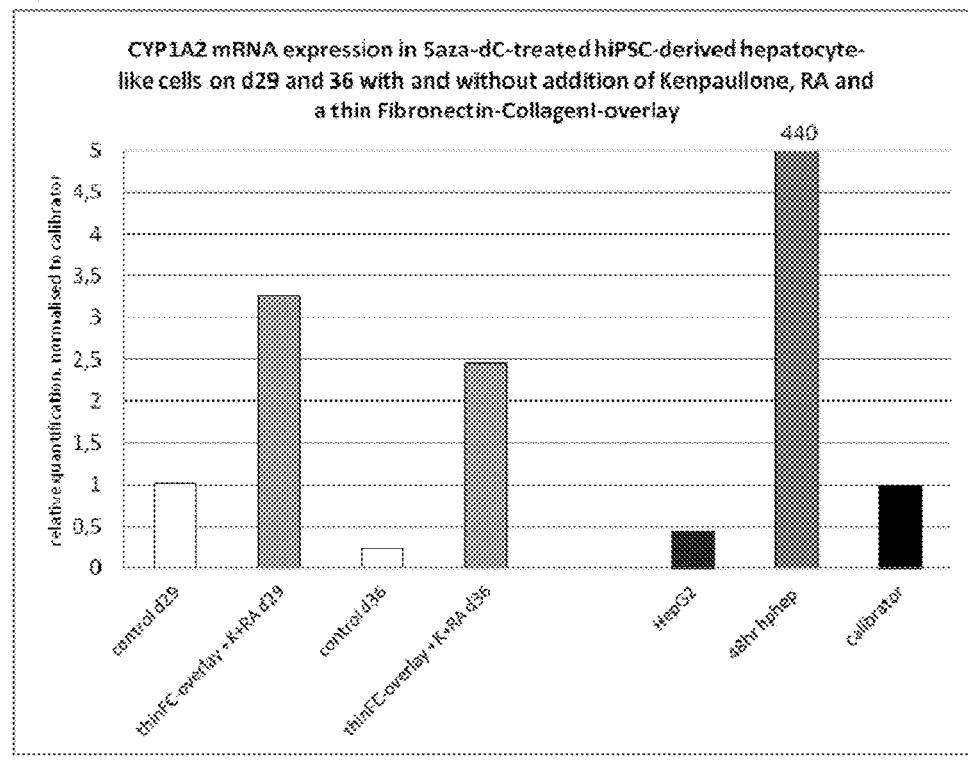

Figure 11:
Fig. 11A) The morphology of 5aza-dC-treated hESC-derived hepatocyte-like cells on d28 with and without the addition of Kenpaullone, RA and a thin Fibronectin-Collagen I-overlay.
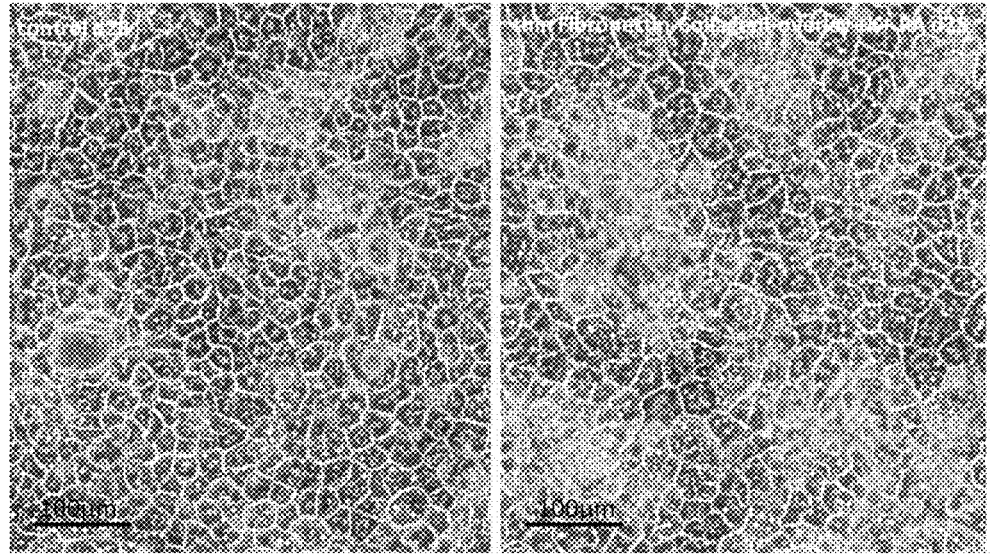
Fig. 11B) The morphology of 5aza-dC-treated hESC-derived hepatocyte-like cells on d35 with and without the addition of Kenpaullone, RA and a thin Fibronectin-Collagen I-overlay.
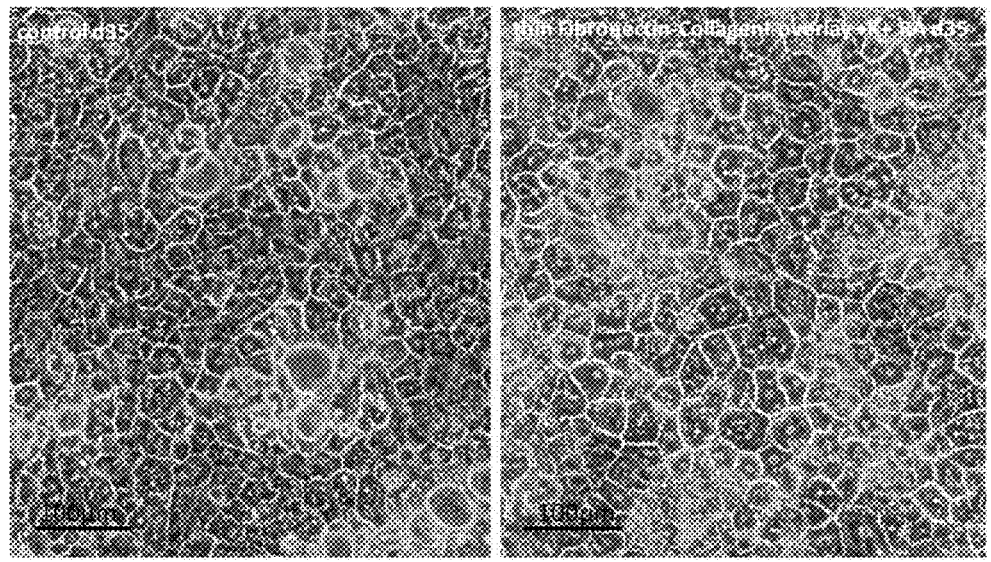

Fig. 11C) The morphology of 5aza-dC-treated hESC-derived hepatocyte-like cells on d42 with and without the addition of Kenpaullone, RA and a thin Fibronectin-Collagen I-overlay.
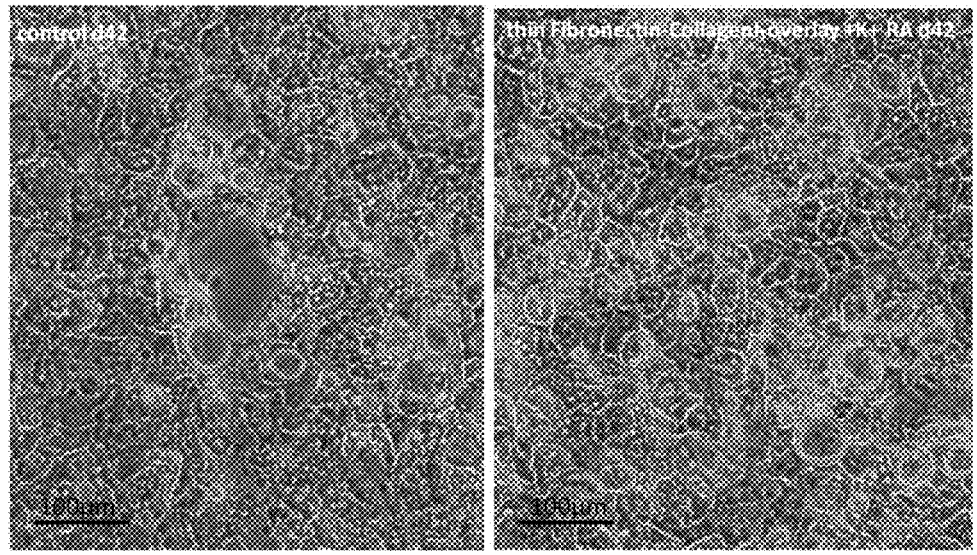
Fig. 11D) The morphology of 5aza-dC-treated hiPSC-derived hepatocyte-like cells on d28 with and without the addition of Kenpaullone, RA and a thin Fibronectin-Collagen I-overlay.
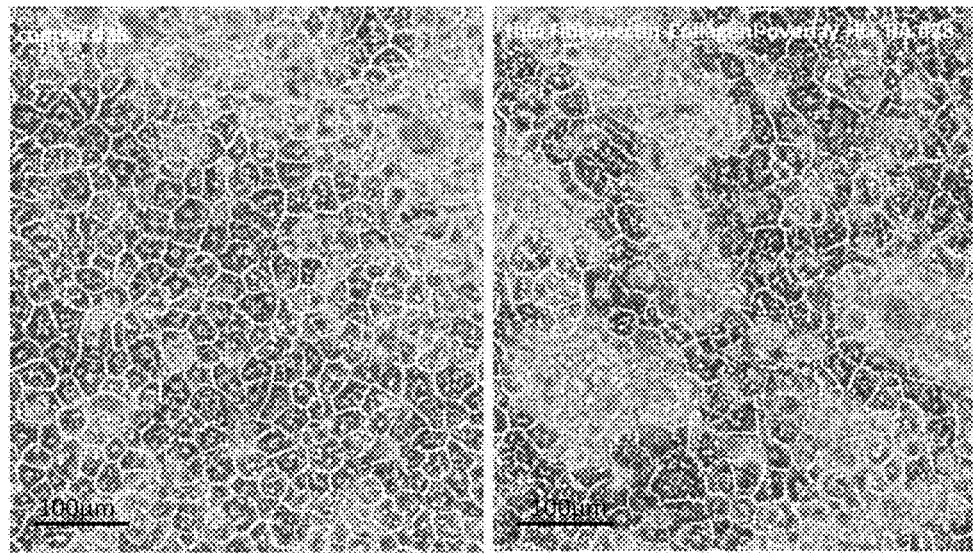

Fig. 11E) The morphology of 5aza-dC-treated hiPSC-derived hepatocyte-like cells on d35 with and without the addition of Kenpaullone, RA and a thin Fibronectin-Collagen I-overlay.
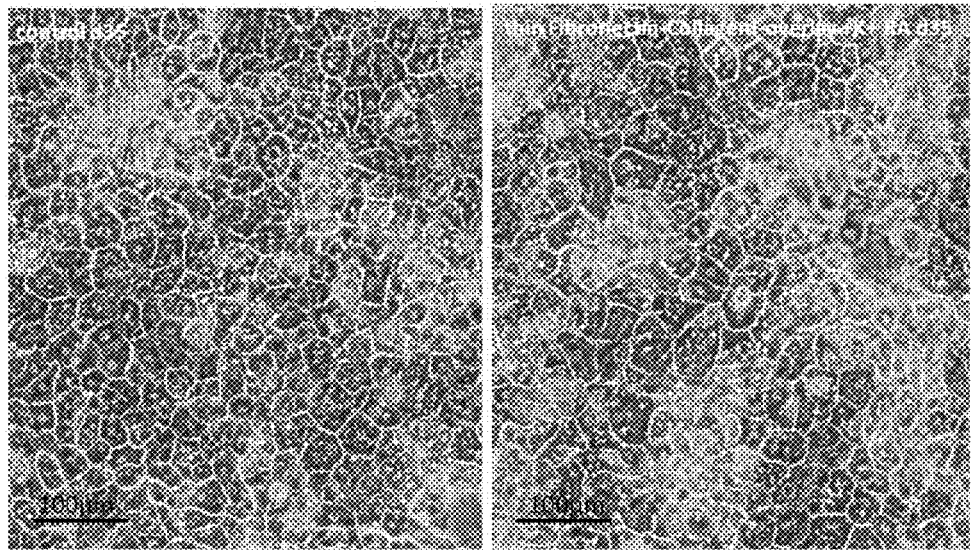
Fig. 11F) The morphology of 5aza-dC-treated hiPSC-derived hepatocyte-like cells on d42 with and without the addition of Kenpaullone, RA and a thin Fibronectin-Collagen I-overlay.
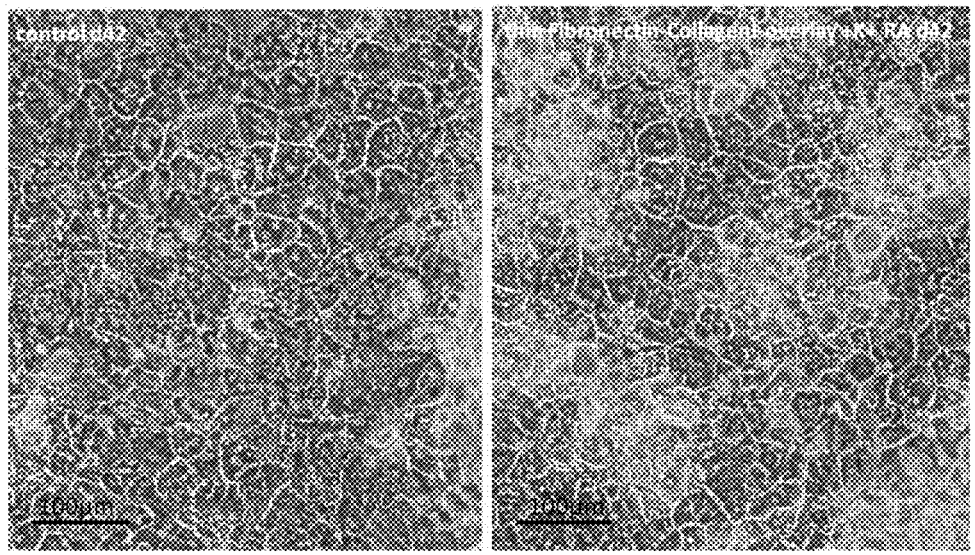

Figure 13:
Fig. 13A1) control          Fig. 13A2) 10nM 5aza-dC d2-3
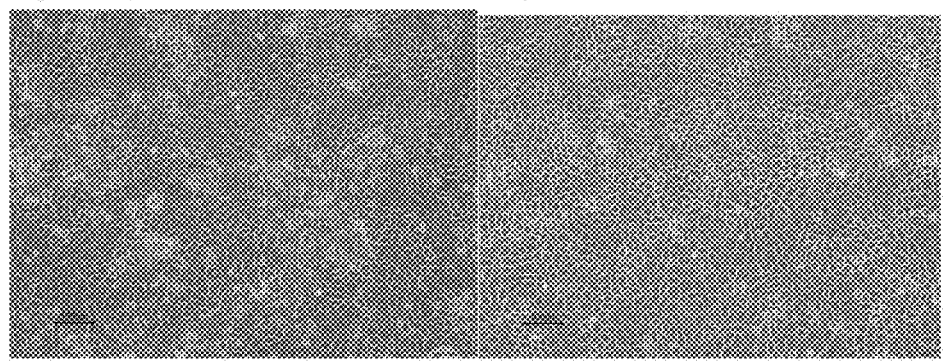
Fig. 13B1) control          Fig. 13B2) 10nM 5aza-dC d2-3
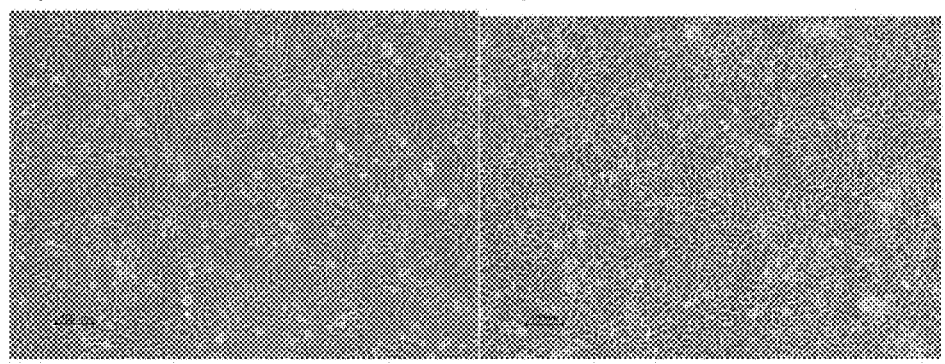
Fig. 13C1) control: Oct4-immunstaining and DAPI nuclear staining
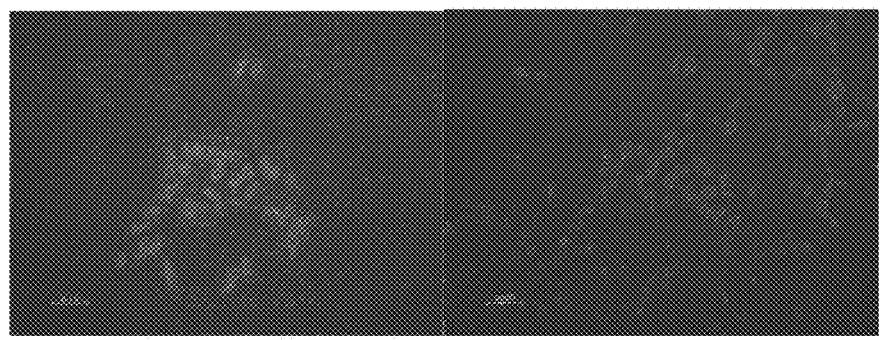

Fig. 13C2) 10nM 5aza-dC d2-3: Oct4-immunstaining and DAPI nuclear staining
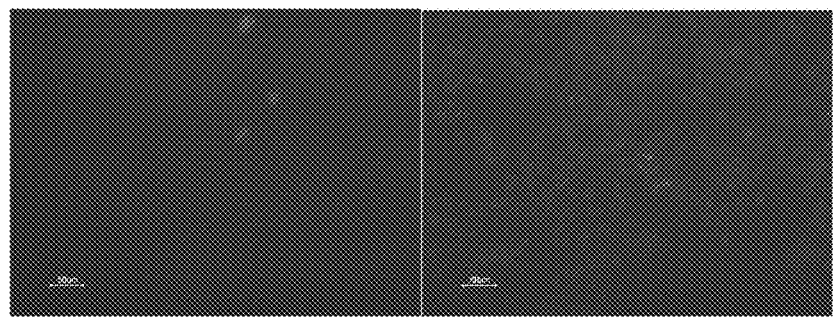

Fig. 13D1)
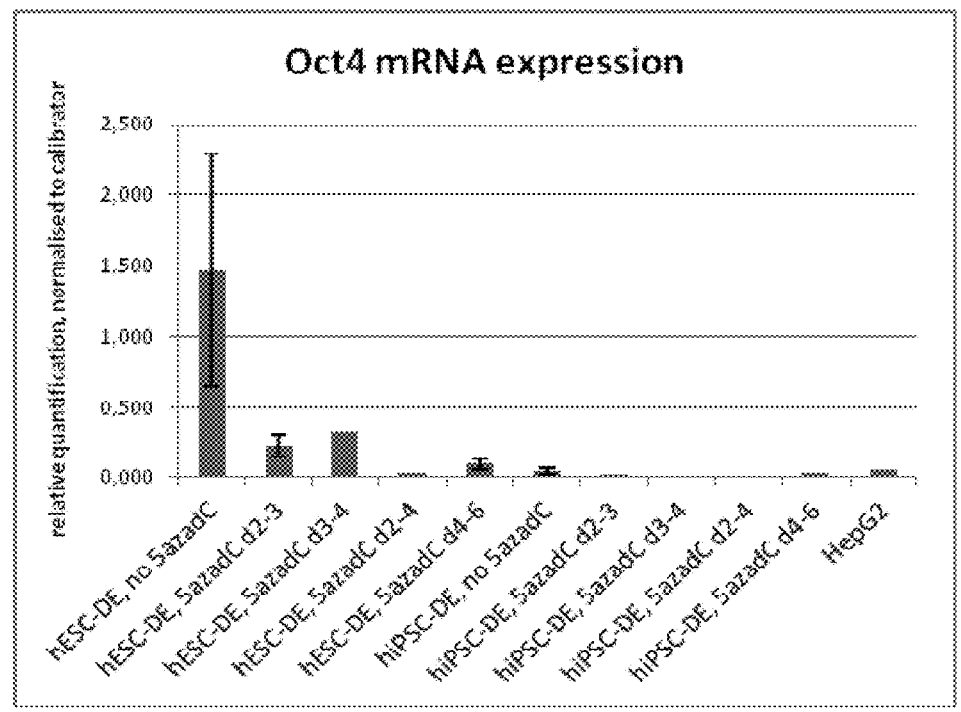
Fig. 13D2)
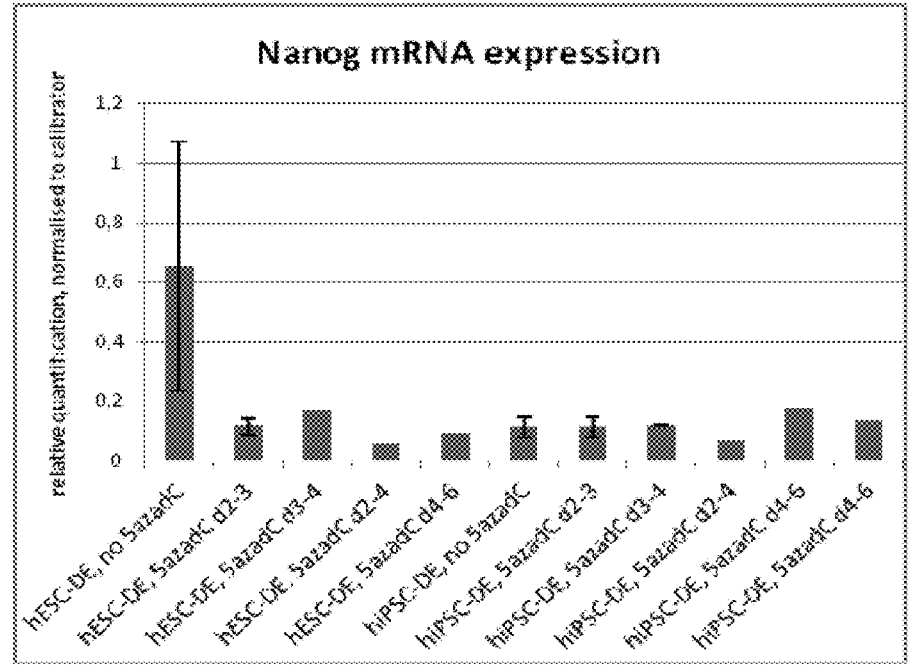

Fig. 13D3)
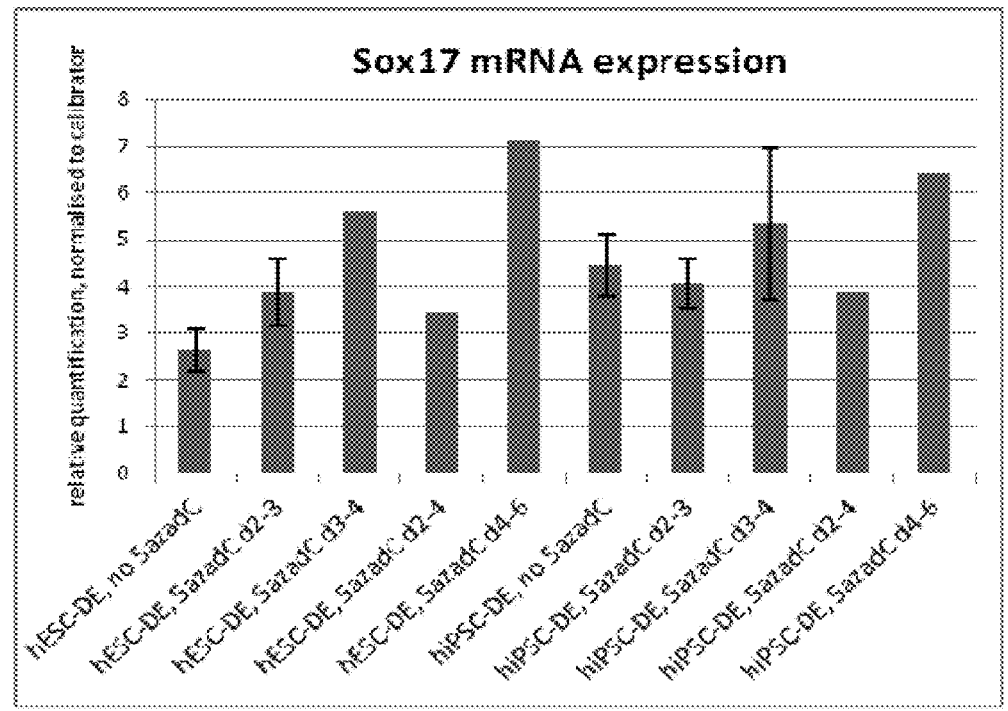
Fig. 13D4)
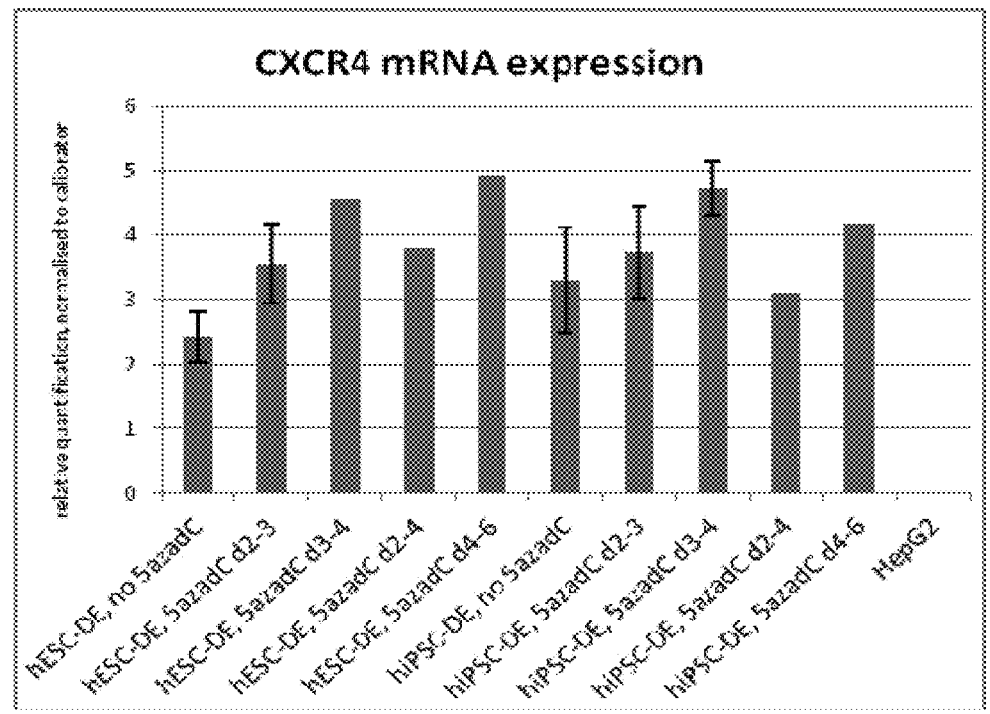

Fig. 13D5)
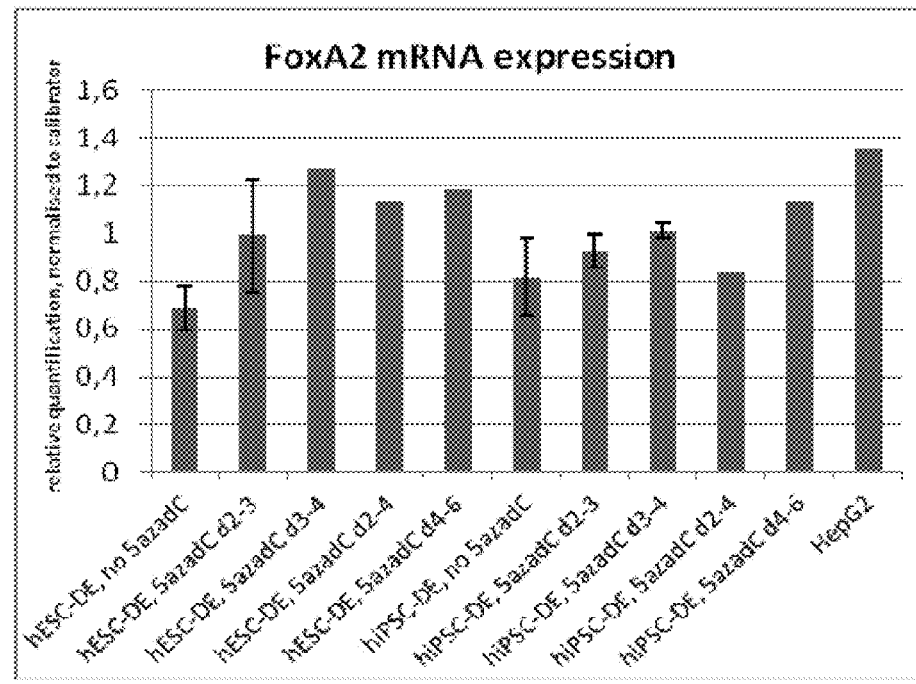
Fig. 13D6
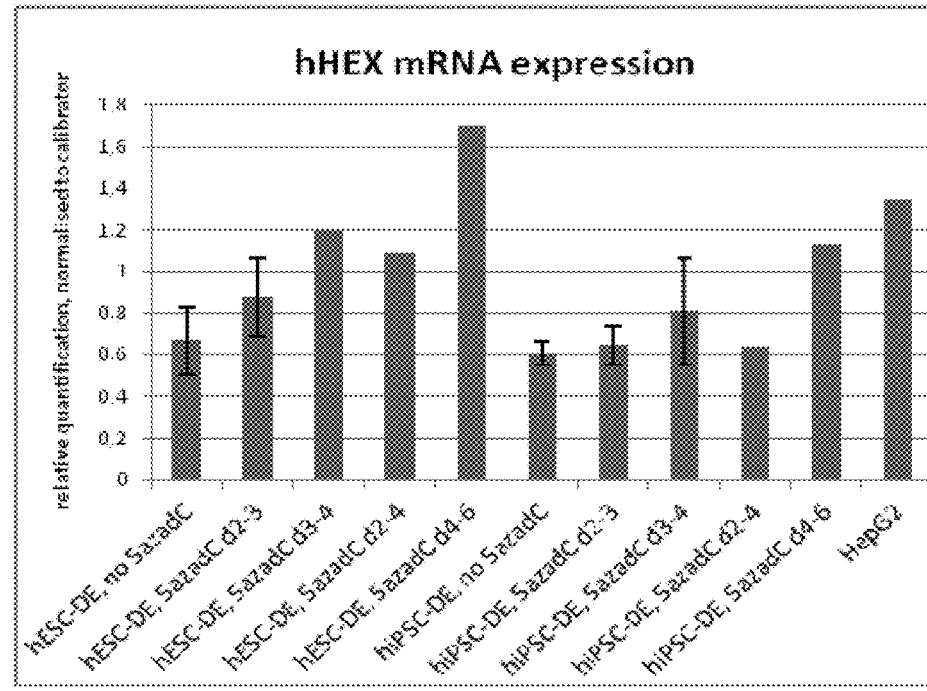

Fig. 13D7)
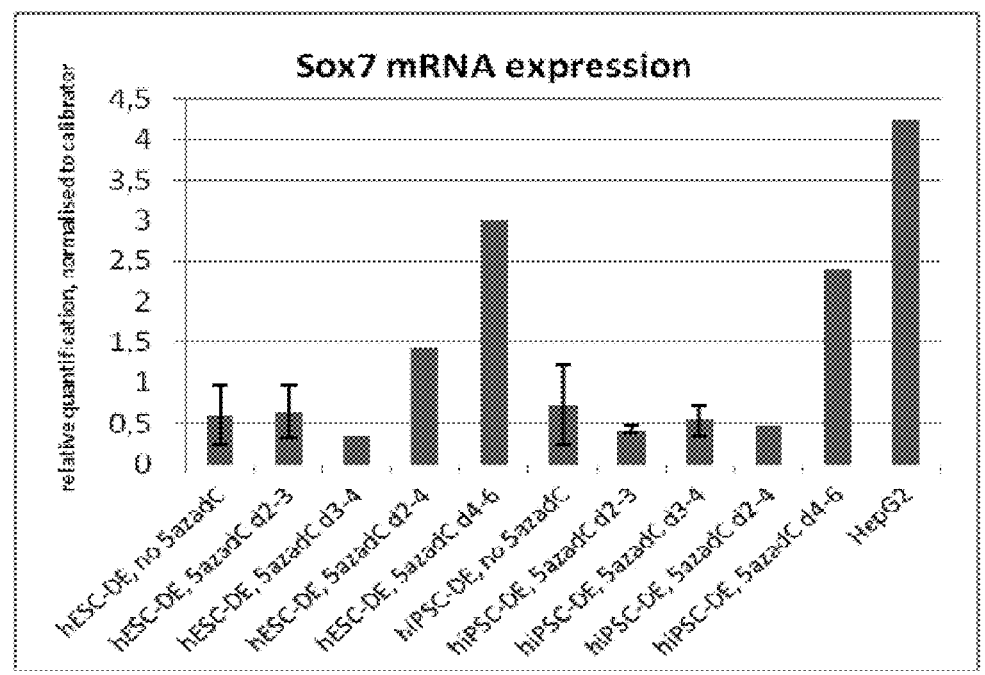

Figure 14:
Fig. 14A)
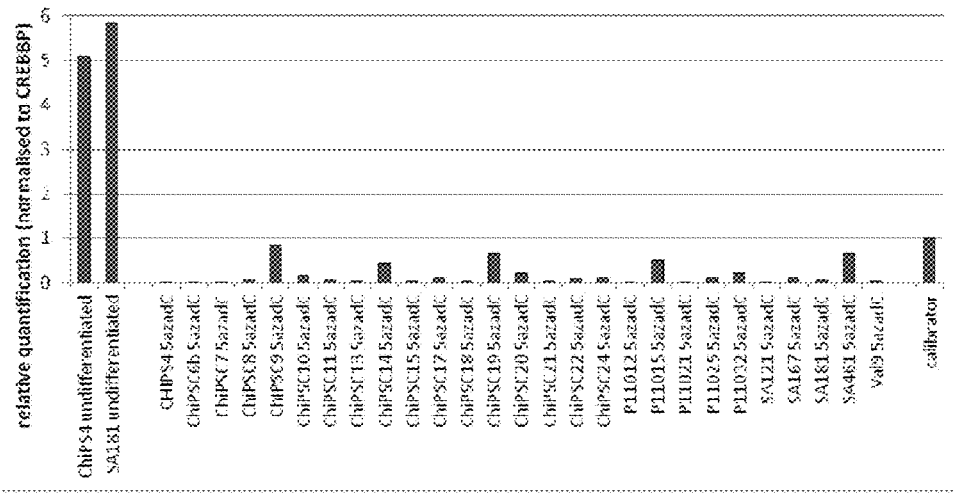
Fig. 14B)
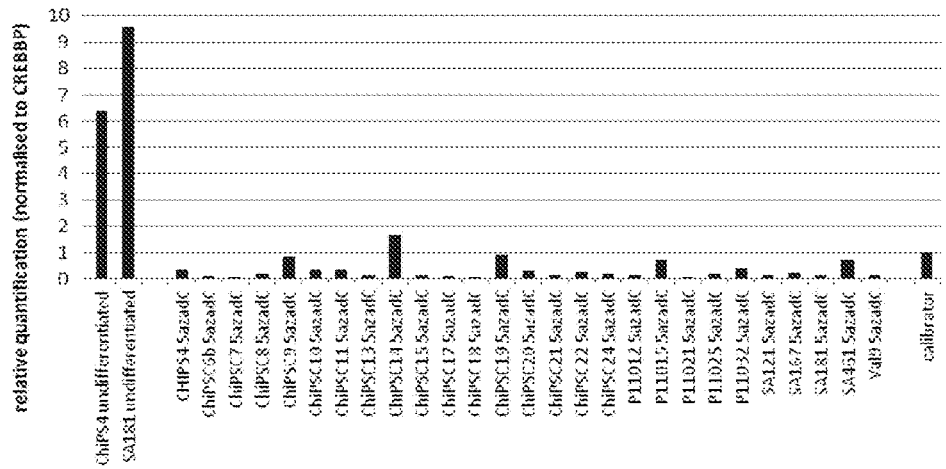

Figure 15:
Fig. 15A)
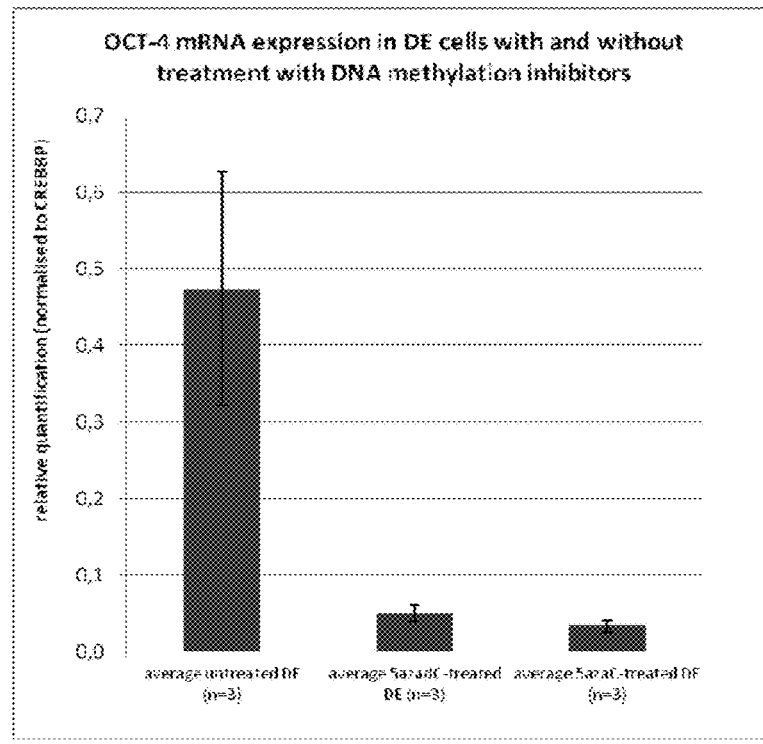
Fig. 15B)
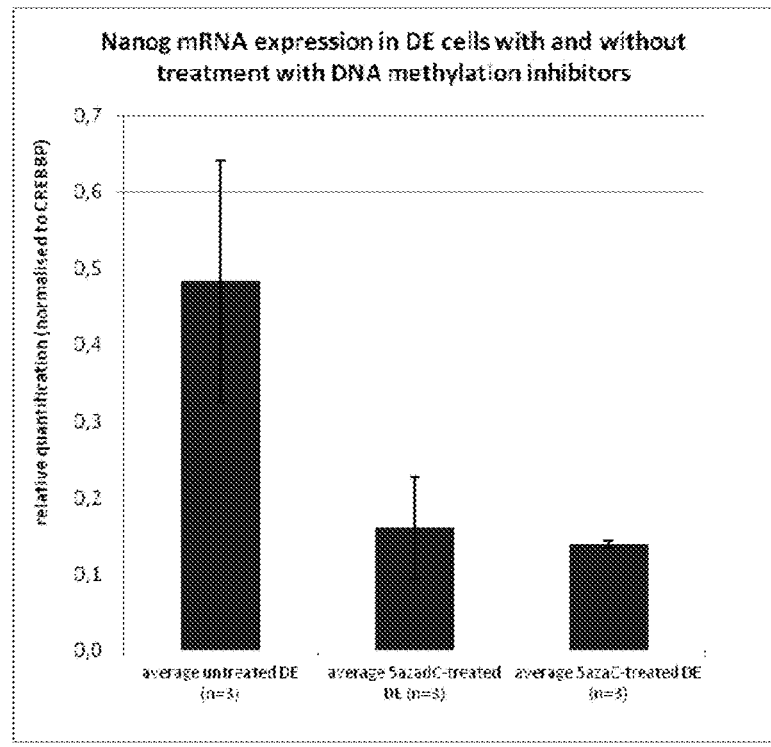

Figure 16:
Fig. 16A-1)
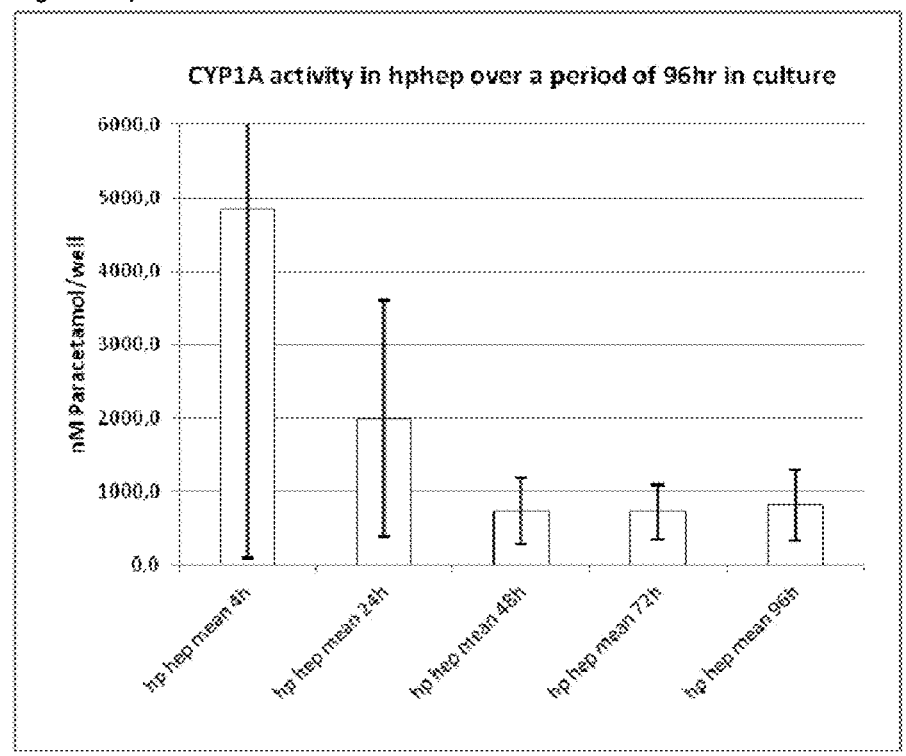
Fig. 16A-2)
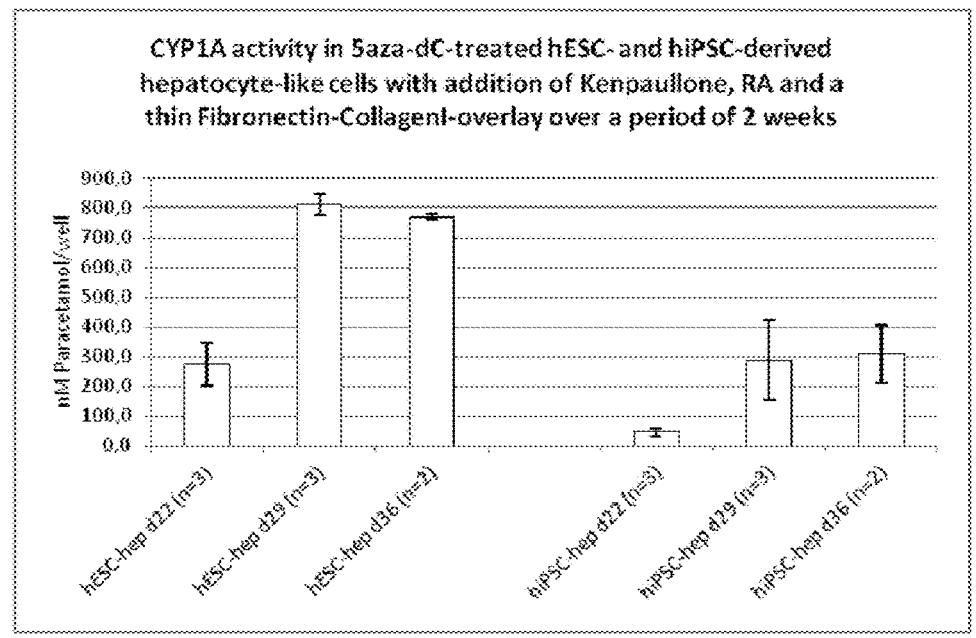

Fig. 16A-3)
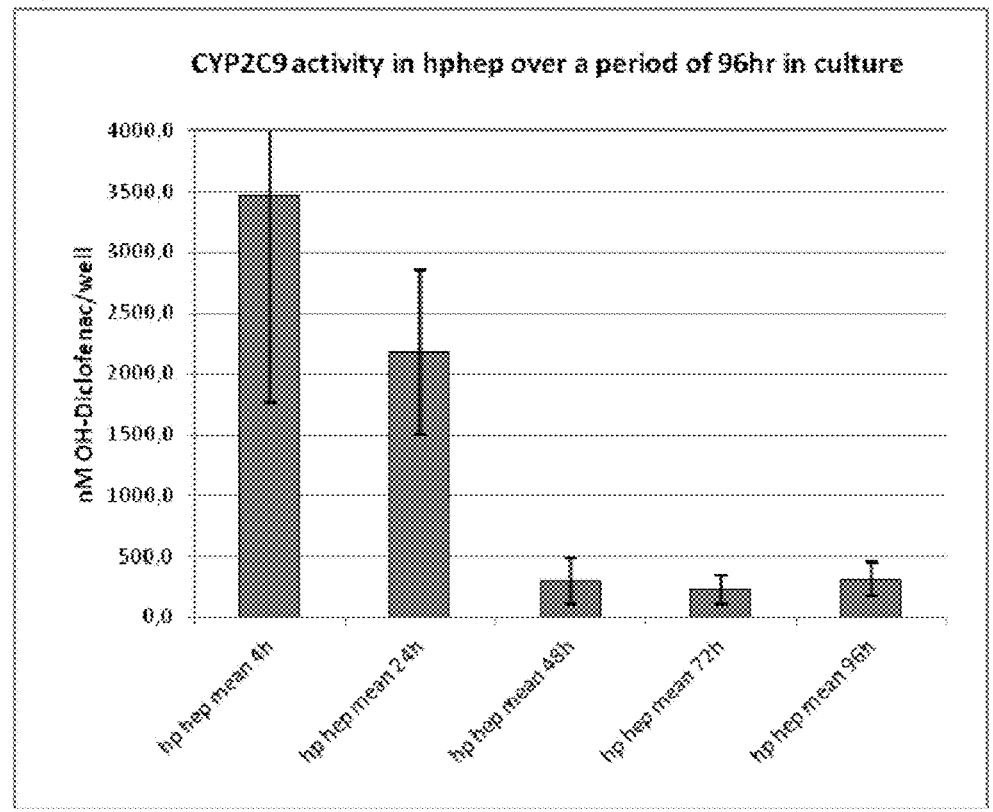
Fig. 16A-4)
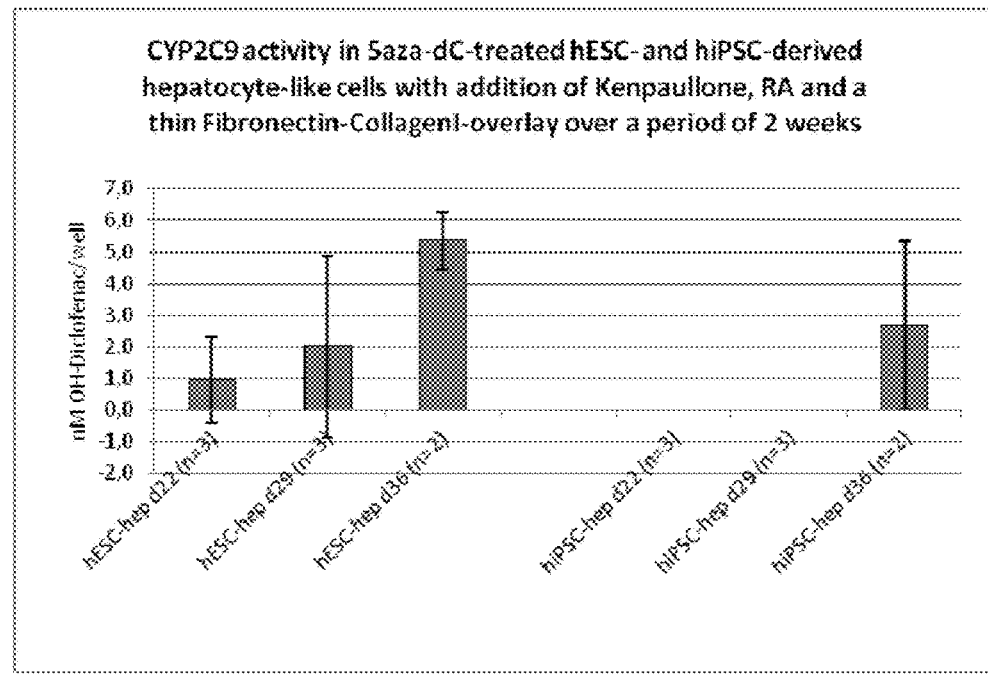

Fig. 16A-5)
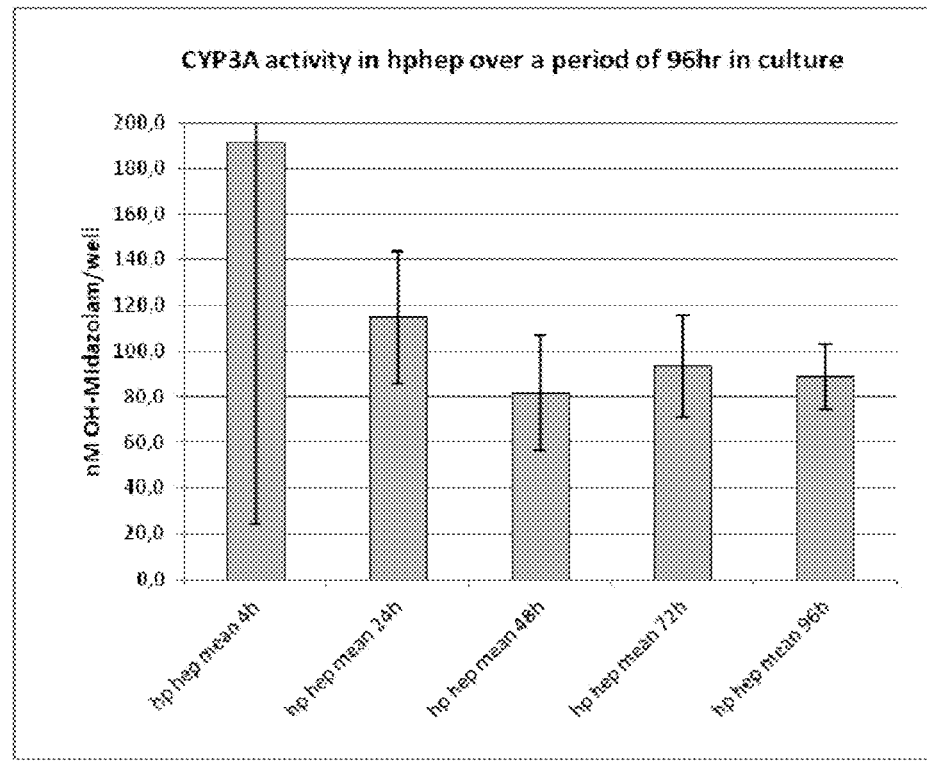
Fig. 16A-6)
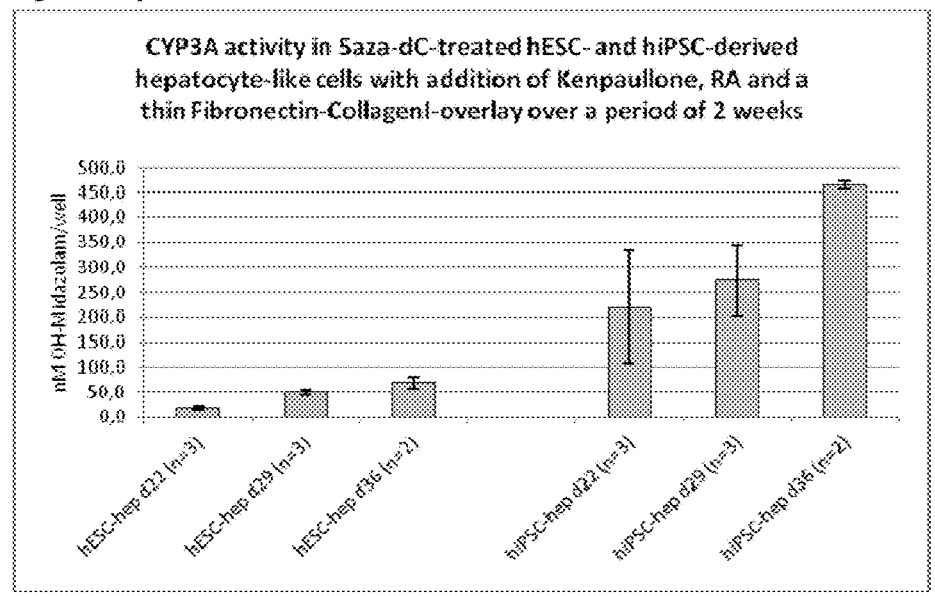

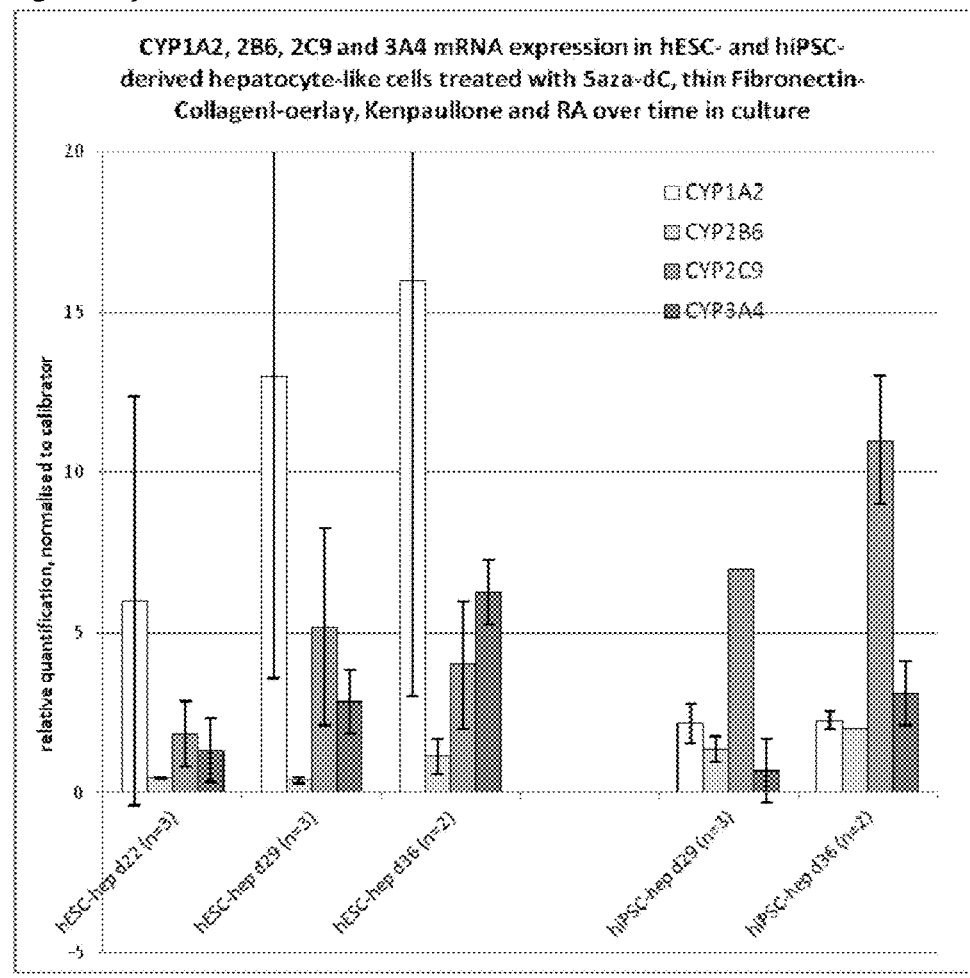
Fig. 16B-1)

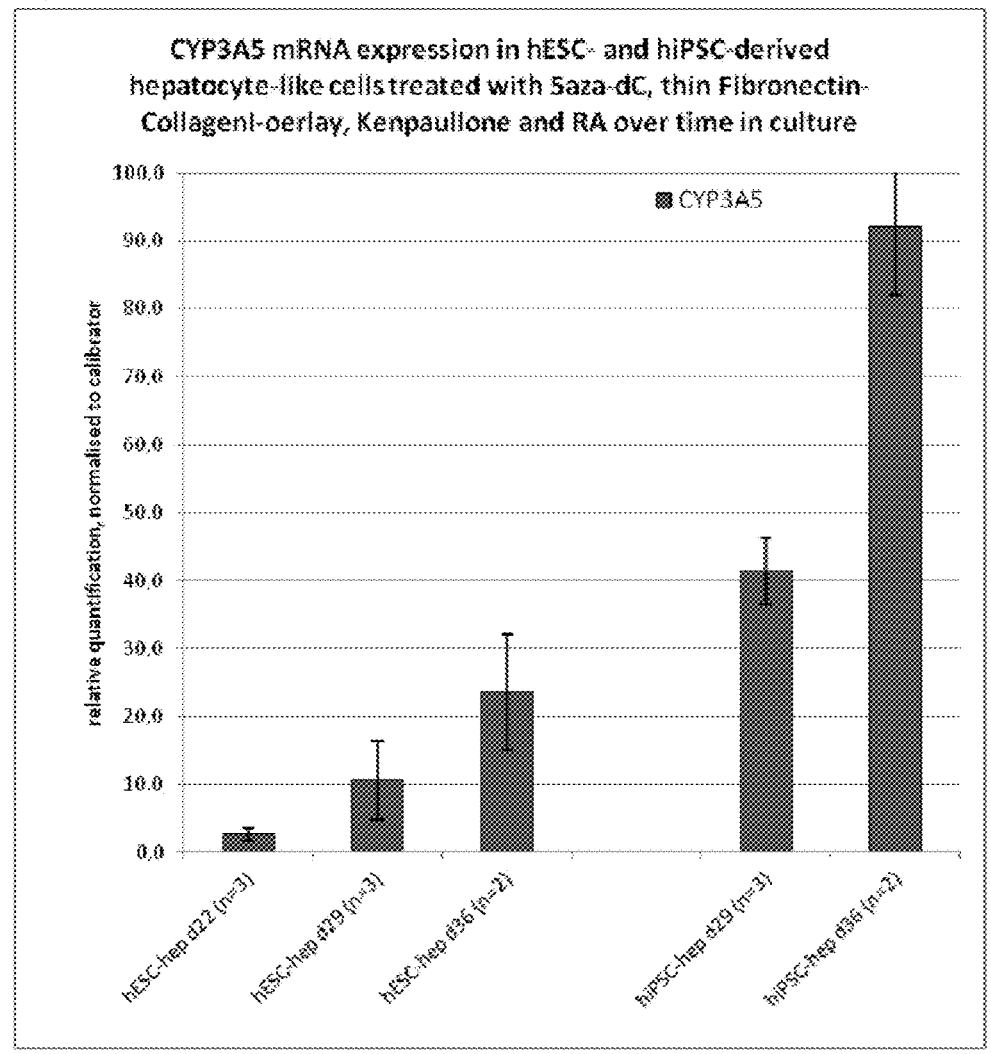
Fig. 16B-2)

Fig. 16B-3)
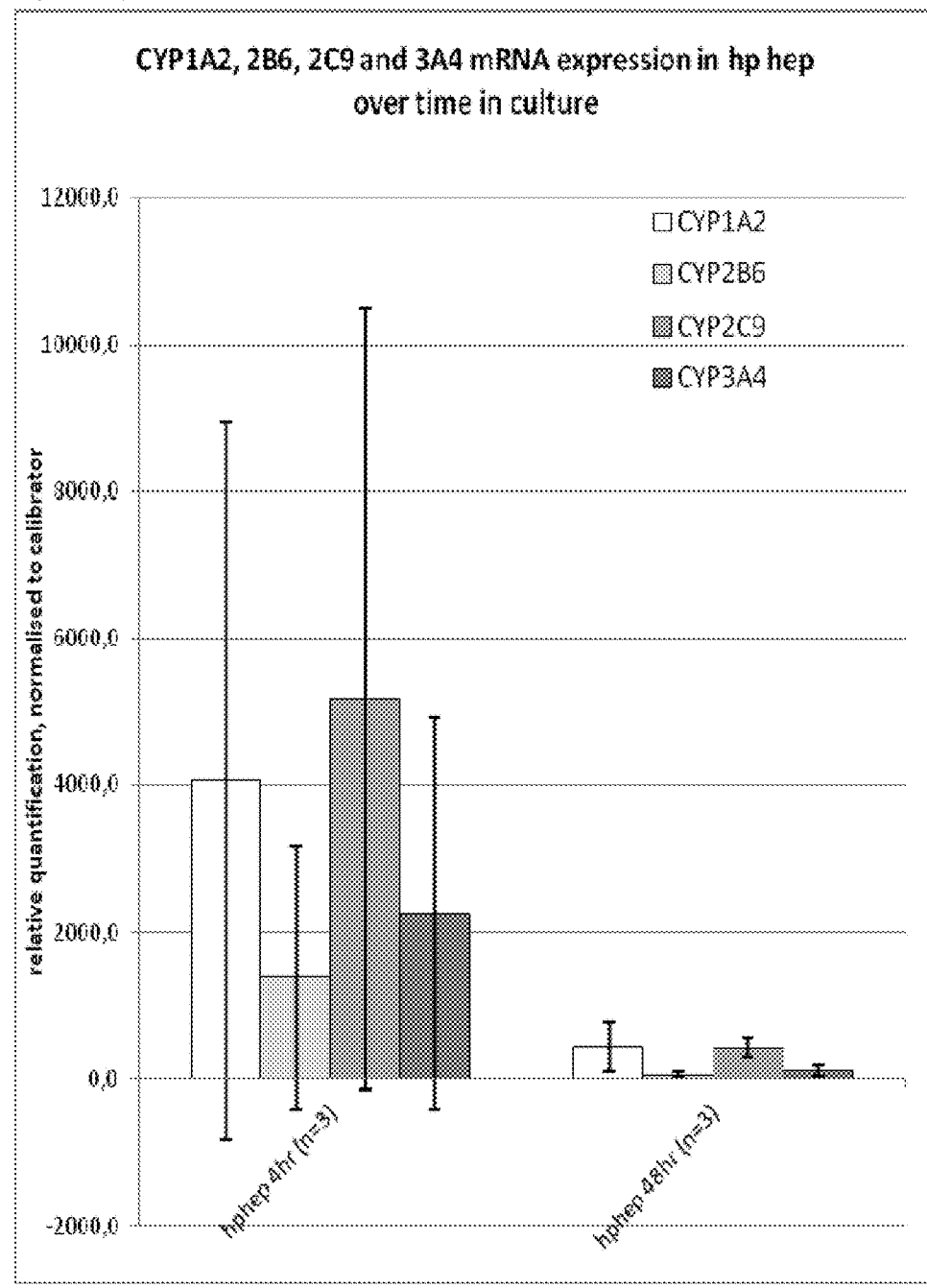

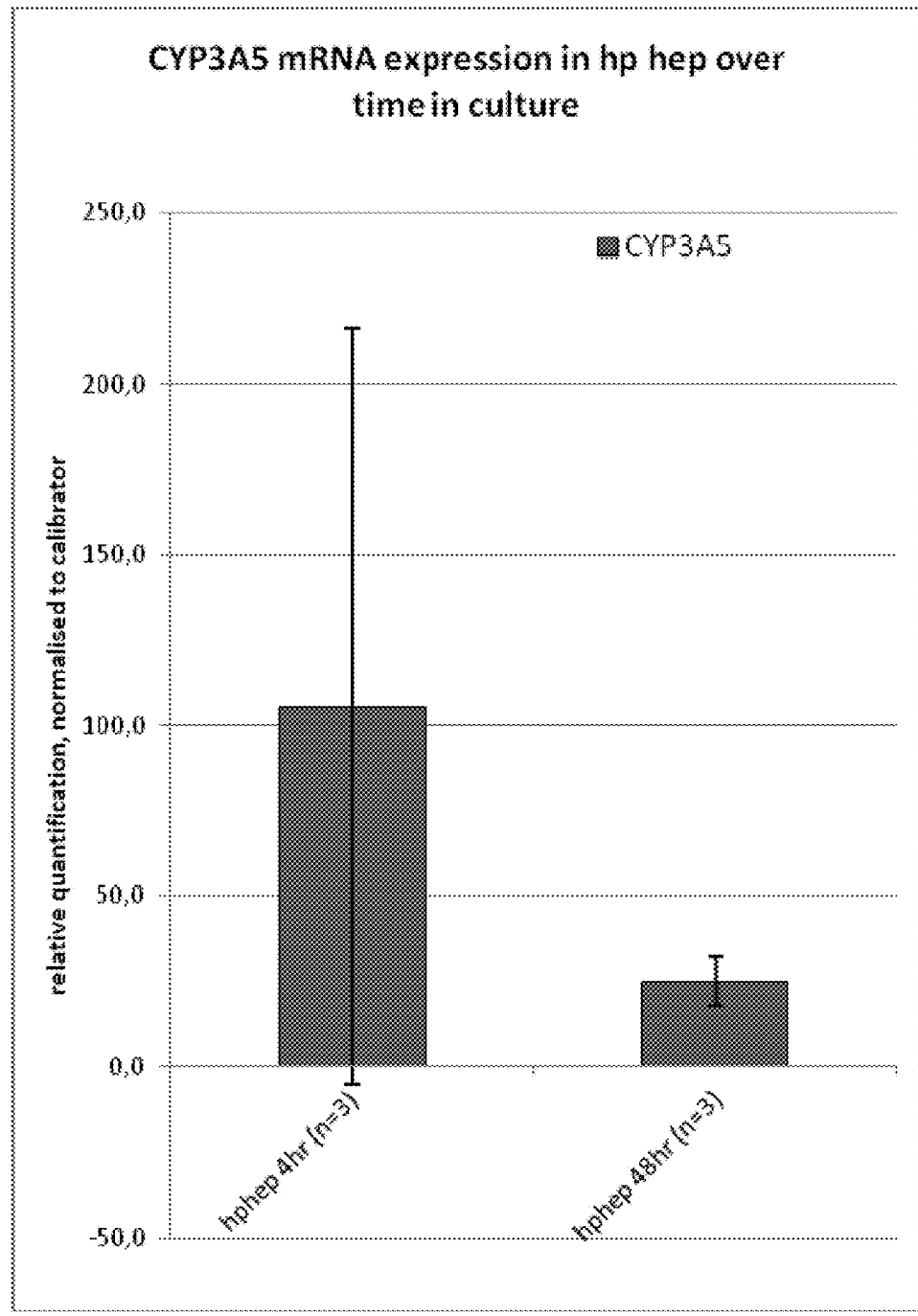
Fig. 16B-4)

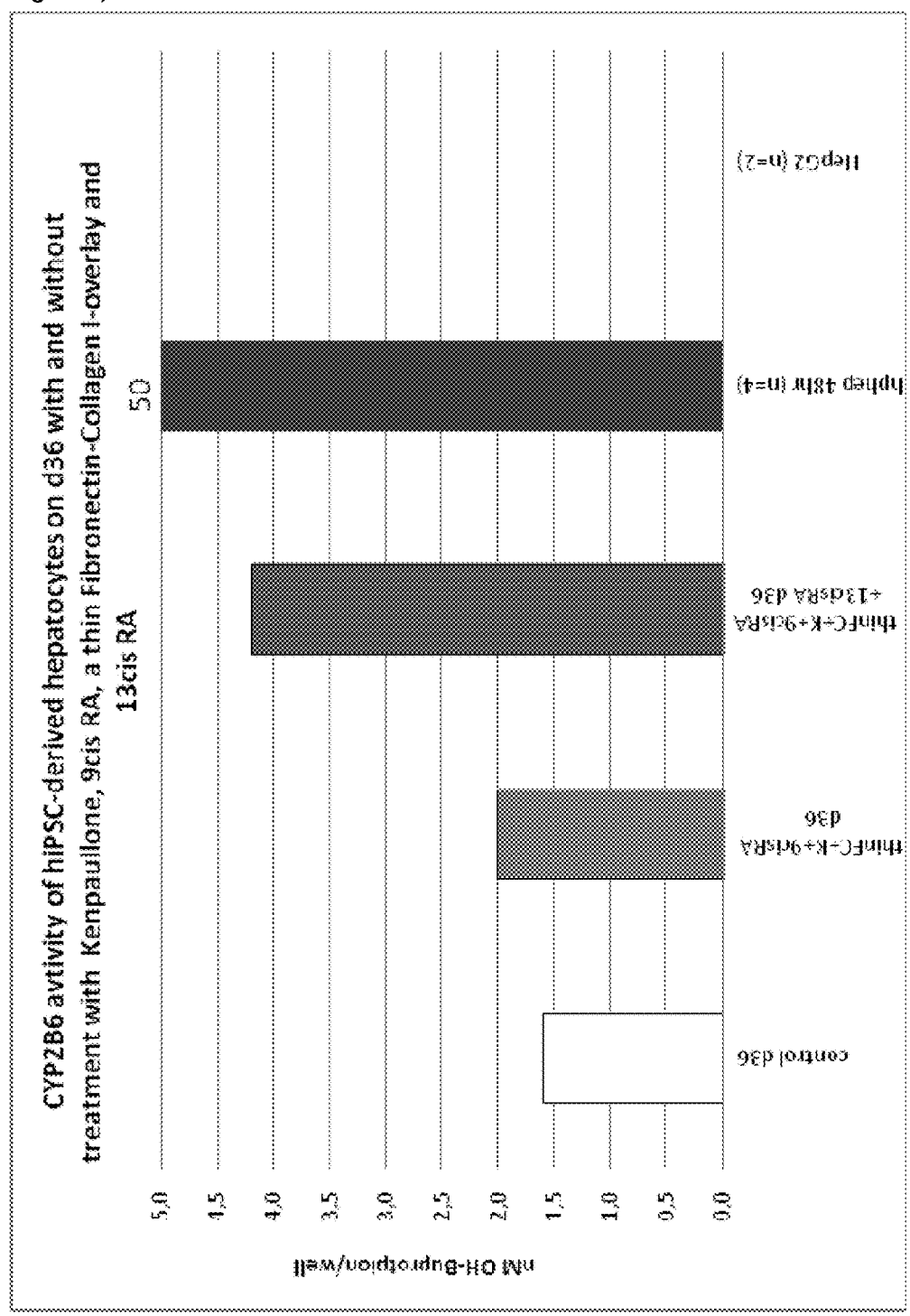

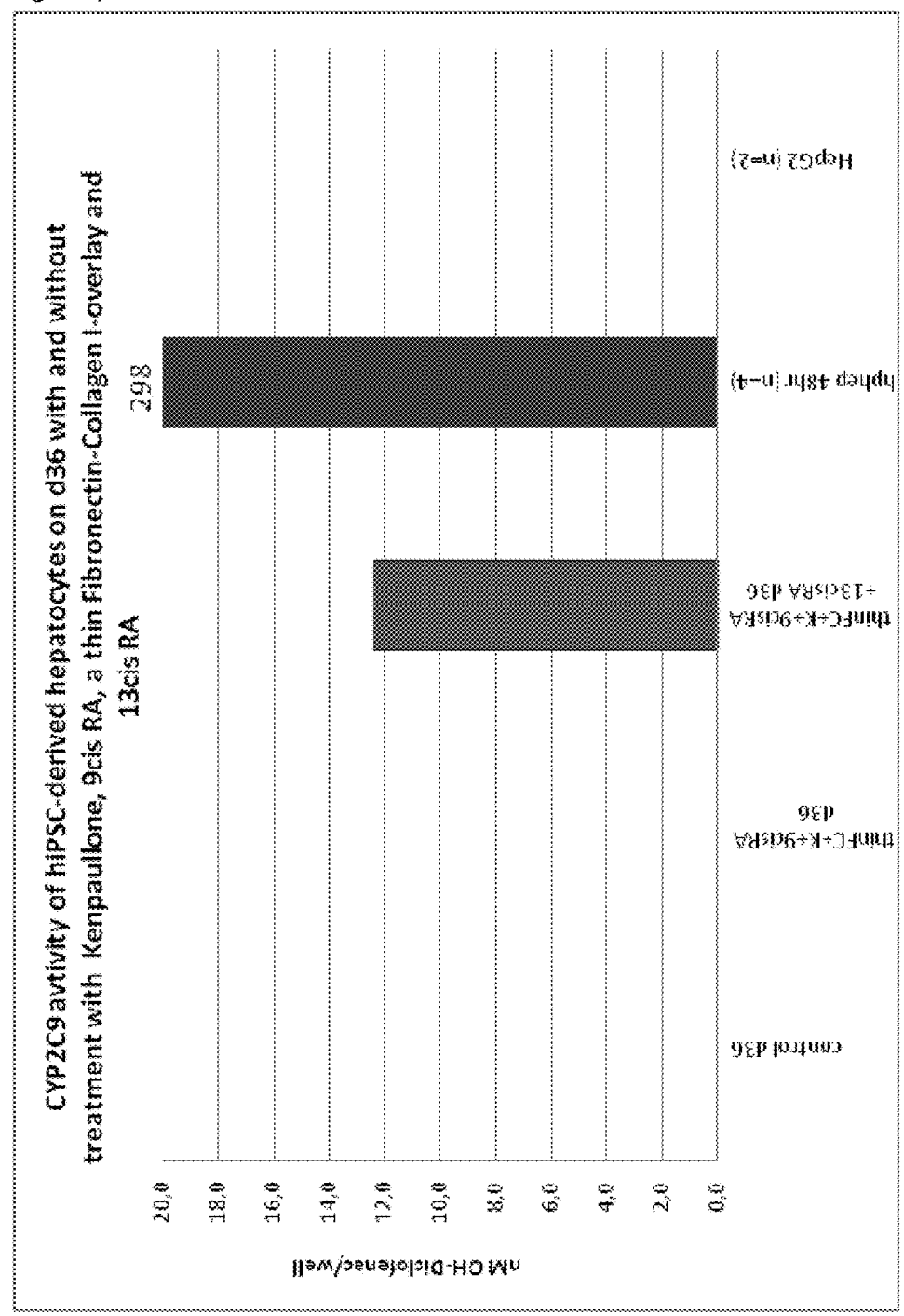

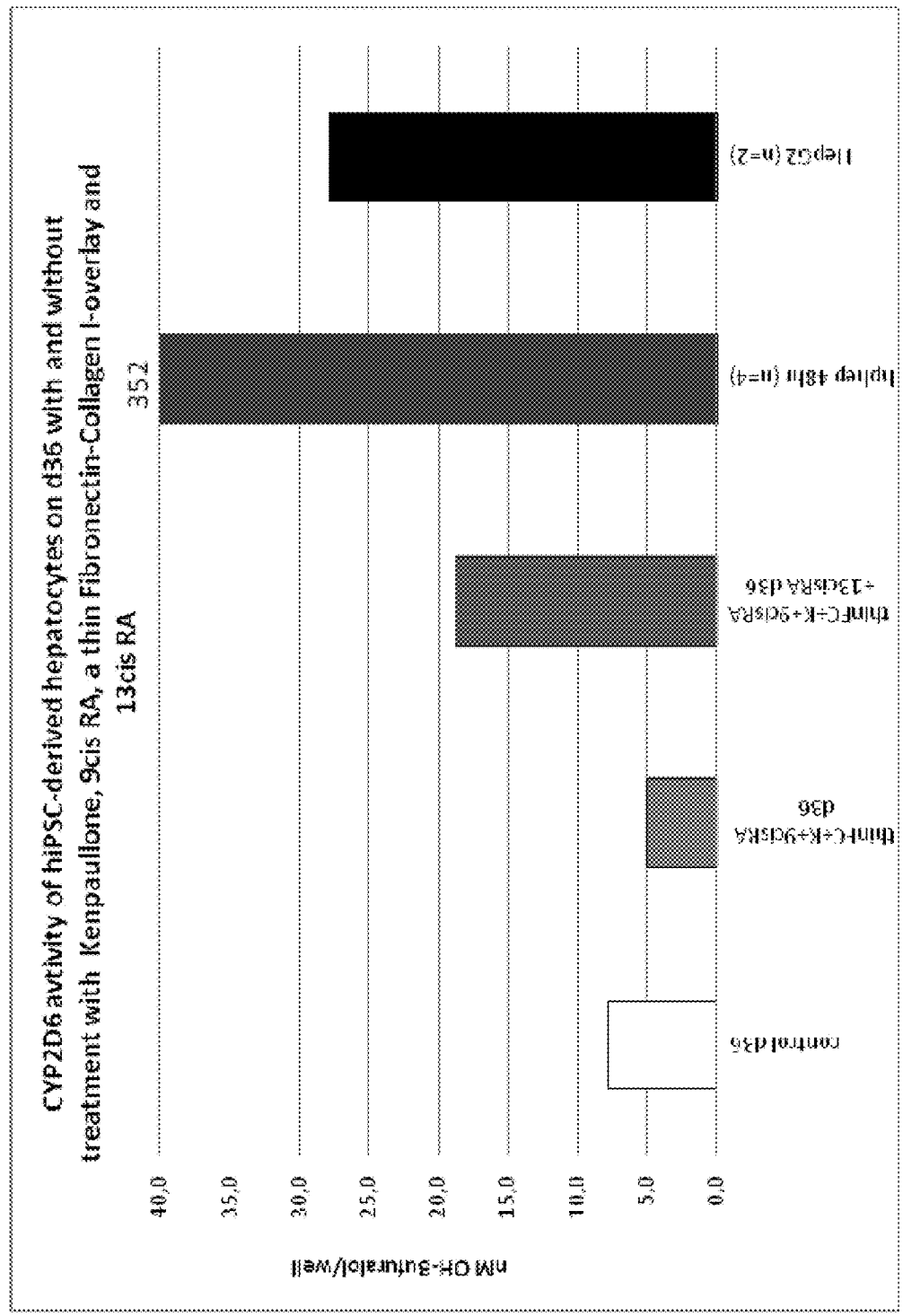

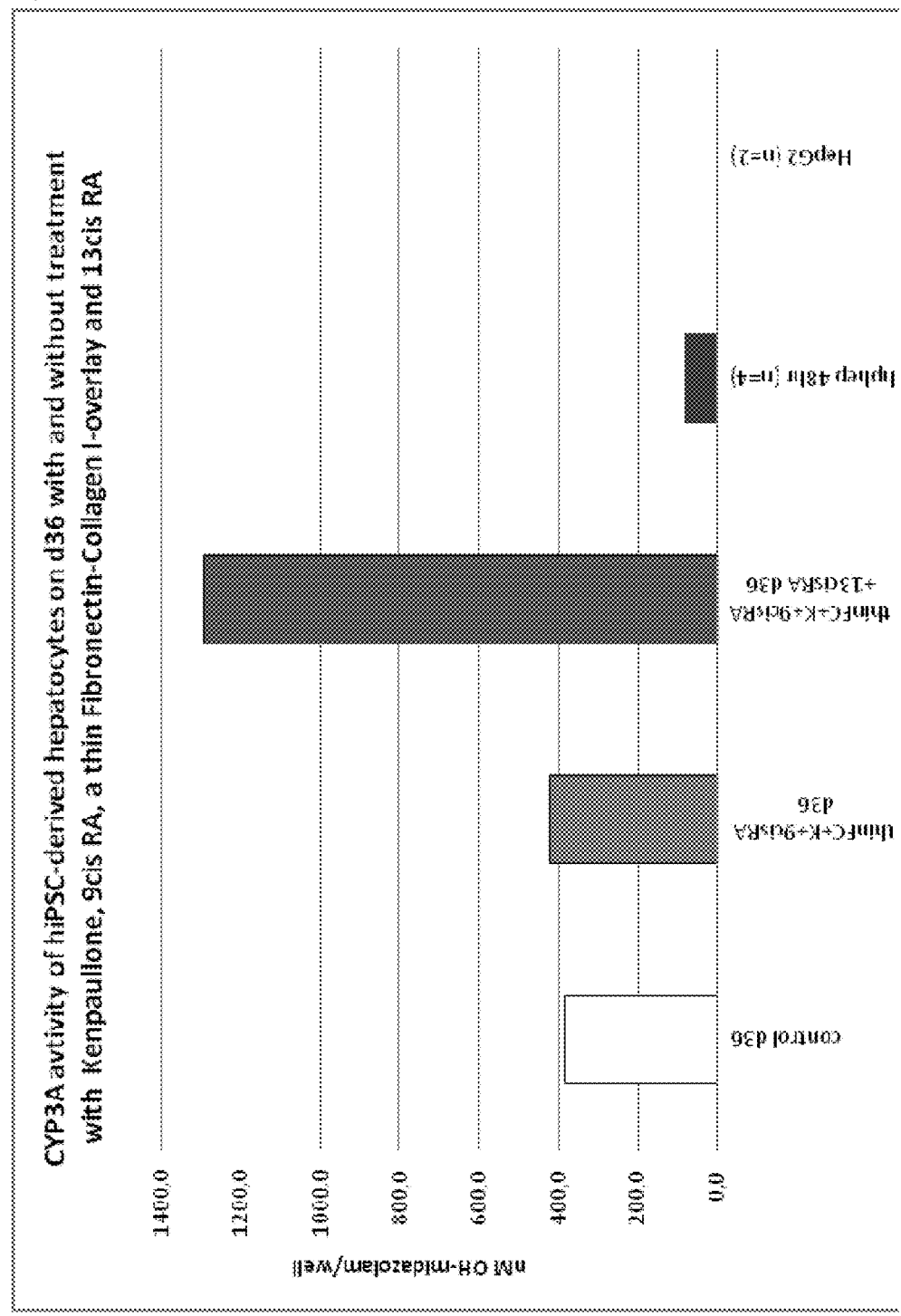

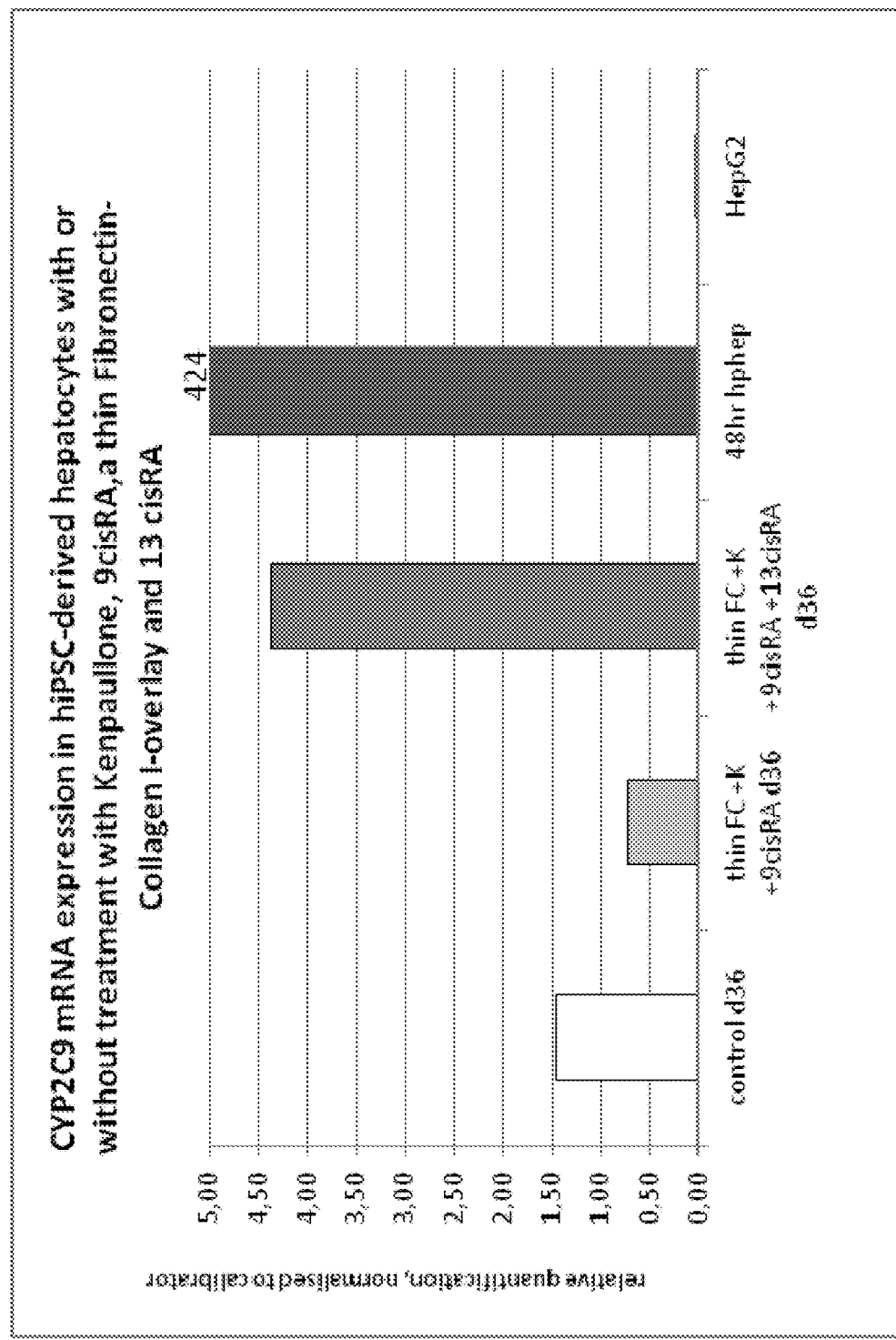

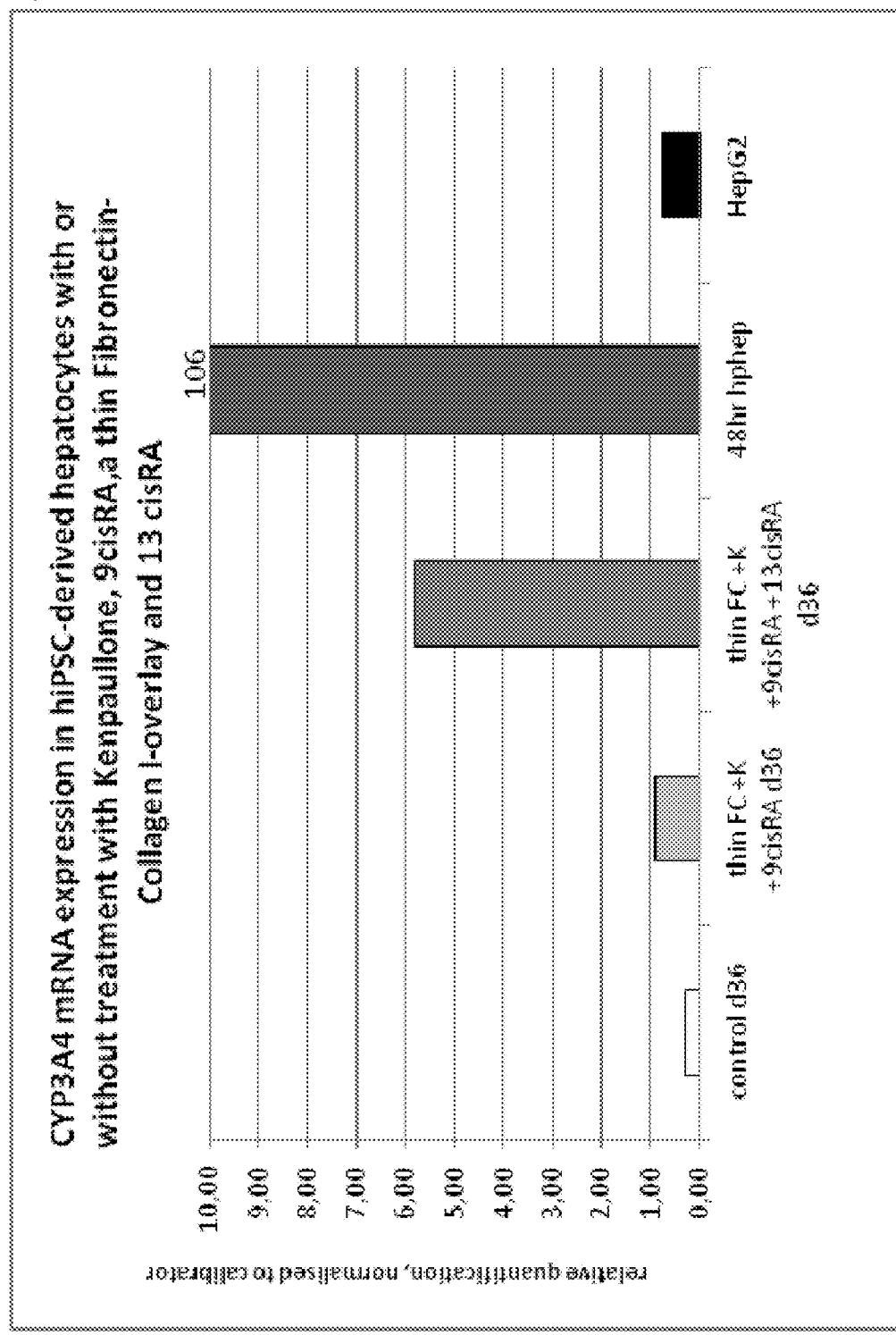

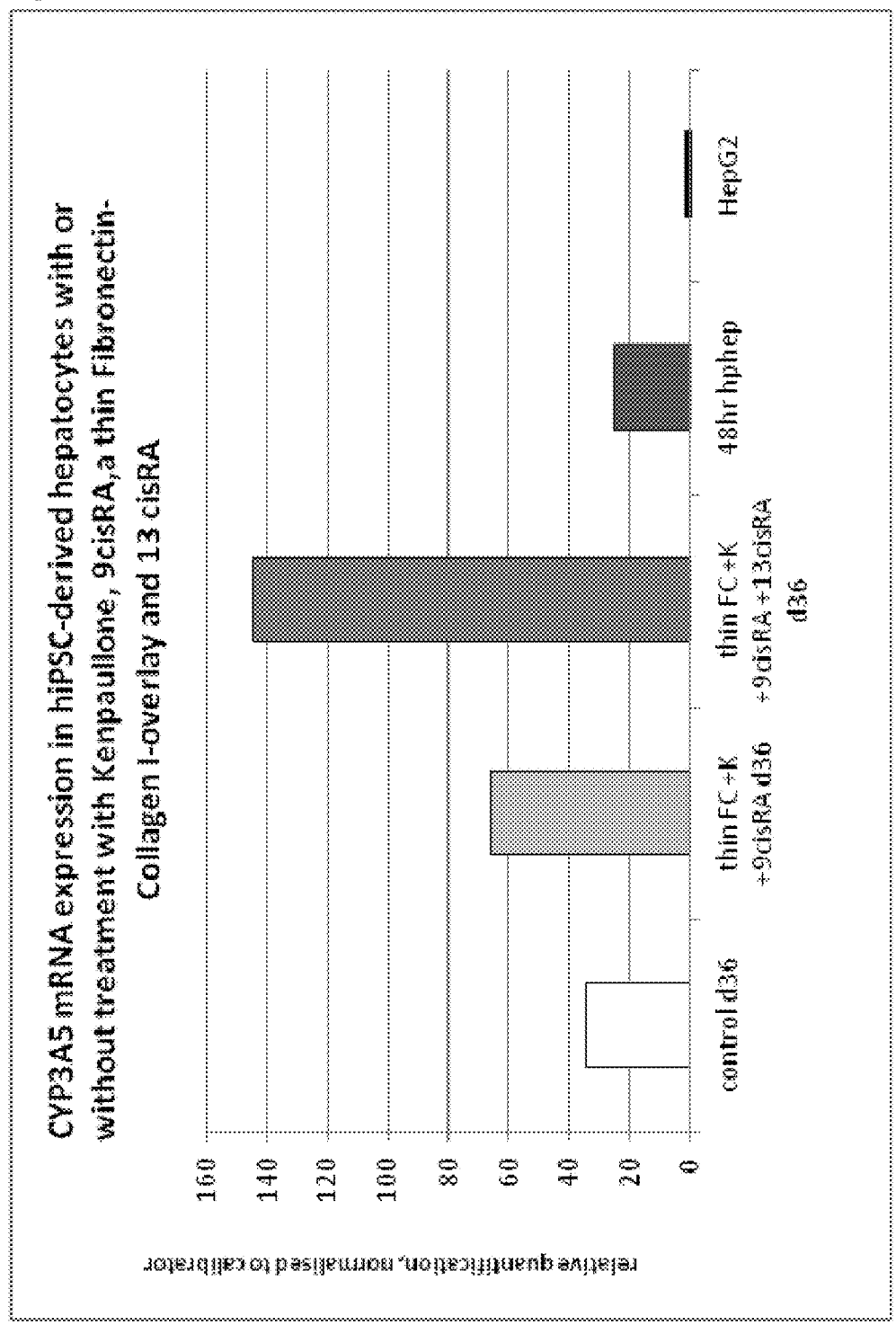
Fig. 18D) CYP3A5 mRNA expression in hiPSC-derived hepatocytes with or without treatment with Kenpaullone, 9cisRA, a thin Fibronectin-Collagen 1-overlay and 13 cisRA

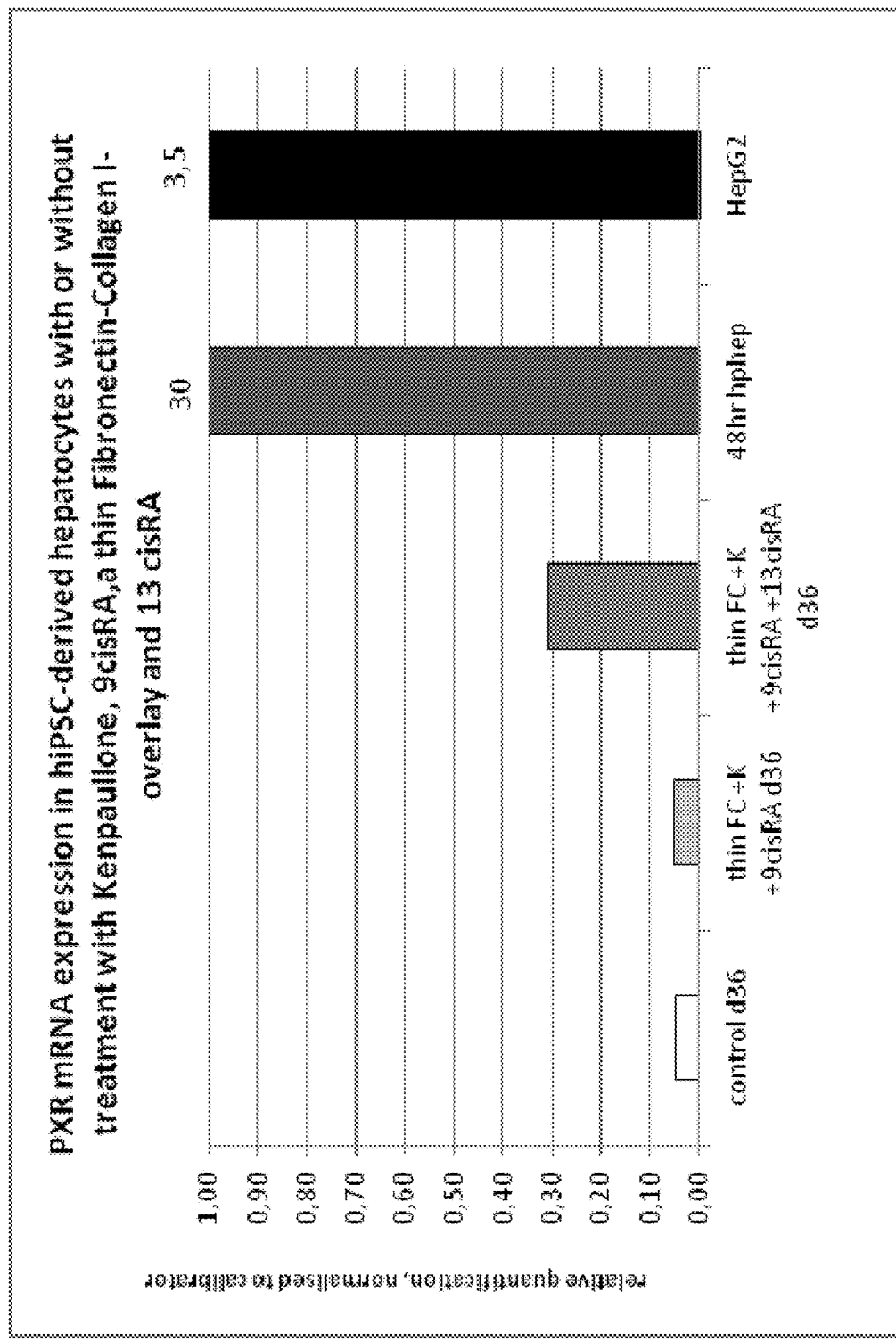

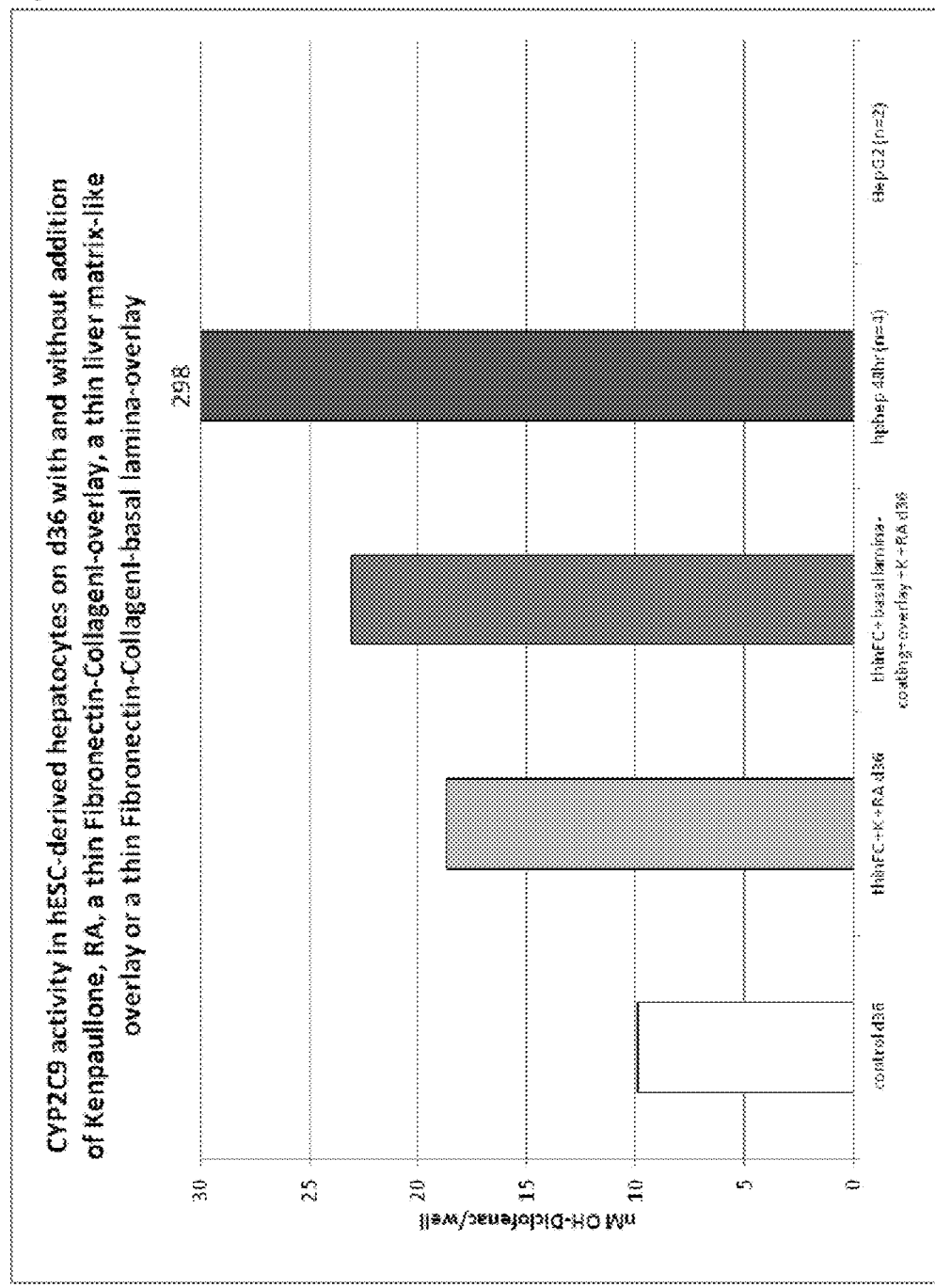

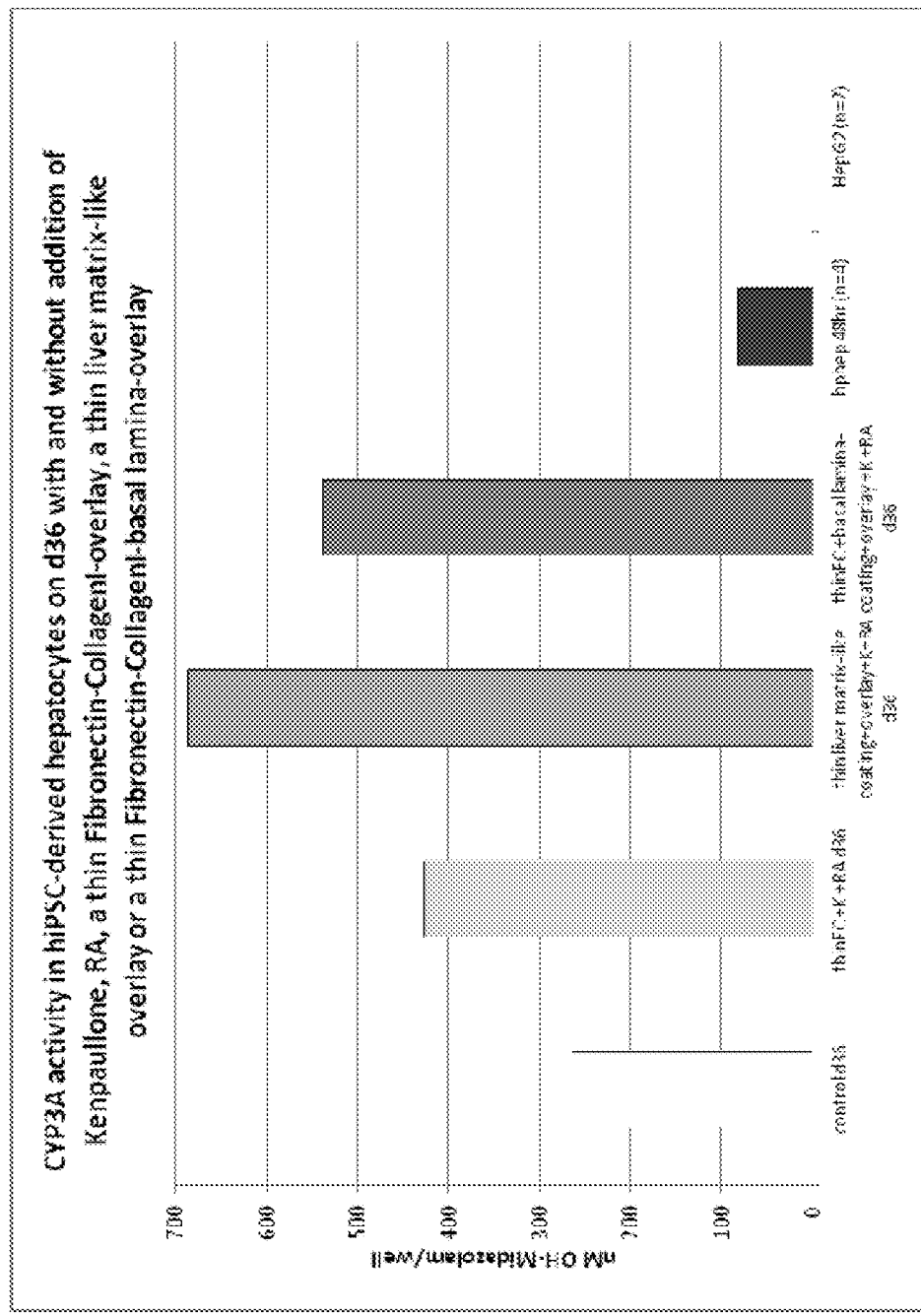

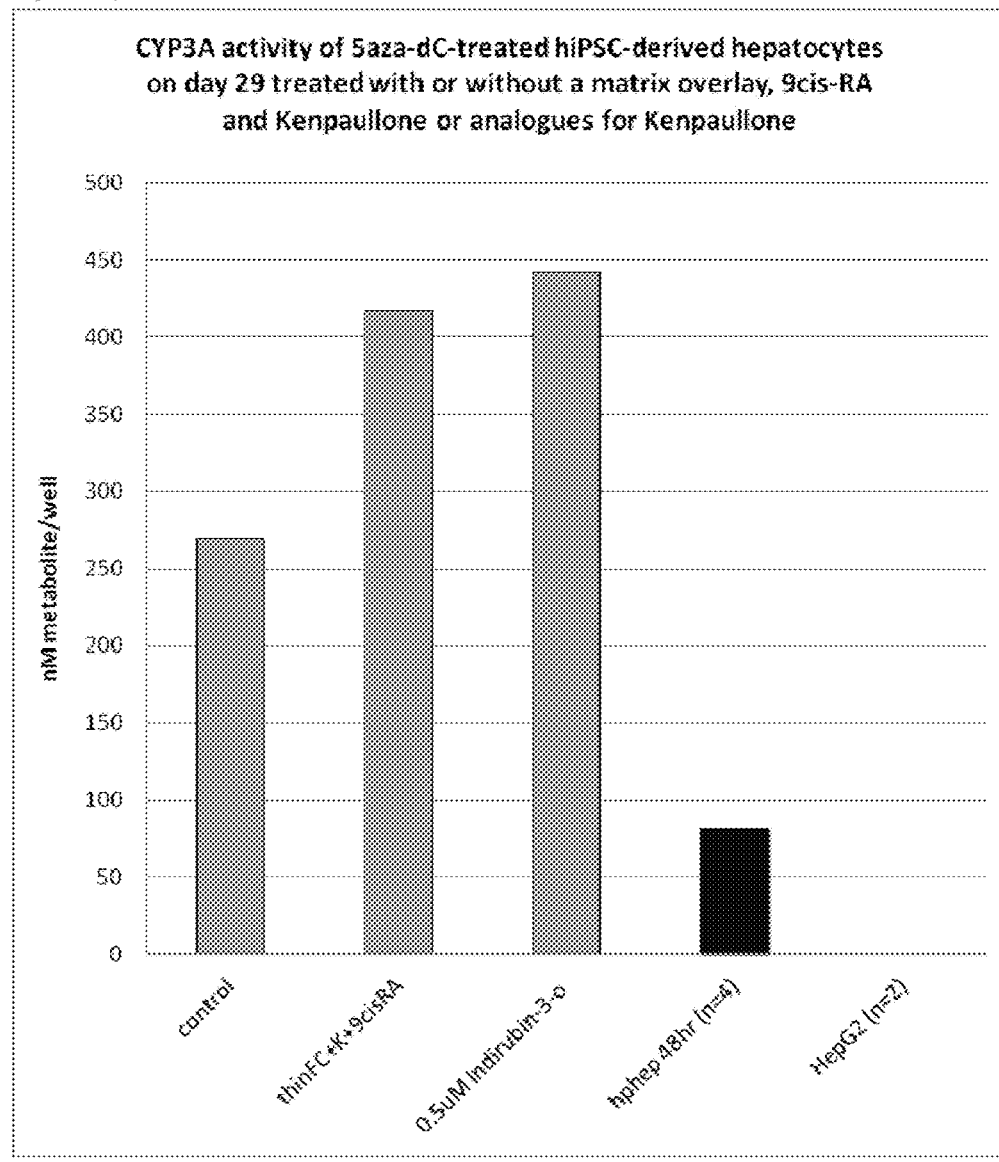
Fig. 21A2)

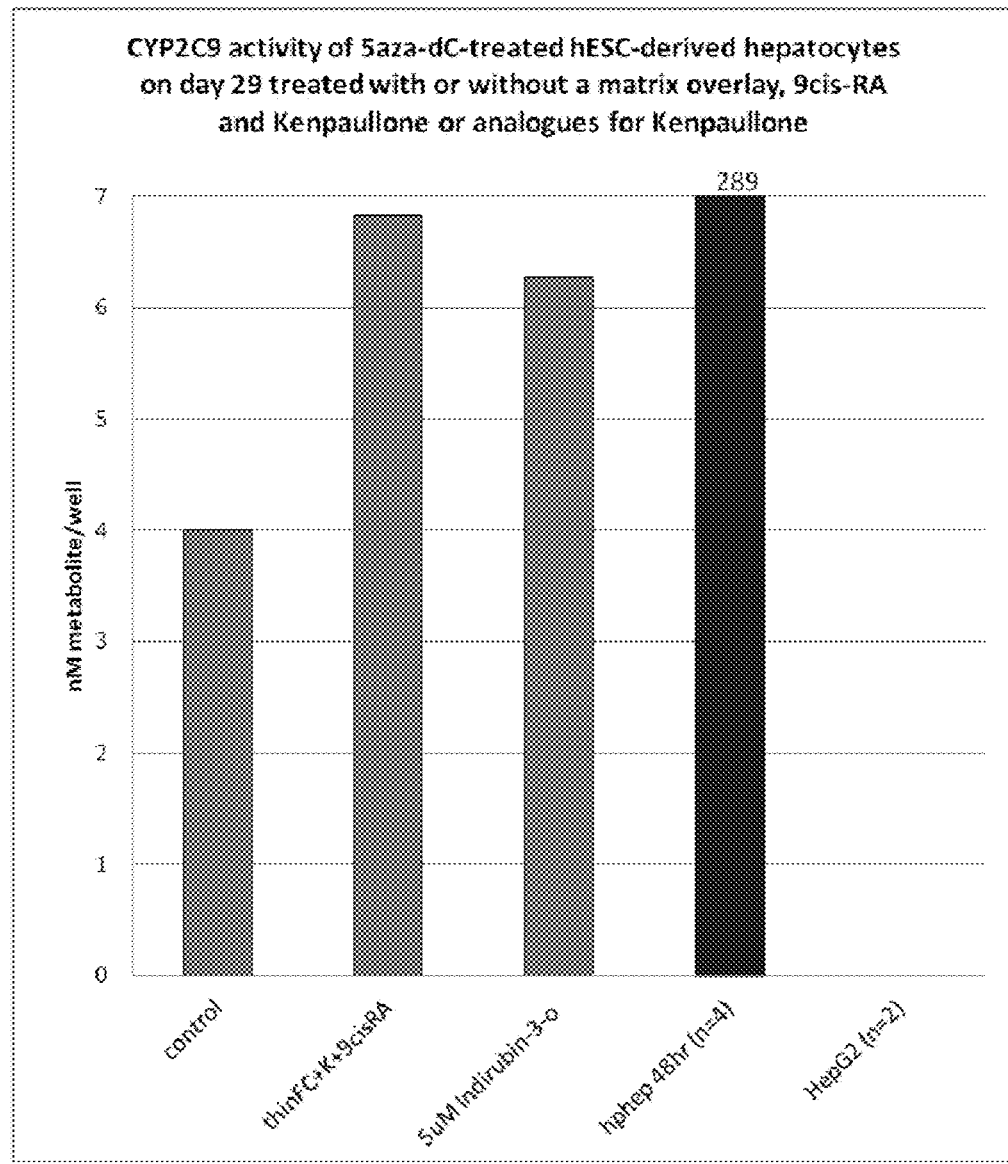
Fig. 21B1)

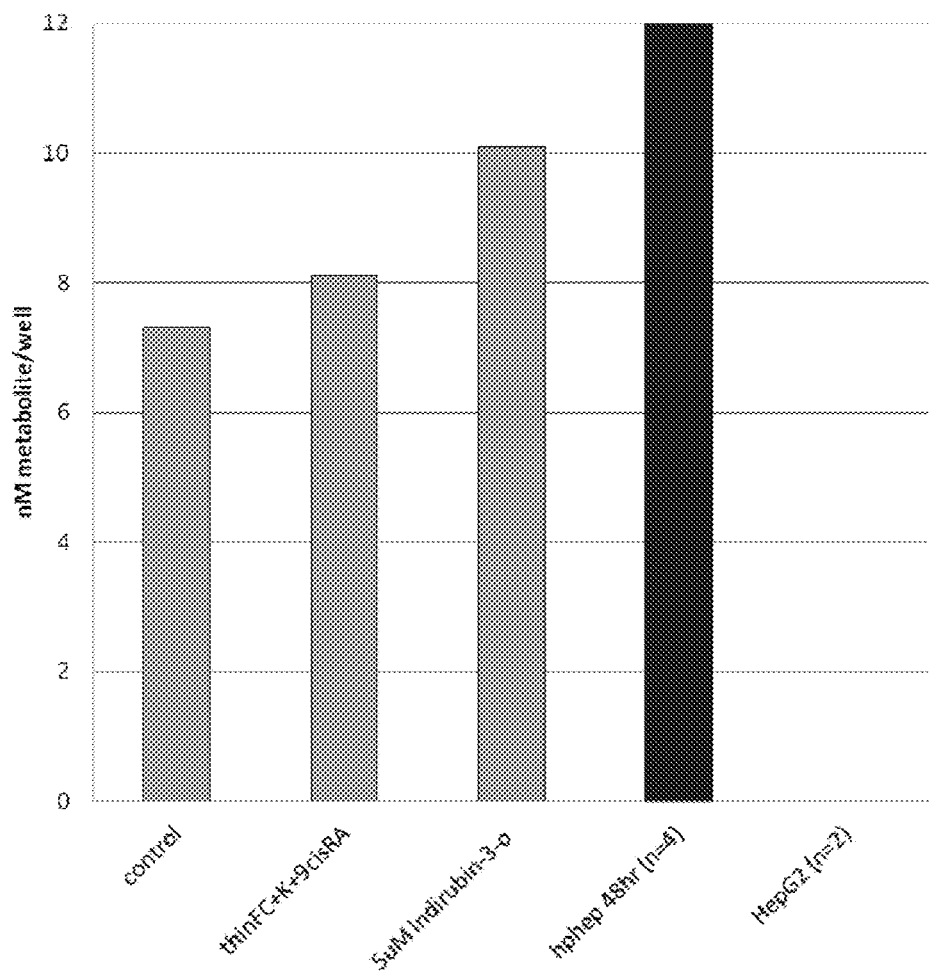
Fig. 21B2)

MATURATION OF HEPATOCYTE-LIKE CELLS DERIVED FROM HUMAN PLURIPOTENT STEM CELLS

CROSS REFERENCE TO RELATED APPLICATIONS

This application is the U.S. National Phase filing of PCT International Application No. PCT/EP2013/075017, filed Nov. 28, 2013, which claims priority to Denmark Application No. PA201270741, filed Nov. 29, 2012, Denmark Application No. PA201270740, filed Nov. 29, 2012, U.S. Provisional Patent Application No. 61/731,266, filed Nov. 29, 2012, and U.S. Provisional Patent Application No. 61/731,281, filed Nov. 29, 2012. The contents of the foregoing applications are incorporated herein by reference in their entireties.

TECHNICAL FIELD

The present invention relates to directed differentiation and maturation of hepatocyte-like cells. The hepatocyte-like cells obtained in accordance with the present invention show a phenotype which is more similar to that of primary hepatocytes than previously shown. In particular, the present invention relates to exposure of hepatocyte-like cells to an activator of a retinoic acid responsive receptor, such as retinoic acid (RA), optionally in combination with an inhibitor of GSK-3 (Glycogen synthase kinase 3) or activator of Wnt signalling and/or with the overlay of the cells with one or more components characteristic of the mammalian extracellular matrix (matrix overlay). The present invention also relates to exposure of hepatocyte-like cells to an activator of a retinoic acid responsive receptor, such as retinoic acid (RA), optionally in combination with an inhibitor of a cyclin dependent kinase (CDK) and/or with the overlay of the cells with one or more components characteristic of the mammalian extracellular matrix (matrix overlay). The inventors have, as disclosed herein, found that exposing hepatocyte-like cells to an activator of a retinoic acid responsive receptor leads to the development of more mature and functional features for the hepatocyte-like cells as well as to more pure and homogenous populations of hepatocyte-like cells, compared to currently available state of the art methods.

BACKGROUND OF THE INVENTION

The development of novel pharmaceuticals faces a number of challenges, not least the problem of overcoming adverse toxicological effects. Indeed, adverse liver reactions remain the most prominent side effect. Metabolism and ultimate clearance of the majority of small molecule drugs occurs in the liver, and thus one of the main areas of focus in drug development concerns whether such compounds or their metabolites possess any hepatotoxic effect. Moreover, it is also of paramount importance to discover whether the secondary metabolites of such compounds also display any cytotoxic effects before the drug can begin clinical trial programmes.

Accordingly there is an urgent need for a model hepatic system that mimics human liver cells and that is able to predict effects of candidate molecules in the development of new drugs or chemicals. Traditionally, researchers have been forced to rely on primary liver-derived hepatocytes for such screening but these have a number of serious drawbacks including difficulty of maintaining the cells in long term culture and difficulty of obtaining consistent, homogeneous cell populations. A solution to this has been offered in the form of hepatocyte-like cells derived from human pluripotent stem cells. Human pluripotent stem cells (hPS) have already begun to revolutionise the ways in which relevant human cell types can be obtained. The possibility to indefinitely propagate pluripotent human embryonic-derived stem (hES) cells and human induced pluripotent stem (hiPS) cells and subsequently differentiate them into the desired target cell types is now providing a stable and virtually unlimited supply of cells for a range of applications in vivo and in vitro.

Unfortunately, currently available hepatocyte cell types do not always accurately model the hepatic environment, due to differences in morphology and function. For example, one often used alternative to primary cells are hepatic cell lines which often contain very low levels of (or totally lack) metabolising enzymes and have expression of other important proteins substantially different from the native hepatocyte in vivo. This is of particular relevance in relation to drug metabolism since one of the major deficiencies in hepatic cell lines is the absence or abnormally high expression of drug transporter proteins which are essential for drug screening purposes. Other available hepatic cell lines suffer from having a morphology and physiology which is more reminiscent of fetal or juvenile hepatocytes than the more clinically relevant adult hepatocytes. For these reasons there is a strong need to develop hepatocyte cell lines which are not only easy to culture and propagate but which also possess a more mature phenotype and which behave in a manner more akin to adult primary hepatocytes.

Derivation of hepatocyte-like cells from pluripotent stem cells is well established in the art. For in vitro purposes, several groups have developed protocols for deriving hepatocyte-like cells from hES cells (Hay et al., 2007; Hay et al., 2008; Brolen et al. 2010; Funakoshi et al. 2011) as well from hiPS cells (U.S. Pat. No. 8,148,151B; Song et al. 2009; Sullivan et al. 2010; Si-Tayeb et al. 2010; Chen et al. 2012). However, common to all of these is a specific low mRNA and protein expression of genes typical for mature hepatocytes, like phase I and II genes (e.g. CYP1A2, 2B6, 2C9, 2D6, 3A4), nuclear receptors (e.g. CAR and PXR), and other adult hepatic markers (e.g. Albumin). In addition, these hESC- and hiPSC-derived hepatocyte-like cells have high expression of fetal hepatic genes like α-fetoprotein (AFP) and CYP3A7, with the result that the cell types described therein have a fetal and not adult phenotype (for overview see e.g. Baxter et al. 2010). Furthermore, in most of the published studies on hESC- and hiPSC-derived hepatocyte-like cells, expression and functionality of drug transporters has not been investigated at all.

The modulation of RA signalling has been previously shown to be of importance during early hepatocyte differentiation and in particular at the stage when definitive endoderm (DE) is specified to become hepatic endoderm (Touboul et al 2010). Furthermore, RA-response elements have been identified in a number of genes important during early hepatocyte specification such as AFP and HNF4α (see Qian et al 2000; Magee et al 1998 and Hatzis et al 2001). However, at this early stage RA is known to have diverse effects and has also been found to be important in the derivation of pancreatic endoderm from pluripotent stem cells (Mfopou et al 2010). US Patent Application Publication US2012/0143316A1 discloses the use of all-trans retinoic acid in inducing hepatic differentiation from endoderm-like cells. As becomes evident, all of these disclosures relate to the modulation of RA signalling during endodermal and early hepatocyte differentiation. However, none of these documents teaches or suggests the applicability of retinoic acid as an hepatocyte maturation promoting agent, let alone its use at a late stage in hepatocyte differentiation.

The use of GSK 3 inhibitors have previously been described for early differentiation towards endoderm. WO08094597 (Dalton) describes a method of producing mesendoderm from primate pluripotent stem cells (pPSC) by contacting the pPSC with an effective amount of GSK3 inhibitor in a differentiation media. WO2007050043 (Stanton) describes a method for producing a mesodermal or an endodermal cell from a pluripotent stem cell, comprising a Wnt-signalling pathway in the pluripotent stem cell. US2006003446 (Keller) describes a way of making a cell population enriched for endoderm cells culturing embryonic stem cells in the absence of serum and in the presence of activin and an inhibitor of Wnt-signalling. Modulation of Wnt signalling through the use of a GSK3 inhibitor has also been shown to be beneficial in specifying hepatocyte cell fate when DE cells are exposed to this treatment (WO2011/116930). Again, all of these disclosures relate to modulation of GSK3 signalling at relatively early stages in endodermal or hepatic specification.

Culturing of cells on certain matrix components has been known to affect their growth and, in the case of multipotent cells, to affect their ultimate differentiation. For example, pluripotent stem cells have been shown to undergo epithelial to mesenchymal transition and thence develop into cardiac cell types through overlaying of the stem cells with certain matrix components (WO2011060342). Moreover, culturing of adult primary hepatocytes in defined "sandwich" of matrix components has long been known to help them maintain their phenotype and metabolic activity (Dunn et al 1991), (Page et al 2007).

SUMMARY OF THE INVENTION

Present invention describes improved methods by which hepatocyte-like cells derived from human pluripotent stem (hPS) cells, such as but not limited to hiPS-cells and hES-cells, may be further matured into hepatocyte-like cells possessing a phenotype more closely resembling that of ex vivo primary liver hepatocytes.

The present invention provides in a first aspect a method for promoting the maturation of human hepatocyte-like cells whereby said hepatocyte-like cells are exposed to an activator of a retinoic acid responsive receptor, such as retinoic acid, optionally in combination with exposure to an inhibitor of GSK3 signalling or activator of Wnt signalling and/or with an overlay of the cells with one or more components characteristic of the mammalian extracellular matrix (matrix overlay).

Thus, a method for promoting the maturation of human hepatocyte-like cells is provided, the method comprising:
Exposing said human hepatocyte-like cells to an activator of a retinoic acid responsive receptor.

The method for promoting the maturation of human hepatocyte-like cells may further comprise culturing human hepatic progenitor cells under differentiation conditions to obtain said hepatocyte-like cells.

The present invention provides in a second aspect a method for producing human hepatocyte-like cells whereby human hepatic progenitor cells are cultured under differentiation conditions to obtain hepatocyte-like cells, and the obtained hepatocyte-like cells are exposed to an activator of a retinoic acid responsive receptor, such as retinoic acid, optionally in combination with exposure to an inhibitor of GSK3 signalling or activator of Wnt signalling and/or with an overlay of the cells with one or more components characteristic of the mammalian extracellular matrix (matrix overlay).

Thus, a method for producing human hepatocyte-like cells is provided, the method comprising:
Culturing human hepatic progenitor cells under differentiation conditions to obtain hepatocyte-like cells, and
Exposing said hepatocyte-like cells to an activator of a retinoic acid responsive receptor.

The present inventors have surprisingly found that the exposure of hepatocyte-like cells to an activator of a retinoic acid responsive receptor, such as retinoic acid, improves the gene and protein expression of a number of markers for mature hepatocytes, notably adult isoforms of HNF4α, CYP1A2, CYP2B6, CYP2C9, CYP3A4, CYP3A5, CAR, GSTA1-1, and NTCP, and thus leads to hepatocyte-like cells with a phenotype more closely resembling that of primary hepatocytes. Moreover, a surprising synergistic effect was found for exposure to an activator of a retinoic acid responsive receptor, a GSK3-inhibitor and an overlay with one or more components characteristic of the mammalian extracellular matrix making the phenotype of the hepatocyte-like cells even more similar to human primary hepatocytes. In addition to improved expression of hepatic genes and functions, the morphology of the hepatocyte-like cells is improved, e.g. the cell-cell contacts are enhanced, and the life span of the hepatocyte-like cells is prolonged by 7-10 days (FIG. 8).

The activator of a retinoic acid responsive receptor, such as retinoic acid, may be present throughout the differentiation of the hepatic progenitor cells into hepatocyte-like cells and further maturation of the obtained hepatocyte-like cells ("differentiation and maturation"), which may take up to 35 days. Thus, the differentiating and maturing hepatic cells may be continuously/long term exposed to the activator of a retinoic acid responsive receptor during the differentiation and maturation. Alternatively, the hepatocyte-like cells may be exposed to said activator of a retinoic acid responsive receptor for a continuous period of time longer than 4 hours and no longer than 72 hours, such as, e.g., for a continuous period of 5, 24 or 48 hours. The hepatocyte-like cells may also be exposed to said activator of a retinoic acid responsive receptor for at least two, such as at least three, at least four or at least 5, continuous periods of time longer than 4 hours and no longer than 72 hours, such for continuous periods of 5, 24 or 48 hours. The at least two continuous periods of time are normally separated by a period of non-exposure to said activator of a retinoic acid responsive receptor. Such period of non-exposure may have a duration from several hours to several days, such as from 12 to 24 hours or 1 to 10 day, such as from 1 to 2 days. In this context, the activator of a retinoic acid responsive receptor may be added to the culture medium at any time point during the maturation of the hepatocyte-like cells. The hepatocyte-like cells may be exposed to the activator of a retinoic acid responsive receptor at a time t≥7 days after initiation of the differentiation of hepatic progenitor cells into hepatocyte-like cells. Thus, hepatocyte-like cells may be exposed to the activator of a retinoic acid responsive receptor at day 7, 9 or 12 after initiation of the differentiation of hepatic progenitor cells into hepatocyte-like cells.

The methods of the present invention may also comprise the initial generation of hepatic progenitor cells by culturing hPS cells under differentiation conditions (also referred herein as "initial hepatic differentiation"). Thus, hPS cells are initially differentiated into said hepatic progenitor cells.

This initial culturing or differentiation may include the culturing of the hPS cells under differentiation conditions to obtain cells of the definitive endoderm (DE cells) (pre-endodermal step), and further culturing the obtained DE cells under differentiation conditions to obtain hepatic progenitor cells (pre-hepatic step). Accordingly, hPS cells may thus be first differentiated into definitive endoderm, followed by the further differentiation of the definitive endoderm into hepatic progenitor cells.

Further, during the initial differentiation of hPS cells into endodermal and/or hepatic progenitor cells, the differentiating hPS cells may be exposed to a DNA demethylating agent, such as 5-aza-2-deoxycytidine or 5-azacytidine, to demethylate sections of the genome and allow transcriptional activation of genes. The exposure to said DNA demethylating agent may take place during the differentiation of the hPS cells into DE cells, i.e. during the pre-endodermal step. The cells are then cultured through endodermal stage until hepatic progenitor stage is reached, i.e. until hepatic progenitor cells are obtained, at which point the further differentiation and maturation of hepatocyte-like cells including the exposure to the activator of a retinoic acid responsive receptor, either alone or in combination with GSK-3 inhibition or activation of Wnt signalling and/or matrix overlay, is carried out.

The treatment of differentiating hPS cells with a DNA demethylating agent has surprisingly been found to lead to an improved morphology and yield of DE cells. Moreover, the exposure to the demethylating agent provides for more pure and homogenous DE populations with lower expression of stem cell markers like Oct4, compared to currently available state of the art methods (see FIG. 13 A to D). Further, an increased gene expression of a number of markers characteristic for definitive endoderm, such as sox17, cxcr4 and hhex (see FIG. 13 D), is seen for these endodermal cells. It is believed to be the first time that such effects are shown for DNA demethylation and the application of growth factors involved in the differentiation of hPS cells towards definitive endoderm whose action at a genomic level may be enhanced by the widespread absence of methylation. Moreover, a strong synergistic effect on the maturation of hepatocyte-like cells is seen when treating cells with a DNA demethylating agent during early endodermal development before exposing the obtained hepatic progenitor cells to an activator of a retinoic acid responsive receptor, either alone or in combination with a GSK3-inhibitor and/or matrix overlay.

As a result of the methods according to the present invention, hepatocyte-like cells are obtained having a phenotype more closely resembling that of primary hepatocytes. Analysis of cells subsequent to the maturation period reveals a distinct increase in the expression levels of certain markers for mature hepatocytes, notably but not limited to adult isoforms of HNF4α, CYP1A2, CYP2B6, CYP2C9, CYP3A4, CYP3A5, CAR, GSTA1-1, and NTCP (see for example FIGS. 1B, 4B+C, 6, 9, 10, 12). Moreover, in contrast to primary hepatocytes, the hepatocyte-like cells obtained by an early stage demethylation treatment and late stage exposure to an activator of a retinoic acid responsive receptor, a GSK3-inhibitor (or activator of Wnt signalling) and a matrix overlay display a stable or increasing expression of hepatic genes like CYPs over time in culture. In cultured primary hepatocytes, CYP activity and mRNA expression is rapidly decreasing over time whereas the opposite is observed for hepatocyte-like cells according to the invention (see FIG. 16). Another widely used hepatic cell type are HepG2 which display much lower CYP activity than hepatocyte-like cells according to the invention.

The present invention provides a method for promoting the maturation of human hepatocyte-like cells whereby said hepatocyte-like cells are exposed to an activator of a retinoic acid responsive receptor, such as retinoic acid, optionally in combination with exposure to an CDK inhibitor and/or with an overlay of the cells with one or more components characteristic of the mammalian extracellular matrix (matrix overlay).

Thus, a method for promoting the maturation of human hepatocyte-like cells is provided, the method comprising:
Exposing said human hepatocyte-like cells to an activator of a retinoic acid responsive receptor.

The method for promoting the maturation of human hepatocyte-like cells may further comprise culturing human hepatic progenitor cells under differentiation conditions to obtain said hepatocyte-like cells.

The present invention further provides a method for producing human hepatocyte-like cells whereby human hepatic progenitor cells are cultured under differentiation conditions to obtain hepatocyte-like cells, and the obtained hepatocyte-like cells are exposed to an activator of a retinoic acid responsive receptor, such as retinoic acid, optionally in combination with exposure to an CDK inhibitor and/or with an overlay of the cells with one or more components characteristic of the mammalian extracellular matrix (matrix overlay).

Thus, a method for producing human hepatocyte-like cells is provided, the method comprising:
Culturing human hepatic progenitor cells under differentiation conditions to obtain hepatocyte-like cells, and
Exposing said hepatocyte-like cells to an activator of a retinoic acid responsive receptor.

As noted above, the present inventors have surprisingly found that the exposure of hepatocyte-like cells to an activator of a retinoic acid responsive receptor, such as retinoic acid, improves the gene and protein expression of a number of markers for mature hepatocytes, notably adult isoforms of HNF4α, CYP1A2, CYP2B6, CYP2C9, CYP3A4, CYP3A5, CAR, GSTA1-1, and NTCP, and thus leads to hepatocyte-like cells with a phenotype more closely resembling that of primary hepatocytes. Moreover, a surprising synergistic effect was found for exposure to an activator of a retinoic acid responsive receptor, a CDK inhibitor and an overlay with one or more components characteristic of the mammalian extracellular matrix making the phenotype of the hepatocyte-like cells even more similar to human primary hepatocytes. In addition to improved expression of hepatic genes and functions, the morphology of the hepatocyte-like cells is improved, e.g. the cell-cell contacts are enhanced, and the life span of the hepatocyte-like cells is prolonged by 7-10 days (FIG. 8).

Again, the activator of a retinoic acid responsive receptor, such as retinoic acid, may be present throughout the differentiation of the hepatic progenitor cells into hepatocyte-like cells and further maturation of the obtained hepatocyte-like cells ("differentiation and maturation"), which may take up to 35 days. Thus, the differentiating and maturing hepatic cells may be continuously/long term exposed to the activator of a retinoic acid responsive receptor during the differentiation and maturation. Alternatively, the hepatocyte-like cells may be exposed to said activator of a retinoic acid responsive receptor for a continuous period of time longer than 4 hours and no longer than 72 hours, such as, e.g., for a continuous period of 5, 24 or 48 hours. The hepatocyte-like cells may also be exposed to said activator of a retinoic acid responsive receptor for at least two, such as at least three, at least four or at least 5, continuous periods of time longer than 4 hours and no longer than 72 hours, such for continuous periods of 5, 24 or 48 hours. The at least two continuous periods of time are normally separated by a period of non-exposure to said activator of a retinoic acid responsive receptor. Such period of non-exposure may have a duration from several hours to several days, such as from 12 to 24 hours or 1 to 10 day, such as from 1 to 2 days. In this context, the activator of a retinoic acid responsive receptor may be added to the culture medium at any time point during the maturation of the hepatocyte-like cells. The hepatocyte-like cells may be exposed to the activator of a retinoic acid responsive receptor at a time t≥7 days after initiation of the differentiation of hepatic progenitor cells into hepatocyte-like cells. Thus, hepatocyte-like cells may be exposed to the activator of a retinoic acid responsive receptor at day 7, 9 or 12 after initiation of the differentiation of hepatic progenitor cells into hepatocyte-like cells.

The methods of the present invention may also comprise the initial generation of hepatic progenitor cells by culturing hPS cells under differentiation conditions (also referred herein as "initial hepatic differentiation"). Thus, hPS cells are initially differentiated into said hepatic progenitor cells. This initial culturing or differentiation may include the culturing of the hPS cells under differentiation conditions to obtain cells of the definitive endoderm (DE cells) (pre-endodermal step), and further culturing the obtained DE cells under differentiation conditions to obtain hepatic progenitor cells (pre-hepatic step). Accordingly, hPS cells may thus be first differentiated into definitive endoderm, followed by the further differentiation of the definitive endoderm into hepatic progenitor cells.

Further, during the initial differentiation of hPS cells into endodermal and/or hepatic progenitor cells, the differentiating hPS cells may be exposed to a DNA demethylating agent, such as 5-aza-2-deoxycytidine or 5-azacytidine, to demethylate sections of the genome and allow transcriptional activation of genes. The exposure to said DNA demethylating agent may take place during the differentiation of the hPS cells into DE cells, i.e. during the pre-endodermal step. The cells are then cultured through endodermal stage until hepatic progenitor stage is reached, i.e. until hepatic progenitor cells are obtained, at which point the further differentiation and maturation of hepatocyte-like cells including the exposure to the activator of a retinoic acid responsive receptor, either alone or in combination with CDK inhibition and/or matrix overlay, is carried out.

The treatment of differentiating hPS cells with a DNA demethylating agent has surprisingly been found to lead to an improved morphology and yield of DE cells. Moreover, the exposure to the demethylating agent provides for more pure and homogenous DE populations with lower expression of stem cell markers like Oct4, compared to currently available state of the art methods (see FIG. 13 A to D). Further, an increased gene expression of a number of markers characteristic for definitive endoderm, such as sox17, cxcr4 and hhex (see FIG. 13 D), is seen for these endodermal cells. It is believed to be the first time that such effects are shown for DNA demethylation and the application of growth factors involved in the differentiation of hPS cells towards definitive endoderm whose action at a genomic level may be enhanced by the widespread absence of methylation. Moreover, a strong synergistic effect on the maturation of hepatocyte-like cells is seen when treating cells with a DNA demethylating agent during early endodermal development before exposing the obtained hepatic progenitor cells to an activator of a retinoic acid responsive receptor, either alone or in combination with a CDK inhibitor and/or matrix overlay.

As a result of the methods according to the present invention, hepatocyte-like cells are obtained having a phenotype more closely resembling that of primary hepatocytes. Analysis of cells subsequent to the maturation period reveals a distinct increase in the expression levels of certain markers for mature hepatocytes, notably but not limited to adult isoforms of HNF4α, CYP1A2, CYP2B6, CYP2C9, CYP3A4, CYP3A5, CAR, GSTA1-1, and NTCP (see for example FIGS. 1B, 4B+C, 6, 9, 10, 12). Moreover, in contrast to primary hepatocytes, the hepatocyte-like cells obtained by an early stage demethylation treatment and late stage exposure to an activator of a retinoic acid responsive receptor, a CDK inhibitor and a matrix overlay display a stable or increasing expression of hepatic genes like CYPs over time in culture. In cultured primary hepatocytes, CYP activity and mRNA expression is rapidly decreasing over time whereas the opposite is observed for hepatocyte-like cells according to the invention (see FIG. 16). Another widely used hepatic cell type are HepG2 which display much lower CYP activity than hepatocyte-like cells according to the invention.

Thus, in further aspects, the invention relates to a hepatocyte-like cell(s) obtained by the methods of the invention and to a cell composition(s) comprising, or consisting of, said hepatocyte-like cell(s), In another aspect, the present invention relates to the further use of the hepatocyte-like cell(s) or cell composition(s) of the invention in medicine, in particular regenerative medicine. In other words, of the hepatocyte-like cell(s) or cell composition(s) of the invention are for use in medicine, in particular for use in regenerative medicine. Particularly, the hepatocyte-like cell(s) or cell composition(s) of the invention are for use in the prevention and/or treatment of pathologies and/or disorders caused by tissue degeneration. The hepatocyte-like cell(s) or cell composition(s) of the invention are also for use in the prevention and/or treatment of liver disorders. The hepatocyte-like cell(s) or cell composition(s) of the invention are also for use in the prevention and/or treatment of metabolic pathologies and/or diseases. As such the hepatocyte-like cell(s) or cell composition(s) of the invention may be used for the manufacture of a medicament or medicinal product, such as in the form of replacement tissue or cell injection, in particular for the prevention and/or treatment of pathologies and/or disorders caused by tissue degeneration. The hepatocyte-like cell(s) or cell composition(s) of the invention may also be used for the manufacture of a medicament or medicinal product/or for the prevention and/or treatment of liver disorders. The hepatocyte-like cell(s) or cell composition(s) of the invention may be used for the manufacture of a medicament or medicinal product for the prevention and/or treatment of metabolic pathologies and/or diseases. Also included in this aspect of the invention are methods for treatment of pathologies and/or disorders mentioned herein, comprising the administration of an effective amount of the hepatocyte-like cell(s) or cell composition(s) of the invention to a subject in need thereof.

In other aspects, the invention provides the further uses of the hepatocyte-like cell(s) or cell composition(s) of the invention in pharmaceutical and toxicological screening, such as drug discovery processes or toxicity testing; for studying drug transporters or drug metabolizing enzymes, as in vitro models for studying hepatogenesis; and for studying human hepatoregenerative disorders.

In a further aspect, the invention relates to the use of an activator of a retinoic acid responsive receptor for maturing human hepatocyte-like cells. Also included in this aspect is the use of an activator of a retinoic acid responsive receptor in combination with an inhibitor of GSK3 signalling and/or a matrix overlay for maturing human hepatocyte-like cells. Further included in this aspect is the use of an activator of a retinoic acid responsive receptor in combination with an activator of Wnt signalling and/or a matrix overlay for maturing human hepatocyte-like cells. Also included in this aspect is the use of an activator of a retinoic acid responsive receptor in combination with a CDK inhibitor and/or a matrix overlay for maturing human hepatocyte-like cells.

In yet a further aspect, the invention relates to kits useful in carrying out the methods of the invention. Included in this aspect are kits which comprise at least one activator of a retinoic acid responsive receptor and at least one selected from GSK3 inhibitor, activator of Wnt signalling, CDK inhibitor and extracellular matrix (ECM) component or ECM component mixture. It is understood that the details given herein with respect to the components employed in the methods of the invention also apply to the components comprised by the kits of the invention.

In yet a further aspect, the invention relates to compositions. Such compositions are particularly useful for maturing human hepatocyte-like cells in accordance with the invention. Included in this aspect are compositions which comprise at least one activator of a retinoic acid responsive receptor and at least one selected from GSK3 inhibitor, activator of Wnt signalling and CDK inhibitor. It is understood that the details given herein with respect to the components employed in the methods of the invention also apply to the components comprised by the compositions of the invention.

DETAILED DESCRIPTION OF THE INVENTION

The invention provides methods for maturing human hepatocyte-like cells by exposing the cells to an activator of a retinoic acid receptor, either alone or in combination with exposure to an inhibitor of GSK3 signalling or an activator of Wnt signalling and/or with overlaying of the cells with one or more components of the mammalian extracellular matrix (matrix overlay). The methods may further comprise culturing of human hepatic progenitor cells in a supportive culture and differentiation medium to obtain said hepatocyte-like cells where the cells are exposed to an activator of a retinoic acid responsive receptor, either alone or in combination with exposure to an inhibitor of GSK3 signalling or activator of Wnt signalling and/or with overlaying of the cells with one or more components of the mammalian extracellular matrix (matrix overlay).

The invention also provides methods for maturing human hepatocyte-like cells by exposing the cells to an activator of a retinoic acid receptor, either alone or in combination with exposure to a CDK inhibitor and/or with overlaying of the cells with one or more components of the mammalian extracellular matrix (matrix overlay). The methods may further comprise culturing of human hepatic progenitor cells in a supportive culture and differentiation medium to obtain said hepatocyte-like cells where the cells are exposed to an activator of a retinoic acid responsive receptor, either alone or in combination with exposure to a CDK inhibitor and/or with overlaying of the cells with one or more components of the mammalian extracellular matrix (matrix overlay).

The starting material in the present invention may be any cell having a hepatic cell fate, developed to any stage beyond the endodermal stage, such as but not limited to fetal hepatocytes and hepatic progenitor cells.

As outlined above, the present invention provides a method for promoting the maturation of human hepatocyte-like cells whereby said hepatocyte-like cells are exposed to an activator of a retinoic acid responsive receptor, such as retinoic acid, optionally in combination with exposure to an inhibitor of GSK3 signalling or activator of Wnt signalling and/or with an overlay of the cells with one or more components characteristic of the mammalian extracellular matrix (matrix overlay).

The method for promoting the maturation of human hepatocyte-like cells may thus be described as comprising the step:

Exposing said human hepatocyte-like cells to an activator of a retinoic acid responsive receptor.

The method for promoting the maturation of human hepatocyte-like cells may further comprise the step of culturing human hepatic progenitor cells under differentiation conditions to obtain said hepatocyte-like cells.

The present invention also provides a method for producing human hepatocyte-like cells whereby human hepatic progenitor cells are cultured under differentiation conditions to obtain hepatocyte-like cells, and the obtained hepatocyte-like cells are exposed to an activator of a retinoic acid responsive receptor, such as retinoic acid, optionally in combination with exposure to an inhibitor of GSK3 signalling or activator of Wnt signalling and/or with an overlay of the cells with one or more components characteristic of the mammalian extracellular matrix (matrix overlay).

The method for producing human hepatocyte-like cells may thus be described as comprising the following steps:

Culturing human hepatic progenitor cells under differentiation conditions to obtain hepatocyte-like cells, and Exposing said hepatocyte-like cells to an activator of a retinoic acid responsive receptor.

The present invention also provides a method for promoting the maturation of human hepatocyte-like cells whereby said hepatocyte-like cells are exposed to an activator of a retinoic acid responsive receptor, such as retinoic acid, optionally in combination with exposure to a CDK inhibitor and/or with an overlay of the cells with one or more components characteristic of the mammalian extracellular matrix (matrix overlay).

The method for promoting the maturation of human hepatocyte-like cells may thus be described as comprising the step:

Exposing said human hepatocyte-like cells to an activator of a retinoic acid responsive receptor.

The method for promoting the maturation of human hepatocyte-like cells may further comprise the step of culturing human hepatic progenitor cells under differentiation conditions to obtain said hepatocyte-like cells.

The present invention also provides a method for producing human hepatocyte-like cells whereby human hepatic progenitor cells are cultured under differentiation conditions to obtain hepatocyte-like cells, and the obtained hepatocyte-like cells are exposed to an activator of a retinoic acid responsive receptor, such as retinoic acid, optionally in combination with exposure to CDK inhibitor and/or with an overlay of the cells with one or more components characteristic of the mammalian extracellular matrix (matrix overlay).

The method for producing human hepatocyte-like cells may thus be described as comprising the following steps:

Culturing human hepatic progenitor cells under differentiation conditions to obtain hepatocyte-like cells, and Exposing said hepatocyte-like cells to an activator of a retinoic acid responsive receptor.

Human hepatic progenitor cells may thus be used as starting material according to the invention. The hepatic progenitor starting material may, for example, be an established cell line of hepatic progenitor cells or may be prepared de novo, such as from hPS cells or endodermal cells.

The differentiation and maturation of hepatocyte-like cells may be divided into two phases, i.e. a first phase where the hepatic progenitor cells differentiate into hepatocyte-like cells ("hepatic progenitor phase"), and a second phase where the obtained hepatocyte-like cells further mature (maturation phase) During the maturation phase the obtained hepatocyte-like cells exhibit an increased gene and protein expression of characteristic markers for hepatocytes.

Suitable conditions for differentiating hepatic progenitor cells into hepatocyte-like cells from hES cells (Hay et al., 2007; Hay et al., 2008; Brolen et al. 2010; Funakoshi et al. 2011) and from hiPS cells (U.S. Pat. No. 8,148,151B; Song et al. 2009; Sullivan et al. 2010; Si-Tayeb et al. 2010; Chen et al. 2012) are known. WO 2009/013254 A1, for example, describes suitable basic protocols to obtain hepatocyte-like cells from hepatic progenitor cells (Embodiments 1 to 4).

Generally, hepatic progenitor cells are cultured in a differentiation medium comprising one or more growth factors, such as HGF, and/or one or more differentiation inducer, such as dimethylsulfoxide (DMSO), dexamethazone (DexM), omeprazole, Oncostatin M (OSM), rifampicin, desoxyphenobarbital, ethanol or isoniazide. The concentration of the one or more growth factors, such as HGF, is usually in the range of about 10 to about 300 ng/ml, such as about 20 to about 250 ng/ml, about 50 to about 250 ng/ml, about 100 to about 250 ng/ml, about 150 to about 250 ng/ml, about 50 to about 200 ng/ml, about 50 to about 150 ng/ml or about 50 to about 100 ng/ml; or may be about 100 ng/ml, about 150 ng/ml, about 200 ng/ml, about 250 ng/ml or about 300 ng/ml. The concentration of the one or more differentiation inducer may vary depending on the particular compound used. The concentration of DMSO, for example, is usually in the range of about 0.1 to about 2% v/v, such as about 0.1 to about 1.5% v/v, about 0.1 to about 1% v/v, about 0.25 to about 1% v/v, about 0.25 to about 0.75% v/v, about 0.5 to about 1.5% v/v, or about 0.5 to about 1% v/v. The concentration of OSM, for example, is usually in the range of about 1 to about 20 ng/ml, such as about 1 to about 15 ng/ml, about 5 to about 15 ng/ml, or about 7.5 to about 12.5 ng/ml. The concentration of DexM, for example, is usually in the range of about 0.05 to about 1 µM, such as about 0.05 to about 0.5 µM, about 0.05 to about 0.2 µM, about 0.05 to about 0.1 µM or about 0.1 to about 0.5 µM.

The differentiation medium may further comprise serum, such as FBS or FCS, and/or one or more bone morphogenetic proteins (BMPs), such as bone morphogenetic protein 2 (BMP2) and/or bone morphogenetic protein 4 (BMP4). The concentration of serum, if present, is usually in the range of about 0.1 to about 5% v/v, such as about 0.1 to about 0.5%, 0.2 to 3% v/v, about 0.5 to about 2.5% v/v, about 0.5 to 1% v/v or about 1 to about 2.5% v/v. The concentration of the one or more BMPs, if present, is usually in the range of about 50 to about 300 ng/ml, such as about 50 to about 250 ng/ml, about 100 to about 250 ng/ml, about 150 to about 250 ng/ml, about 50 to about 200 ng/ml, about 100 to about 200 ng/ml or about 150 to about 200 ng/ml.

The differentiation medium may further comprise other supplements such as PEST and/or GlutaMAX. The concentration of PEST is usually in the range of about 0.1 to about 0.5% v/v, such as about 0.1 to about 0.25% v/v. The concentration of GlutaMAX is usually in the range of about 0.5 to about 1.5% v/v, such as about 0.75 to 1.25% v/v, e.g. about 1% v/v.

The culture medium forming the basis for the differentiation medium may be any culture medium suitable for culturing human hepatic progenitor cells such as RPMI 1640 or advanced medium, Dulbecco's Modified Eagle Medium (DMEM), HCM medium, HBM medium, Waymouth medium or Williams E based medium. Thus, the differentiation medium may be RPMI 1640 or advanced medium comprising or supplemented with the above-mentioned components. Alternatively, the differentiation medium may be DMEM comprising or supplemented with the above-mentioned components. As a further alternative, the differentiation medium may thus be HCM or HBM medium comprising or supplemented with the above-mentioned components. As a further alternative, the differentiation medium may thus be Waymouth medium or Williams E based medium comprising or supplemented with the above-mentioned components.

The differentiation of human hepatic progenitor cells and further maturation of the obtained hepatocyte-like cells ("differentiation and maturation") normally takes up to 35 days in total. Thus, in order to obtain hepatocyte-like cells, the human hepatic progenitor cells are cultured in differentiation medium for up to 35 days. For example, the human hepatic progenitor cells may be cultured in differentiation medium for any time between about 7 to about 35 days. They may thus also be cultured for about 10 to about 30 days. They may also be cultured for about 10 to about 25 days. Alternatively, they may be cultured for about 10 to about 20 days or for about 10 to about 15 days. They may also be cultured for about 15 to about 35 days. Thus, they may also be cultured for about 15 to about 30 days. Alternatively, they may be cultured for about 15 to about 25 days. They may also be cultured for about 15 to about 20 days. During the culturing the differentiation medium is usually exchanged for fresh medium every second or third day.

Under the above described conditions, hepatocyte-like cells are obtained from hepatic progenitor cells on or after 7 days of culture. Thus, the differentiation and maturation of hepatocyte-like cells may be divided into a hepatic progenitor phase of 7 days, whereby hepatic progenitor cells differentiate into hepatocyte-like cells, and a maturation phase lasting until the end of the total culture period (e.g., until day 35), whereby the obtained hepatocyte-like cells further mature.

The activator of a retinoic acid responsive receptor employed in the methods of the invention may be any compound capable of binding to and activating a human retinoic acid receptor (RAR) and/or human retinoid X receptor (RXR), such as, e.g., a compound capable of binding to and activating both RAR and RXR.

A suitable activator of a retinoic acid responsive receptor for use in the invention is retinoic acid, such as 9-cis-retinoic acid and 13-cis-retinoic acid or other retinoic isomers, including all-trans-retinoic acid, 7-cis retinoic acid and 11-cis-retinoic acid, or an analogue of retinoic acid, such as TTNPB, AM580, retilloic acid or CBS-211A, or a retinoid.

Accordingly, 9-cis-retinoic acid may be used as the activator of a retinoic acid responsive receptor in accordance with the present invention. Alternatively, or in addition, 13-cis-retinoic acid may also be used as the activator of a retinoic acid responsive receptor in accordance with the present invention. 13-cis retinoic acid may also be used as the activator of a retinoic acid responsive receptor in accordance with the present invention.

9-cis-retinoic acid, for example, has been reported to be the only retinoic acid stereoisomer that binds to and activates both RXR and RAR (Allenby et al.; Idres et al.). However, another report stated that also 11-cis-retinoic acid, 13-cis-retinoic acid and all trans retinoic acid can bind to RXR but with much lower affinity than 9-cis-retinoic acid (Heyman et al.). Taken together, these reports suggest that 9-cis-retinoic acid may be the major RXR activator compared to other RA isomers. Thus, the activator of a retinoic acid responsive receptor for use in the present invention may be a retinoic acid, an analogue of retinoic acid or a retinoid capable of binding to and activating both RAR and RXR, such as, e.g., 9-cis-retinoic acid or an analogue thereof.

Further, all-trans-retinoic acid, 7-cis retinoic acid, 11-cis retinoic acid or 13-cis retinoic acid may be used as activator of a retinoic acid responsive receptor. Those isomers have been shown to specifically bind RAR, but not to RXR (Allenby et al.; Idres et al.) or with much lower affinity to RXR than 9-cis-retinoic acid (Heyman et al). Thus, the activator of a retinoic acid responsive receptor for use in the present invention may be a retinoic acid, an analogue of retinoic acid or a retinoid capable of binding to and activating RAR and not or weakly RXR, such as, e.g. all trans retinoic acid or an analogue of all-trans-retinoic acid, or 7-cis retinoic acid or an analogue of 7-cis retinoic acid, or 11-cis retinoic acid or an analogue of 11-cis retinoic acid, or 13-cis retinoic acid or an analogue of 13-cis retinoic acid.

The activator of a retinoic acid responsive receptor for use in the present invention may also be a retinoid capable of binding to and activating only RXR and not RAR, such as, e.g. Bexarotene (LGD1069), LG100268 or SR11237.

As noted above, an analogue of retinoic acid, such as, e.g., TTNPB, AM580, retilloic acid or CBS-211A, may also be used as the activator of a retinoic acid responsive receptor. Thus, the retinoic acid analogue TTNPB may be used as the activator of a retinoic acid responsive receptor. Alternatively, the retinoic acid analogue AM580 may be used as the activator of a retinoic acid responsive receptor.

Also envisaged is the use of a small molecule, lipid, polypeptide or protein, which binds to and activates a human retinoic acid receptor (RAR) and/or retinoid X receptor (RXR), as activator of a retinoic acid responsive receptor. Non-limiting examples of such compounds are Ch 55, AC 261066, AC 55649, CD1530, CD437, CD3254, AM80, BMS 753, BMS 961, Adapalene, Tazarotene, Docosahexaenoic acid, and Fluorobexarotene, which are all known agonists of RAR or RXR.

Optionally, the hepatocyte-like cells may be exposed to one or more further activators of a retinoic acid responsive receptor. Thus, the hepatocyte-like cells may not only be exposed to one activator of a retinoic acid responsive receptor, but may also be exposure to one or more further activators of a retinoic acid responsive receptor, such as to a combination of two, three or four of those mentioned above. The hepatocyte-like cells may, for instance, be exposed to both 9-cis-retinoic acid and 13-cis-retinoic acid.

In one aspect of the invention, the differentiating and maturing hepatic cells are continuously/long term exposed to the activator of a retinoic acid responsive receptor during the differentiation and maturation of the hepatocyte-like cells. Thus, the activator of a retinoic acid responsive receptor may be present in the differentiation medium throughout the differentiation and maturation period.

The differentiating and maturing hepatic cells may, for example, be exposed to the activator of a retinoic acid responsive receptor for up to about 35 days. They may, for example, be exposed to the activator of a retinoic acid responsive receptor for about 10 days to about 30 days. They may also be exposed to the activator of a retinoic acid responsive receptor for about 10 days to about 25 days. They may also be exposed to the activator of a retinoic acid responsive receptor for about 10 days to about 20 days. They may also be exposed to the activator of a retinoic acid responsive receptor for about 10 days to about 15 days. They may also be exposed to the activator of a retinoic acid responsive receptor for about 15 days to about 35 days. They may also be exposed to the activator of a retinoic acid responsive receptor for about 15 days to about 30 days. They may also be exposed to the activator of a retinoic acid responsive receptor for about 15 days to about 25 days. They may also be exposed to the activator of a retinoic acid responsive receptor for about 15 days to about 20 days.

In another aspect of the invention, the hepatocyte-like cells are exposed to the activator of a retinoic acid responsive receptor for a continuous period of time longer than 4 hours and no longer than 72 hours. Thus, the activator of a retinoic acid responsive receptor may be added to, and thus is present, in the differentiation medium for a continuous period of time longer than 4 hours and no longer than 72 hours during the differentiation and maturation period.

The continuous period of time of exposure may be for about 5 to about 10 hours. The continuous period of time of exposure may also be for about 5 to about 12 hours. The continuous period of time of exposure may also be for about 5 to about 18 hours. The continuous period of time of exposure may also be for about 5 to about 24 hours. The continuous period of time of exposure may also be for about 5 to about 48 hours. Thus, the continuous period of time of exposure may be for about 5 hours. The continuous period of time of exposure may also be for about 12 to about 18 hours. The continuous period of time of exposure may also be for about 12 to about 24 hours. The continuous period of time of exposure may also be for about 12 to about 48 hours. The continuous period of time of exposure may also be for about 12 to about 72 hours. Thus, the continuous period of time of exposure may be for about 12 hours. The continuous period of time of exposure may also be for about 18 to about 24 hours. The continuous period of time of exposure may also be for about 18 to about 48 hours. The continuous period of time of exposure may also be for about 18 to about 72 hours. Thus, the continuous period of time of exposure may be for about 18 hours. The continuous period of time of exposure may also be for about 24 to about 48 hours. The continuous period of time of exposure may also be for about 24 to about 72 hours. Thus, the continuous period of time of exposure may be for about 24 hours. The continuous period of time of exposure may also be for about 48 to 72 hours. Thus, the continuous period of time of exposure may be for about 48 hours or about 72 hours.

The continuous period of time of exposure may, for example, be for about 5, about 10, about 12, about 18, about 24, about 48 or about 72 hours. The continuous period of time of exposure may be for about 5. It may also be for about 24. Alternatively, the continuous period of time of exposure may be for about 48.

As shown, for instance, in Example 4 (FIG. 2), exposing hepatocyte-like cells to an activator of a retinoic acid responsive receptor, here 9-cis-retinoic acid, for, e.g., 5, 24 and 48 hours, leads to an increase in CYP1A, CYP2C9 and 3A activities when compared to untreated cells. Further, after exposing hepatocyte-like cells to an activator of a retinoic acid responsive receptor for 5 or 24 hours, an increase of mRNA expression of the adult hepatic gene CYP3A4 and a strong decrease of the fetal hepatic gene CYP3A7 is immediately observed (see Example 5, FIG. 3).

The hepatocyte-like cells may not only be exposed to an activator of a retinoic acid responsive receptor once for continuous period of time longer than 4 hours and no longer than 72 hours, but may also be exposed to said activator of a retinoic acid responsive receptor for at least two, such as at least three, at least four or at least five, continuous periods of time longer than 4 hours and no longer than 72 hours, such as, e.g., for continuous periods of 5, 24 or 48 hours. Thus, the hepatocyte-like cells may, for example, be exposed to an activator of a retinoic acid responsive receptor for two continuous periods of time longer than 4 hours and no longer than 72 hours. The hepatocyte-like cells may also be exposed to an activator of a retinoic acid responsive receptor for three continuous periods of time longer than 4 hours and no longer than 72 hours. The hepatocyte-like cells may also be exposed to an activator of a retinoic acid responsive receptor for four continuous periods of time longer than 4 hours and no longer than 72 hours. The hepatocyte-like cells may also be exposed to an activator of a retinoic acid responsive receptor for five continuous periods of time longer than 4 hours and no longer than 72 hours.

As shown in Example 4, repeated exposure to an activator of a retinoic acid responsive receptor has a stronger increasing effect on, e.g., CYP1A and CYP2C9 than a single exposure.

After this continuous period of time of exposure, the differentiation medium is exchanged with one lacking the activator of a retinoic acid responsive receptor, and the cultivation of the differentiating cells is continued. Thus, in a protocol where hepatocyte-like cells are exposed to an activator of a retinoic acid responsive receptor for at least two continuous periods of time of exposure as defined above, the at least two continuous periods of time or exposure are separated by a period of non-exposure to said activator of a retinoic acid responsive receptor. Such period of non-exposure may have a duration from several hours to several days, such as from 12 to 24 hours or from 1 to 10 day. The period of non-exposure may have a duration of from 1 to 2 days. The period of non-exposure may also have a duration from 1 to 5 days. The period of non-exposure may also have a duration from 2 to 5 days. The period of non-exposure may, for instance, have a duration of 1 day. The period of non-exposure may also have a duration of 2 days. The period of non-exposure may, for instance, have a duration of 5 days.

In accordance with the invention, the activator of a retinoic acid responsive receptor may be added to the differentiation medium at any time point once hepatocyte-like cells have been obtained, such as, e.g., after 7, 9, 11, 13, 15, 20, 25 and/or 30 days of culturing.

Thus, the activator of a retinoic acid responsive receptor may, for instance, be added to the differentiation medium for the continuous period of time longer than 4 hours and no longer than 72 hours between day 7 and day 30 of the differentiation and maturation, such as, e.g., between day 7 and day 15. The activator of a retinoic acid responsive receptor may thus be added to the differentiation medium for the continuous period of time longer than 4 hours and no longer than 72 hours between day 7 and day 9 of the differentiation and maturation.

Accordingly, the activator of a retinoic acid responsive receptor may also be added to the differentiation medium for the continuous period of time longer than 4 hours and no longer than 72 hours at day 7 of the differentiation and maturation. The activator of a retinoic acid responsive receptor may also be added to the differentiation medium for the continuous period of time longer than 4 hours and no longer than 72 hours at day 9 of the differentiation and maturation. The activator of a retinoic acid responsive receptor may also be added to the differentiation medium for the continuous period of time longer than 4 hours and no longer than 72 hours at day 11 of the differentiation and maturation. The activator of a retinoic acid responsive receptor may also be added to the differentiation medium for the continuous period of time longer than 4 hours and no longer than 72 hours at day 13 of the differentiation and maturation. The activator of a retinoic acid responsive receptor may also be added to the differentiation medium for the continuous period of time longer than 4 hours and no longer than 72 hours at day 15 of the differentiation and maturation. The activator of a retinoic acid responsive receptor may also be added to the differentiation medium for the continuous period of time longer than 4 hours and no longer than 72 hours at day 20 of the differentiation and maturation. The activator of a retinoic acid responsive receptor may also be added to the differentiation medium for the continuous period of time longer than 4 hours and no longer than 72 hours at day 25 of the differentiation and maturation. The activator of a retinoic acid responsive receptor may also be added to the differentiation medium for the continuous period of time longer than 4 hours and no longer than 72 hours at day 30 of the differentiation and maturation.

The activator of a retinoic acid responsive receptor may also be added to the differentiation medium for the continuous period of time longer than 4 hours and no longer than 72 hours at days 7 and 9 of the differentiation and maturation. The activator of a retinoic acid responsive receptor may also be added to the differentiation medium for the continuous period of time longer than 4 hours and no longer than 72 hours at days 7, 9 and 11 of the differentiation and maturation. The activator of a retinoic acid responsive receptor may also be added to the differentiation medium for the continuous period of time longer than 4 hours and no longer than 72 hours at days 1, 6, 9, 11 and 16 of the differentiation and maturation. The activator of a retinoic acid responsive receptor may also be added to the differentiation medium for the continuous period of time longer than 4 hours and no longer than 72 hours at days 7, 9, 11 and 16 of the differentiation and maturation. The activator of a retinoic acid responsive receptor may also be added to the differentiation medium for the continuous period of time longer than 4 hours and no longer than 72 hours at days 7, 9, 11, 13 and 16 of the differentiation and maturation. The activator of a retinoic acid responsive receptor may also be added to the differentiation medium for the continuous period of time longer than 4 hours and no longer than 72 hours at days 1, 7, 9, 11 and 16 of the differentiation and maturation. The activator of a retinoic acid responsive receptor may also be added to the differentiation medium for the continuous period of time longer than 4 hours and no longer than 72 hours at days 1, 3, 7, 9, 11 and 16 of the differentiation and maturation.

The hepatocyte-like cells are generally to be exposed to the activator of a retinoic acid responsive receptor at a concentration in the range of about 0.1 to about 5 µM, such as, e.g, in the range of about 0.5 to about 1.5 µM.

The hepatocyte-like cells may thus be exposed to the activator of a retinoic acid responsive receptor at a concentration in the range of about 0.1 to about 2.5 µM. The hepatocyte-like cells may also be exposed to the activator of a retinoic acid responsive receptor at a concentration in the range of about 0.1 to about 1.5 µM. The hepatocyte-like cells may also be exposed to the activator of a retinoic acid responsive receptor at a concentration in the range of about 0.1 to about 1 µM. The hepatocyte-like cells may also be exposed to the activator of a retinoic acid responsive receptor at a concentration in the range of about 0.1 to about 0.5 µM. The hepatocyte-like cells may also be exposed to the activator of a retinoic acid responsive receptor at a concentration in the range of about 0.1 to about 0.3 µM. The hepatocyte-like cells may also be exposed to the activator of a retinoic acid responsive receptor at a concentration in the range of about 0.2 to about 5 µM. The hepatocyte-like cells may also be exposed to the activator of a retinoic acid responsive receptor at a concentration in the range of about 0.2 to about 2.5 µM. The hepatocyte-like cells may also be exposed to the activator of a retinoic acid responsive receptor at a concentration in the range of about 0.2 to about 1.5 µM. The hepatocyte-like cells may also be exposed to the activator of a retinoic acid responsive receptor at a concentration in the range of about 0.5 to about 5 µM. The hepatocyte-like cells may also be exposed to the activator of a retinoic acid responsive receptor at a concentration in the range of about 0.5 to about 3 µM. The hepatocyte-like cells may also be exposed to the activator of a retinoic acid responsive receptor at a concentration in the range of about 0.5 to about 2.5 µM. The hepatocyte-like cells may also be exposed to the activator of a retinoic acid responsive receptor at a concentration in the range of about 0.5 to about 2 µM. The hepatocyte-like cells may also be exposed to the activator of a retinoic acid responsive receptor at a concentration in the range of about 0.5 to about 1.5 µM. The hepatocyte-like cells may also be exposed to the activator of a retinoic acid responsive receptor at a concentration in the range of about 0.5 to about 1 µM. The hepatocyte-like cells may also be exposed to the activator of a retinoic acid responsive receptor at a concentration in the range of about 0.75 to about 5 µM. The hepatocyte-like cells may also be exposed to the activator of a retinoic acid responsive receptor at a concentration in the range of about 0.75 to about 3 µM. The hepatocyte-like cells may also be exposed to the activator of a retinoic acid responsive receptor at a concentration in the range of about 0.75 to about 2.5 µM. The hepatocyte-like cells may also be exposed to the activator of a retinoic acid responsive receptor at a concentration in the range of about 0.75 to about 2 µM. The hepatocyte-like cells may also be exposed to the activator of a retinoic acid responsive receptor at a concentration in the range of about 0.75 to about 1.5 µM. The hepatocyte-like cells may also be exposed to the activator of a retinoic acid responsive receptor at a concentration in the range of about 0.75 to about 1.25 µM. The hepatocyte-like cells may also be exposed to the activator of a retinoic acid responsive receptor at a concentration in the range of about 1 to about 2.5 µM. The hepatocyte-like cells may also be exposed to the activator of a retinoic acid responsive receptor at a concentration in the range of about 1 to about 2 µM. The hepatocyte-like cells may also be exposed to the activator of a retinoic acid responsive receptor at a concentration in the range of about 1 to about 1.5 µM.

Thus, the hepatocyte-like cells may be exposed to the activator of a retinoic acid responsive receptor at a concentration of about 0.1 µM. The hepatocyte-like cells may also be exposed to the activator of a retinoic acid responsive receptor at a concentration of about 0.2 µM. The hepatocyte-like cells may also be exposed to the activator of a retinoic acid responsive receptor at a concentration of about 0.5 µM. The hepatocyte-like cells may also be exposed to the activator of a retinoic acid responsive receptor at a concentration of about 0.75 µM. The hepatocyte-like cells may also be exposed to the activator of a retinoic acid responsive receptor at a concentration of about 1 µM. The hepatocyte-like cells may also be exposed to the activator of a retinoic acid responsive receptor at a concentration of about 1.25 µM. The hepatocyte-like cells may also be exposed to the activator of a retinoic acid responsive receptor at a concentration of about 1.5 µM. The hepatocyte-like cells may also be exposed to the activator of a retinoic acid responsive receptor at a concentration of about 1.75 µM. The hepatocyte-like cells may also be exposed to the activator of a retinoic acid responsive receptor at a concentration of about 2 µM. The hepatocyte-like cells may also be exposed to the activator of a retinoic acid responsive receptor at a concentration of about 2.5 µM. The hepatocyte-like cells may also be exposed to the activator of a retinoic acid responsive receptor at a concentration of about 3 µM. The hepatocyte-like cells may also be exposed to the activator of a retinoic acid responsive receptor at a concentration of about 3.5 µM. The hepatocyte-like cells may also be exposed to the activator of a retinoic acid responsive receptor at a concentration of about 4 µM. The hepatocyte-like cells may also be exposed to the activator of a retinoic acid responsive receptor at a concentration of about 5 µM.

In case that, for instance, 9-cis-retinoic acid is employed as the activator of a retinoic acid responsive receptor according to the invention, it may be exposed to the hepatocyte-like cells at a concentration in the range of about 0.1 to about 2.5 µM, such as, e.g., in the range of about 0.1 to about 0.5 µM, such as, e.g., at about 0.2 µM.

The hepatocyte-like cells may thus be exposed to 9-cis-retinoic acid at a concentration in the range of about 0.1 to about 2 µM. The hepatocyte-like cells may also be exposed to 9-cis-retinoic acid at a concentration in the range of about 0.1 to about 1.5 µM. The hepatocyte-like cells may thus be exposed to 9-cis-retinoic acid at a concentration in the range of about 0.1 to about 1 µM. The hepatocyte-like cells may thus be exposed to 9-cis-retinoic acid at a concentration in the range of about 0.1 to about 0.75 µM. The hepatocyte-like cells may thus be exposed to 9-cis-retinoic acid at a concentration in the range of about 0.1 to about 0.5 µM. The hepatocyte-like cells may thus be exposed to 9-cis-retinoic acid at a concentration in the range of about 0.1 to about 0.3 µM. The hepatocyte-like cells may also be exposed to 9-cis-retinoic acid at a concentration in the range of about 0.2 to about 2.5 µM. The hepatocyte-like cells may also be exposed to 9-cis-retinoic acid at a concentration in the range of about 0.2 to about 1.5 µM. The hepatocyte-like cells may also be exposed to 9-cis-retinoic acid at a concentration in the range of about 0.5 to about 2.5 µM. The differentiating hepatic progenitor cells may also be exposed to 9-cis-retinoic acid at a concentration in the range of about 0.5 to about 2 µM. The hepatocyte-like cells may also be exposed to 9-cis-retinoic acid at a concentration in the range of about 0.5 to about 1.5 µM. The hepatocyte-like cells may also be exposed to 9-cis-retinoic acid at a concentration in the range of about 0.5 to about 1 µM. The hepatocyte-like cells may also be exposed to 9-cis-retinoic acid at a concentration in the range of about 0.75 to about 2.5 µM. The hepatocyte-like cells may also be exposed to 9-cis-retinoic acid at a concentration in the range of about 0.75 to about 2 µM. The hepatocyte-like cells may also be exposed to 9-cis-retinoic acid at a concentration in the range of about 0.75 to about 1.5

μM. The hepatocyte-like cells may also be exposed to 9-cis-retinoic acid at a concentration in the range of about 0.75 to about 1.25 μM. The hepatocyte-like cells may also be exposed to 9-cis-retinoic acid at a concentration in the range of about 1 to about 2.5 μM. The hepatocyte-like cells may also be exposed to 9-cis-retinoic acid at a concentration in the range of about 1 to about 2 μM. The hepatocyte-like cells may also be exposed to 9-cis-retinoic acid at a concentration in the range of about 1 to about 1.5 μM.

Thus, the hepatocyte-like cells may be exposed to 9-cis-retinoic acid at a concentration of about 0.1 μM. The hepatocyte-like cells may also be exposed to 9-cis-retinoic acid at a concentration of about 0.2 μM. The hepatocyte-like cells may also be exposed to 9-cis-retinoic acid at a concentration of about 0.5 μM. The differentiating hepatic progenitor cells may also be exposed to 9-cis-retinoic acid at a concentration of about 0.75 μM. The hepatocyte-like cells may also be exposed to 9-cis-retinoic acid at a concentration of about 1 μM. The hepatocyte-like cells may also be exposed to 9-cis-retinoic acid at a concentration of about 1.25 μM. The hepatocyte-like cells may also be exposed to 9-cis-retinoic acid at a concentration of about 1.5 μM. The differentiating hepatic progenitor cells may also be exposed to 9-cis-retinoic acid at a concentration of about 1.75 μM. The hepatocyte-like cells may also be exposed to 9-cis-retinoic acid at a concentration of about 2 μM.

Similar concentrations may be used in case that, for instance, 13-cis-retinoic acid is employed as the activator of a retinoic acid responsive receptor according to the invention.

In addition to being exposed to the activator of a retinoic acid responsive receptor, the hepatocyte-like cells may optionally also be exposed to a GSK-3 inhibitor or activator of Wnt signalling and/or to an overlay of one or more components characteristic of the mammalian extracellular matrix (matrix overlay). Thus, the exposure to the activator of a retinoic acid responsive receptor is combined with the exposure to a GSK-3 inhibitor or with the exposure to a matrix overlay, or both. The exposure to the activator of a retinoic acid responsive receptor may also be combined with the exposure to an activator of Wnt signalling or with the exposure to a matrix overlay, or both. The additional exposure of the differentiating hepatic progenitor cells to a GSK-3 inhibitor or activator of Wnt signalling and/or to a matrix overlay has shown to further improve the mature and functional features for the hepatocyte-like cells (FIG. 4).

The GSK-3 inhibitor employed in the methods of the invention may be any compound capable of inhibiting the GSK-3 signalling. Suitable GSK-3 inhibitors for use in the invention are 9-Bromo-7,12-dihydro-indolo[3,2-d][1]benzazepin-6(5H)-one, also known as Kenpaullone or NSC 664704; 1-Aza-Kenpaullone (9-Bromo-7,12-dihydro-pyrido[3',2':2,3]azepino[4,5-b]indol-6(5H)-one); Alsterpaullone (9-Nitro-7,12-dihydroindolo-[3,2-d][1]benzazepin-6(5)-one); 4-(2,6-dichlorobenzamido)-N-(piperidin-4-yl)-1H-pyrazole-3-carboxamide also known as AT-7519; N-(5-((5-tert-butyloxazol-2-yl)methylthio)thiazol-2-yl)piperidine-4-carboxamide also known as SNS-032 (BMS-387032); 4-(1-isopropyl-2-methyl-1H-imidazol-5-yl)-N-(4-(methylsulfonyl)phenyl)pyrimidin-2-amine also known as AZD5438; (2'Z,3'£)-6-Bromoindirubin-3'-oxime, also known as BIO (GSK3 Inhibitor IX); (2'Z,3'E)-6-Bromoindirubin-3'-acetoxime, also known as BIO-Acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); N-(4-Methoxybenzyl)-N'-(5-nitro-1,3-thiazol-2-yl)urea, also known as AR-AO 14418 (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWSI 19 pyrrolopyrimidine compound (GSK3beta Inhibitor XII); L803 H-KEAPPAP-PQSpP-NH2 or its myristoylated form (GSK3beta Inhibitor XIII); 2-Chloro-1-(4,5-dibromo-thiophen-2-yl)-ethanone (GSK3beta Inhibitor VI); Aminopyrimidine CHIR99021; 3-(2,4-Dichlorophenyl)-4-(1-methyl-1H-indol-3-yl)-1H-pyrrole-2,5-dione, also known as SB216763; and Indirubin-3'-monoxime. The GSK-3 inhibitor may be selected from the above group.

Other suitable GSK-3 inhibitors which may be employed in the methods of the invention are 3F8 (5-Ethyl-7,8-dimethoxy-1H-pyrrolo[3,4-c]-isoquinoline-1,3-(2H)-dione), A1070722, anorganic ions like Beryllium, Copper, Lithium, Mercury, Tungstate (Wolfram), and Zinc, AR-A 014418, AZD2858, Axin GID-25 residues (peptide), bisindolylmaleimides, CHIR98014 (CT98014), CHIR98023 (CT98023), FRATide-39 residues (peptide), Halomethylketone derivatives, e.g. HMK-32, KT5720, L803-mts (peptide) and variants, LY20900314, NP-12 (Tideglusib, NP031112), NP00111, NP031115, Polyoxygenated bis-7-azaindolyl-maleimides, R031-8220, SB415286 (maleimide), TC-G24, TCS2002, TCS21311, TDZD-8, TOS119 and TWS119 (difluoroacetate). The GSK-3 inhibitor may be selected from the above group The GSK-3 inhibitor may, for instance, be one selected from Kenpaullone, 1-Aza-Kenpaullone, Alsterpaullone, Aminopyrimidine CHIR99021 and Indirubin-3'-monoxime.

The GSK-3 inhibitor employed in the methods of the invention may be Kenpaullone 9-Bromo-7,12-dihydro-indolo[3,2-d][1]benzazepin-6(5H)-one. The GSK-3 inhibitor may also be 1-Aza-Kenpaullone. The GSK-3 inhibitor may also be Alsterpaullone. The GSK-3 inhibitor may also be AT-7519. The GSK-3 inhibitor may also be SNS-032 (BMS-387032). The GSK-3 inhibitor may also be AZD5438. The GSK-3 inhibitor may also be BIO (2'Z,3'£)-6-Bromoindirubin-3'-oxime. The GSK-3 inhibitor may also be BIO-Acetoxime (2'Z,3'E)-6-Bromoindirubin-3'-acetoxime. The GSK-3 inhibitor may also be (5-Methyl-1H-pyrazol-3-yl)-(2-phenylquinazolin-4-yl)amine. The GSK-3 inhibitor may also be Pyridocarbazole-cyclopenadienylruthenium complex. The GSK-3 inhibitor may also be TDZD-8 4-Benzyl-2-methyl-1,2,4-thiadiazolidine-3,5-dione. The GSK-3 inhibitor may also be 2-Thio(3-iodobenzyl)-5-(1-pyridyl)[1,3,4]-oxadiazole. The GSK-3 inhibitor may also be OTDZT 2,4-Dibenzyl-5-oxothiadiazolidine-3-thione. The GSK-3 inhibitor may also be alpha-4-Dibromoacetophenone. The GSK-3 inhibitor may also be AR-AO 14418 N-(4-Methoxybenzyl)-N'-(5-nitro-1,3-thiazol-2-yl)urea. The GSK-3 inhibitor may also be 3-(1-(3-Hydroxypropyl)-1H-pyrrolo[2,3-b]pyridin-3-yl]-4-pyrazin-2-yl-pyrrole-2,5-dione. The GS K-3 inhibitor may also be TWSI 19 pyrrolopyrimidine compound. The GSK-3 inhibitor may also be L803 H-KEAPPAPPQSpP-NH2 or its myristoylated form. The GSK-3 inhibitor may also be 2-Chloro-1-(4,5-dibromo-thiophen-2-yl)-ethanone. The GSK-3 inhibitor may also be Aminopyrimidine CHIR99021. The GSK-3 inhibitor may also be SB216763 3-(2,4-Dichlorophenyl)-4-(1-methyl-1H-indol-3-yl)-1H-pyrrole-2,5-dione. The GSK-3 inhibitor may also be Indirubin-3'-monoxime.

The hepatocyte-like cells may not only be exposed to one GSK-3 inhibitor, but may also be exposed to one or more further GSK-3 inhibitors, such as to a combination of two, three or four of those mentioned above.

The hepatocyte-like cells may generally be exposed to the GSK-3 inhibitor at a concentration in the range of about 0.01 to about 10 µM.

Thus, the hepatocyte-like cells may be exposed to the GSK-3 inhibitor at a concentration in the range of about 0.05 to about 5 µM. The hepatocyte-like cells may thus be exposed to the GSK-3 inhibitor at a concentration in the range of about 0.05 to about 2.5 µM. The hepatocyte-like cells may also be exposed to the GSK-3 inhibitor at a concentration in the range of about 0.05 to about 2 µM. The hepatocyte-like cells may also be exposed to the GSK-3 inhibitor at a concentration in the range of about 0.05 to about 1.5 µM. The hepatocyte-like cells may also be exposed to the GSK-3 inhibitor at a concentration in the range of about 0.05 to about 1 µM. The hepatocyte-like cells may also be exposed to the GSK-3 inhibitor at a concentration in the range of about 0.05 to about 0.5 µM. The hepatocyte-like cells may be exposed to the GSK-3 inhibitor at a concentration in the range of about 0.1 to about 5 µM. The hepatocyte-like cells may thus be exposed to the GSK-3 inhibitor at a concentration in the range of about 0.1 to about 2.5 µM. The hepatocyte-like cells may also be exposed to the GSK-3 inhibitor at a concentration in the range of about 0.1 to about 2 µM. The hepatocyte-like cells may also be exposed to the GSK-3 inhibitor at a concentration in the range of about 0.1 to about 1.5 µM. The hepatocyte-like cells may also be exposed to the GSK-3 inhibitor at a concentration in the range of about 0.1 to about 1 µM. The hepatocyte-like cells may also be exposed to the GSK-3 inhibitor at a concentration in the range of about 0.1 to about 0.5 µM.

The hepatocyte-like cells may also be exposed to the GSK-3 inhibitor at a concentration in the range of about 0.25 to about 5 µM. The hepatocyte-like cells may also be exposed to the GSK-3 inhibitor at a concentration in the range of about 0.25 to about 2.5 µM. The hepatocyte-like cells may also be exposed to the GSK-3 inhibitor at a concentration in the range of about 0.25 to about 1.5 µM. The hepatocyte-like cells may also be exposed to the GSK-3 inhibitor at a concentration in the range of about 0.25 to about 1 µM. The hepatocyte-like cells may also be exposed to the GSK-3 inhibitor at a concentration in the range of about 0.25 to about 0.75 µM. The hepatocyte-like cells may also be exposed to the GSK-3 inhibitor at a concentration in the range of about 0.25 to about 0.5 µM. The hepatocyte-like cells may also be exposed to the GSK-3 inhibitor at a concentration in the range of about 0.5 to about 5 µM. The hepatocyte-like cells may also be exposed to the GSK-3 inhibitor at a concentration in the range of about 0.5 to about 2.5 µM. The hepatocyte-like cells may also be exposed to the GSK-3 inhibitor at a concentration in the range of about 0.5 to about 2 µM. The hepatocyte-like cells may also be exposed to the GSK-3 inhibitor at a concentration in the range of about 0.5 to about 1.5 µM. The hepatocyte-like cells may also be exposed to the GSK-3 inhibitor at a concentration in the range of about 0.5 to about 1 µM. The hepatocyte-like cells may also be exposed to the GSK-3 inhibitor at a concentration in the range of about 0.75 to about 5 µM. The hepatocyte-like cells may also be exposed to the GSK-3 inhibitor at a concentration in the range of about 0.75 to about 2.5 µM. The hepatocyte-like cells may also be exposed to the GSK-3 inhibitor at a concentration in the range of about 0.75 to about 2.0 µM. The hepatocyte-like cells may also be exposed to the GSK-3 inhibitor at a concentration in the range of about 0.75 to about 1.5 µM. The hepatocyte-like cells may also be exposed to the GSK-3 inhibitor at a concentration in the range of about 0.75 to about 1 µM. The hepatocyte-like cells may also be exposed to the GSK-3 inhibitor at a concentration in the range of about 1 to about 5 µM. The hepatocyte-like cells may also be exposed to the GSK-3 inhibitor at a concentration in the range of about 1 to about 4 µM. The hepatocyte-like cells may also be exposed to the GSK-3 inhibitor at a concentration in the range of about 1 to about 3 µM. The hepatocyte-like cells may also be exposed to the GSK-3 inhibitor at a concentration in the range of about 1 to about 2.5 µM. The hepatocyte-like cells may also be exposed to the GSK-3 inhibitor at a concentration in the range of about 1 to about 2 µM. The hepatocyte-like cells may also be exposed to the GSK-3 inhibitor at a concentration in the range of about 1 to about 1.5 µM.

In case that, for instance, Kenpaullone is employed as the GSK3-inhibitor, the hepatocyte-like cells may be exposed to it at a concentration in the range of about 0.05 to about 5 µM, such as, e.g., in the range of about 0.5 to about 1.5 µM.

The hepatocyte-like cells may be exposed to Kenpaullone at a concentration in the range of about 0.05 to about 2 µM. The hepatocyte-like cells may also be exposed to Kenpaullone at a concentration in the range of about 0.05 to about 1.5 µM. The hepatocyte-like cells may also be exposed to Kenpaullone at a concentration in the range of about 0.05 to about 1 µM. The hepatocyte-like cells may also be exposed to Kenpaullone at a concentration in the range of about 0.05 to about 0.5 µM. The hepatocyte-like cells may be exposed to Kenpaullone at a concentration in the range of about 0.1 to about 2 µM. The hepatocyte-like cells may also be exposed to Kenpaullone at a concentration in the range of about 0.1 to about 1.5 µM. The hepatocyte-like cells may also be exposed to Kenpaullone at a concentration in the range of about 0.1 to about 1 µM. The hepatocyte-like cells may also be exposed to Kenpaullone at a concentration in the range of about 0.1 to about 0.5 µM. The hepatocyte-like cells may also be exposed to Kenpaullone at a concentration in the range of about 0.25 to about 2.5 µM. The hepatocyte-like cells may also be exposed to Kenpaullone at a concentration in the range of about 0.25 to about 1.5 µM. The hepatocyte-like cells may also be exposed to Kenpaullone at a concentration in the range of about 0.25 to about 1 µM. The hepatocyte-like cells may also be exposed to Kenpaullone at a concentration in the range of about 0.25 to about 0.75 µM. The hepatocyte-like cells may also be exposed to Kenpaullone at a concentration in the range of about 0.25 to about 0.5 µM. The hepatocyte-like cells may also be exposed to Kenpaullone at a concentration in the range of about 0.5 to about 2.5 µM. The hepatocyte-like cells may also be exposed to Kenpaullone at a concentration in the range of about 0.5 to about 2 µM. The hepatocyte-like cells may also be exposed to Kenpaullone at a concentration in the range of about 0.5 to about 1.5 µM. The hepatocyte-like cells may also be exposed to Kenpaullone at a concentration in the range of about 0.5 to about 1 µM. The hepatocyte-like cells may also be exposed to Kenpaullone at a concentration in the range of about 0.75 to about 2.5 µM. The hepatocyte-like cells may also be exposed to Kenpaullone at a concentration in the range of about 0.75 to about 2.0 µM. The hepatocyte-like cells may also be exposed to Kenpaullone at a concentration in the range of about 0.75 to about 1.5 µM. The hepatocyte-like cells may also be exposed to Kenpaullone at a concentration in the range of about 0.75 to about 1 µM. The hepatocyte-like cells may also be exposed to Kenpaullone at a concentration in the range of about 1 to about 2.5 µM. The hepatocyte-like cells may also be exposed to Kenpaullone at a concentration in the range of about 1 to about 2 µM. The hepatocyte-like cells may also be exposed to Kenpaullone at a concentration in the range of about 1 to about 1.5 µM.

Similar concentrations may be used in case that, for instance, 1-Aza-Kenpaullone or Alsterpaullone is employed as the GSK-3 inhibitor according to the invention.

Besides inhibiting GSK3, the GSK-3 inhibitor used according to the invention may further exhibit inhibitory activity towards a cyclin dependent kinase (CDK), such as CDK2. Examples of such dual inhibitor are Kenpaullone, AT-7519, SNS-032 (BMS-387032) and AZD5438. Further examples of such dual inhibitor are 1-Aza-Kenpaullone, Alsterpaullone and Indirubin-3'-monoxime. Yet further examples of such dual inhibitor are 2-bromo-9-nitropaullone, 2-bromo-9-trifluoromethylpaullone, 2-bromopaullone, 2-iodo-9-trifluoromethylpaullone, 2-iodopaullone, 2-phenyl-4-(2-thienyl)-5H-pyrido[2±3-d][1]benzazepine-6(7H)-thione, 2-[2-(1-hydroxycyclohexyl)-ethinyl]-9-trifluoromethyl-paullone, 2,3-dimethoxy-9-nitropaullone, 2,3-dimethoxy-9-trifluormethylpaullone, 2,3-dimethoxypaullone, 2-(3-hydroxy-1-propinyl)-9-trifluoromethylpaullone, 2,9-dibromo-paullone, 3-(6-oxo-9-trifluoromethyl-5,6,7,12-tetrahydro-indolo[2±3-d][1]benzazepin-2-yl)-propionitrile, 4-methoxypaullone, 4-(4-chlorophenyl)-2-(2-naphthyl)-5H-pyrido[2±3-d][1]benzazepine-6(7H)-thione, 5-benzyl-9-bromopaullone, 5-iodo-indirubin.3-monoxime, 5,6,7,12-tetrahydro-benzo[6±7]cyclohept[1,2-b]indole, 6 bromo indirubin, 8,10-dichloropaullone, 9-bromo-2,3-dihydroxypaullone, 9-bromo-2,3-dimethoxypaullone, 9-bromo-4-hydroxypaullone, 9-bromo-4-methoxypaullone, 9-bromo-5-ethylpaullone, 9-bromo-5-(methyloxycarbonylmethyl)paullone, 9-bromo-5-methylpaullone, 9-bromo-5,6,7,12-tetrahydro-benzo[6±7]cyclohept[1,2-b]indole, 9-bromo-5,7-bis-(tert.-butyloxycarbonyl)-paullone, 9-bromo-5,7,12-tri-(tert.-butyloxycarbonyl)-paullone, 9-bromo-5,12-bis-(tert.-butyloxycarbonyl)-paullone, 9-bromo-7,12-dihydro-6-(hydroxyamino)-indolo[2±3-d][1]benzazepine, 9-bromo-7,12-dihydro-6-methylthio-indolo[2±3-d][1]benzazepine, 9-bromo-7,12-dihydro-indolo[2±3-d][1]benzazepine-6(5H)-thione, 9-bromo-12-(2-hydroxyethyl)-paullone, 9-bromo-12-(2-propenyl)-paullone, 9-bromo-12-ethylpaullone, 9-bromo-12-methylpaullone, 9-bromo-12-methyloxycarbonyl-methylpaullone, 9-bromo-12-(tert.-butyloxycarbonyl)-paullone, 9-chloropaullone, 9-cyanopaullone, 9-cyano-2,3-dimethoxypaullone, 9-fluoropaullone, 9-methoxypaullone, 9-methylpaullone, 9-oxo-thiazolo[5,4-f]quinazoline-2-carbonitril derivatives, 9-trifluoromethylpaullone, 10-bromopaullone, 11-bromopaullone, 11-chloropaullone, 11-ethylpaullone, 11-methylpaullone, Aloisines (=6-phenyl[5H] pyrrolo[2,3-6]pyrazines); e.g. Aloisine A, AZD1080, bis-indole indirubin, Debromohymenialdisine, Dibromocantharelline, (E)-3-(6-oxo-9-trifluoromethyl-5,6,7,12-tetrahydro-indolo[2±3-d][1]benzazepin-2-yl)-acrylic acid methyl ester, (E)-2-(3-oxo-1-butenyl)-9-trifluoromethyl-paullone, (E)-3-(6-oxo-9-trifluoromethyl-5,6,7,12-tetrahydro-indolo[2±3-d][1]benzazepin-2-yl)-acrylonitrile, Indirubin, Hymenidin, Hymenialdisine, Manzamines, e.g. Manzamine A, Meridiamins, Paullone, Pyrazolo[3,4-b]pyridine derivatives, Pryazolo[3,4-b]quinoxaline derivatives and thiazolo[5,4-f]quinazolino-9-one derivatives.

As an alternative to a GSK3 inhibitor, the hepatocyte-like cells may be exposed to an activator of Wnt signalling. The activator of Wnt signalling employed in the methods of the present invention, may be any compound activating Wnt signalling.

Suitable activators of Wnt signalling for use in the present invention are Wnt proteins, such as, e.g., Wnt1, Wnt2, Wnt2B/13, Wnt3A, Wnt3, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16, which may be recombinant in nature.

The activator of Wnt signalling may thus be selected from the above group of Wnt proteins. The activator of Wnt signalling may, for instance, be Wnt3A. The activator of Wnt signalling may also be Wnt5A.

The hepatocyte-like cells may generally be exposed to the activator of Wnt signalling at a concentration in the range of about 0.05 to about 10 ng/ml.

Thus, the hepatocyte-like cells may be exposed to the activator of Wnt signalling at a concentration in the range of about 0.05 to about 5 ng/ml. The hepatocyte-like cells may also be exposed to the activator of Wnt signalling at a concentration in the range of about 0.1 to about 5 ng/ml. The hepatocyte-like cells may also be exposed to the activator of Wnt signalling at a concentration in the range of about 0.5 to about 5 ng/ml. The hepatocyte-like cells may also be exposed to the activator of Wnt signalling at a concentration in the range of about 1 to about 5 ng/ml. The hepatocyte-like cells may also be exposed to the activator of Wnt signalling at a concentration in the range of about 2 to about 5 ng/ml. The hepatocyte-like cells may also be exposed to the activator of Wnt signalling at a concentration in the range of about 0.1 to about 2.5 ng/ml. The hepatocyte-like cells may also be exposed to the activator of Wnt signalling at a concentration in the range of about 0.1 to about 2 ng/ml. The hepatocyte-like cells may also be exposed to the activator of Wnt signalling at a concentration in the range of about 0.5 to about 2.5 ng/ml. The hepatocyte-like cells may also be exposed to the activator of Wnt signalling at a concentration in the range of about 0.5 to about 2 ng/ml. The hepatocyte-like cells may also be exposed to the activator of Wnt signalling at a concentration in the range of about 0.5 to about 1.5 ng/ml. The hepatocyte-like cells may also be exposed to the activator of Wnt signalling at a concentration in the range of about 1 to about 2.5 ng/ml.

In case that, for instance, Wnt3A is employed as the activator of Wnt signalling, the hepatocyte-like cells may be exposed to it at a concentration in the range of about 0, 05 to about 10 ng/ml, such as, e.g., in the range of about 0.5 to about 2.5 µM.

Thus, the hepatocyte-like cells may be exposed to Wnt3A at a concentration in the range of about 0.05 to about 5 ng/ml. The hepatocyte-like cells may also be exposed to Wnt3A at a concentration in the range of about 0.1 to about 5 ng/ml. The hepatocyte-like cells may also be exposed to Wnt3A at a concentration in the range of about 0.5 to about 5 ng/ml. The hepatocyte-like cells may also be exposed to Wnt3A at a concentration in the range of about 1 to about 5 ng/ml. The hepatocyte-like cells may also be exposed Wnt3A at a concentration in the range of about 2 to about 5 ng/ml. The hepatocyte-like cells may also be exposed to Wnt3A at a concentration in the range of about 0.1 to about 2.5 ng/ml. The hepatocyte-like cells may also be exposed to Wnt3A at a concentration in the range of about 0.1 to about 2 ng/ml. The hepatocyte-like cells may also be exposed to Wnt3A at a concentration in the range of about 0.5 to about 2.5 ng/ml. The hepatocyte-like cells may also be exposed to Wnt3A at a concentration in the range of about 0.5 to about 2 ng/ml. The hepatocyte-like cells may also be exposed to Wnt3A at a concentration in the range of about 0.5 to about 1.5 ng/ml. The hepatocyte-like cells may also be exposed to Wnt3A at a concentration in the range of about 1 to about 2.5 ng/ml.

The hepatocyte-like cells may not only be exposed to one activator of Wnt signalling, but may also be exposure to one or more further activators of Wnt signalling, such as to a combination of two, three or four of those mentioned above.

In addition to being exposed to the activator of a retinoic acid responsive receptor, the hepatocyte-like cells may optionally also be exposed to a CDK inhibitor and/or to an overlay of one or more components characteristic of the mammalian extracellular matrix (matrix overlay). Thus, the exposure to the activator of a retinoic acid responsive receptor is combined with the exposure to a CDK inhibitor or with the exposure to a matrix overlay, or both. The additional exposure of the differentiating hepatic progenitor cells to a CDK inhibitor and/or to a matrix overlay has shown to further improve the mature and functional features for the hepatocyte-like cells (FIG. 4).

The CDK inhibitor employed in the methods of the invention may be any compound capable of inhibiting the function (e.g., the activity) of a cyclin dependent kinase (CDK). The CDK inhibitor employed in the methods of the invention may, for instance, be an inhibitor of one or more of CDK1, CDK2, CDK4, CDK5, CDK6, CDK7, and CDK9. The CDK inhibitor employed in the methods of the invention may be an inhibitor of cyclin dependent kinase 2 (CDK2). The CDK inhibitor employed in the methods of the invention may, for instance, be an inhibitor of CDK1 and CDK2. The CDK inhibitor employed in the methods of the invention may, for instance, be an inhibitor of CDK2 and CDK5. The CDK inhibitor employed in the methods of the invention may, for instance, be an inhibitor of CDK1, CDK2 and CDK5.

Suitable CDK inhibitors for use in the invention are 9-Bromo-7,12-dihydro-indolo[3,2-d]-[1]benzazepin-6(5H)-one, also known as Kenpaullone or NSC 664704; (R)-2-(6-(benzylamino)-9-isopropyl-9H-purin-2-ylamino)butan-1-ol also known as Roscovitine; 2-(2-chlorophenyl)-5,7-dihydroxy-8-((3S,4R)-3-hydroxy-1-methylpiperidin-4-yl)-4H-chromen-4-one also known as Flavopiridol; 4-(2,6-dichlorobenzamido)-N-(piperidin-4-yl)-1H-pyrazole-3-carboxamide also known as AT-7519; 6-acetyl-8-cyclopentyl-5-methyl-2-(5-(piperazin-1-yl)pyridin-2-ylamino)pyrido[2,3-d]pyrimidin-7(8H)-one hydrochloride also known as PD 0332991 HCl; N-(5-((5-tert-butyloxazol-2-yl)methylthio) thiazol-2-yl)piperidine-4-carboxamide also known as SNS-032 (BMS-387032); JNJ-7706621; N-(6,6-dimethyl-5-(1-methylpiperidine-4-carbonyl)-1,4,5,6-tetrahydropyrrolo[3,4-c]pyrazol-3-yl)-3-methylbutanamide also known as PHA-793887; Dinaciclib (SCH727965); (4-butoxy-1H-pyrazolo[3,4-b]pyridin-5-yl)(2,6-difluoro-4-methylphenyl)methanone also known as BMS-265246; N,1,4,4-tetramethyl-8-(4-(4-methylpiperazin-1-yl)phenylamino)-4,5-dihydro-1H-pyrazolo[4,3-h]quinazoline-3-carboxamide also known as PHA-848125; 2-(pyridin-4-yl)-6,7-dihydro-1H-pyrrolo[3,2-c]pyridin-4(5H)-one also known as PHA-767491; SCH 900776; 2-(2-chlorophenyl)-5,7-dihydroxy-8-((3S,4R)-3-hydroxy-1-methylpiperidin-4-yl)-4H-chromen-4-one hydrochloride also known as Flavopiridol HCl; (4-amino-2-(1-(methylsulfonyl)piperidin-4-ylamino)pyrimidin-5-yl) (2,3-difluoro-6-methoxyphenyl)methanone also known as R547; (2S)-1-(5-(3-methyl-1H-indazol-5-yl)pyridin-3-yloxy)-3-phenylpropan-2-amine also known as A-674563; 4-(1-isopropyl-2-methyl-1H-imidazol-5-yl)-N-(4-(methylsulfonyl)phenyl)pyrimidin-2-amine also known as AZD5438; N5-(6-aminohexyl)-N7-benzyl-3-isopropylpyrazolo[1,5-a]pyrimidine-5,7-diamine hydrochloride also known as BS-181 HCl; CY-202; AG-024322; P276-00; ZK 304709; GPC-286199; and BAY 80-3000. The CDK inhibitor may be selected from the above group.

Other suitable CDK inhibitors which may be employed in the methods of the invention are 2-hydroxybohemine, A674563, Aminopurvanolol, BAY1000394, BMS-265246, BS-181 Butyrolactone I, CR8 S-isomer, Diaciclib (SCH727965), JNJ-7706621, N9-isopropyl-olomoucine, NU6140, NU6102, Olomoucine II, Oxindole I, P276-00, PD332991, PHA-793887, PHA-767491, PHA-848125, PNU112455A, Purvanolol A and B, R547, (R)-DRF053 and SCH900776 (MK-8776). The CDK inhibitor may be selected from the above group.

The CDK inhibitor employed in the methods of the invention may, for instance, be Kenpaullone. Kenpaullone is known to be an inhibitor of CDK2. The CDK inhibitor may also be Roscovitine. The CDK inhibitor may also be Flavopiridol. The CDK inhibitor may also be AT-7519. The CDK inhibitor may also be PD 0332991 HCl. The CDK inhibitor may also be SNS-032 (BMS-387032). The CDK inhibitor may also be JNJ-7706621. The CDK inhibitor may also be PHA-793887. The CDK inhibitor may also be Dinaciclib (SCH727965). The CDK inhibitor may also be BMS-265246. The CDK inhibitor may also be PHA-848125. The CDK inhibitor may also be PHA-767491. The CDK inhibitor may also be SCH 900776. The CDK inhibitor may also be Flavopiridol HCl. The CDK inhibitor may also be R547. The CDK inhibitor may also be A-674563. The CDK inhibitor may also be AZD5438. The CDK inhibitor may also be BS-181 HCl. The CDK inhibitor may also be CY-202. The CDK inhibitor may also be AG-024322. The CDK inhibitor may also be P276-00. The CDK inhibitor may also be ZK 304709. The CDK inhibitor may also be GPC-286199. The CDK inhibitor may also be BAY 80-3000.

The CDK inhibitor may be selected from the group consisting of: Kenpaullone, SNS-032(BMS-387032), AT-7519 and AZD5438.

The CDK inhibitor may be selected from the group consisting of: Kenpaullone, 1-Aza-Kenpaullone, Indirubin-3'-monoxime, Alsterpaullone, SNS-032(BMS-387032), AT-7519 and AZD5438.

The hepatocyte-like cells may not only be exposed to one CDK inhibitor, but may also be exposure to one or more further CDK inhibitors, such as to a combination of two, three or four of those mentioned above.

The hepatocyte-like cells may generally be exposed to the CDK inhibitor at a concentration in the range of about 0.01 to about 10 μM.

Thus, the hepatocyte-like cells may be exposed to the CDK inhibitor at a concentration in the range of about 0.05 to about 5 μM. The hepatocyte-like cells may thus be exposed to the CDK inhibitor at a concentration in the range of about 0.05 to about 2.5 μM. The hepatocyte-like cells may also be exposed to the CDK inhibitor at a concentration in the range of about 0.05 to about 2 μM. The hepatocyte-like cells may also be exposed to the CDK inhibitor at a concentration in the range of about 0.05 to about 1.5 μM. The hepatocyte-like cells may also be exposed to the CDK inhibitor at a concentration in the range of about 0.05 to about 1 μM. The hepatocyte-like cells may also be exposed to the CDK inhibitor at a concentration in the range of about 0.05 to about 0.5 μM. The hepatocyte-like cells may be exposed to the CDK inhibitor at a concentration in the range of about 0.1 to about 5 μM. The hepatocyte-like cells may thus be exposed to the CDK inhibitor at a concentration in the range of about 0.1 to about 2.5 µM. The hepatocyte-like cells may also be exposed to the CDK inhibitor at a concentration in the range of about 0.1 to about 2 µM. The hepatocyte-like cells may also be exposed to the CDK inhibitor at a concentration in the range of about 0.1 to about 1.5 µM. The hepatocyte-like cells may also be exposed to the CDK inhibitor at a concentration in the range of about 0.1 to about 1 µM. The hepatocyte-like cells may also be exposed to the CDK inhibitor at a concentration in the range of about 0.1 to about 0.5 µM.

The hepatocyte-like cells may also be exposed to the CDK inhibitor at a concentration in the range of about 0.25 to about 5 µM. The hepatocyte-like cells may also be exposed to the CDK inhibitor at a concentration in the range of about 0.25 to about 2.5 µM. The hepatocyte-like cells may also be exposed to the CDK inhibitor at a concentration in the range of about 0.25 to about 1.5 µM. The hepatocyte-like cells may also be exposed to the CDK inhibitor at a concentration in the range of about 0.25 to about 1 µM. The hepatocyte-like cells may also be exposed to the CDK inhibitor at a concentration in the range of about 0.25 to about 0.75 µM. The hepatocyte-like cells may also be exposed to the CDK inhibitor at a concentration in the range of about 0.25 to about 0.5 µM. The hepatocyte-like cells may also be exposed to the CDK inhibitor at a concentration in the range of about 0.5 to about 5 µM. The hepatocyte-like cells may also be exposed to the CDK inhibitor at a concentration in the range of about 0.5 to about 2.5 µM. The hepatocyte-like cells may also be exposed to the CDK inhibitor at a concentration in the range of about 0.5 to about 2 µM. The hepatocyte-like cells may also be exposed to the CDK inhibitor at a concentration in the range of about 0.5 to about 1.5 µM. The hepatocyte-like cells may also be exposed to the CDK inhibitor at a concentration in the range of about 0.5 to about 1 µM. The hepatocyte-like cells may also be exposed to the CDK inhibitor at a concentration in the range of about 0.75 to about 5 µM. The hepatocyte-like cells may also be exposed to the CDK inhibitor at a concentration in the range of about 0.75 to about 2.5 µM. The hepatocyte-like cells may also be exposed to the CDK inhibitor at a concentration in the range of about 0.75 to about 2.0 µM. The hepatocyte-like cells may also be exposed to the CDK inhibitor at a concentration in the range of about 0.75 to about 1.5 µM. The hepatocyte-like cells may also be exposed to the CDK inhibitor at a concentration in the range of about 0.75 to about 1 µM. The hepatocyte-like cells may also be exposed to the CDK inhibitor at a concentration in the range of about 1 to about 5 µM. The hepatocyte-like cells may also be exposed to the CDK inhibitor at a concentration in the range of about 1 to about 4 µM. The hepatocyte-like cells may also be exposed to the CDK inhibitor at a concentration in the range of about 1 to about 3 µM. The hepatocyte-like cells may also be exposed to the CDK inhibitor at a concentration in the range of about 1 to about 2.5 µM. The hepatocyte-like cells may also be exposed to the CDK inhibitor at a concentration in the range of about 1 to about 2 µM. The hepatocyte-like cells may also be exposed to the CDK inhibitor at a concentration in the range of about 1 to about 1.5 µM.

In case that, for instance, Kenpaullone is employed as the CDK inhibitor, the hepatocyte-like cells may be exposed to it at a concentration in the range of about 0.05 to about 5 µM, such as, e.g., in the range of about 0.5 to about 1.5 µM.

The hepatocyte-like cells may be exposed to Kenpaullone at a concentration in the range of about 0.05 to about 2 µM. The hepatocyte-like cells may also be exposed to Kenpaullone at a concentration in the range of about 0.05 to about 1.5 µM. The hepatocyte-like cells may also be exposed to Kenpaullone at a concentration in the range of about 0.05 to about 1 µM. The hepatocyte-like cells may also be exposed to Kenpaullone at a concentration in the range of about 0.05 to about 0.5 µM. The hepatocyte-like cells may be exposed to Kenpaullone at a concentration in the range of about 0.1 to about 2 µM. The hepatocyte-like cells may also be exposed to Kenpaullone at a concentration in the range of about 0.1 to about 1.5 µM. The hepatocyte-like cells may also be exposed to Kenpaullone at a concentration in the range of about 0.1 to about 1 µM. The hepatocyte-like cells may also be exposed to Kenpaullone at a concentration in the range of about 0.1 to about 0.5 µM. The hepatocyte-like cells may also be exposed to Kenpaullone at a concentration in the range of about 0.25 to about 2.5 µM. The hepatocyte-like cells may also be exposed to Kenpaullone at a concentration in the range of about 0.25 to about 1.5 µM. The hepatocyte-like cells may also be exposed to Kenpaullone at a concentration in the range of about 0.25 to about 1 µM. The hepatocyte-like cells may also be exposed to Kenpaullone at a concentration in the range of about 0.25 to about 0.75 µM. The hepatocyte-like cells may also be exposed to Kenpaullone at a concentration in the range of about 0.25 to about 0.5 µM. The hepatocyte-like cells may also be exposed to Kenpaullone at a concentration in the range of about 0.5 to about 2.5 µM. The hepatocyte-like cells may also be exposed to Kenpaullone at a concentration in the range of about 0.5 to about 2 µM. The hepatocyte-like cells may also be exposed to Kenpaullone at a concentration in the range of about 0.5 to about 1.5 µM. The hepatocyte-like cells may also be exposed to Kenpaullone at a concentration in the range of about 0.5 to about 1 µM. The hepatocyte-like cells may also be exposed to Kenpaullone at a concentration in the range of about 0.75 to about 2.5 µM. The hepatocyte-like cells may also be exposed to Kenpaullone at a concentration in the range of about 0.75 to about 2.0 µM. The hepatocyte-like cells may also be exposed to Kenpaullone at a concentration in the range of about 0.75 to about 1.5 µM. The hepatocyte-like cells may also be exposed to Kenpaullone at a concentration in the range of about 0.75 to about 1 µM. The hepatocyte-like cells may also be exposed to Kenpaullone at a concentration in the range of about 1 to about 2.5 µM. The hepatocyte-like cells may also be exposed to Kenpaullone at a concentration in the range of about 1 to about 2 µM. The hepatocyte-like cells may also be exposed to Kenpaullone at a concentration in the range of about 1 to about 1.5 µM.

Besides inhibiting CDK, the CDK inhibitor used according to the invention may further exhibit inhibitory activity towards Glycogen synthase kinase 3 (GSK-3), especially GSK-3 beta. Examples of such dual inhibitor are Kenpaullone, SNS-032 (BMS-387032), AT-7519 and AZD5438 which inhibit both CDK2 and GSK3. Further examples of such dual inhibitor are 1-Aza-Kenpaullone, Alsterpaullone and Indirubin-3'-monoxime. Further examples of such dual inhibitor are 1-Aza-Kenpaullone, Alsterpaullone and Indirubin-3'-monoxime. Yet further examples of such dual inhibitor are 2-bromo-9-nitropaullone, 2-bromo-9-trifluoromethylpaullone, 2-bromopaullone, 2-iodo-9-trifluoromethylpaullone, 2-iodopaullone, 2-phenyl-4-(2-thienyl)-5H-pyrido[2±3-d][1]benzazepine-6(7H)-thione, 2-[2-(1-hydroxycyclohexyl)-ethinyl]-9-trifluoromethyl-paullone, 2,3-dimethoxy-9-nitropaullone, 2,3-dimethoxy-9-trifluormethylpaullone, 2,3-dimethoxypaullone, 2-(3-hydroxy-1-propinyl)-9-trifluoromethylpaullone, 2,9-dibromo-paullone, 3-(6-oxo-9-trifluoromethyl-5,6,7,12-tetrahydro-indolo[2±3-d][1]benzazepin-2-yl)-propionitrile, 4-methoxypaullone, 4-(4- chlorophenyl)-2-(2-naphthyl)-5H-pyrido[2±3-d][1]benzazepine-6(7H)-thione, 5-benzyl-9-bromopaullone, 5-iodoindirubin.3-monoxime, 5,6,7,12-tetrahydro-benzo[6±7]cyclohept[1,2-b]indole, 6 bromo indirubin, 8,10-dichloropaullone, 9-bromo-2,3-dihydroxypaullone, 9-bromo-2,3-dimethoxypaullone, 9-bromo-4-hydroxypaullone, 9-bromo-4-methoxypaullone, 9-bromo-5-ethylpaullone, 9-bromo-5-(methyloxycarbonylmethyl)paullone, 9-bromo-5-methylpaullone, 9-bromo-5,6,7,12-tetrahydro-benzo[6±7]cyclohept[1,2-b]indole, 9-bromo-5,7-bis-(tert.-butyloxycarbonyl)-paullone, 9-bromo-5,7,12-tri-(tert.-butyloxycarbonyl)-paullone, 9-bromo-5,12-bis-(tert.-butyloxycarbonyl)-paullone, 9-bromo-7,12-dihydro-6-(hydroxyamino)-indolo[2±3-d][1]benzazepine, 9-bromo-7,12-dihydro-6-methylthio-indolo[2±3-d][1]benzazepine, 9-bromo-7,12-dihydro-indolo[2±3-d][1]benzazepine-6(5H)-thione, 9-bromo-12-(2-hydroxyethyl)-paullone, 9-bromo-12-(2-propenyl)-paullone, 9-bromo-12-ethylpaullone, 9-bromo-12-methylpaullone, 9-bromo-12-methyloxycarbonyl-methylpaullone, 9-bromo-12-(tert.-butyloxycarbonyl)-paullone, 9-chloropaullone, 9-cyanopaullone, 9-cyano-2,3-dimethoxypaullone, 9-fluoropaullone, 9-methoxypaullone, 9-methylpaullone, 9-oxothiazolo[5,4-f]quinazoline-2-carbonitril derivatives, 9-trifluoromethylpaullone, 10-bromopaullone, 11-bromopaullone, 11-chloropaullone, 11-ethyl paullone, 11-methylpaullone, Aloisines (=6-phenyl[5H]pyrrolo[2,3-6]pyrazines); e.g. Aloisine A, AZD1080, bis-indole indirubin, Debromohymenialdisine, Dibromocantharelline, (E)-3-(6-oxo-9-trifluoromethyl-5,6,7,12-tetrahydro-indolo[2±3-d][1]benzazepin-2-yl)-acrylic acid methyl ester, (E)-2-(3-oxo-1-butenyl)-9-trifluoromethylpaullone, (E)-3-(6-oxo-9-trifluoromethyl-5,6,7,12-tetrahydro-indolo[2±3-d][1]benzazepin-2-ylyacrylonitrile, Indirubin, Hymenidin, Hymenialdisine, Manzamines, e.g. Manzamine A, Meridiamins, Paullone, Pyrazolo[3,4-b]pyridine derivatives, Pryazolo[3,4-b]quinoxaline derivatives and thiazolo[5,4-f]quinazolino-9-one derivatives.

It is also contemplated by the present invention that the hepatocyte-like cells being expose to a GSK3 inhibitor or activator of Wnt signalling are further exposed to a CDK inhibitor. This is particularly of interest if the GSK inhibitor employed does not exhibit inhibitory activity towards a cyclin dependent kinase (CDK), Likewise, is contemplated by the present invention that the hepatocyte-like cells being expose to a CDK inhibitor are further exposed to a GSK3 inhibitor or activator of Wnt signalling. This is particularly of interest if the CDK inhibitor employed does not exhibit inhibitory activity towards Glycogen synthase kinase 3 (GSK-3), Accordingly, the present invention further provides a method for promoting the maturation of human hepatocyte-like cells whereby said hepatocyte-like cells are exposed to an activator of a retinoic acid responsive receptor, such as retinoic acid, optionally in combination with exposure to an inhibitor of GSK3 signalling or activator of Wnt signalling and a CDK inhibitor, further optionally in combination with an overlay of the cells with one or more components characteristic of the mammalian extracellular matrix (matrix overlay).

The method for promoting the maturation of human hepatocyte-like cells may thus be described as comprising the step:

Exposing said human hepatocyte-like cells to an activator of a retinoic acid responsive receptor, optionally in combination with exposure to a CDK inhibitor and a GSK3 inhibitor or activator of Wnt signalling, further optionally in combination with exposure to an overlay of the cells with one or more components characteristic of the mammalian extracellular matrix (matrix overlay).

Moreover, the present invention further provides a method for producing human hepatocyte-like cells whereby human hepatic progenitor cells are cultured under differentiation conditions to obtain hepatocyte-like cells, and the obtained hepatocyte-like cells are exposed to an activator of a retinoic acid responsive receptor, such as retinoic acid, optionally in combination with exposure to an inhibitor of GSK3 signalling or activator of Wnt signalling and a CDK inhibitor, further optionally in combination with an overlay of the cells with one or more components characteristic of the mammalian extracellular matrix (matrix overlay).

The method for producing human hepatocyte-like cells may thus be described as comprising the following steps:

Culturing human hepatic progenitor cells under differentiation conditions to obtain hepatocyte-like cells, and Exposing said hepatocyte-like cells to an activator of a retinoic acid responsive receptor, optionally in combination with exposure to a CDK inhibitor and a GSK3 inhibitor or activator of Wnt signalling, further optionally in combination with exposure to an overlay of the cells with one or more components characteristic of the mammalian extracellular matrix (matrix overlay).

By way of example, if hepatocyte-like cells are to be exposed to an activator of a retinoic acid responsive receptor in combination with a GSK3 inhibitor and a CDK inhibitor, the GSK3 inhibitor may be CHIR99021 and the CDK inhibitor may be Roscovitine or Flavopiridol. However, it is understood that any other GSK3 inhibitor or CDK inhibitor, especially of those specifically mentioned herein, may be employed instead.

Matrix overlays consisting of Collagen I or Matrigel (a basement membrane mix extracted from the Engelbreth-Holm-Swarm mouse sarcoma) have been used for culturing primary hepatocytes for several decades (e.g. Dunn et al. 1991; Page et al. 2007), since it was found that primary hepatocytes maintain a better functionality and live longer in a so called sandwich configuration, with one extracellular matrix (ECM) layer below the cells and one ECM layer on top of the cells. Classically, Collagen I and Matrigel overlays are thick, containing e.g. 125 µg Matrigel/cm$^2$ or 50 µg Collagen I/cm$^2$. However, this is not reflecting the physiological composition or thickness of the liver ECM (compare e.g. Turner et al. 2011; Wang et al. 2011).

The matrix overlay employed in the methods of the invention is a novel, more physiological combination of component present in the ECM of the adult liver and comprises, or is composed of, one or more ECM components, which form part of the normal mammalian extracellular matrix environment. Suitable ECM components for use as matrix overlay in the present invention are collagen, such as collagen I, II, III, IV, V or VI, fibronectin, elastin, chondroitin sulfate proteoglycan, dermatan sulfate proteoglycan, heparin proteoglycan, heparan sulfate proteoglycan, such as glypicans, syndecans or perlecans, glycosaminoglycans, nidogen/entactin, laminins, biglycan, tenascin, hyaluronans, or other ECM components, or ECM component mixtures comprising, or consisting of, e.g., collagens, laminin, fibronectin, tenascin, proteoglycans, and glycosaminoglycans.

Accordingly, the hepatocyte-like cells may be exposed to a matrix overlay comprising, or composed of, one or more, such as two, three, four, five, six, seven, eight, nine or ten, or up to 20 of the above mentioned ECM components. Thus, the hepatocyte-like cells may be exposed to a matrix overlay comprising, or composed of, two of the above mentioned ECM components. The hepatocyte-like cells may also be exposed to a matrix overlay comprising, or composed of, three of the above mentioned ECM components. The hepatocyte-like cells may also be exposed to a matrix overlay comprising, or composed of, four of the above mentioned ECM components. The hepatocyte-like cells may also be exposed to a matrix overlay comprising, or composed of, five of the above mentioned ECM components. The hepatocyte-like cells may also be exposed to a matrix overlay comprising, or composed of, six of the above mentioned ECM components. The hepatocyte-like cells may also be exposed to a matrix overlay comprising, or composed of, seven of the above mentioned ECM components. The hepatocyte-like cells may also be exposed to a matrix overlay comprising, or composed of, eight of the above mentioned ECM components. The hepatocyte-like cells may also be exposed to a matrix overlay comprising, or composed of, nine of the above mentioned ECM components. The hepatocyte-like cells may also be exposed to a matrix overlay comprising, or composed of, ten of the above mentioned ECM components.

For example, the hepatocyte-like cells may be exposed to a matrix overlay comprising, or composed of, collagen and fibronectin (collagen-fibronectin-matrix overlay), such as a matrix overlay comprising, or composed of, collagen I and fibronectin (collagen I-fibronectin-matrix overlay). The hepatocyte-like cells may also be exposed to a matrix overlay comprising, or composed of, collagen, such as collagen I, and laminin (collagen-laminin-matrix overlay). The hepatocyte-like may also be exposed to a matrix overlay comprising, or composed of, collagen, such as collagen I, nidogen and laminin (collagen-nidogen-laminin-matrix overlay). The hepatocyte-like cells may also be exposed to a matrix overlay comprising, or composed of, collagen, such as collagen I, fibronectin and laminin (collagen-fibronectin-laminin-matrix overlay). The hepatocyte-like cells may also be exposed to a matrix overlay comprising, or composed of, fibronectin and laminin (fibronectin-laminin-matrix overlay). The hepatocyte-like cells may also be exposed to a matrix overlay comprising, or composed of, Fibronectin, nidogen and laminin (Fibronectin-nidogen-laminin-matrix overlay).

The hepatocyte-like cells may also be exposed to a matrix overlay comprising, or composed of, fibronectin, collagen I, collagen IV, collagen VI, nidogen, biglycan and laminin (fibronectin-collagen I, IV, VI-Nidogen-biglycan-laminin-matrix overlay).

The hepatocyte-like cells may also be exposed to a matrix overlay comprising, or composed of, fibronectin, collagen I, collagen IV, nidogen, biglycan and laminin (fibronectin-collagen I, IV-nidogen-biglycan-laminin-matrix overlay).

The hepatocyte-like cells may also be exposed to a matrix overlay comprising collagen, such as collagen I, laminin, fibronectin, proteoglycans and glycosaminoglycans (collagen, laminin, fibronectin, proteoglycans and glycosaminoglycans matrix overlay). The hepatocyte-like cells may also be exposed to a matrix overlay comprising collagen, such as collagen I, laminin, fibronectin, and proteoglycans (collagen, laminin, fibronectin, and proteoglycans matrix overlay).

The hepatocyte-like cells may also be exposed to a matrix overlay comprising collagen, such as collagen I, laminin, fibronectin, tenascin, elastin, proteoglycans and glycosaminoglycans (collagen, laminin, fibronectin, tenascin, elastin, proteoglycans and glycosaminoglycans matrix overlay).

The matrix overlay employed in the methods of the invention is thin compared to the thick matrices so far used. The thickness of the matrix overlay thereby correlates with the concentration of the ECM components employed. Suitable concentrations for the present matrix overlay are e.g. 0.01-30 µg, such as 0.01-20 µg, ECM component/cm$^2$.

Thus, each ECM component may be present in the matrix overlay at a concentration from about 0.1 to about 20 µg ECM component/cm$^2$. Each ECM component may also be present in the matrix overlay at a concentration from about 0.1 to about 15 µg ECM component/cm$^2$. Each ECM component may also be present in the matrix overlay at a concentration from about 0.1 to about 12.5 µg protein component/cm$^2$. Each ECM component may also be present in the matrix overlay at a concentration from about 0.1 to about 10 µg ECM component/cm$^2$. Each ECM component may also be present in the matrix overlay at a concentration from about 0.1 to about 5 µg ECM component/cm$^2$. Each ECM component may also be present in the matrix overlay at a concentration from about 0.1 to about 2.5 µg ECM component/cm$^2$. Each ECM component may also be present in the matrix overlay at a concentration from about 0.2 to about 20 µg ECM component/cm$^2$. Each ECM component may also be present in the matrix overlay at a concentration from about 0.2 to about 15 µg ECM component/cm$^2$. Each ECM component may also be present in the matrix overlay at a concentration from about 0.2 to about 12.5 µg ECM component/cm$^2$. Each ECM component may also be present in the matrix overlay at a concentration from about 0.2 to about 10 µg ECM component/cm$^2$. Each ECM component may also be present in the matrix overlay at a concentration from about 0.2 to about 5 µg ECM component/cm$^2$. Each ECM component may also be present in the matrix overlay at a concentration from about 0.5 to about 25 µg ECM component/cm$^2$. Each ECM component may also be present in the matrix overlay at a concentration from about 0.5 to about 20 µg ECM component/cm$^2$. Each protein component may also be present in the matrix overlay at a concentration from about 0.5 to about 15 µg protein component/cm$^2$. Each protein component may also be present in the matrix overlay at a concentration from about 0.5 to about 10 µg protein component/cm$^2$. Each protein component may also be present in the matrix overlay at a concentration from about 0.5 to about 7.5 µg protein component/cm$^2$. Each protein component may also be present in the matrix overlay at a concentration from about 0.5 to about 5 µg protein component/cm$^2$. Each protein component may also be present in the matrix overlay at a concentration from about 0.5 to about 2.5 µg protein component/cm$^2$. Each protein component may also be present in the matrix overlay at a concentration from about 0.5 to about 1.5 µg protein component/cm$^2$. Each protein component may also be present in the matrix overlay at a concentration from about 0.5 to about 1 µg protein component/15 cm$^2$. Each ECM component may be present in the matrix overlay at a concentration from about 1 to about 20 µg ECM component/cm$^2$. Each ECM component may also be present in the matrix overlay at a concentration from about 1 to about 15 µg ECM component/cm$^2$. Each ECM component may also be present in the matrix overlay at a concentration from about 1 to about 12.5 µg protein component/cm$^2$. Each ECM component may also be present in the matrix overlay at a concentration from about 1 to about 10 µg ECM component/cm$^2$. Each ECM component may also be present in the matrix overlay at a concentration from about 1 to about 5 µg ECM component/cm$^2$. Each ECM component may also be present in the matrix overlay at a concentration from about 1 to about 2.5 µg ECM component/cm². Each ECM component may also be present in the matrix overlay at a concentration from about 2 to about 20 µg ECM component/cm². Each ECM component may also be present in the matrix overlay at a concentration from about 2 to about 15 µg ECM component/cm². Each ECM component may also be present in the matrix overlay at a concentration from about 2 to about 12.5 µg ECM component/cm². Each ECM component may also be present in the matrix overlay at a concentration from about 2 to about 10 µg ECM component/cm². Each ECM component may also be present in the matrix overlay at a concentration from about 2 to about 5 µg ECM component/cm². Each ECM component may also be present in the matrix overlay at a concentration from about 5 to about 25 µg ECM component/cm². Each ECM component may also be present in the matrix overlay at a concentration from about 5 to about 20 µg ECM component/cm². Each protein component may also be present in the matrix overlay at a concentration from about 5 to about 15 µg protein component/cm². Each protein component may also be present in the matrix overlay at a concentration from about 5 to about 10 µg protein component/cm². Each protein component may also be present in the matrix overlay at a concentration from about 5 to about 7.5 µg protein component/cm².

Collagen I may, for example, be present in the matrix overlay at a concentration from about 2 to about 20 µg/cm², such as from about 5 to about 15 µg/cm².

Collagen IV may, for example, be present in the matrix overlay at a concentration from about 0.01 to 10 µg/cm², such as from about 0.05 to about 10 µg/cm².

Collagen VI may, for example, be present in the matrix overlay at a concentration form about 0.01 to about 15 µg/cm², such as from about 0.01 to about 10 µg/cm² or from about 0.1 to about 15 µg/cm².

Fibronectin may, for example, be present in the matrix overlay at a concentration from about 2 to about 30 µg/cm², such as from about 2 to about 20 µg/cm².

Nidogen may, for example, be present in the matrix overlay at a concentration from about 0.01 to about 10 µg/cm², such as from about 0.05 to about 10 µg/cm².

Laminin may, for example, be present in the matrix overlay at a concentration from about 0.01 to about 10 µg/cm², such as from about 0.05 to about 10 µg/cm².

Biglycan may, for example, be present in the matrix overlay at a concentration from about 0.01 to about 10 µg/cm², such as from about 0.1 to about 10 µg/cm².

It is to be understood that the above concentrations in "µg/cm²" are with respect to the respective component in its dry state.

Generally, cells may be cultured on a coating as growth support which covers the surface of the culture vessel. Gelatine or fibronectin based coating are widely used as growth support. Thus, the cells, in particular the hepatic progenitor cells and hepatocyte-like cells, may be cultured on a gelatin or fibronectin based coating. However, the cells may also be cultured on a coating which has a composition similar or identical to a matrix overlay as defined above. For example, when a matrix overlay is to be employed, the cells may be cultured on a coating which has a composition which is identical to that of the employed matrix overlay. Accordingly, a so-called "sandwich" type culture environment is provided.

As an optional pre-step, the hepatic progenitor cells used in the methods of the invention may initially be derived from human pluripotent stem (hPS) cells, such as human embryonic stem (hES) cells or human induced pluripotent stem cells (hiPS). The methods of the invention may thus further comprise as an initial step the culturing of hPS cells under differentiation conditions to obtain said hepatic progenitor cells. Thus, hPS cells are initially differentiated into said hepatic progenitor cells. This step is referred to herein as initial hepatic differentiation.

As indicated above, the human pluripotent stem cells which may also be used as starting material to obtain the endodermal and/or hepatic progenitor cells may be human embryonic stem cells. Various techniques for obtaining such hES cells are known to the skilled person. Preferably, however, the hES cells for use according to the invention are ones which have been derived (or obtained) without destruction of the human embryo, such as by employing the single blastomere removal technique described in e.g. Chung et al (2008), further described by Mercader et al. in Essential Stem Cell Methods (First Edition, 2009). Suitable hES cell lines for use are, for example, the cell lines SA167, SA181, SA461 (Cellartis AB, Göteborg, Sweden) which are listed in the NIH stem cell registry, the UK Stem Cell bank and the European hESC registry and are available on request. Other suitable cell lines for use are those established by Klimanskaya et al. (2006), such as cell lines MA01 and MA09, and Chung et al. (2008), such as cell lines MA126, MA127, MA128 and MA129, which all are listed with the International Stem Cell Registry (assigned to Advanced Cell Technology, Inc. Worcester, Mass., USA).

Alternatively, the human pluripotent stem cells which may be used as starting material to obtain the endodermal and/or hepatic progenitor cells may be human induced pluripotent stem cells. Various techniques for obtaining such hiPS cells have been described in the scientific literature, and are thus known to the skilled person [see, e.g., Takahashi et al. (2007); Zhou et al. (2009); Yu and Thomson in Essentials of Stem Cell Biology ($2^{nd}$ Edition].

It is also envisaged that the endodermal and/or hepatic progenitor cells may also be derived from other pluripotent stem cells such as adult stem cells, cancer stem cells or from other embryonic, fetal, juvenile or adult sources.

Suitable conditions for differentiating hPS cells into hepatic progenitor cells are known (see, e.g., Hay 2008, Brolen 2010 and Duan 2010). WO 2009/013254 A1, for example, describes suitable protocols to obtain hepatic progenitor cells (Embodiments 1 to 4).

The hPS cells are normally cultured for up to 14 days in suitable differentiation medium in order to obtain hepatic progenitor cells. For example, the hPS cells may be cultured in suitable differentiation medium for about 10 to about 14 days, such as for about 11 to 14 days.

The initial hepatic differentiation may be defined by including a pre-endodermal step, i.e. the culturing of the hPS cells under differentiation conditions to obtain cells of the definitive endoderm (DE cells), which is followed by a pre-hepatic step, i.e. the culturing of the obtained DE cells under differentiation conditions to obtain the hepatic progenitor cells. Accordingly, hPS cells are first differentiated into definitive endoderm, followed by the further differentiation of the definitive endoderm into hepatic progenitor cells.

Generally, in order to obtain endodermal cells, hPS cells are cultured in a differentiation medium comprising activin, such as activin A or B. The differentiation medium may further include a histone deacetylase (HDAC) inhibitor, such as Sodium Butyrate (NaB), Phenylbutyrate (PB), valproate, trichostatin A, Entinostat or Panobinstat. The differentiation medium may further comprise one or more growth factors, such as FGF1, FGF2 and FGF4, and/or serum, such as FBS or FCS. The differentiation medium may comprise a GSK3- inhibitor, such as, e.g., CHIR99021, or an activator of Wnt signalling, such as Wnt3A. The differentiation medium may further comprise a PI3K (Phosphoinositide 3-kinase) inhibitor, such as LY294002.

The concentration of activin is usually in the range of about 50 to about 150 ng/ml, such as about 80 to about 120 ng/ml. Activin may, for example, be present in the differentiation medium at a concentration of about 50 ng/ml or about 100 ng/ml. The concentration of the HDAC inhibitor is usually in the range of about 0.5 to about 2 mM. The HDAC inhibitor may, for example, be present in the differentiation medium at a concentration of about 0.5 mM or about 1 mM. The concentration of the one or more growth factors may vary depending on the particular compound used. The concentration of FGF2, for example, is usually in the range of about 2 to about 50 ng/ml, such as about 2 to about 10 ng/ml. FGF2 may, for example, be present in the differentiation medium at a concentration of about 4 or about 5 ng/ml. The concentration of FGF1, for example, is usually in the range of about 50 to about 200 ng/ml, such as about 80 to about 120 ng/ml. FGF1 may, for example, be present in the differentiation medium at a concentration of about 100 ng/ml. The concentration of FGF4, for example, is usually in the range of about 20 to about 40 ng/ml. FGF4 may, for example, be present in the differentiation medium at a concentration of about 30 ng/ml. The concentration of serum, if present, is usually in the range of about 0.1 to about 2% v/v, such as about 0.1 to about 0.5%, about 0.2 to about 1.5% v/v, about 0.2 to about 1% v/v, about 0.5 to 1% v/v or about 0.5 to about 1.5% v/v. Serum may, for example, be present in the differentiation medium at a concentration of about 0.2% v/v, about 0.5% v/v or about 1% v/v. The concentration of the GSK3 inhibitor, if present, is usually in the range of about 0.1 to about 10 µM, such as about 0.05 to about 5 µM. The concentration of the activator of Wnt signalling, if present, is usually in the range of about 0.05 to about 10 ng/ml, such as about 0, 5 to about 5 µM. The concentration of the PI3K inhibitor, for example, is usually in the range of about 0.1 to 10 µM, such as about 1 to 5 µM.

The differentiation medium may further comprise other supplements such as PEST and/or GlutaMAX. The differentiation medium may also further comprise a ROCK inhibitor. The concentration of PEST is usually in the range of about 0.1 to about 0.5% v/v, such as about 0.1 to about 0.25% v/v. The concentration of GlutaMAX is usually in the range of about 0.5 to about 1.5% v/v, such as about 0.75 to 1.25% v/v, e.g. about 1% v/v. The differentiation medium may also further comprise a ROCK inhibitor. The concentration of the ROCK inhibitor is usually in the range of about 1 to about 10 µM, such as about 2.5 to about 7.5 µM, e.g., about 5 µM.

The culture medium forming the basis for the differentiation medium may be any culture medium suitable for culturing hPS cells such as RPMI 1640 or advanced medium, Dulbecco's Modified Eagle Medium (DMEM), HCM medium, HBM medium or Williams E based medium. Thus, the differentiation medium may be RPMI 1640 or advanced medium comprising or supplemented with the above-mentioned components. Alternatively, the differentiation medium may be DMEM comprising or supplemented with the above-mentioned components. The differentiation medium may thus also be HCM medium comprising or supplemented with the above-mentioned components. The differentiation medium may thus also be HBM medium comprising or supplemented with the above-mentioned components. The differentiation medium may thus also be Williams E based medium comprising or supplemented with the above-mentioned components.

For endodermal differentiation, hPS cells are normally cultured for up to 10 days in an activin containing differentiation medium as described above. The hPS cells may, for example, be cultured in said differentiation medium for about 4 to about 10 days, such as for about 7 to about 9 days.

Thereafter, the obtained DE cells are further cultured in a differentiation medium comprising DMSO to obtain hepatic progenitor cells. Alternatively, the obtained DE cells may be cultured in a differentiation medium comprising one or more growth factors, such as FGF1, FGF2 and FGF4, and one or more bone morphogenic proteins, such as BMP2 and BMP4. The differentiation medium may further comprise HGF, EGF and/or serum.

The concentration of DMSO is usually in the range of about 0.1% to about 2% v/v, such as about 0.5% to about 1.5% v/v. DMSO may, for example, be present in the differentiation medium at a concentration of about 1%. The concentration of the one or more growth factors may vary depending on the particular compound used. The concentration of FGF2, for example, is usually in the range of about 2 to about 50 ng/ml, such as about 2 to about 10 ng/ml. FGF2 may, for example, be present in the differentiation medium at a concentration of 4 or 5 ng/ml. The concentration of FGF1, for example, is usually in the range of about 50 to about 200 ng/ml, such as about 80 to about 120 ng/ml. FGF1 may, for example, be present in the differentiation medium at a concentration of about 100 ng/ml. The concentration of FGF4, for example, is usually in the range of about 20 to about 40 ng/ml. FGF4 may, for example, be present in the differentiation medium at a concentration of about 30 ng/ml. The concentration of HGF, if present, is usually in the range of about 10 to about 30 ng/ml. HGF may, for example, be present in the differentiation medium at a concentration of about 20 ng/ml. The concentration of EGF, if present is usually in the range of about 5 to about 15 ng/ml. EGF may, for example, be present in the differentiation medium at a concentration of about 10 ng/ml. The concentration of serum, if present, is usually in the range of about 0.1 to about 2% v/v, such as such as about 0.1 to about 0.5%, about 0.2 to about 1.5% v/v, about 0.2 to about 1% v/v, about 0.5 to 1% v/v or about 0.5 to about 1.5% v/v. Serum may, for example, be present in the differentiation medium at a concentration of about 0.2% v/v, about 0.5% v/v or about 1% v/v.

The differentiation medium may further comprise other supplements such as PEST and/or GlutaMAX. The concentration of PEST is usually in the range of about 0.1 to about 0.5% v/v, such as about 0.1 to about 0.25% v/v. The concentration of GlutaMAX is usually in the range of about 0.5 to about 1.5% v/v, such as about 0.75 to 1.25% v/v, e.g. about 1% v/v.

The culture medium forming the basis for the differentiation medium may be any culture medium suitable for culturing human endodermal cells such as RPMI 1640 or advanced medium, Dulbecco's Modified Eagle Medium (DMEM), HCM medium, HBM medium or Williams E based medium. Thus, the differentiation medium may be RPMI 1640 or advanced medium comprising or supplemented with the above-mentioned components. Alternatively, the differentiation medium may be DMEM comprising or supplemented with the above-mentioned components. The differentiation medium may thus also be HCM medium comprising or supplemented with the above-mentioned components. The differentiation medium may thus also be HBM medium comprising or supplemented with the above-mentioned components. The differentiation medium may thus also be Williams E based medium comprising or supplemented with the above-mentioned components.

For differentiation into hepatic progenitor cells, DE cells are normally cultured for up to 7 days in differentiation medium as described above. The DE cells may, for example, be cultured in differentiation medium for about 4 to about 7 days.

Basic, non-limiting culture conditions for obtaining DE cells, hepatic progenitor cells and hepatocyte-like cells are provided in Example 2 herein.

The differentiating hPS cells may also be exposed to a DNA demethylating agent. Cells may be exposed to (or treated with) said agent at any stage between pluripotent stem cell stage and definitive endodermal stage. Thus, the exposure to said DNA demethylating agent may take place during the differentiation of the hPS cells into DE cells, i.e. during the pre-endodermal step. The cells are then cultured through endodermal stage until hepatic progenitor stage is reached, i.e. until hepatic progenitor cells are obtained, at which point the further differentiation and maturation into hepatocyte-like cells including the exposure to the activator of a retinoic acid responsive receptor, either alone or in combination with GSK-3 inhibition or activation of Wnt signalling and/or a CDK inhibitor and/or a matrix overlay, is carried out.

The DNA demethylating agent employed in the methods according to the invention may be any compound that interferes with DNA methyltransferase enzyme activity. Suitable DNA demethylating agents are ones of the nucleoside-analog type, such as cytidine analogues, e.g. 5-aza-2-deoxycytidine (decitabine), 5-azacytidine (azacitidine) or zebularine, and of the non-nucleoside type, such as procaine, RG108, S-5-adenosyl-L-homocysteine, Caffeic acid, Chlorogenic acid, Epogallocatechin gallate, Hydralazine hydrochloride, Procainamide hydrochloride or Psammaplin A.

Thus, the DNA demethylating agent employed in the methods of the invention may be one of the nucleoside-analogue type. Alternatively, the DNA demethylating agent employed in the methods of the invention may be one of the non-nucleoside type.

Accordingly, the DNA demethylating agent employed in the methods of the invention may be a cytidine analogue, such as e.g. 5-aza-2-deoxycytidine (decitabine), 5-azacytidine (azacitidine), zebularine, Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide.

The DNA demethylating agent employed in the methods of the invention may thus be a cytidine analogue selected from the group consisting of 5-aza-2-deoxycytidine (decitabine), 5-azacytidine (azacitidine), 5-fluoro-2-deoxycytidine, 5,6-dihydro-5-azacytidine, 2'-deoxy-5,6-dihydro-5-azacytidine, 6-azacytidine and 2',2'-Difluoro-deoxycytidine (gemcitabine).

The DNA demethylating agent employed in the methods of the invention may thus be a cytidine analogue selected from the group consisting of 5-aza-2-deoxycytidine (decitabine) and 5-azacytidine (azacitidine), Alternatively, the DNA demethylating agent employed in the methods of the invention may be a cytidine analogue which is not 5-aza-2-deoxycytidine (decitabine) or 5-azacytidine (azacitidine).

Accordingly, the DNA demethylating agent employed in the methods of the invention may be 5-aza-2-deoxycytidine. The DNA demethylating agent may also be 5-azacytidine. The DNA demethylating agent may also be zebularine. The DNA demethylating agent may also be Pseudoisocytidine. The DNA demethylating agent may also be 5-fluoro-2-deoxycytidine. The DNA demethylating agent may also be 5,6-dihydro-5-azacytidine. The DNA demethylating agent may also be 2'-deoxy-5,6-dihydro-5-azacytidine. The DNA demethylating agent may also be 6-azacytidine. The DNA demethylating agent may also be 2',2'-Difluoro-deoxycytidine (gemcitabine). The DNA demethylating agent may also be Cytosine-beta-D-arabinofurasonide. The DNA demethylating agent may also be procaine. The DNA demethylating agent may also be RG108. The DNA demethylating agent may also be S-5-adenosyl-L-homocysteine. The DNA demethylating agent may also be Caffeic acid. The DNA demethylating agent may also be Chlorogenic acid. The DNA demethylating agent may also be Epogallocatechin gallate. The DNA demethylating agent may also be Hydralazine hydrochloride. The DNA demethylating agent may also be Procainamide hydrochloride. The DNA demethylating agent may also be Psammaplin A.

The differentiating hPS cells may not only be exposed to one DNA demethylating agent, but may also be exposure to one or more further DNA demethylating agents, such as to a combination of two, three or four of those mentioned above.

The differentiating hPS cells may generally be exposed to the DNA demethylating agent at a concentration in the range of about 1 nM to about 10 µM, such as in the range of about 1 nM to about 5 µM.

Thus, the differentiating hPS cells may be exposed to the DNA demethylating agent at a concentration in the range of about 1 nM to about 1 µM. The differentiating hPS cells may thus be exposed to the DNA demethylating agent at a concentration in the range of about 1 nM to about 500 nM. The differentiating hPS cells may also be exposed to the DNA demethylating agent at a concentration in the range of about 1 nM to about 250 nM. The differentiating hPS cells may also be exposed to the DNA demethylating agent at a concentration in the range of about 1 nM to about 100 nM. The differentiating hPS cells may thus be exposed to the DNA demethylating agent at a concentration in the range of about 1 nM to about 50 nM. The differentiating hPS cells may thus be exposed to the DNA demethylating agent at a concentration in the range of about 1 nM to about 25 nM. The differentiating hPS cells may thus be exposed to the DNA demethylating agent at a concentration in the range of about 1 nM to about 15 nM. The differentiating hPS cells may also be exposed to the DNA demethylating agent at a concentration in the range of about 1 nM to about 10 nM. The differentiating hPS cells may also be exposed to the DNA demethylating agent at a concentration in the range of about 5 nM to about 500 nM. The differentiating hPS cells may thus be exposed to the DNA demethylating agent at a concentration in the range of about 5 nM to about 250 nM. The differentiating hPS cells may also be exposed to the DNA demethylating agent at a concentration in the range of about 5 nM to about 100 nM. The differentiating hPS cells may also be exposed to the DNA demethylating agent at a concentration in the range of about 5 nM to about 50 nM. The differentiating hPS cells may also be exposed to the DNA demethylating agent at a concentration in the range of about 5 nM to about 25 nM. The differentiating hPS cells may also be exposed to the DNA demethylating agent at a concentration in the range of about 5 nM to about 15 nM, such as in the range of about 10 nM. The differentiating hPS cells may also be exposed to the DNA demethylating agent at a concentration in the range of about 7.5 nM to about 250 nM. The differentiating hPS cells may also be exposed to the DNA demethylating agent at a concentration in the range of about 7.5 nM to about 100 nM. The differentiating hPS cells may also be exposed to the DNA demethylating agent at a concentration in the range of about 7.5 nM to about 50 nM. The differentiating hPS cells may also be exposed to the DNA demethylating agent at a concentration in the range of about 7.5 nM to about 25 nM. The differentiating hPS cells may also be exposed to the DNA demethylating agent at a concentration in the range of about 7.5 nM to about 12.5 nM.

In case that, for instance, 5-aza-2-deoxycytidine is employed as the DNA demethylating agent, the differentiating hPS cells may be exposed to it at a concentration in the range of 1 nM to about 1 μM. The differentiating hPS cells may thus be exposed to 5-aza-2-deoxycytidine at a concentration in the range of about 1 nM to about 500 nM. The differentiating hPS cells may also be exposed to 5-aza-2-deoxycytidine at a concentration in the range of about 1 nM to about 250 nM. The differentiating hPS cells may also be exposed to 5-aza-2-deoxycytidine at a concentration in the range of about 1 nM to about 100 nM. The differentiating hPS cells may thus be exposed to 5-aza-2-deoxycytidine at a concentration in the range of about 1 nM to about 50 nM. The differentiating hPS cells may thus be exposed to 5-aza-2-deoxycytidine at a concentration in the range of about 1 nM to about 25 nM. The differentiating hPS cells may thus be exposed to 5-aza-2-deoxycytidine at a concentration in the range of about 1 nM to about 15 nM. The differentiating hPS cells may also be exposed to 5-aza-2-deoxycytidine at a concentration in the range of about 1 nM to about 10 nM. The differentiating hPS cells may also be exposed to 5-aza-2-deoxycytidine at a concentration in the range of about 5 nM to about 500 nM. The differentiating hPS cells may thus be exposed to 5-aza-2-deoxycytidine at a concentration in the range of about 5 nM to about 250 nM. The differentiating hPS cells may also be exposed to 5-aza-2-deoxycytidine at a concentration in the range of about 5 nM to about 100 nM. The differentiating hPS cells may also be exposed to 5-aza-2-deoxycytidine at a concentration in the range of about 5 nM to about 50 nM. The differentiating hPS cells may also be exposed to 5-aza-2-deoxycytidine at a concentration in the range of about 5 nM to about 25 nM. The differentiating hPS cells may also be exposed to 5-aza-2-deoxycytidine at a concentration in the range of about 5 nM to about nM, such as in the range of about 10 nM. The differentiating hPS cells may also be exposed to 5-aza-2-deoxycytidine at a concentration in the range of about 7.5 nM to about 250 nM. The differentiating hPS cells may also be exposed to 5-aza-2-deoxycytidine at a concentration in the range of about 7.5 nM to about 100 nM. The differentiating hPS cells may also be exposed to 5-aza-2-deoxycytidine at a concentration in the range of about 7.5 nM to about 50 nM. The differentiating hPS cells may also be exposed to 5-aza-2-deoxycytidine at a concentration in the range of about 7.5 nM to about 25 nM. The differentiating hPS cells may also be exposed to 5-aza-2-deoxycytidine at a concentration in the range of about 7.5 nM to about 12.5 nM.

Similar concentrations may be used in case that 5-azacytidine or zebularine are employed as the DNA demethylating agent. Similar concentrations may also be used in case of other cytidine analogues, such as, e.g. Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide, in particular 5-fluoro-2-deoxycytidine, 5,6-dihydro-5-azacytidine, 2'-deoxy-5,6-dihydro-5-azacytidine, 6-azacytidine or 2',2'-Difluoro-deoxycytidine (gemcitabine).

The differentiating hPS cells are usually exposed to the DNA demethylating agent of the nucleoside-analog type (e.g. 5aza-2deoxycytidine, 5-azacytidine, zebularine) when they show greatest proliferative capacity as evidenced by cell doubling time, such as between day 2 and 7 of differentiation. Thus, the DNA demethylating agent may be added to the differentiation medium on day 2 of differentiation. The DNA demethylating agent may also be added to the differentiation medium on day 3 of differentiation. The DNA demethylating agent may also be added to the differentiation medium on day 4 of differentiation. The DNA demethylating agent may also be added to the differentiation medium on day 5 of differentiation. The DNA demethylating agent may also be added to the differentiation medium on day 6 of differentiation. DNA demethylation agents of the non-nucleoside type (e.g. procaine, RG108, S-5-adenosyl-L-homocysteine) can be added at any time in the differentiation protocol since they do not require cell proliferation to have an effect.

As shown in FIG. 13 (Example 10) herein, treatment of differentiating hPS cells with a DNA demethylating agent surprisingly leads to an improved morphology and yield of DE cells. Moreover, treatment with a DNA demethylating agent also surprisingly led to a significant down-regulation of expression of the stem cell marker Oct4 in DE cells (FIG. 13 C and D) and to an improved expression of DE specific markers SOX17, CXCR4 and HHEX (FIG. 13 D). This aspect of the invention is believed to be the first time that a specific synergistic effect has been shown between DNA demethylation and the application of specific growth factors whose action at a genomic level may be enhanced by the widespread absence of methylation. Moreover, a strong synergistic effect on the maturation of hepatocyte-like cells is seen when treating cells with a DNA demethylating agent during early endodermal development before exposing the obtained hepatic progenitor cells to an activator of a retinoic acid responsive receptor, a GSK3 inhibitor/20 activator of Wnt signalling or CDK inhibitor and/or a matrix overlay (Example 8; FIGS. 9, 10, and 12).

Further, the hepatocyte-like cells of the present invention may be obtained under xeno-free conditions. As such, the starting material employed in the methods of the invention may thus be xeno-free, such as xeno-free hPS cells or cell lines, or xeno-free hepatic progenitor cells or cell lines which have been obtained or established under animal-free conditions. Moreover, throughout the methods of the invention cells may be cultured completely under xeno-free conditions, giving rise to truly xeno-free hepatocyte-like cells. Such cells or cell line would be better suited to therapeutic or regenerative medicine applications and could be distinguished from a non-xeno free composition by the presence in non-xeno free cells of the non-human sialic acid Neu5Gc or other non-human markers (Martin et al 2005).

As a result of the methods of the present invention, hepatocyte-like cells obtained with more mature and functional features compared to currently available state of the art methods.

The hepatocyte-like cell(s) obtained by employing the methods of the invention show elevated expression of hepatocyte-associated genes such as e.g. CYP1A2, CYP3A4, CYP2C9, CYP7A1, CYP2B6, CYP3A5, MRP2, CAR, NTCP, GSTA-1, PXR and adult isoforms of HNF4a. They further show increased metabolic activity, as evidenced by increased activity of CYP enzymes such as CYP1A1/2, 2C9 and 3A4/5/7 to metabolise drugs such as paracetamol and Diclofenac or UGT enzymes (UDP-glucuronyltransferases) such as UGT1A1, UGT1A9 and UGT2B7. The hepatocyte-like cell (s) of the invention show also a prolonged longevity compared to untreated control cells. The hepatocyte-like cell(s) obtained by employing the methods of the invention also show cytochrome P450 activities exceeding a fold change of at least 1.5, such as e.g. 2, when compared to cultures where 5aza-deoxycytodine, retinoic acid, Kenpaullone and a matrix overlay is not used.

Moreover, the obtained populations of hepatocyte-like cells or cell compositions are more pure and homogenous compared to ones obtained by following currently available state of the art methods.

The cell composition(s) of the invention may further be characterized in that at least 70% such as e.g. 75%, 80%, 90% or 95% of the cells are hepatocyte-like cells of the present invention.

The hepatocyte-like cells obtained by employing the methods of the invention and principles as laid out in present invention may be used to a multitude of purposes comprising drug discovery processes, toxicity test, for studying drug transporters, drug metabolizing enzyme, as in vitro models for studying hepatogenesis, such as, e.g., early hepatogenesis, for studying human hepatoregenerative disorders, for in vitro hepatotoxicity testing.

Further the hepatocyte-like cells obtained by employing the methods of the invention may be used for therapeutic purposes comprising: in a medicament, for the manufacture of a medicament or medicinal product for the prevention and/or treatment of pathologies and/or diseases caused by tissue degeneration, such as, e.g., the degeneration of liver tissue. The hepatocyte-like cells of the present invention may also be used for the manufacture of a medicament or medicinal product for the treatment of liver disorders. Liver disorders are, for example, auto immune disorders including primary biliary cirrhosis; metabolic disorders including dyslipidemia; liver disorders caused by e.g. alcohol abuse; diseases caused by viruses such as, e.g., hepatitis B, hepatitis C, and hepatitis A; liver necrosis caused by acute toxic reactions to e. g. pharmaceutical drugs; and tumour removal in patients suffering from e. g. hepatocellular carcinoma.

Alternatively, the hepatocyte-like cells obtained by employing the methods of the invention may be used for the manufacture of a medicament or medicinal product for the treatment and/or prevention of metabolic pathologies and/or diseases.

The medicament or medicinal product may, for example, be in the form of a replacement tissue or cell injection.

The differentiation and maturation of hepatocyte-like cells in accordance to the invention may be useful for obtaining metabolically improved hepatocyte-like cells, for studying maturation towards hepatocyte-like cells or for screening a compound for its ability to modulate hepatocellular function, comprising exposing in vitro derived hepatocyte-like cells obtained according to the directions provided herein to the compound, determining any phenotypic or metabolic changes in the cells that result from contact with the compound, and correlating the change with an ability to modulate hepatocellular function.

The invention also provides kits. Such kits are particularly useful in carrying out the methods of the invention, e.g, for maturing human hepatocyte-like cells in accordance with the invention. A kit according to the invention comprises at least one activator of a retinoic acid responsive receptor and at least one selected from GSK3 inhibitor, activator of Wnt signalling, CDK inhibitor and extracellular matrix (ECM) component or ECM component mixture.

Accordingly, a kit of the invention may comprise at least one activator of a retinoic acid responsive receptor, at least one GSK3 inhibitor, and optionally at least one extracellular matrix (ECM) component or ECM component mixture.

A kit of the invention may also comprise at least one activator of a retinoic acid responsive receptor, at least one activator of Wnt signalling, and optionally at least one extracellular matrix (ECM) component or ECM component mixture.

A kit of the invention may also comprise at least one activator of a retinoic acid responsive receptor, at least one CDK inhibitor, and optionally at least one extracellular matrix (ECM) component or ECM component mixture.

A kit of the invention may also comprise at least one activator of a retinoic acid responsive receptor, at least one CDK inhibitor and at least one GSK3 inhibitor or activator of Wnt signalling, and optionally at least one extracellular matrix (ECM) component or ECM component mixture.

A kit of the invention may also comprise at least one activator of a retinoic acid responsive receptor and at least one extracellular matrix (ECM) component or ECM component mixture.

As noted above, it is understood that the details given herein with respect to the components employed in the methods of the invention also apply to the components comprised by the kits of the invention.

Hence, the at least one activator of a retinoic acid responsive receptor comprised by a kit of the invention may, for instance, be a retinoic acid, such as 9-cis-retinoic acid.

The at least one GSK-3 inhibitor comprised by a kit of the invention may, for instance, be one selected from Kenpaullone 1-Aza-Kenpaullone, Alsterpaullone, Aminopyrimidine CHIR99021 and Indirubin-3'-monoxime.

The at least one GSK-3 inhibitor comprised by a kit of the invention may, for instance, be one selected from Kenpaullone, 1-Aza-Kenpaullone, Alsterpaullone, Indirubin-3'-monoxime. 2-bromo-9-nitropaullone, 2-bromo-9-trifluoromethylpaullone, 2-bromopaullone, 2-iodo-9-trifluoromethylpaullone, 2-iodopaullone, 2-phenyl-4-(2-thienyl)-5H-pyrido[2±3-d][1]benzazepine-6(7H)-thione, 2-[2-(1-hydroxycyclohexyl)-ethinyl]-9-trifluoromethyl-paullone, 2,3-dimethoxy-9-nitropaullone, 2,3-dimethoxy-9-trifluormethylpaullone, 2,3-dimethoxypaullone, 2-(3-hydroxy-1-propinyl)-9-trifluoromethylpaullone, 2,9-dibromo-paullone, 3-(6-oxo-9-trifluoromethyl-5,6,7,12-tetrahydro-indolo[2±3-d][1]benzazepin-2-yl)-propionitrile, 4-methoxypaullone, 4-(4-chlorophenyl)-2-(2-naphthyl)-5H-pyrido[2±3-d][1]benzazepine-6(7H)-thione, 5-benzyl-9-bromopaullone, 5-iodo-indirubin.3-monoxime, 5,6,7,12-tetrahydro-benzo[6±7]cyclohept[1,2-b]indole, 6 bromo indirubin, 8,10-dichloro-paullone, 9-bromo-2,3-dihydroxypaullone, 9-bromo-2,3-dimethoxypaullone, 9-bromo-4-hydroxypaullone, 9-bromo-4-methoxypaullone, 9-bromo-5-ethylpaullone, 9-bromo-5-(methyloxycarbonylmethyl)paullone, 9-bromo-5-methylpaullone, 9-bromo-5,6,7,12-tetrahydro-benzo[6±7]cyclohept[1,2-b]indole, 9-bromo-5,7-bis-(tert.-butyloxycarbonyl)-paullone, 9-bromo-5,7,12-tri-(tert.-butyloxycarbonyl)-paullone, 9-bromo-5,12-bis-(tert.-butyloxycarbonyl)-paullone, 9-bromo-7,12-dihydro-6-(hydroxyamino)-indolo[2±3-d][1]benzazepine, 9-bromo-7,12-dihydro-6-methylthio-indolo[2±3-d][1]benzazepine, 9-bromo-7,12-dihydro-indolo[2±3-d][1]benzazepine-6(5H)-thione, 9-bromo-12-(2-hydroxyethyl)-paullone, 9-bromo-12-(2-propenyl)-paullone, 9-bromo-12-ethylpaullone, 9-bromo-12-methylpaullone, 9-bromo-12-methyloxycarbonyl-methylpaullone, 9-bromo-12-(tert.-butyloxycarbonyl)-paullone, 9-chloropaullone, 9-cyanopaullone, 9-cyano-2,3-dimethoxypaullone, 9-fluoropaullone, 9-methoxypaullone, 9-methylpaullone, 9-oxo-thiazolo[5,4-f]quinazoline-2-carbonitril derivatives, 9-trifluoromethylpaullone, 10-bromopaullone, 11-bromopaullone, 11-chloropaullone, 11-ethylpaullone, 11-methylpaullone, Aloisines (=6-phenyl[5H]pyrrolo[2,3-6]pyrazines); e.g. Aloisine A, AZD1080, bis-indole indirubin, Debromohymenialdisine, Dibromocantharelline, (E)-3-(6-oxo-9-trifluoromethyl-5,6,7,12-tetrahydro-indolo[2±3-d][1]benzazepin-2-yl)-acrylic acid methyl ester, (E)-2-(3-oxo-1-butenyl)-9-trifluoromethyl-paullone, (E)-3-(6-oxo-9-trifluoromethyl-5,6,7,12-tetrahydro-indolo[2±3-d][1]benzazepin-2-yl)-acrylonitrile, Indirubin, Hymenidin, Hymenialdisine, Manzamines, e.g. Manzamine A, Meridiamins, Paullone, Pyrazolo[3,4-b]pyridine derivatives, Pryazolo[3,4-b]quinoxaline derivatives and thiazolo[5,4-f]quinazolino-9-one derivatives.

The at least one activator of Wnt signalling comprised by a kit of the invention may, for instance, be one selected from the group of Wnt proteins dislosed above. It may, for instance, be Wnt3A or Wnt5A.

The at least one CDK inhibitor comprised by a kit of the invention may, for instance, be one selected from Kenpaullone, 1-Aza-Kenpaullone, Alsterpaullone, Indirubin-3'-monoxime, SNS-032(BMS-387032), AT-7519 and AZD5438.

The at least one CDK inhibitor comprised by a kit of the invention may, for instance, be one selected from Kenpaullone, 1-Aza-Kenpaullone, Alsterpaullone, Indirubin-3'-monoxime. 2-bromo-9-nitropaullone, 2-bromo-9-trifluoromethylpaullone, 2-bromopaullone, 2-iodo-9-trifluoromethylpaullone, 2-iodopaullone, 2-phenyl-4-(2-thienyl)-5H-pyrido[2±3-d][1]benzazepine-6(7H)-thione, 2-[2-(1-hydroxycyclohexyl)-ethinyl]-9-trifluoromethyl-paullone, 2,3-dimethoxy-9-nitropaullone, 2,3-dimethoxy-9-trifluormethylpaullone, 2,3-dimethoxypaullone, 2-(3-hydroxy-1-propinyl)-9-trifluoromethylpaullone, 2,9-dibromo-paullone, 3-(6-oxo-9-trifluoromethyl-5,6,7,12-tetrahydro-indolo[2±3-d][1]benzazepin-2-yl)-propionitrile, 4-methoxypaullone, 4-(4-chlorophenyl)-2-(2-naphthyl)-5H-pyrido[2±3-d][1]benzazepine-6(7H)-thione, 5-benzyl-9-bromopaullone, 5-iodo-indirubin.3-monoxime, 5,6,7,12-tetrahydro-benzo[6±7]cyclohept[1,2-b]indole, 6 bromo indirubin, 8,10-dichloropaullone, 9-bromo-2,3-dihydroxypaullone, 9-bromo-2,3-dimethoxypaullone, 9-bromo-4-hydroxypaullone, 9-bromo-4-methoxypaullone, 9-bromo-5-ethylpaullone, 9-bromo-5-(methyloxycarbonylmethyl)paullone, 9-bromo-5-methylpaullone, 9-bromo-5,6,7,12-tetrahydro-benzo[6±7]cyclohept[1,2-b]indole, 9-bromo-5,7-bis-(tert.-butyloxycarbonyl)-paullone, 9-bromo-5,7,12-tri-(tert.-butyloxycarbonyl)-paullone, 9-bromo-5,12-bis-(tert.-butyloxycarbonyl)-paullone, 9-bromo-7,12-dihydro-6-(hydroxyamino)-indolo[2±3-d][1]benzazepine, 9-bromo-7,12-dihydro-6-methylthio-indolo[2±3-d][1]benzazepine, 9-bromo-7,12-dihydro-indolo[2±3-d][1]benzazepine-6(5H)-thione, 9-bromo-12-(2-hydroxyethyl)-paullone, 9-bromo-12-(2-propenyl)-paullone, 9-bromo-12-ethylpaullone, 9-bromo-12-methylpaullone, 9-bromo-12-methyloxycarbonyl-methylpaullone, 9-bromo-12-(tert.-butyloxycarbonyl)-paullone, 9-chloropaullone, 9-cyanopaullone, 9-cyano-2,3-dimethoxypaullone, 9-fluoropaullone, 9-methoxypaullone, 9-methylpaullone, 9-oxothiazolo[5,4-f]quinazoline-2-carbonitril derivatives, 9-trifluoromethylpaullone, 10-bromopaullone, 11-bromopaullone, 11-chloropaullone, 11-ethylpaullone, 11-methylpaullone, Aloisines (=6-phenyl[5H]pyrrolo[2,3-6]pyrazines); e.g. Aloisine A, AZD1080, bis-indole indirubin, Debromohymenialdisine, Dibromocantharelline, (E)-3-(6-oxo-9-trifluoromethyl-5,6,7,12-tetrahydro-indolo[2±3-d][1]benzazepin-2-ylacrylic acid methyl ester, (E)-2-(3-oxo-1-butenyl)-9-trifluoromethylpaullone, (E)-3-(6-oxo-9-trifluoromethyl-5,6,7,12-tetrahydro-indolo[2±3-d][1]benzazepin-2-ylacrylonitrile, Indirubin, Hymenidin, Hymenialdisine, Manzamines, e.g. Manzamine A, Meridiamins, Paullone, Pyrazolo[3,4-b]pyridine derivatives, Pryazolo[3,4-b]quinoxaline derivatives and thiazolo[5,4-f]quinazolino-9-one derivatives.

The at least one ECM component comprised by a kit of the invention may, for instance, be one selected from collagen, such as collagen I, II, III, IV, V or VI, fibronectin, elastin, chondroitin sulfate proteoglycan, dermatan sulfate proteoglycan, heparin proteoglycan, heparan sulfate proteoglycan, such as glypicans, syndecans or perlecans, glycosaminoglycans, nidogen/entactin, laminins, biglycan, tenascin, and hyaluronans.

A kit of the invention may comprise a ECM component mixture comprising, or composed of, two, three, four, five, six, seven, eight, nine or ten, or up to 20 of the ECM components mentioned herein. Thus, a kit of the invention may comprise a ECM component mixture comprising, or composed of, two of the ECM components mentioned herein. A kit of the invention may also comprise a ECM component mixture comprising, or composed of, three of the ECM components mentioned herein. A kit of the invention may also comprise a ECM component mixture comprising, or composed of, four of the ECM components mentioned herein. A kit of the invention may also comprise a ECM component mixture comprising, or composed of, five of the ECM components mentioned herein. A kit of the invention may also comprise a ECM component mixture comprising, or composed of, six of the ECM components mentioned herein. A kit of the invention may also comprise a ECM component mixture comprising, or composed of, seven of the ECM components mentioned herein. A kit of the invention may also comprise a ECM component mixture comprising, or composed of, eight of the ECM components mentioned herein. A kit of the invention may also comprise a ECM component mixture comprising, or composed of, nine of the ECM components mentioned herein. A kit of the invention may also comprise a ECM component mixture comprising, or composed of, ten of the ECM components mentioned herein.

For example, a kit of the invention may comprise a ECM component mixture comprising, or composed of, collagen and fibronectin, such as a ECM component mixture comprising, or composed of, collagen I and fibronectin. A kit of the invention may comprise a ECM component mixture comprising, or composed of, collagen, such as collagen I, and laminin. A kit of the invention may comprise a ECM component mixture comprising, or composed of, collagen, such as collagen I, nidogen and laminin. A kit of the invention may comprise a ECM component mixture comprising, or composed of, collagen, such as collagen I, fibronectin and laminin. A kit of the invention may comprise a ECM component mixture comprising, or composed of, fibronectin and laminin. A kit of the invention may comprise a ECM component mixture comprising, or composed of, Fibronectin, nidogen and laminin.

A kit of the invention may comprise a ECM component mixture comprising, or composed of, fibronectin, collagen I, collagen IV, collagen VI, nidogen, biglycan and laminin.

A kit of the invention may comprise a ECM component mixture comprising, or composed of, fibronectin, collagen I, collagen IV, nidogen, biglycan and laminin.

A kit of the invention may comprise a ECM component mixture comprising, or composed of, collagen, such as collagen I, laminin, fibronectin, proteoglycans and glycosaminoglycans. A kit of the invention may comprise a ECM component mixture comprising, or composed of, collagen, such as collagen I, laminin, fibronectin, and proteoglycans.

A kit of the invention may comprise a ECM component mixture comprising, or composed of, collagen, such as collagen I, laminin, fibronectin, tenascin, elastin, proteoglycans and glycosaminoglycans.

Accordingly, a kit of the invention may comprise 9-cis-retinoic acid and Kenpaullone. Such kit may further comprise a ECM component mixture as disclosed above, such as, a ECM component mixture comprising, or composed of, collagen and fibronectin, such as a ECM component mixture comprising, or composed of, collagen I and fibronectin.

A kit of the invention may comprise 9-cis-retinoic acid and Indirubin-3'-monoxime. Such kit may further comprise a ECM component mixture as disclosed above, such as, a ECM component mixture comprising, or composed of, collagen and fibronectin, such as a ECM component mixture comprising, or composed of, collagen I and fibronectin.

A kit of the invention may further comprise at least one DNA demethylating agent. The DNA demthylating agent, if comprised by the kit of the invention, may be a cytidine analogue, such as e.g. 5-aza-2-deoxycytidine (decitabine), 5-azacytidine (azacitidine), zebularine, Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide.

The at least one DNA demthylating agent may, for instance, be 5-aza-2-deoxycytidine (decitabine). The at least one DNA demethylating agent may also be 5-azacytidine (azacitidine).

A kit of the invention may further comprise human pluripotent stem cells. Hence, a kit of the invention may comprise human embryonic stem cells or human induced pluripotent stem cells. The human pluripotent stem cells may suitably be provided as a cell suspension, and may be provided in a frozen state.

A kit of the invention may further comprise definitive endoderm cells (DE cells). The DE cells may suitably be provided as a cell suspension, and may be provided in a frozen state.

The components of a kit of the invention may be provided in the same or separate containers. For instance, the at least one activator of a retinoic acid responsive receptor and the at least one GSK3 inhibitor, the at least one activator of Wnt signalling or the at least one CDK inhibitor may be provided in the same container. If an at least one extracellular matrix (ECM) component or ECM component mixture is also comprised by the kit, such ECM component or ECM component mixture may be generally provided in a separate container. Hence, while the at least one activator of a retinoic acid responsive receptor and the at least one GSK3 inhibitor, the at least one activator of Wnt signalling or the at least one CDK inhibitor may be provided in the same container, at least one extracellular matrix (ECM) component or ECM component mixture is provided in a different container.

Likewise, if human pluripotent stem cells or definitive endoderm cells (DE cells) are comprised by a kit, the human pluripotent stem cells or DE cells are generally provide in a container which is different from the container(s) containing the other components.

The invention also provides compositions. Such compositions are particularly useful for maturing human hepatocyte-like cells in accordance with the invention. A composition of the invention comprises at least one activator of a retinoic acid responsive receptor and at least one selected from GSK3 inhibitor, activator of Wnt signalling and CDK inhibitor.

Accordingly, a composition of the invention may comprise at least one activator of a retinoic acid responsive receptor and at least one GSK-3 inhibitor, and optionally at least one CDK inhibitor.

A composition of the invention may also comprise at least one activator of a retinoic acid responsive receptor and at least one activator of Wnt signalling, and optionally at least one CDK inhibitor.

A composition of the invention may also comprise at least one activator of a retinoic acid responsive receptor and at least one CDK inhibitor, and optionally at least one GSK3 inhibitor or at least one activator of Wnt signalling.

As noted above, it is understood that the details given herein with respect to the components employed in the methods of the invention also apply to the components comprised by the composition of the invention.

Hence, the at least one activator of a retinoic acid responsive receptor comprised by a composition of the invention may, for instance, be a retinoic acid, such as 9-cis-retinoic acid.

The at least one GSK-3 inhibitor comprised by a composition of the invention may, for instance, be one selected from Kenpaullone, 1-Aza-Kenpaullone, Alsterpaullone, Aminopyrimidine CHIR99021 and Indirubin-3'-monoxime.

The at least one GSK-3 inhibitor comprised by a composition of the invention may, for instance, be one selected from Kenpaullone, 1-Aza-Kenpaullone, Alsterpaullone, Indirubin-3'-monoxime. 2-bromo-9-nitropaullone, 2-bromo-9-trifluoromethylpaullone, 2-bromopaullone, 2-iodo-9-trifluoromethylpaullone, 2-iodopaullone, 2-phenyl-4-(2-thienyl)-5H-pyrido[2±3-d][1]benzazepine-6(7H)-thione, 2-[2-(1-hydroxycyclohexyl)-ethinyl]-9-trifluoromethyl-paullone, 2,3-dimethoxy-9-nitropaullone, 2,3-dimethoxy-9-trifluormethylpaullone, 2,3-dimethoxypaullone, 2-(3-hydroxy-1-propinyl)-9-trifluoromethylpaullone, 2,9-dibromo-paullone, 3-(6-oxo-9-trifluoromethyl-5,6,7,12-tetrahydro-indolo[2±3-d][1]benzazepin-2-yl)-propionitrile, 4-methoxypaullone, 4-(4-chlorophenyl)-2-(2-naphthyl)-5H-pyrido[2±3-d][1]benzazepine-6(7H)-thione, 5-benzyl-9-bromopaullone, 5-iodo-indirubin.3-monoxime, 5,6,7,12-tetrahydro-benzo[6±7]cyclohept[1,2-b]indole, 6 bromo indirubin, 8,10-dichloropaullone, 9-bromo-2,3-dihydroxypaullone, 9-bromo-2,3-dimethoxypaullone, 9-bromo-4-hydroxypaullone, 9-bromo-4-methoxypaullone, 9-bromo-5-ethylpaullone, 9-bromo-5-(methyloxycarbonylmethyl)paullone, 9-bromo-5-methylpaullone, 9-bromo-5,6,7,12-tetrahydro-benzo[6±7]cyclohept[1,2-b]indole, 9-bromo-5,7-bis-(tert.-butyloxycarbonyl)-paullone, 9-bromo-5,7,12-tri-(tert.-butyloxycarbonyl)-paullone, 9-bromo-5,12-bis-(tert.-butyloxycarbonyl)-paullone, 9-bromo-7,12-dihydro-6-(hydroxyamino)-indolo[2±3-d][1]benzazepine, 9-bromo-7,12-dihydro-6-methylthio-indolo[2±3-d][1]benzazepine, 9-bromo-7,12-dihydro-indolo[2±3-d][1]benzazepine-6(5H)-thione, 9-bromo-12-(2-hydroxyethyl)-paullone, 9-bromo-12-(2-propenyl)-paullone, 9-bromo-12-ethylpaullone, 9-bromo-12-methylpaullone, 9-bromo-12-methyloxycarbonyl-methylpaullone, 9-bromo-12-(tert.-butyloxycarbonyl)-paullone, 9-chloropaullone, 9-cyanopaullone, 9-cyano-2,3-dimethoxypaullone, 9-fluoropaullone, 9-methoxypaullone, 9-methylpaullone, 9-oxo-thiazolo[5,4-f]quinazoline-2-carbonitril derivatives, 9-trifluoromethylpaullone, 10-bromopaullone, 11-bromopaullone, 11-chloropaullone, 11-ethylpaullone, 11-methylpaullone, Aloisines (=6-phenyl[5H]pyrrolo[2,3-6]pyrazines); e.g. Aloisine A, AZD1080, bis-indole indirubin, Debromohymenialdisine, Dibromocantharelline, (E)-3-(6-oxo-9-trifluoromethyl-5,6,7,12-tetrahydro-indolo[2±3-d][1]benzazepin-2-yl)-acrylic acid methyl ester, (E)-2-(3-oxo-1-butenyl)-9-trifluoromethylpaullone, (E)-3-(6-oxo-9-trifluoromethyl-5,6,7,12-tetrahydro-indolo[2±3-d][1]benzazepin-2-ylyacrylonitrile, Indirubin, Hymenidin, Hymenialdisine, Manzamines, e.g. Manzamine A, Meridiamins, Paullone, Pyrazolo[3,4-b]pyridine derivatives, Pryazolo[3,4-b]quinoxaline derivatives and thiazolo[5,4-f]quinazolino-9-one derivatives.

The at least one activator of Wnt signalling comprised by a composition of the invention may, for instance, be one selected from the group of Wnt proteins dislosed above. It may, for instance, be Wnt3A or Wnt5A.

The at least one CDK inhibitor comprised by a composition of the invention may, for instance, be one selected from Kenpaullone, 1-Aza-Kenpaullone, Alsterpaullone, Indirubin-3'-monoxime, SNS-032(BMS-387032), AT-7519 and AZD5438.

The at least one CDK inhibitor comprised by a composition of the invention may, for instance, be one selected from Kenpaullone, 1-Aza-Kenpaullone, Alsterpaullone, Indirubin-3'-monoxime. 2-bromo-9-nitropaullone, 2-bromo-9-trifluoromethylpaullone, 2-bromopaullone, 2-iodo-9-trifluoromethylpaullone, 2-iodopaullone, 2-phenyl-4-(2-thienyl)-5H-pyrido[2±3-d][1]benzazepine-6(7H)-thione, 2-[2-(1-hydroxycyclohexyl)-ethinyl]-9-trifluoromethyl-paullone, 2,3-dimethoxy-9-nitropaullone, 2,3-dimethoxy-9-trifluormethylpaullone, 2,3-dimethoxypaullone, 2-(3-hydroxy-1-propinyl)-9-trifluoromethylpaullone, 2,9-dibromo-paullone, 3-(6-oxo-9-trifluoromethyl-5,6,7,12-tetrahydro-indolo[2±3-d][1]benzazepin-2-yl)-propionitrile, 4-methoxypaullone, 4-(4-chlorophenyl)-2-(2-naphthyl)-5H-pyrido[2±3-d][1]benzazepine-6(7H)-thione, 5-benzyl-9-bromopaullone, 5-iodo-indirubin.3-monoxime, 5,6,7,12-tetrahydro-benzo[6±7]cyclohept[1,2-b]indole, 6 bromo indirubin, 8,10-dichloropaullone, 9-bromo-2,3-dihydroxypaullone, 9-bromo-2,3-dimethoxypaullone, 9-bromo-4-hydroxypaullone, 9-bromo-4-methoxypaullone, 9-bromo-5-ethylpaullone, 9-bromo-5-(methyloxycarbonylmethyl)paullone, 9-bromo-5-methylpaullone, 9-bromo-5,6,7,12-tetrahydro-benzo[6±7]cyclohept[1,2-b]indole, 9-bromo-5,7-bis-(tert.-butyloxycarbonyl)-paullone, 9-bromo-5,7,12-tri-(tert.-butyloxycarbonyl)-paullone, 9-bromo-5,12-bis-(tert.-butyloxycarbonyl)-paullone, 9-bromo-7,12-dihydro-6-(hydroxyamino)-indolo[2±3-d][1]benzazepine, 9-bromo-7,12-dihydro-6-methylthio-indolo[2±3-d][1]benzazepine, 9-bromo-7,12-dihydro-indolo[2±3-d][1]benzazepine-6(5H)-thione, 9-bromo-12-(2-hydroxyethyl)-paullone, 9-bromo-12-(2-propenyl)-paullone, 9-bromo-12-ethylpaullone, 9-bromo-12-methyl-paullone, 9-bromo-12-methyloxycarbonyl-methylpaullone, 9-bromo-12-(tert.-butyloxycarbonyl)-paullone, 9-chloro-paullone, 9-cyanopaullone, 9-cyano-2,3-dimethoxypaullone, 9-fluoropaullone, 9-methoxypaullone, 9-methylpaullone, 9-oxo-thiazolo[5,4-f]quinazoline-2-carbonitril derivatives, 9-trifluoromethylpaullone, 10-bromopaullone, 11-bromopaullone, 11-chloropaullone, 11-ethylpaullone, 11-methylpaullone, Aloisines (=6-phenyl[5H]pyrrolo[2,3-6]pyrazines); e.g. Aloisine A, AZD1080, bis-indole indirubin, Debromohymenialdisine, Dibromocantharelline, (E)-3-(6-oxo-9-trifluoromethyl-5,6,7,12-tetrahydro-indolo[2±3-d][1]benzazepin-2-yl)-acrylic acid methyl ester, (E)-2-(3-oxo-1-butenyl)-9-trifluoromethylpaullone, (E)-3-(6-oxo-9-trifluoromethyl-5,6,7,12-tetrahydro-indolo[2±3-d][1]benzazepin-2-ylyacrylonitrile, Indirubin, Hymenidin, Hymenialdisine, Manzamines, e.g. Manzamine A, Meridiamins, Paullone, Pyrazolo[3,4-b]pyridine derivatives, Pryazolo[3,4-b]quinoxaline derivatives and thiazolo[5,4-f]quinazolino-9-one derivatives.

Accordingly, a composition of the invention may comprise 9-cis-retinoic acid and Kenpaullone.

A composition of the invention may comprise 9-cis-retinoic acid and Indirubin-3'-monoxime.

A composition of the invention may comprise 13-cis-retinoic acid and kenpaullone.

A composition of the invention may comprise 13-cis-retinoic acid and Indirubin-3'-monoxime.

DEFINITIONS

As used herein, "pluripotent" or "pluripotency" refers to the potential to form all types of specialized cells of the three germ layers (endoderm, mesoderm, and ectoderm); and is to be distinguished from "totipotent" or "totipotency", that is the ability to form a complete embryo capable of giving rise to offsprings.

As used herein, "human pluripotent stem cells" (hPSC) refers to human cells that have the capacity, under appropriate conditions, to self-renew as well as the ability to form any type of specialized cells of the three germ layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells, (see, e.g., Thomson et al. (1998), Heins et. al. (2004), as well as induced pluripotent stem cells [see, e.g. Takahashi et al., (2007); Zhou et al. (2009); Yu and Thomson in Essentials of Stem Cell Biology ($2^{nd}$ Edition]. The various methods described herein may utilise hPS cells from a variety of sources. For example, hPS cells suitable for use may have been obtained from developing embryos by use of a non-destructive technique such as by employing the single blastomere removal technique described in e.g. Chung et al (2008), further described by Mercader et al. in Essential Stem Cell Methods (First Edition, 2009). Additionally or alternatively, suitable hPS cells may be obtained from established cell lines or may be adult stem cells.

As used herein "hiPS cells" refers to human induced pluripotent stem cells. hiPS cells are a type of pluripotent stem cells derived from non-pluripotent cells—typically adult somatic cells—by induction of the expression of genes associated with pluripotency, such as SSEA-3, SSEA-4, TRA-1-60, TRA-1-81, Oct-4, Sox2, Nanog and Lin28.

As used herein "definitive endoderm (DE)" and "definitive endoderm cells (DE cells)" refers to cells exhibiting protein and/or gene expression as well as morphology typical to cells of the definitive endoderm or a composition comprising a significant number of cells resembling the cells of the definitive endoderm. The definitive endoderm is the germ cell layer which gives rise to cells of the intestine, pancreas, liver and lung. DE cells may generally be characterized, and thus identified, by a positive gene and protein expression of the endodermal markers FOXA2, CXCR4, HHEX, SOX17, GATA4 and GATA6. The two markers SOX17 and CXCR4 are specific for DE and not detected in hPSC, hepatic progenitor cells or hepatocytes. Lastly, DE cells do not exhibit gene and protein expression of the undifferentiated cell markers Oct4, SSEA-3, SSEA-4, TRA-1-60, TRA-1-81, but can show low Nanog expression.

As used herein, "hepatic progenitors" or "hepatic progenitor cells" refers to cells which have entered the hepatic cell path and give rise to hepatocyte. "Hepatic progenitors"

are thus distinguished from "endodermal cells" in that they have lost the potential to develop into cells of the intestine, pancreas and lung. "Hepatic progenitors" may generally be characterized, and thus identified, by a positive gene and protein expression of the early hepatic markers EpCAM, c-Met (HGF-receptor), AFP, CK19, HNF6, C/EBPα and β. They do not exhibit gene and protein expression of the DE-markers CXCR4 and SOX17. Lastly, "hepatic progenitors" do not exhibit gene and protein expression of the undifferentiated cell markers Oct4, SSEA-3, SSEA-4, TRA-1-60 and TRA-1-81 nor the mature hepatic markers CYP1A2, CYP2C9, CYP19, CYP3A4, CYP2B6 and PXR.

As used herein, "hepatocyte" or "hepatocyte-like cells" refers to fully differentiated hepatic cells. "Hepatocytes" or "hepatocytes-like cells" may generally be described, and thus identified, by a positive gene and protein expression of the mature hepatic markers CYP1A2, CYP3A4, CYP2C9, CYP2C19, CYP2B6, GSTA1-1, OATP-2, NTCP, Albumin, PXR, CAR, and HNF4α(isoforms 1+2) among others. Further, "hepatocytes" or "hepatocyte-like cells do not exhibit gene and protein expression of the undifferentiated cell markers Oct4, SSEA-3, SSEA-4, TRA-1-60 and TRA-1-81. Compared to DE cells, "hepatocytes" or "hepatocyte-like cells do not exhibit gene and protein expression of the DE cell markers SOX17 and CXCR4. Compared to "hepatic progenitors", "hepatocytes" or "hepatocyte-like cells do not exhibit gene and protein expression of the hepatic progenitor markers Cytokeratin 19 and AFP.

As meant herein, a gene or protein shall be interpreted as being "expressed", if in an experiment measuring the expression level of said gene or protein, the determined expression level is higher than three times the standard deviation of the determination, wherein the expression level and the standard deviation are determined in 10 separate determinations of the expression level. The determination of the expression level in the 10 separate determinations is preferably corrected for background-signal.

As used herein HDAC inhibitors refers to Histone deacetylase inhibitors, such as Sodium Butyrate ("NaB"), Phenyl Butyrate ("PB"), Trichostatin A and Valproic Acid ("VA").

As used herein, "GSK inhibitor" refers to a compound which inhibits GSK (especially GSK3, including GSK3alpha or GSK3beta).

As used herein, "activator of Wnt signalling" refers to a compound which activates Wnt signalling.

As used herein, a DNA demethylating agent is intended to mean a compound that interferes with DNA methyltransferase enzyme activity, such as nucleoside analogues, like cytidine analogs, notably 5-aza-2-deoxycytidine (decitabine) and 5-azacytidine (azacitidine), and non-nucleoside types, such as RG108, S-5-Adenosyl-L-homocysteine, and procaine.

As used herein "CYP" is intended to mean Cytochrome P, and more specifically Cytochrome P 450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

As used herein, the term "GST" is intended to mean glutathione transferase, and examples of subtypes thereof are GST A1-1, GST M1-1, and GST P1-1.

As used herein the term "UGT" is intended to mean uridine diphosphoglucuronosyltransferase, which is a group of liver enzymes catalyzing glucuronidation activities.

As used herein the term "NTCP" is taken to mean Na+-taurocholate cotransporting polypeptide, a Sodium/bile acid co-transporter encoded by the gene SLC10A1

As used herein the term "CAR" is taken to mean Constitutive androstane receptor

The term "functional drug metabolising enzymes" is intended to mean functional enzymes belonging to the phase I and phase II enzymes that perform chemical modifications of xenobiotics and drugs, so called drug or xenobiotic metabolism.

As used herein, the term "functional activity" means effective measurable hepatic cell function, such as a measurable transportation of drugs for drug transporters and a measurable metabolism of enzymes for the Cytochrome P450s (CYPs), commonly detected in primary human hepatocytes.

As used herein, the term "extraembryonic endoderm (ExE)" is intended to mean the differentiated endodermal cells that, as to the opposite of the definitive endoderm, will constitute the compartments outside the embryo in the human development, such as the yolk sac.

As used herein, the term "AAT" is intended to mean the liver marker alpha-anti-trypsin.

As used herein, the term "AFP" is intended to mean the liver marker alpha-fetoprotein.

As used herein, the term "BSEP" is intended to mean the bile transporter bile salt export pump.

As used herein, the term "CK" is intended to mean the liver marker cytokeratin (used interchangeably) with different subtypes such as Cytokeratin 18 (CK18/KRT18), Cytokeratin 19 (CK19/KRT19), Cytokeratin 8 (CK8) and Cytokeratin 7 (CK7).

As used herein, the term "FGF" means fibroblast growth factor, preferably of human and/or recombinant origin, and subtypes belonging thereto are e.g. "bFGF" (means basic fibroblast growth factor, sometimes also referred to as FGF2) and FGF4. "aFGF" means acidic fibroblast growth factor (sometimes also referred to as FGF1).

As used herein, the term "BMP" means Bone Morphogenic Protein, preferably of human and/or recombinant origin, and subtypes belonging thereto are e.g. BMP4 and BMP2.

As used herein, the term "HGF" means Hepatocyte Growth Factor, preferably of human and/or recombinant origin.

As used herein, the term "EGF" means Epidermal Growth Factor, preferably or human and/or recombinant origin.

As used herein, the "HNF4alpha", or "HNF4a", used interchangeably are intended to mean hepatocyte nuclear factor 4 also known as NR2A1 (nuclear receptor subfamily 2, group A, member 1), a transcription factor regulating gene expression in endodermal derived tissue, e.g. the liver, pancreatic islets, and adipocytes. The encoded protein controls the expression of several genes, including hepatocyte nuclear factor 1 alpha.

As used herein, the term "MDR" is intended to mean multi-drug resistance transporter. MDR 1 and 3 are members of the ATP-binding cassette (ABC) family of transporters and both are drug efflux transporters. MDR 1 is important in regulating the traffic of drugs, peptides and xenobiotics into the body and in protecting the body against xenobiotic insults and drug toxicity, while MDR 3 is essential for phospholipid secretion into bile.

As used herein, the term "Activin" is intended to mean a TGF-beta family member that exhibits a wide range of biological activities including regulation of cellular proliferation and differentiation such as "Activin A" or "Activin B". Activin belongs to the common TGF-beta superfamiliy of ligands.

As used herein, the term "activator of a retinoic acid responsive receptor" is intended to mean a compound capable of binding to and activating a human retinoic acid receptor (RAR) and/or retinoid X receptor (RXRs).

As used herein, the term "retinoic acid receptor" or "RAR" is intended to mean a member of the family of retinoic acid receptors, in particular RAR-alpha, RAR-beta, and RAR-gamma, which are encoded by the RARA, RARB, RARG genes, respectively. Each receptor isoform has several splice variants: two for alpha, four for beta, and two for gamma. These isoforms are also included in the definition of a "retinoic acid receptor".

As used herein, the term "retinoid X receptor" is intended to mean a member of the family of retinoid X receptors, in particular RXR-alpha, RXR-beta, and RXR-gamma, which are encoded by the RXRA, RXRB, RXRG genes, respectively.

As used herein, the term "retinoic acid" is intended to mean a retinoic acid isomer, including but not limited to all-trans-retinoic acid, 7-cis-retinoic acid, 9-cis retinoic acid, 11-cis-retinoic acid and 13-cis retinoic.

As used herein, the term "inhibitor of a cyclin dependent kinase" or "CDK inhibitor" is intended to mean a compound capable of inhibiting the function (e.g., the activity) of a cyclin dependent kinase, such as cyclin dependent kinase 2 (CDK2).

As used herein, the term "ROCK inhibitor" is intended to mean an inhibitor of ROCK Rho-associated protein kinase activity As used herein, the term "matrix" is intended to refer to any component, either isolated or in combination, which forms part of the normal mammalian extracellular matrix environment. Such matrix components include, but are not limited to, collagen, fibronectin, and laminin and may be from natural or synthetic sources.

As used herein, the term "overlay" is intended to refer to a layer of, e.g., extracellular matrix components, which is applied on top of the cultured cells.

As used herein, the term "coating" is intended to refer to a layer of, e.g., extracellular matrix components, which covers the surface of a culture vessel and on which the cells are cultured.

As used herein the term "xeno-free" is intended to mean complete circumvention of direct or in-direct exposure to non-human animal components.

As used herein, the term "hepatocellular toxicity" indicates cellular responses such as necrotic toxicity, apoptosis, mitochondrial toxicity, phospholipidosis, steatosis and bile acid transport.

BRIEF DESCRIPTION OF THE DRAWINGS

FIG. 1A. Expression of HNF4α in hESC-derived hepatocytes exposed to varying lengths of retinoic acid treatments.

FIG. 1B. Ratio of expression of HNF4α1-3 isoforms to HNF4α4-9 isoforms in hESC-derived hepatocytes on day 23 with and without different RA treatments.

FIG. 1C. HNF4α mRNA expression in hESC-derived hepatocytes on day 23 immediately after a 5 hour RA-pulse and 7 days later.

FIG. 2A. Functional expression of CYP1A and CYP3A in hESC-derived hepatocytes exposed to varying lengths of retinoic acid treatments on day 21 (measured on day 23).

FIG. 2D. Functional expression of CYP1A and CYP3A in hESC-derived hepatocytes with and without different RA treatments on days 21, 22 or 23 (measured on day 23).

FIG. 3A. mRNA expression of CYP3A4 in hESC-derived hepatocytes exposed to 5hr of retinoic acid treatment on days 21 or 24hr of retinoic acid treatment on day 22-23 (measured on days 21, 23 and 30)

FIG. 3B. mRNA expression of CYP3A7 in hESC-derived hepatocytes exposed to 5hr of retinoic acid treatment on days 21 or 24hr of retinoic acid treatment on day 22-23 (measured on days 21 and 23).

FIG. 4A. Functional expression of CYP enzymes in hESC-derived hepatocytes exposed to retinoic acid Kenpaullone and/or matrix overlay.

FIG. 4C. Functional expression of CYP enzymes in hiPS-derived hepatocytes exposed to retinoic acid in combination with Kenpaullone and matrix overlay.

FIG. 5A. mRNA expression of NTCP in hESC-derived hepatocyte-like cells (derived with basic protocol B) exposed to retinoic acid, Kenpaullone and a matrix overlay.

FIG. 5B. mRNA expression of GSTA1-1 in hESC-derived hepatocyte-like cells (derived with basic protocol B) exposed to retinoic acid, Kenpaullone and a matrix overlay.

FIG. 5C. mRNA expression of CAR in hESC-derived hepatocyte-like cells (derived with basic protocol B) exposed to retinoic acid, Kenpaullone and a matrix overlay.

FIG. 5D. mRNA expression of CYP2B6 in hESC-derived hepatocyte-like cells (derived with basic protocol B) exposed to retinoic acid, Kenpaullone and a matrix overlay.

FIG. 5E. mRNA expression of CYP2C9 in hESC-derived hepatocyte-like cells (derived with basic protocol B) exposed to retinoic acid, Kenpaullone and a matrix overlay.

FIG. 5F. mRNA expression of CYP3A4 in hESC-derived hepatocyte-like cells (derived with basic protocol B) exposed to retinoic acid, Kenpaullone and a matrix overlay.

FIG. 6A. mRNA expression of CYP2B6 in hESC- and hiPSC-derived hepatocyte-like cells (derived with basic protocols C and D, respectively) exposed to retinoic acid, Kenpaullone and a matrix overlay.

FIG. 6C. mRNA expression of CYP3A5 in hESC- and hiPSC-derived hepatocyte-like cells (derived with basic protocols C and D, respectively) exposed to retinoic acid, Kenpaullone and a matrix overlay.

FIG. 6D. mRNA expression of CAR in hESC- and hiPSC-derived hepatocyte-like cells (derived with basic protocols C and D, respectively) exposed to retinoic acid, Kenpaullone and a matrix overlay.

FIG. 6E. mRNA expression of GSTA1-1 in hESC- and hiPSC-derived hepatocyte-like cells (derived with basic protocols C and D, respectively) exposed to retinoic acid, Kenpaullone and a matrix overlay.

FIG. 7A. Morphology of hESC-derived hepatocyte-like cells (derived with basic protocol B) on d28 with and without the addition of a thin Fibronectin-Collagen I-overlay.

FIG. 7B. Morphology of hESC-derived hepatocyte-like cells (derived with basic protocol B) on d35 with and without the addition of a thin Fibronectin-Collagen I-overlay.

FIG. 7C. Morphology of hESC-derived hepatocyte-like cells (derived with basic protocol B) on d43 with and without the addition of a thin Fibronectin-Collagen I-overlay.

FIG. 8A. Morphology of hESC-derived hepatocyte-like cells (derived with basic protocol C) on d30 with and without the addition of Kenpaullone, RA and a thin Fibronectin-Collagen I-overlay.

FIG. 8B. Morphology of hESC-derived hepatocyte-like cells (derived with basic protocol C) on d35 with and without the addition of Kenpaullone, RA and a thin Fibronectin-Collagen I-overlay.

FIG. 8C. Morphology of hiPSC-derived hepatocyte-like cells (derived with basic protocol D) on d28 with and without the addition of Kenpaullone, RA and a thin Fibronectin-Collagen I-overlay.

FIG. 8D. Morphology of hiPSC-derived hepatocyte-like cells (derived with basic protocol D) on d36 with and without the addition of Kenpaullone, RA and a thin Fibronectin-Collagen I-overlay.

FIG. 9B. mRNA expression of CYP3A4 in hESC- and hiPSC-derived hepatocyte-like cells (derived with basic protocols C and D, respectively) treated early with 5-aza-deoxycytidine and exposed late to retinoic acid, Kenpaullone and a matrix overlay.

FIG. 9C. mRNA expression of CYP3A5 in hESC- and hiPSC-derived hepatocyte-like cells (derived with basic protocols C and D, respectively) treated early with 5-aza-deoxycytidine and exposed late to retinoic acid, Kenpaullone and a matrix overlay.

FIG. 9F. mRNA expression of NTCP in hESC- and hiPSC-derived hepatocyte-like cells (derived with basic protocols C and D, respectively) treated early with 5-aza-deoxycytidine and exposed late to retinoic acid, Kenpaullone and a matrix overlay.

FIG. 9G. mRNA expression of CYP1A2 in hiPSC-derived hepatocyte-like cells (derived with basic protocol D) treated early with 5-aza-deoxycytidine and exposed late to retinoic acid, Kenpaullone and a matrix overlay.

FIG. 11A. Morphology of 5aza-dC-treated hESC-derived hepatocyte-like cells (derived with basic protocol C) on d28 with and without the addition of Kenpaullone, RA and a thin Fibronectin-Collagen I-overlay.

FIG. 11B. Morphology of 5aza-dC-treated hESC-derived hepatocyte-like cells (derived with basic protocol C) on d35 with and without the addition of Kenpaullone, RA and a thin Fibronectin-Collagen I-overlay.

FIG. 11C. Morphology of 5aza-dC-treated hESC-derived hepatocyte-like cells (derived with basic protocol C) on d42 with and without the addition of Kenpaullone, RA and a thin Fibronectin-Collagen I-overlay.

FIG. 11D. Morphology of 5aza-dC-treated hiPSC-derived hepatocyte-like cells (derived with basic protocol D) on d28 with and without the addition of Kenpaullone, RA and a thin Fibronectin-Collagen I-overlay.

FIG. 11E. Morphology of 5aza-dC-treated hiPSC-derived hepatocyte-like cells (derived with basic protocol D) on d35 with and without the addition of Kenpaullone, RA and a thin Fibronectin-Collagen I-overlay.

FIG. 11F. Morphology of 5aza-dC-treated hiPSC-derived hepatocyte-like cells (derived with basic protocol D) on d42 with and without the addition of Kenpaullone, RA and a thin Fibronectin-Collagen I-overlay.

FIG. 13A1. Morphology of hESC-derived definitive endodermal cells (derived with basic protocol C) without a 5-aza-deoxycytidine treatment during the pre-endodermal phase (day 0-7 of the protocol).

FIG. 13A2. Morphology of hESC-derived definitive endodermal cells (derived with basic protocol C) with a 5-aza-deoxycytidine treatment during the pre-endodermal phase (day 0-7 of the protocol).

FIG. 13B1. Morphology of hiPSC-derived definitive endodermal cells (derived with basic protocol D) without a 5-aza-deoxycytidine treatment during the pre-endodermal phase (day 0-7 of the protocol).

FIG. 13B2. Morphology of hiPSC-derived definitive endodermal cells (derived with basic protocol D) with a 5-aza-deoxycytidine treatment during the pre-endodermal phase (day 0-7 of the protocol).

FIG. 13C1. Oct4-immunstaining and DAPI nuclear staining of hiPSC-derived definitive endodermal cells (derived with basic protocol D) without a 5-aza-deoxycytidine treatment during the pre-endodermal phase (day 0-7 of the protocol).

FIG. 13C2. Oct4-immunstaining and DAPI nuclear staining of hiPSC-derived definitive endodermal cells (derived with basic protocol D) with a 5-aza-deoxycytidine treatment during the pre-endodermal phase (day 0-7 of the protocol).

FIG. 13D1. mRNA expression of stem cell marker Oct4 in hESC- and hiPSC-derived definitive endodermal cells (derived with basic protocols C and D, respectively) with and without a 5-aza-deoxycytidine treatment during the pre-endodermal phase (day 0-7 of the protocol).

FIG. 13D2. mRNA expression of stem cell marker Nanog in hESC- and hiPSC-derived definitive endodermal cells (derived with basic protocols C and D, respectively) with and without a 5-deoxycytidine treatment during the pre-endodermal phase (day 0-7 of the protocol).

FIG. 13D3. mRNA expression of DE marker Sox17 in hESC- and hiPSC-derived definitive endodermal cells (derived with basic protocols C and D, respectively) with and without a 5-deoxycytidine treatment during the pre-endodermal phase (day 0-7 of the protocol).

FIG. 13D4. mRNA expression of DE marker Cxcr4 in hESC- and hiPSC-derived definitive endodermal cells (derived with basic protocols C and D, respectively) with and without a 5-deoxycytidine treatment during the pre-endodermal phase (day 0-7 of the protocol).

FIG. 13D5. mRNA expression of DE marker FoxA2 in hESC- and hiPSC-derived definitive endodermal cells (derived with basic protocols C and D, respectively) with and without a 5-deoxycytidine treatment during the pre-endodermal phase (day 0-7 of the protocol).

FIG. 13D6. mRNA expression of DE marker hHEX in hESC- and hiPSC-derived definitive endodermal cells (derived with basic protocols C and D, respectively) with and without a 5-deoxycytidine treatment during the pre-endodermal phase (day 0-7 of the protocol).

FIG. 13D7. mRNA expression of extraembryonic marker Sox7 in hESC- and hiPSC-derived definitive endodermal cells (derived with basic protocols C and D, respectively) with and without a 5-deoxycytidine treatment during the pre-endodermal phase (day 0-7 of the protocol).

FIG. 14A. mRNA expression of stem cell marker Oct4 in definitive endodermal cells derived from 27 different hESC- and hiPSC lines (derived with basic protocols C and D, respectively) with a 5-deoxycytidine treatment during the pre-endodermal phase (day 0-7 of the protocol).

FIG. 14B. mRNA expression of stem cell marker Nanog in definitive endodermal cells derived from 27different hESC- and hiPSC lines (derived with basic protocols C and D, respectively) with a 5-aza-deoxycytidine treatment during the pre-endodermal phase (day 0-7 of the protocol).

FIG. 15A. mRNA expression of stem cell marker Oct4 in definitive endodermal cells derived from 3 hESC- and hiPSC lines (derived with basic protocols C and D, respectively) with or without a treatment with 5aza-deoxycytidine or 5azacytidine during the pre-endodermal phase (day 0-7 of the protocol).

FIG. 15B. mRNA expression of stem cell marker Nanog in definitive endodermal cells derived from 3hESC- and hiPSC lines (derived with basic protocols C and D, respectively) with or without a treatment with 5-deoxycytidine or 5cytidine during the pre-endodermal phase (day 0-7of the protocol).

FIG. 16A-1. CYP1A enzyme activity in cryopreserved human primary hepatocytes.

FIG. 16A-2. CYP1A enzyme activity in hESC- and hiPSC-derived hepatocyte-like cells (derived with basic protocols C and D, respectively) with early treatment with 5-deoxycytidine and late exposure to retinoic acid, Kenpaullone and a matrix overlay.

FIG. 16A-3. CYP2C9 enzyme activity in cryopreserved human primary hepatocytes.

FIG. 16A-4. CYP2C9 enzyme activity in hESC- and hiPSC-derived hepatocyte-like cells (derived with basic protocols C and D, respectively) with early treatment with 5-deoxycytidine and late exposure to retinoic acid, Kenpaullone and a matrix overlay.

FIG. 16A-5. CYP3A enzyme activity in cryopreserved human primary hepatocytes.

FIG. 16A-6. CYP3A enzyme activity in hESC- and hiPSC-derived hepatocyte-like cells (derived with basic protocols C and D, respectively) with early treatment with 5-deoxycytidine and late exposure to retinoic acid, Kenpaullone and a matrix overlay.

FIG. 16B-1. mRNA expression of CYP1A2, CYP2B6, CYP2C9 and CYP3A4 in hESC- and hiPSC-derived hepatocyte-like cells (derived with basic protocols C and D, respectively) with early treatment with 5-deoxycytidine and late exposure to retinoic acid, Kenpaullone and a matrix overlay.

FIG. 16B-2. mRNA expression of CYP3A5 in hESC- and hiPSC-derived hepatocyte-like cells (derived with basic protocols C and D, respectively) with early treatment with 5-deoxycytidine and late exposure to retinoic acid, Kenpaullone and a matrix overlay.

FIG. 16B-3. mRNA expression of CYP1A2, CYP2B6, CYP2C9 and CYP3A4 in cryopreserved human primary hepatocytes.

FIG. 16B-4. mRNA expression of CYP3A5 in cryopreserved human primary hepatocytes.

FIG. 17B. Functional expression of CYP2B6 in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 17C. Functional expression of CYP2C9 in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 17D. Functional expression of CYP2D6 in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 17E. Functional expression of CYP3A in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 18B. mRNA expression of CYP2C9 in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 18C. mRNA expression of CYP3A4 in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 18D. mRNA expression of CYP3A5 in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 18E. mRNA expression of PXR in hiPSC-derived hepatocyte-like cells (derived with basic protocol D) with early treatment with 5-deoxycytidine and late exposure to one or two activators of a retinoic acid responsive receptor, Kenpaullone and a matrix overlay.

FIG. 19A. Functional expression of CYP2C9 in hiPSC-derived hepatocyte-like cells (derived with basic protocol C) treated early with 5-deoxycytidine and exposed late to retinoic acid, Kenpaullone and a simple or more complex matrix overlay.

FIG. 19C. Functional expression of CYP3A in hiPSC-derived hepatocyte-like cells (derived with basic protocol D) treated early with 5-deoxycytidine and exposed late to retinoic acid, Kenpaullone and a simple or more complex matrix overlay.

FIG. 21A1. Functional expression of CYP2C9 enzyme in hiPSC-derived hepatocyte-like cells (derived with basic protocol D) treated early with 5-deoxycytidine and exposed late to 9cis retinoic acid, Kenpaullone or an analogue to Kenpaullone.

FIG. 21A2. Functional expression of CYP 3A enzyme in hiPSC-derived hepatocyte-like cells (derived with basic protocol D) treated early with 5-deoxycytidine and exposed late to 9cis retinoic acid, Kenpaullone or an analogue to Kenpaullone.

FIG. 21B1. Functional expression of CYP2C9 enzyme in hESC-derived hepatocyte-like cells (derived with basic protocol C) treated early with 5-deoxycytidine and exposed late to 9cis retinoic acid, Kenpaullone or an analogue to Kenpaullone.

FIG. 21B2. Functional expression of CYP3A enzyme in hESC-derived hepatocyte-like cells (derived with basic protocol C) treated early with 5-deoxycytidine and exposed late to 9cis retinoic acid, Kenpaullone or an analogue to Kenpaullone.

EXAMPLES

Figures 2, 2A:
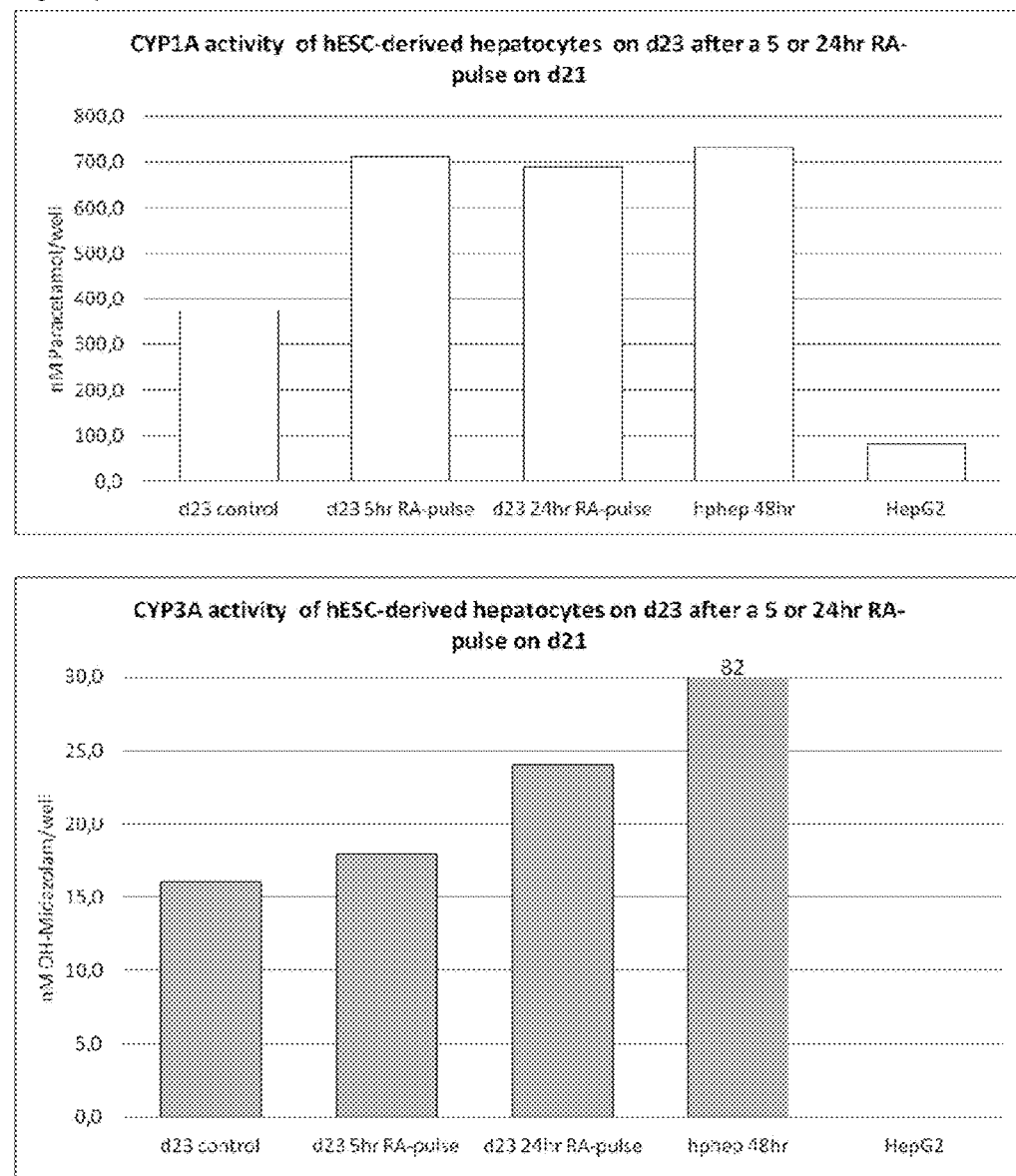

Examples of general culturing and passaging techniques are disclosed in applications WO2004/099394, WO2003/055992, WO/2007/042225, WO2007/140968 and WO2011116930.

As laid out in the following examples, the starting material may comprise any hepatic progenitor cell type, particularly one derived through an initial differentiation towards a definitive or extraembryonic lineage from a human pluripotent stem cell. The starting material may also be any cell of hepatic progenitor lineage.

Example 1

Maintenance of hPS Cell Types

All hPS cells (as defined above) can be used as staring material for this invention. For the examples below in particular hepatocyte-like cells were derived in vitro from undifferentiated human embryonic stem cells (hESC) established on mEF feeder cells (Heins et al 2004) and maintained under feeder-free conditions. The cell lines used for this experiment could be, but are not limited to the hES cell lines SA167, SA181, SA461 (Cellartis AB, Goteborg, Sweden) and they can be propagated as described by Heins et al. 2004. These cell lines are listed in the NIH stem cell registry, the UK Stem Cell bank and the European hESC registry and are available on request.

Along with hPS obtained from hESC, hiPS (human induced pluripotent stem) cells have also been used for the derivation of hepatocytes for the examples of this invention.

The hiPSC line used in this invention was derived as followed: Human dermal fibroblasts (CRL2429, ATCC) were maintained in DMEM supplemented with 10% fetal bovine serum, 1× glutamax, 5 U/ml penicillin and 5 µg/ml streptomycin at 37° C. in a humidified atmosphere of 5% $CO_2$ in air. Fibroblasts were tranduced with recombinant lentiviruses encoding mouse Oct4, Sox2, Klf4 and c-myc and cultured for 5 days. The transduced cells were then dispersed with trypsin and seeded onto mitomycin C treated human dermal fibroblast feeder cells at a density of $5 \times 10^3$ cells/cm$^2$ in their normal growth medium. After 24 hours the medium was replaced with knockout DMEM supplemented with 20% knockout serum replacement, 1× non-essential amino acids, 1× glutamax, 5 U/ml penicillin, 5 µg/ml streptomycin, 100 µM 2-mercaptoethanol and 30 ng/ml bFGF at 37° C. in a humidified atmosphere of 5% $CO_2$ in air. Half of the volume of medium was replaced every day and colonies of iPS cells emerged after approximately 30 days. iPS colonies were picked, expanded in DEF-CS™, and cell banks prepared. The banked cells were then characterised to check for the expression of endogenous Oct4, Sox2, Klf4 and c-Myc, silencing of transgenes, potential to differentiate into cell types representative of all three germ layers in vitro, and to confirm their authenticity by STR profiling and comparison with the parental fibroblast cell line (ATCC). Alternatively to reprogramming using lentivirus, hiPSC lines can also be reprogrammed using retrovirus, Sendai virus, adenovirus, episomal plasmid vectors, proteins and mRNAs or other techniques. Other suitable cell lines for use are those established by Chung et al. (2008), such as cell lines MA126, MA127, MA128 and MA129 (Advanced Cell Technology, Inc. Worcester, Mass., USA), which all are listed with the International stem cell registry. These cell lines have been derived (or obtained) without destruction of the human embryo by employing a single blastomere removal technique.

Example 2

Differentiation of hPS Cell Types to Produce Hepatocyte-Like

Hepatocyte-like cells may be derived from hPS cells by employing the following exemplary basic protocols A, B, C, and D:

Protocol A:

Undifferentiated hPS cells are dissociated and seeded directly in freshly prepared day 0—medium. The different mediums were prepared freshly and added day 0, 1, 2, 3, 4, 5, 7 and then every second or third day during the pre-hepatic phase, and differentiation and maturation phase.

Day 0
RPMI 1640 (+0.1% PEST, +1% Glutamax)
1×B27
100 ng/ml Activin A
1 mM NaB
5 µM ROCK inhibitor
Day 1
RPMI 1640 (+0.1% PEST, +1% Glutamax)
1×B27
100 ng/ml Activin A
1 mM NaB
Day 2-7
RPMI 1640 (+0.1% PEST+1% Glutamax)
1×B27
100 ng/ml Activin A
0.5 mM NaB On day 7 the cells are passaged. The cells are incubated for 3-7 minutes with TrypLE Select at 37° C., the same volume of VitroHES is added and the cell suspension is centrifuged at 200-300 g, 5-6 min. Thereafter, the cells are replated onto a Gelatine-based coating at a cell density of 50 000-350 000 cells/$cm^2$ such as e.g. 100 000-300 000 cells/$cm^2$, preferably 150 000 cells/$cm^2$.

Day7-14 (pre-hepatic)
VitroHES
1% DMSO
Day 14-45 (differentiation and maturation)
WME+SQ (-GA1000)+1% Glutamax+0.1% PEST
0.1 µM DexM
10 ng/ml OsM
20 ng/ml HGF
0.5% DMSO
1.4 µM (2'Z,3'£)-6-Bromoindirubin-3'-oxime (BIO)

Protocol B:

Undifferentiated hPS cells are dissociated and seeded directly in freshly prepared day 0—medium. The different mediums were prepared freshly and added day 0, 1, 2, 3, 4, 5, 7 and then every second or third day during the pre-hepatic phase, and differentiation and maturation phase.

Day 0
RPMI 1640 (+0.1% PEST, +1% Glutamax)
1×B27
100 ng/ml Activin A
1 mM NaB
5 µM ROCK inhibitor
Day 1
RPMI 1640 (+0.1% PEST, +1% Glutamax)
1×B27
100 ng/ml Activin A
1 mM NaB
3 µM CHIR99021
Day 2-7
RPMI 1640 (+0.1% PEST+1% Glutamax)
1×B27
100 ng/ml Activin A
0.5 mM NaB On day 7 the cells are passaged. The cells are incubated for 3-7 minutes with TrypLE Select at 37° C., the same volume of VitroHES is added and the cell suspension is centrifuged at 200-300 g, 5-6 min. Thereafter, the cells are replated onto a Fibronectin-based coating at a cell density of 50 000-350 000 cells/$cm^2$ such as e.g. 100 000-300 000 cells/$cm^2$, preferably 150 000 cells/$cm^2$. For media d7-14 (pre-hepatic) and 14-45 (differentiation and maturation) see Protocol A.

Protocol C:

Undifferentiated hPS cells are dissociated and seeded directly in freshly prepared day 0—medium. The different mediums were prepared freshly and added day 0, 1, 2, 3, 4, 5, 7 and then every second or third day during the pre-hepatic phase, and differentiation and maturation phase. The pre-treatment medium is available from Cellectis AB (Arvid Wallgrens Backe 20, 41346 Gothenburg, Sweden).

Day 0
Pre-treatment medium
3 µM CHIR99021
5 µM ROCK inhibitor
Day 1
Pre-treatment medium
3 µM CHIR99021
Day 2
RPMI 1640 (+0.1% PEST+1% Glutamax)
1×B27
50 ng/ml Activin A
3 µM CHIR99021
5 µM LY294002
Day 3
RPMI 1640 (+0.1% PEST+1% Glutamax)
1×B27
50 ng/ml Activin A
5 µM LY294002
Day 4-7
RPMI 1640 (+0.1% PEST+1% Glutamax)
1×B27
50 ng/ml Activin A For passage d7, media d7-14 (pre-hepatic) and 14-45 (differentiation and maturation) see Protocol B.

Protocol D:

Undifferentiated hPS cells are dissociated and seeded directly in freshly prepared day 0—medium. The different mediums were prepared freshly and added day 0, 1, 2, 3, 4, 5, 7 and then every second or third day during the pre-hepatic phase, and differentiation and maturation phase. The pre-treatment medium is available from Cellectis AB (Arvid Wallgrens Backe 20, 41346 Gothenburg, Sweden).

Day 0
Pre-treatment medium
3 μM CHIR99021
5 μM ROCK inhibitor
Day 1
RPMI 1640 (+0.1% PEST+1% Glutamax)
1×B27
50 ng/ml Activin A
3 μM CHIR99021
5 μM LY294002
Day 2
RPMI 1640 (+0.1% PEST+1% Glutamax)
1×B27
50 ng/ml Activin A
5 μM LY294002
Day 3-7
RPMI 1640 (+0.1% PEST+1% Glutamax)
1×B27
50 ng/ml Activin A For passage d7, media d7-14 (pre-hepatic) and 14-45 (differentiation and maturation) see Protocol B.

Example 3

Effect of Treatment of hESC-Derived Hepatocyte-Like Cells with 9 Cis-Retinoic Acid on Expression of Different HNF4α Isoforms Procedure:

Following the basic protocol A, hepatocyte-like cells derived from hES cells cultured on a Gelatin-based coating were treated with 1 or 2 μM 9 cis-retinoic acid for 5 hr, 24 hr or 48 hr on day 23 of the protocol (i.e. on day 9 of the differentiation and maturation) or long term from day 14 (i.e. starting day 1 of the differentiation and maturation phase) and onwards and analysed immediately after the exposure (FIG. 1 A, B, C) or 7 days later (FIG. C). Three different HNF4α-TaqMan assays were used for analysis of HNF4α expression: one assay detecting all 9 HNF4α isoforms, one assay detecting isoforms 1-3 (including the adult isoforms 1 and 2) and one assay detecting isoforms 4-9 (including the fetal isoforms 7 and 8). Isoforms 3, 4, 5, 6 and 9 are not expressed at all in vivo or at very low levels and can therefore be neglected.

Results:

A) 5 hr RA-exposure strongly increase expression of the adult HNF4a1-3 isoforms, but also increase the expression of the fetal HNF4a4-9 isoforms. 24-, 48 hr-exposure and continuous RA-treatment slightly increase the adult HNF4a1-3 isoforms and slightly decrease the fetal HNF4a4-9 isoforms making the ratio of 1-3 isoforms/4-9 isoforms more similar to hphep, see also FIG. 1B.

B) Human primary hepatocytes (hp hep) have a high ratio of the adult HNF4a isoforms 1-3 to the fetal 4-9 isoforms, whereas HepG2 have a low ratio. 24 hr and 48 hr RA-exposure and long term/continuous treatment increase the 1-3/4-9 ratio of hESC-derived hepatocytes to levels similar as in hp hep. 5 hr exposures do not increase the 1-3/4-9 ratio since also expression of 4-9 isoforms increases (see FIG. 1A). hphep: average of 7 batches freshly isolated hp hep. HepG2: average of 2 batches.

C) A 5 hr exposure with 1 μM RA increases the expression of HNF4α isoforms 1-3 immediately after the exposure (see also A), but 7 days later the expression of isoforms 1-3 is slightly lower in the RA-treated cells than in the untreated control cells. The expression of isoforms 4-9 is slightly lower in the RA-treated cells than in the control immediately after the exposure. 7 days later expression of fetal isoform is raised over control values.

Therefore the optimal culture conditions for producing an increase in the adult isoforms of HNF4a with minimal increase or decrease in fetal isoforms on day 23 involve the continuous treatment or 24 hr or 48 hr exposures of 1 or 2 μM RA on d23, corresponding to an expression profile closest to that of primary human hepatocytes (hp hep). The skilled person wishing to produce cells with an unchanged expression profile might instead select a 5 hr exposure to RA.

Example 4

Effect of Treatment of hESC-Derived Hepatic Progenitors and Hepatocyte-Like Cells with 9 Cis-Retinoic Acid (RA) on CYP Activity Procedure:

Following the basic protocol A, differentiating hES cell derived hepatic progenitors and hepatocyte-like cells cultured on a Gelatin-based coating were treated with 1 μM 9-cis retinoic acid for 5, 24 or 48 hr exposures on days 21, 22 or 23 of the protocol (i.e. on day 7, 8 or 9 of the differentiation and maturation phase; FIG. 2 A, B, D), repeated 5 hr exposures on days 11, 16, 23, 25 and 30 of the protocol (i.e. on day 4 of the pre-hepatic phase and days 2, 9, 11 and 16 of the differentiation and maturation phase; FIG. 2 C), or long term/continuous treatment from day 14 and onwards (i.e.starting on day 1 of the differentiation and maturation phase; FIG. 2D).

Immediately after end of the RA treatment, the cell cultures are subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 26 μM Phenacetin (model substrate for CYP1A), 9 μM Diclofenac (model substrate for CYP2C9) and 3 μM Midazolam (model substrate for CYP3A), is added to the cells (e.g. 220 μl/24 well) and incubated for 16 hr at 37° C. Then supernatant is collected and centrifuged for 20 min at 10.000 rcf at 4° C. Subsequently, 120 μl of the supernatant is transferred into a 96 well plate which is sealed with a tight seal tape and stored at −20 or −80° C. until LC/MS-analysis of metabolite formation: Acetaminophen (Paracetamol) for CYP1A, OH-Diclofenac for CYP2C9 and OH-Midazolam for CYP3A.

Results:

A) After 5 and 24 hr RA-exposures on day 21 of the protocol (i.e. on day 7 of the differentiation and maturation phase), an immediate increase of CYP1A and 3A activity in hESC-derived hepatocytes can be observed: CYP1A activity is on same level as in primary hepatocytes cultured for 48 hr, whereas CYP3A activity is roughly 25% of primary hepatocytes cultured for 48 hr. HepG2 have much lower CYP1A and 3A activity than hESC-derived hepatocytes. On day 23 in the protocol no CYP2C9 activity could be detected in hESC-derived hepatocytes.

Figure 2B:
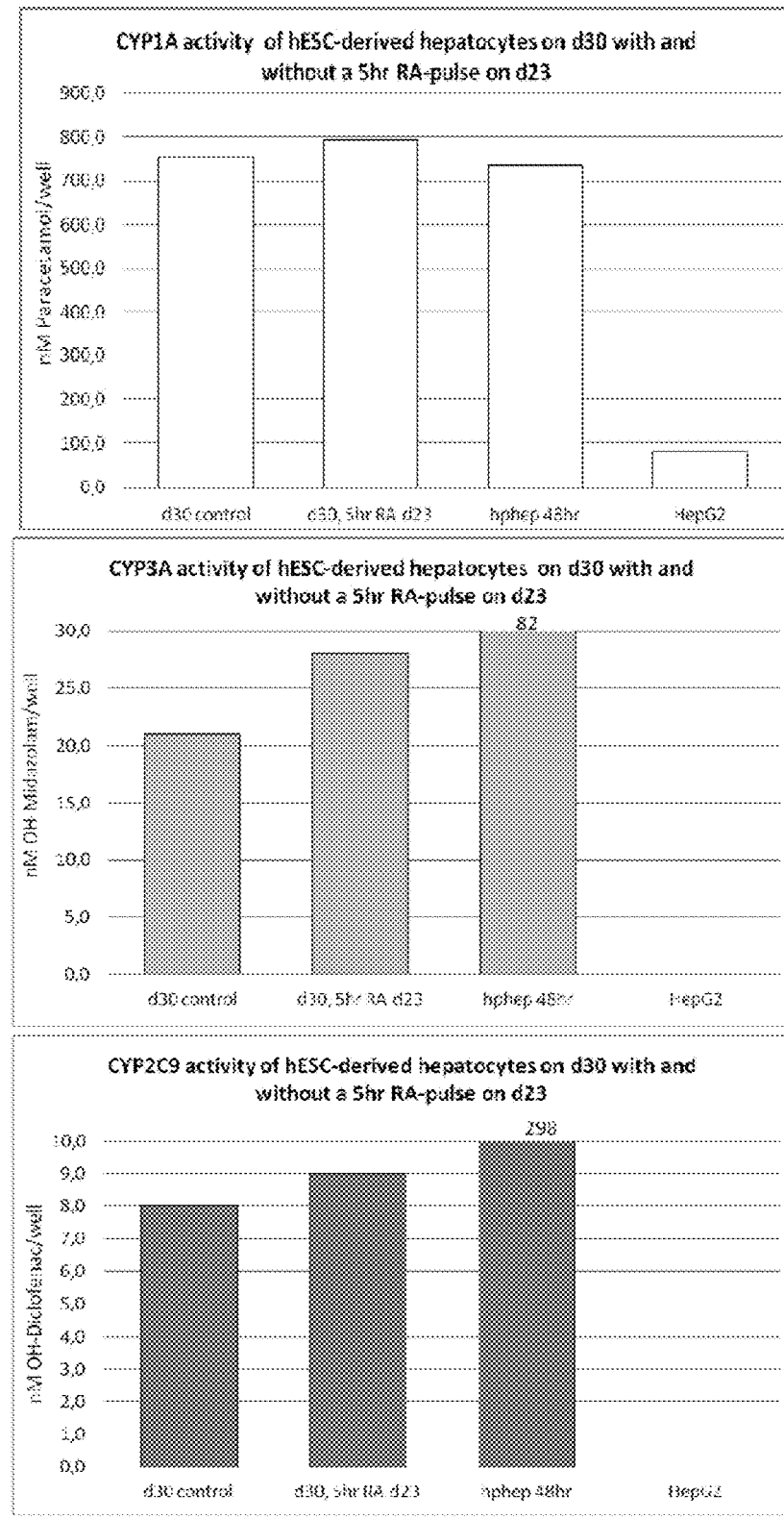
FIG. 2B. Functional expression of CYP1A and CYP3A in hESC-derived hepatocytes exposed to varying lengths of retinoic acid treatments on day 23 (measured on day 30).
Figure 2C:
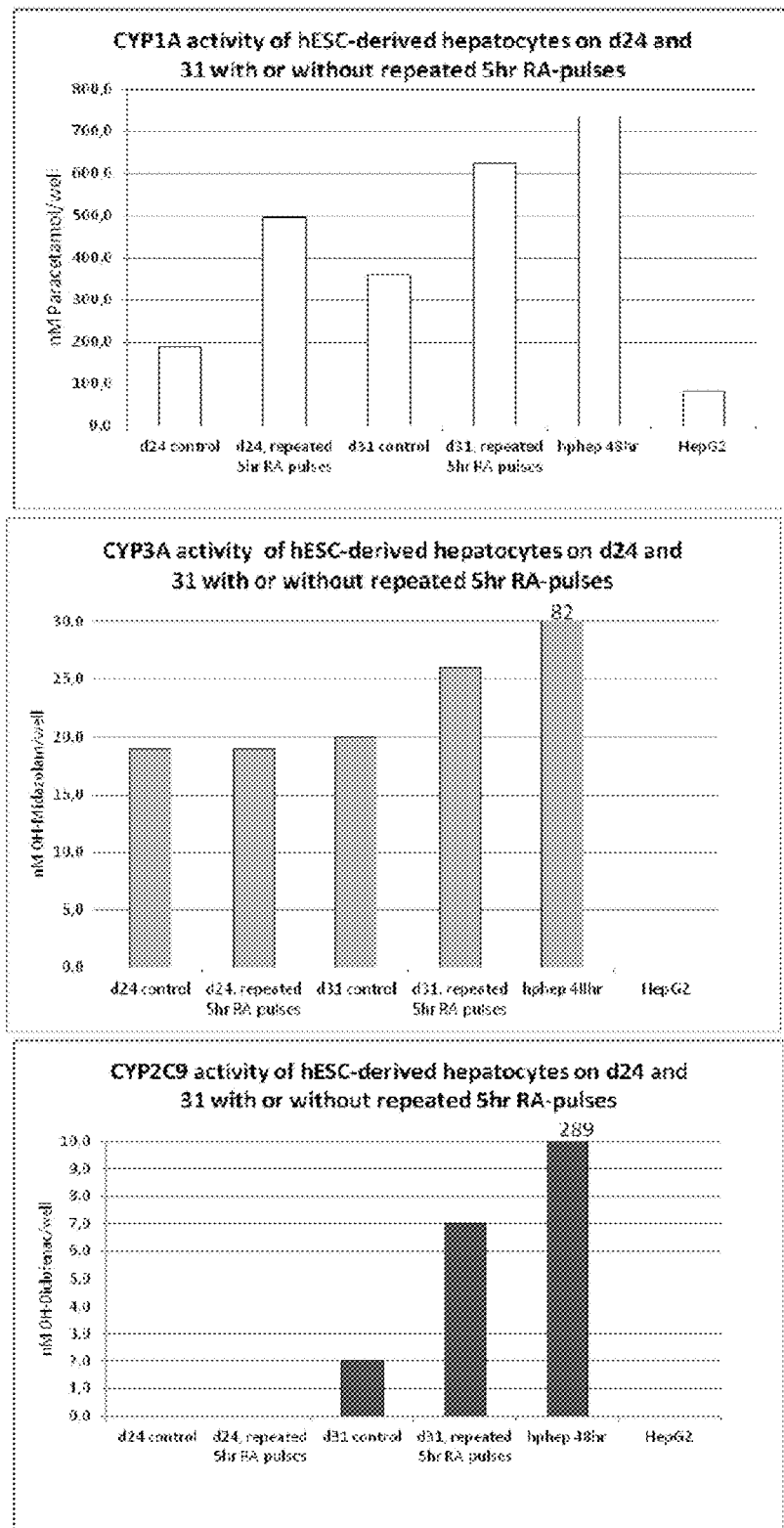
FIG. 2C. Functional expression of CYP1A, CYP3A and CYP2C9 in hESC-derived hepatocytes exposed to varying lengths of retinoic acid treatments on days 24 or 31.

B) 7 days after a single 5 hr RA-exposure on day 23 of the protocol (i.e. on day 9 of the differentiation and maturation phase) hESC-derived hepatocytes still have increased CYP1A, 2C9 and 3A activities compared with untreated cells. However the increase in CYP1A and 2C9 activity is higher after 5 repeated 5 hr exposures (see FIG. 2C).

C) 5 repeated 5 hr RA pulses on days 11, 16, 23, 25 and 30 of the protocol (i.e. on day 4 of the hepatic progenitor step and days 2, 9, 11 and 16 of the maturation step) lead to a significant increase of CYP1A-, 2C9- and 3A-activity on day 31 of the protocol. However, on day 24 of the protocol an increase of CYP1A-, but not of CYP3A-activity could be observed (no CYP2C9-activity detectable on day 24 of the protocol). Thus, repeated 5 hr RA-exposures have a stronger increasing effect on CYP1A and 2C9 activity than one single 5 hr RA-exposure (comp. to FIG. 2B).

D) A comparison of 5, 24, 48 hr exposures and continuous treatment shows that the strongest increase of CYP3A activity is obtained with continuous RA-treatment compared to 5, 24 and 48 hr RA-exposures whereas the strongest increase of CYP1A activity is observed after a 24 hr RA-exposure.

The strongest increase in expression of CYP2C9 is observed with repeated 5 hr exposure commencing on d24 (i.e. day 12 of the differentiation and maturation phase). Therefore the skilled person wishing to effect an increase in a particular CYP gene may select from these pulse conditions according to their gene of interest.

Example 5

Treatment with 9 Cis-Retinoic Acid (RA) Induces a More Adult Phenotype in hESC-Derived Hepatocyte-Like Cells Procedure:

Following the basic protocol A, hES cell derived hepatocyte-like cells cultured on a Gelatin-based coating were treated with 1 μM 9-cis retinoic acid for 5 hr on day 21 of the protocol (i.e. on day 7 of the differentiation and maturation phase) or 24 hr on day 22-23 of the protocol (i.e. on day 8-9 of the differentiation and maturation phase).

Figure 3C:
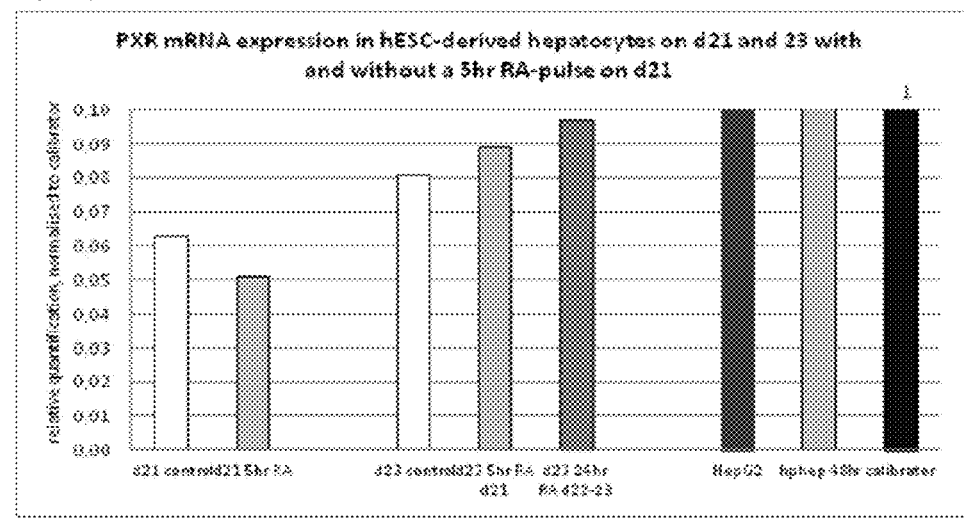
FIG. 3C. mRNA expression of PXR in hESC-derived hepatocytes exposed to 5hr of retinoic acid treatment on days 21 or 24hr of retinoic acid treatment on day 22-23 (measured on days 21 and 23).
Figure 3D:
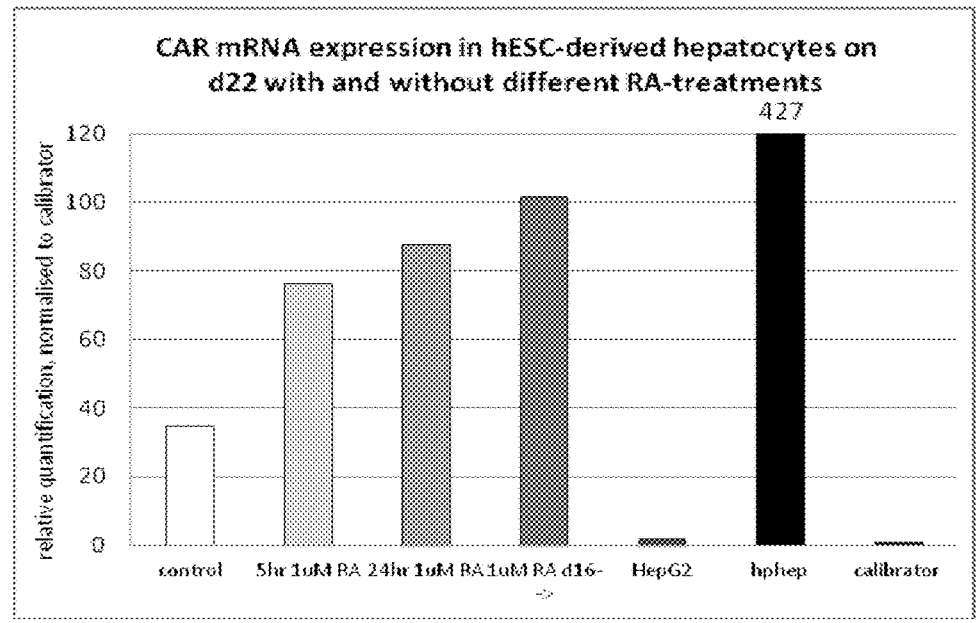
FIG. 3D. mRNA expression of CAR in hESC-derived hepatocytes exposed to 5hr of retinoic acid treatment on days 22, 24hr of retinoic acid treatment on day 21-22 or long-term exposure starting day 16 (measured on days 22).
Figure 3E:
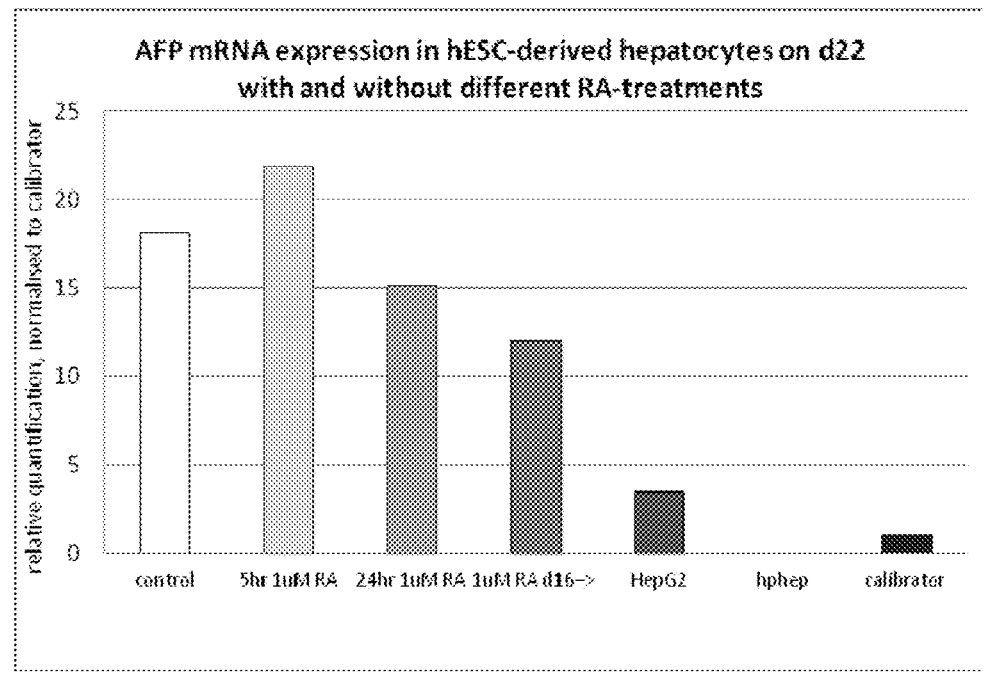
FIG. 3E. mRNA expression of AFP in hESC-derived hepatocytes exposed to 5hr of retinoic acid treatment on days 22, 24hr of retinoic acid treatment on day 21-22 or long-term exposure starting day 16and onwards (measured on days 22).

Cells were harvested on day 21 or 23 of the protocol (i.e. on day 7 or 9 of the differentiation and maturation phase) and gene expression was analysed using qRT-PCR, normalised to the house-keeping gene CREBBP and the results presented as relative quantification normalised to a calibrator (FIG. 3.)

Results:

A) An increase of mRNA expression of the adult hepatic gene CYP3A4 is observed immediately after a 5 RA-exposure on day 21 (i.e. on day 7 of the differentiation and maturation phase) as well as 2 and 7 days later (on day 23 and 30 of the protocol, respectively), Also a 24 hr RA-exposure on day 22-23 of the protocol (i.e. on day 8-9 of the differentiation and maturation phase) lead to an immediate up-regulation of adult CYP3A4 expression on day 23 (i.e. on day 9 of the differentiation and maturation phase).

B) A 5 hr exposure on day 21 (i.e. on day 7 of the differentiation and maturation phase) decreases expression of the fetal hepatic gene CYP3A7 slightly immediately after the exposure on day 21 and strongly 2 days later on day 23 of the protocol (i.e. on day 9 of the differentiation and maturation phase). Similarly, a 24 hr RA-exposure on day 22-23 of the protocol (i.e. on day 8-9 of the differentiation and maturation phase) strongly decreases expression of the fetal hepatic gene CYP3A7 immediately after the exposure on day 23 of the protocol (i.e. on day 9 of the differentiation and maturation phase).

C) A 5 hr exposure on day 21 (i.e. on day 7 of the differentiation and maturation phase) increases mRNA expression of the adult hepatic gene PXR on day 23 (i.e. on day 9 of the differentiation and maturation phase), but not immediately after the 5 hr exposure on day 21 (i.e. on day 7 of the differentiation and maturation phase).

A 24 hr RA-exposure on day 22-23 of the protocol (i.e. on day 8-9 of the differentiation and maturation phase) also increases mRNA expression of the adult hepatic gene PXR expression.

D,E) Continuous/long-term RA treatment leads to higher increase of mRNA expression of the adult hepatic gene CAR (D) and a stronger down-regulation of the fetal hepatic gene α-Fetoprotein (AFP, E) than 5 and 24 hr RA exposures on d22 and day 21-22, respectively (day8 and day 7-8 of the differentiation and maturation phase, respectively).

In this case it can be seen that exposure to RA at d21 (at the end of the hepatic progenitor phase) leads to an increase in the expression of adult genes CYP3A4, CAR and PXR and a decrease in fetal genes AFP and CYP3A7, thus showing that a more mature and adult phenotype is achieved. The skilled person can further refine this method by selecting 5 hr pulse, 24 hours pulse or continuous treatment if there is one specific gene or group of genes from within this set which they wish to up or down regulate.

Example 6

Effect of Treatment of hESC- and hiPSC-Derived Hepatocyte-Like Cells with 9 Cis-Retinoic Acid (RA), Kenpaullone (K) and a Thin Fibronectin-Collagen I-Overlay (thin FC-Overlay) on CYP Activity Procedure:

Following the basic protocol B, differentiating hES cell derived hepatic progenitor cells and hepatocyte-like cells cultured on a Fibronectin-based coating were treated with continuous/long term treatment with 0.2 μM 9cis-retinoic acid and 0.5 μM Kenpaullone starting on day 14 of the protocol (i.e. day 1 of the differentiation and maturation phase) and received thin Fibronectin-Collagen I-overlays on day 14 and 16 of the protocol (i.e. day 1 and 3 of the differentiation and maturation phase) and is refreshed thereafter once a week on day 23, 30, 37 and so on (i.e. on day 9, 16, 23 and so on of the differentiation and maturation phase). This combination of thin Fibronectin-Collagen I-overlay, RA and Kenpaullone is called henceforth "RA+matrix overlay+Kenpaullone".

The thin Fibronectin-Collagen 1-overlay is applied as following: Prepare a 3 mg/ml rat tail Collagen I-solution by diluting the Collagen I stock with 0.02M acetic acid. Pre-warm the cell culture medium to room temperature and add 8 μl of the 3 mg/ml Collagen I-solution per ml medium (=25 μg Collagen I/ml) and 50 μl of a 1 mg/ml Fibronectin solution per ml medium (=50 μg Fibronectin/ml). Remove the old medium from the cultures and add 0.5 ml of the Collagen I and Fibronectin-containing medium per cm$^2$ culture surface (=12.5 μg Collagen I/cm$^2$ and 25 μg Fibronectin/cm$^2$). For refreshing the overlay once a week, add 4 μl of the 3 mg/ml Collagen I-solution per ml medium (=6.25 μg/ml) and 10 μl of a 1 mg/ml Fibronectin solution per ml medium (=5 μg/ml).

For analysing functional expression of CYP enzymes, the cell cultures are subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 26 µM Phenacetin (model substrate for CYP1A), 9 µM Diclofenac (model substrate for CYP2C9) and 3 µM Midazolam (model substrate for CYP3A), is added to the cells (e.g. 220 µl/24 well) and incubated for 16 hr at 37° C. Then supernatant is collected and centrifuged for 20 min at 10.000 rcf at 4° C. Subsequently, 120 µl of the supernatant is transferred into a 96 well plate which is sealed with a tight seal tape and stored at −20 or −80° C. until LC/MS-analysis of metabolite formation: Acetaminophen (Paracetamol) for CYP1A, OH-Diclofenac for CYP2C9 and OH-Midazolam for CYP3A, Results:

The inventors have found that, further to the use of RA alone, the combination of continuous/long term treatment with a thin Fibronectin-Collagen I-overlay, 0.5 µM Kenpaullone, and 0.2 µM RA [henceforth "RA+matrix overlay+Kenpaullone] (starting on day 14 and onwards, i.e. starting on day 1 of the differentiation and maturation phase) reproducibly increases CYP activity in hESC-derived hepatocytes (FIGS. 4 A, B) and hiPSC-derived hepatocytes (FIG. 4 C) and thus induces a more adult hepatocyte phenotype (more similar to human primary hepatocytes)

A) The combination of continuous treatment of hESC-derived hepatocytes treated with 0.2 µM RA and 0.5 µM Kenpaullone (starting on day 14 and onwards) and the application of a thin Fibronectin-Collagen I-overlay is the only experimental group which has both increased CYP2C9- and 3A-activity on day 36 of the protocol (i.e. day 22 of the differentiation and maturation phase). However, some single or double treated groups also showed increase of CYP2C9- and 3A-activity, but none had both high CYP2C9- and 3A-activity. CYP1A activity is highest with overlay alone. HepG2 only show CYP1A activity and no 2C9 or 3A activity.

B,C) The combination of continuous/long term treatment with a thin Fibronectin-Collagen I-overlay, 0.5 µM Kenpaullone, and 0.2 µM RA (starting on day 14 and onwards) reproducibly increases CYP1A, 2C9 and 3A activity in hESC-derived and hiPSC-derived hepatocytes.

The expression levels of various CYP genes and other markers associated with a mature hepatic phenotype have been further examined in the following examples, which provide more detailed guidance for those wishing to improve mature hepatic phenotype using this triple combination.

Example 7

Increase in Expression of Hepatic Phase I and Phase II Enzymes, Drug Transporters and Nuclear Receptors in Hepatocyte-Like Cells Procedure:

Following the basic protocols B (FIG. 5), C (hESC-derived hepatocytes in FIG. 6) or D (hiPSC-derived hepatocytes in FIG. 6), differentiating hPS cell derived hepatic progenitor cells and hepatocyte-like cells cultured on a Fibronectin-based coating were treated with continuous/long term treatment with 0.2 µM 9cis-RA and 0.5 µM Kenpaullone starting on day 14 of the protocol (i.e. on day 1 of the differentiation and maturation phase) and received thin Fibronectin-Collagen I-overlays on day 14 and 16 of the protocol (i.e. on day 1 and 3 of the differentiation and maturation phase) and is refreshed thereafter once a week on day 23, 30, 37 and so on (i.e. on day 9, 16, 23 and so on of the differentiation and maturation phase).

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 µl of the 3 mg/ml Collagen I-solution per ml medium (=25 µg Collagen I/ml) and 50 µl of a 1 mg/ml Fibronectin solution per ml medium (=50 µg Fibronectin/ml). Remove the old medium from the cultures and add 0.5 ml of the Collagen I and Fibronectin-containing medium per $cm^2$ culture surface (=12.5 µg Collagen I/$cm^2$ and 25 µg Fibronectin/$cm^2$). For refreshing the overlay once a week, add 4 µl of the 3 mg/ml Collagen I-solution per ml medium (=6.25 µg/ml) and 10 µl of a 1 mg/ml Fibronectin solution per ml medium (=5 µg/ml).

Figures 5, 5A:
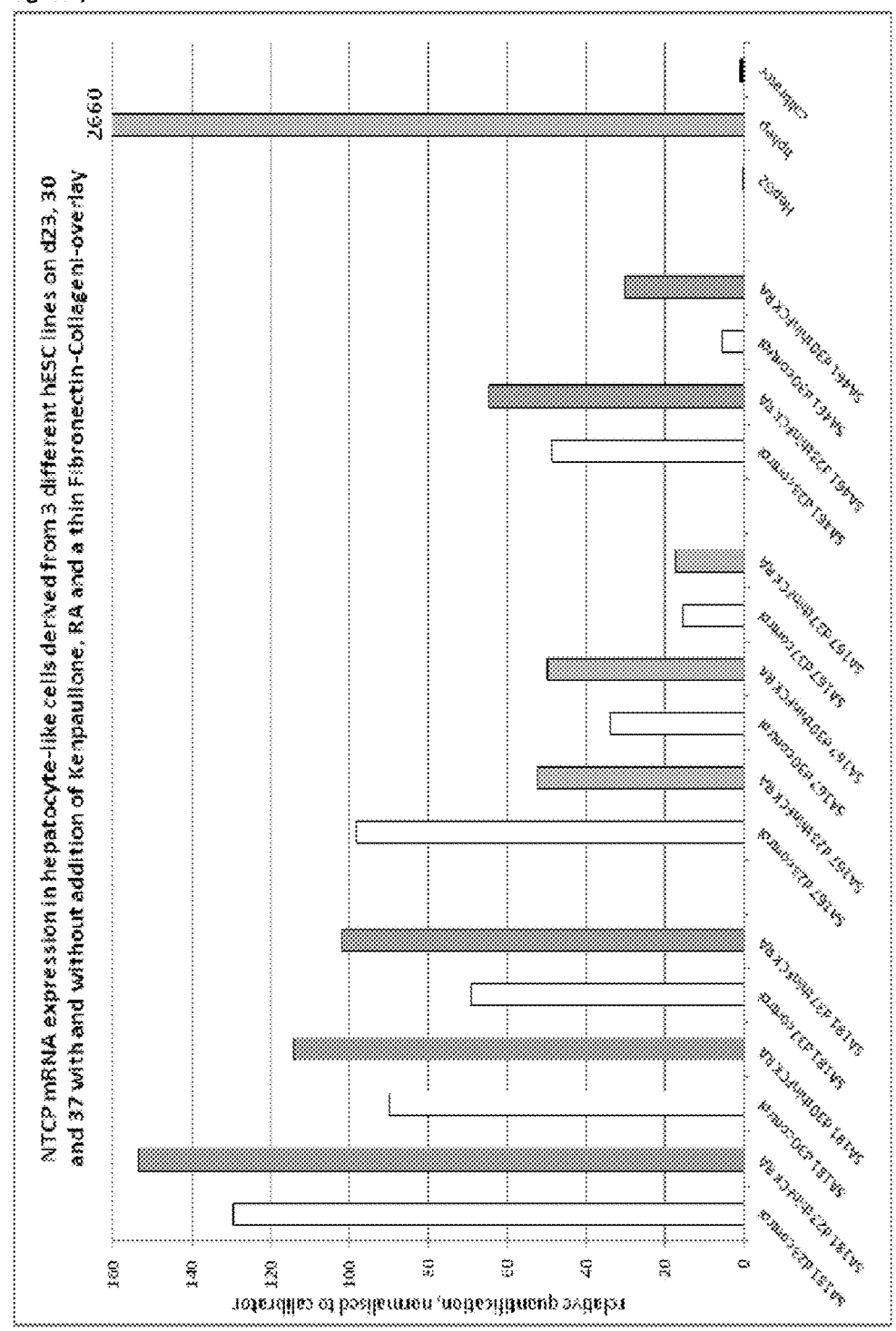
Figures 6, 6A:
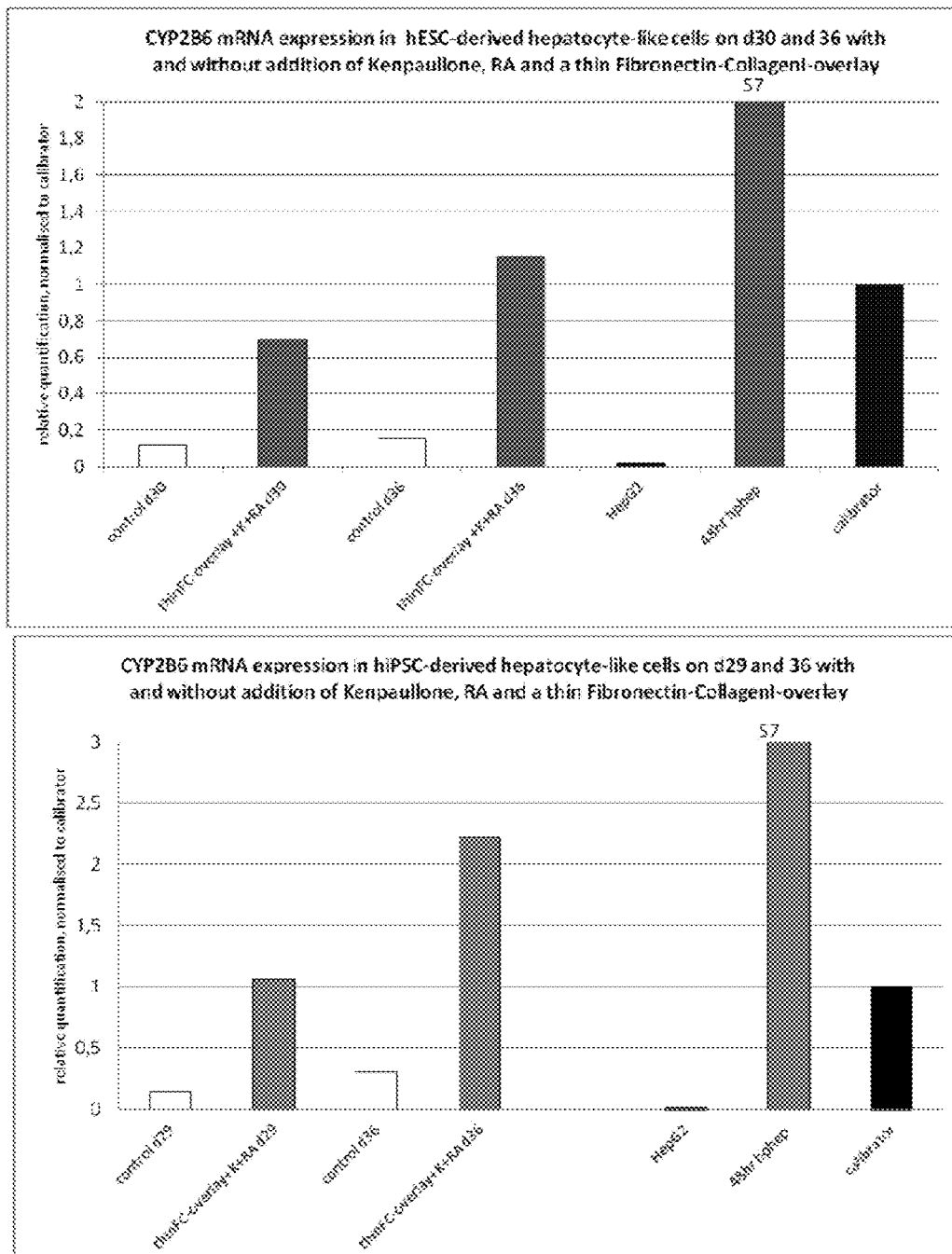
Figure 6B:
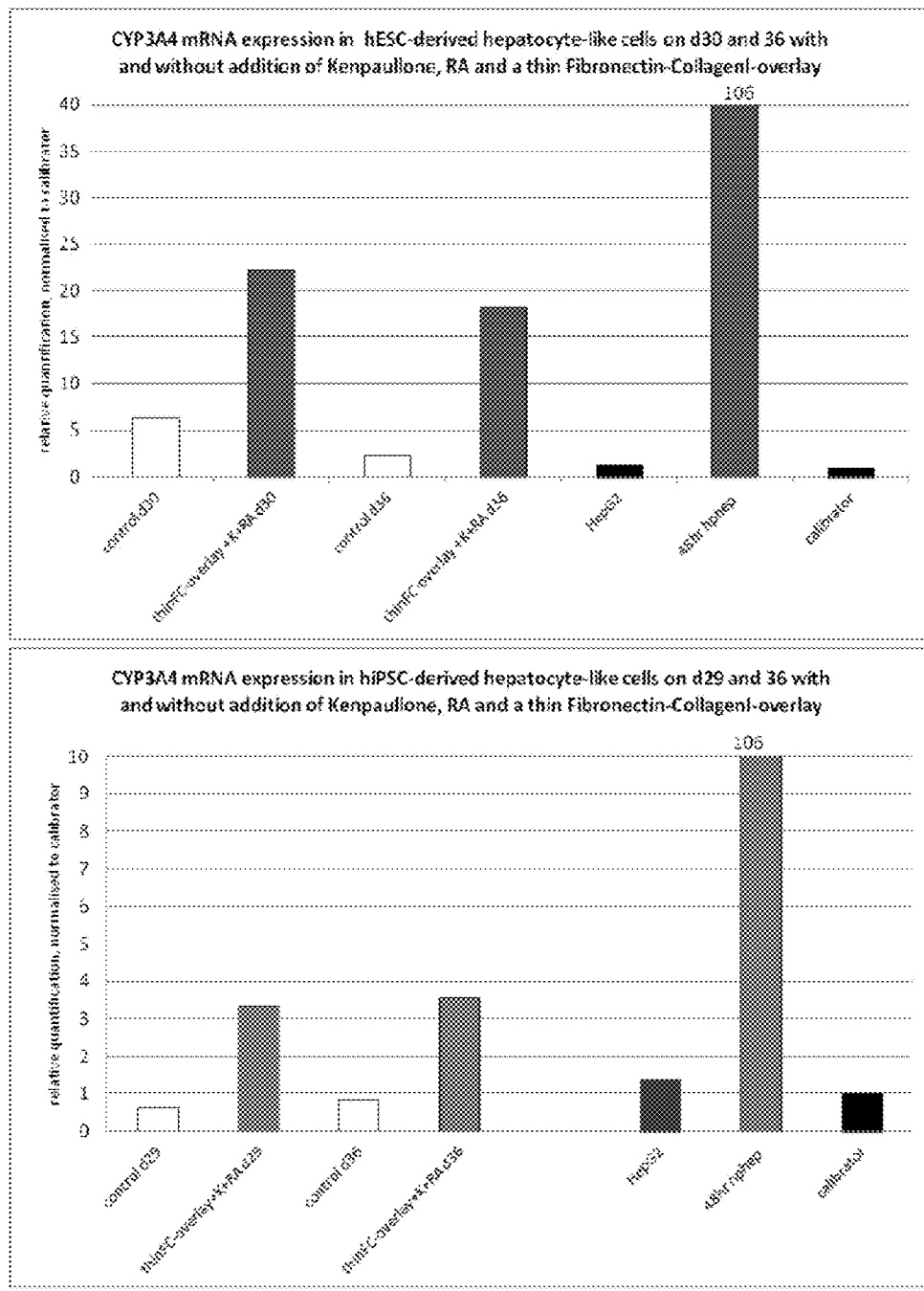
FIG. 6B. mRNA expression of CYP3A4 in hESC- and hiPSC-derived hepatocyte-like cells (derived with basic protocols C and D, respectively) exposed to retinoic acid, Kenpaullone and a matrix overlay.
Figure 6F:
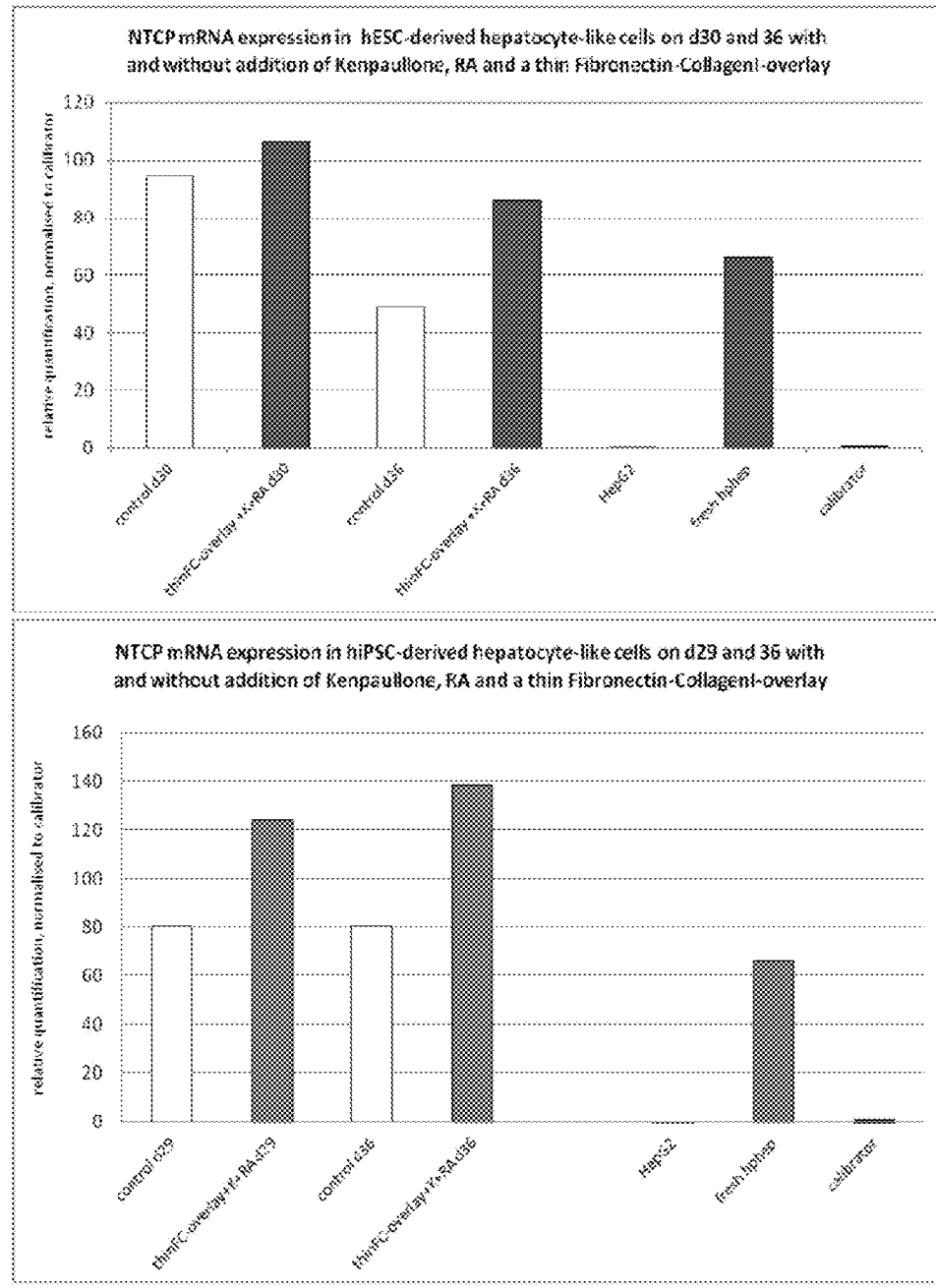
FIG. 6F. mRNA expression of NTCP in hESC- and hiPSC-derived hepatocyte-like cells (derived with basic protocols C and D, respectively) exposed to retinoic acid, Kenpaullone and a matrix overlay.
Figure 6G:
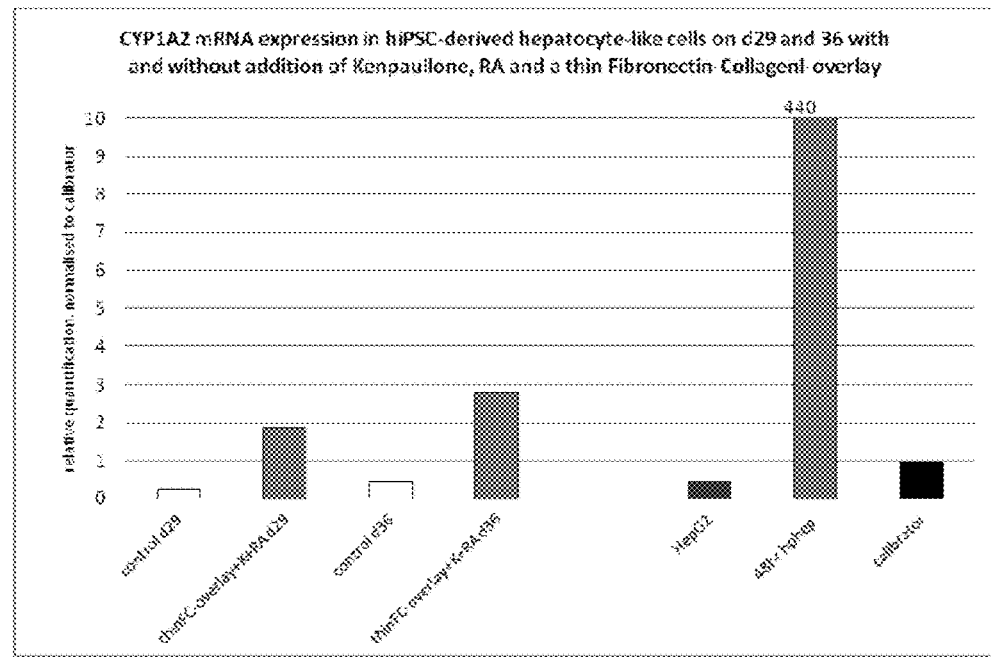
FIG. 6G. mRNA expression of CYP1A2 in hiPSC-derived hepatocyte-like cells (derived with basic protocol D) exposed to retinoic acid, Kenpaullone and a matrix overlay.

Cells were harvested on day 23, 30 and 36/37 of the protocol (i.e. on day 9, 16 and 22/23 of the differentiation and maturation phase) and gene expression was analysed using qRT-PCR, normalised to the house-keeping gene CREBBP, and the results presented as relative quantification normalised to a calibrator (FIGS. 5 and 6).

Results:

FIGS. 5 and 6 summarise results from several experiments where several hESC lines (FIG. 5) or hESC and hiPSC (FIG. 6) from several independent lines were used to generate hepatocyte-like cells. Those were then exposed to a combination of retinoic acid, Kenpaullone and matrix overlay before being assayed by QRT-PCR for mRNA expression of a number of markers for mature hepatocytes including NTCP, GSTA1-1, CAR, CYP2B6, CYP2C9, CYP3A4, CYP3A5, CYP1A2, CYP2D6.

FIG. 5 A-F) Upon treatment with a combination of RA, Kenpaullone and matrix overlay, hepatocyte-like cells derived from three different hESC-lines (SA181, SA167 and SA461; using basic protocol B) showed similar tendencies of increased mRNA expression of the adult hepatic markers NTCP, GSTA1-1, CAR, CYP2B6, CYP2C9, and CYP3A4 on day 23, 30 and 37 of the protocol (i.e. on day 9, 16 and 23 of the differentiation and maturation phase).

FIG. 6 A-G) Upon treatment with a combination of RA, Kenpaullone and matrix overlay, both hepatocyte-like cells derived from hESC and hiPSC (using basic protocols C and D, respectively) showed similar increases of mRNA expression of the adult hepatic markers CYP2B6, CYP3A4, CYP3A5, CAR, GSTA1-1, NTCP and CYP1A2 on day 29 and 36 of the protocol (i.e. on day 15 and 22 of the differentiation and maturation phase).

Figures 4, 4A:
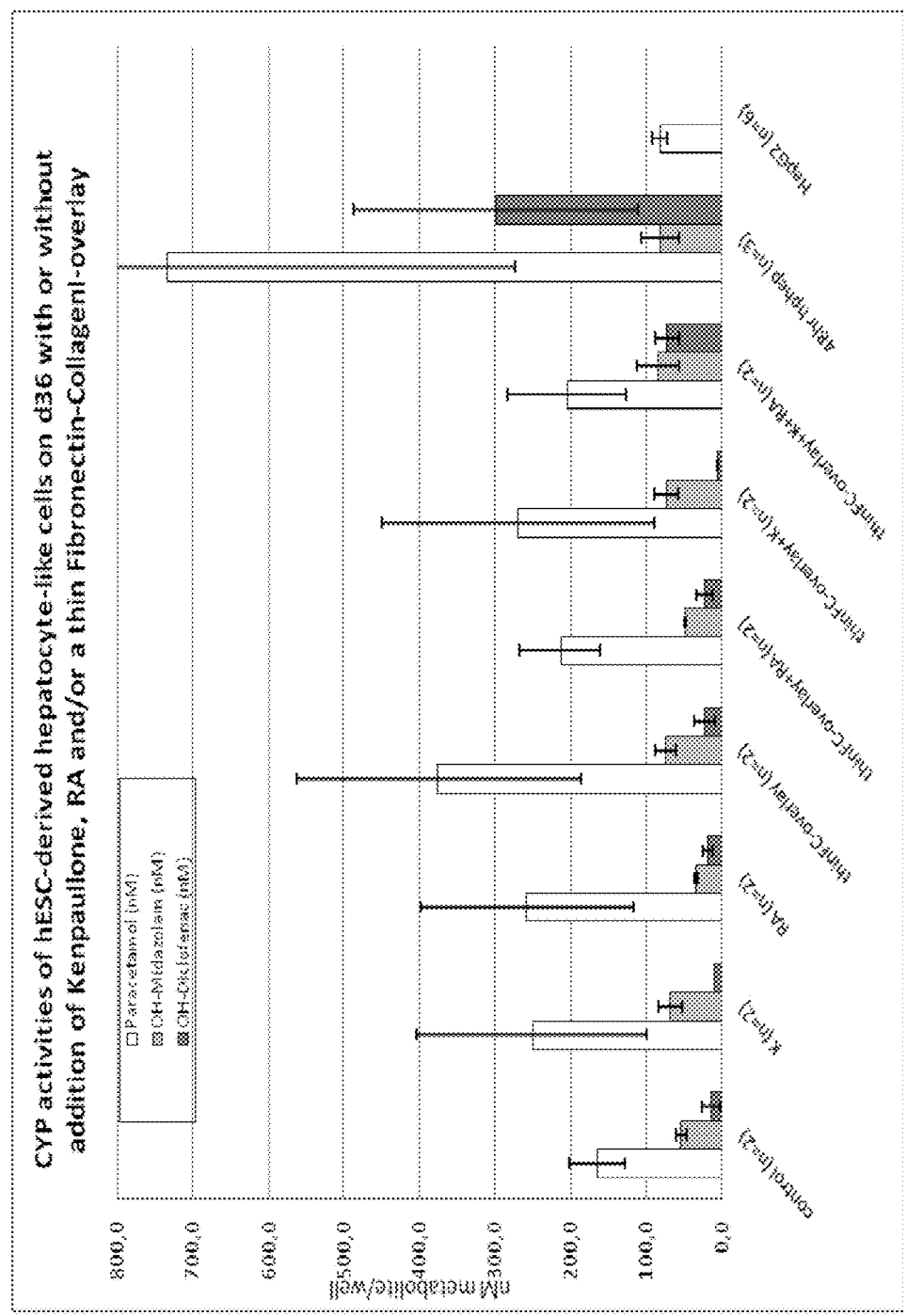
Figure 4B:
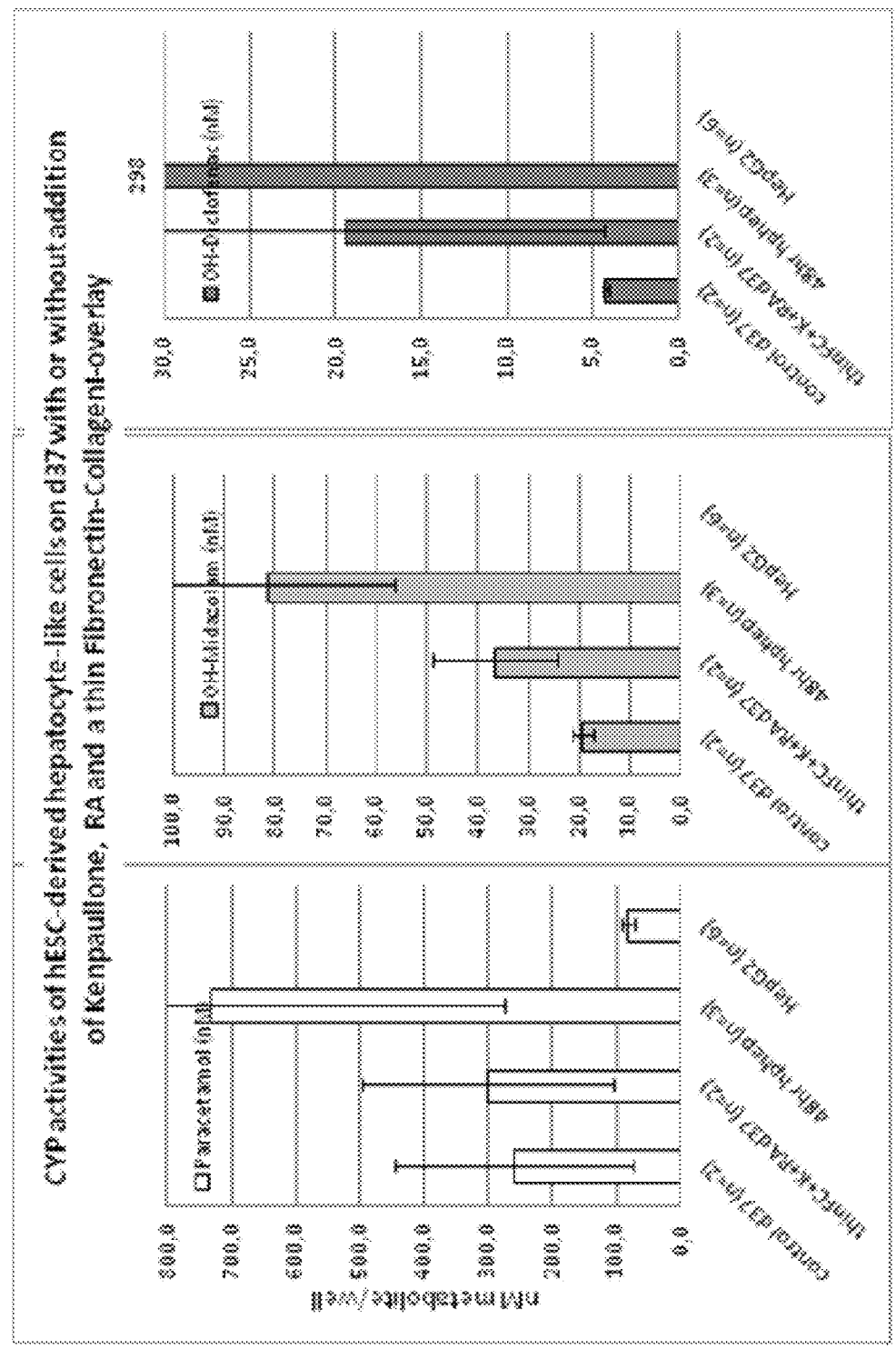
FIG. 4B. Functional expression of CYP enzymes in hESC-derived hepatocytes exposed to retinoic acid in combination with Kenpaullone and matrix overlay.

The combination of Kenpaullone, matrix overlay and RA shows a synergistic effect over exposures with RA alone (see e.g. CYP3A4 mRNA expression in FIG. 3A versus FIG. 5F, or CYP2C9 and 3A activity in FIG. 4A). The effect is consistent across several independent hESC lines and across an hiPS cell line, as illustrated in the paired images of FIG. 6 which compares gene expression in hESC- and hiPS-derived hepatocyte-like cells for a number of genes.

The skilled person may therefore select from a number of sources of pluripotent stem cell lines as starting material to implement the invention. The skilled person may also employ the results obtained in FIGS. 3, 5 and 6 to selectively upregulate one or more gene markers by selecting a treatment (RA exposure alone, or RA+matrix overlay+GSK-3 inhibitor or CDK inhibitor) and a specified time point(s) for treatment according to which markers they wish to upregulate.

Example 8

Increase in Expression of Hepatic Phase I and Phase II Enzymes, Drug Transporters and Nuclear Receptors in Hepatocyte-Like Cells: Pre-Exposure to DNA Demethylation Agent Procedure:

Following the basic protocols C (hESC-derived hepatocytes) or D (hiPSC-derived hepatocytes), differentiating hES and hiPS cells in the pre-endodermal phase were treated with 10 nM of the DNA demethylating agent 5-aza-2-deoxycytidine for 24 hr on day 2 to 3 of the protocol.

Later in the protocol, hPS cell derived hepatic progenitor cells and hepatocyte-like cells cultured on a Fibronectin-based coating were treated with continuous/long term treatment with 0.2 µM 9cis-RA and 0.5 µM Kenpaullone starting on day 14 of the protocol (i.e. on day 1 of the differentiation and maturation phase) and received thin Fibronectin-Collagen I-overlays on day 14 and 16 of the protocol (i.e. on day 1 and 3 of the differentiation and maturation phase) and is refreshed thereafter once a week on day 23, 30, 37 and so on (i.e. on day 9, 16, 23 and so on of the differentiation and maturation phase).

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 µl of the 3 mg/ml Collagen I-solution per ml medium (=25 µg Collagen I/ml) and 50 µl of a 1 mg/ml Fibronectin solution per ml medium (=50 µg Fibronectin/ml). Remove the old medium from the cultures and add 0.5 ml of the Collagen I and Fibronectin-containing medium per $cm^2$ culture surface (=12.5 µg Collagen I/$cm^2$ and 25 µg Fibronectin/$cm^2$). For refreshing the overlay once a week, add 4 µl of the 3 mg/ml Collagen I-solution per ml medium (=6.25 µg/ml) and 10 µl of a 1 mg/ml Fibronectin solution per ml medium (=5 µg/ml).

For analysis of mRNA expression (FIG. 9), cells were harvested on day 29 and 36 of the protocol (i.e. on day 15 and 22 of the differentiation and maturation phase) and gene expression was analysed using qRT-PCR, normalised to the house-keeping gene CREBBP, and the results presented as relative quantification normalised to a calibrator.

Figures 9, 9A:
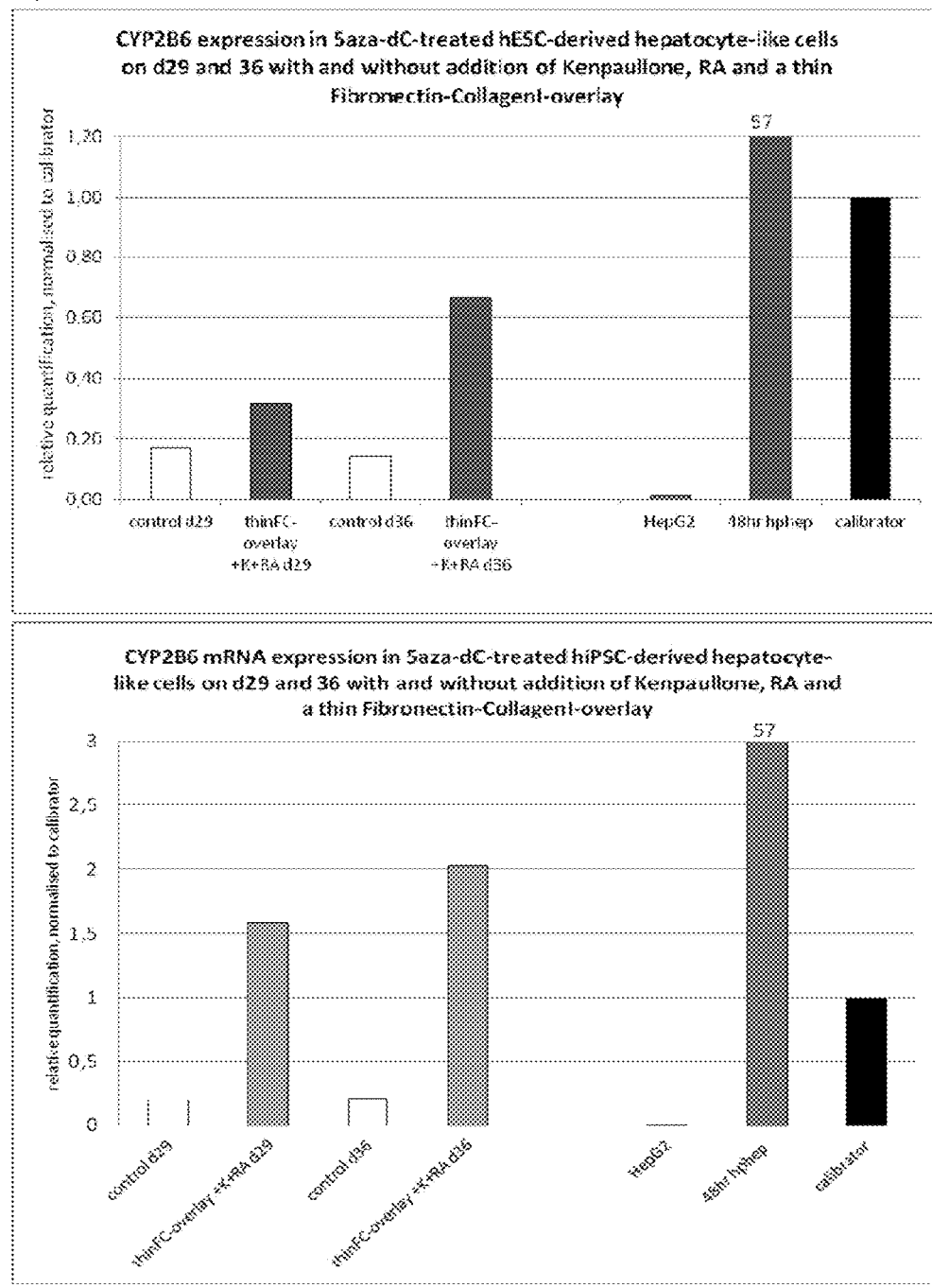
FIG. 9A. mRNA expression of CYP2B6 in hESC- and hiPSC-derived hepatocyte-like cells (derived with basic protocols C and D, respectively) treated early with 5-aza-deoxycytidine and exposed late to retinoic acid, Kenpaullone and a matrix overlay.
Figure 9D:
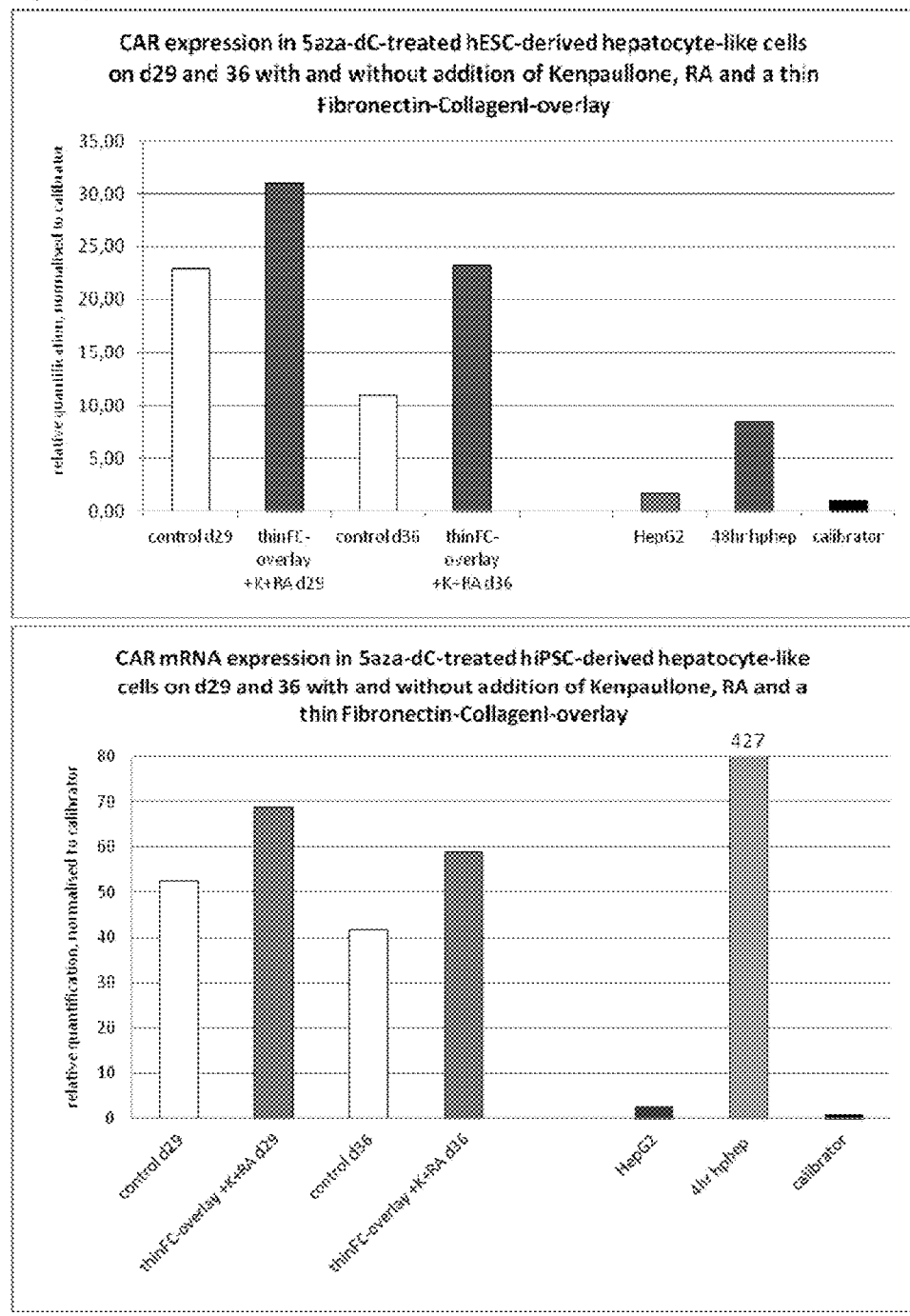
FIG. 9D. mRNA expression of CAR in hESC- and hiPSC-derived hepatocyte-like cells (derived with basic protocols C and D, respectively) treated early with 5-aza-deoxycytidine and exposed late to retinoic acid, Kenpaullone and a matrix overlay.
Figure 9E:
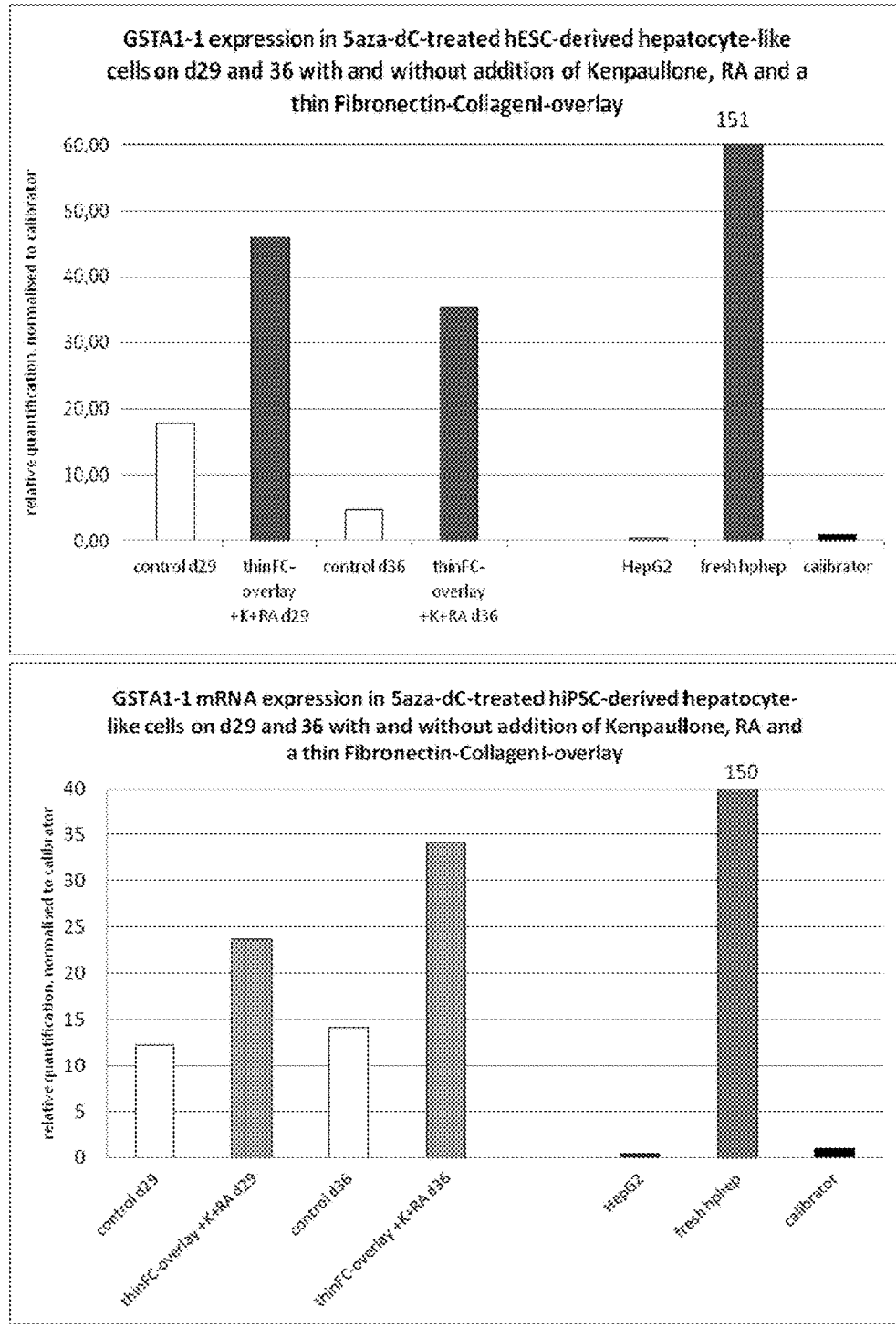
FIG. 9E. mRNA expression of GSTA1-1 in hESC- and hiPSC-derived hepatocyte-like cells (derived with basic protocols C and D, respectively) treated early with 5-aza-deoxycytidine and exposed late to retinoic acid, Kenpaullone and a matrix overlay.
Figures 10, 10A:
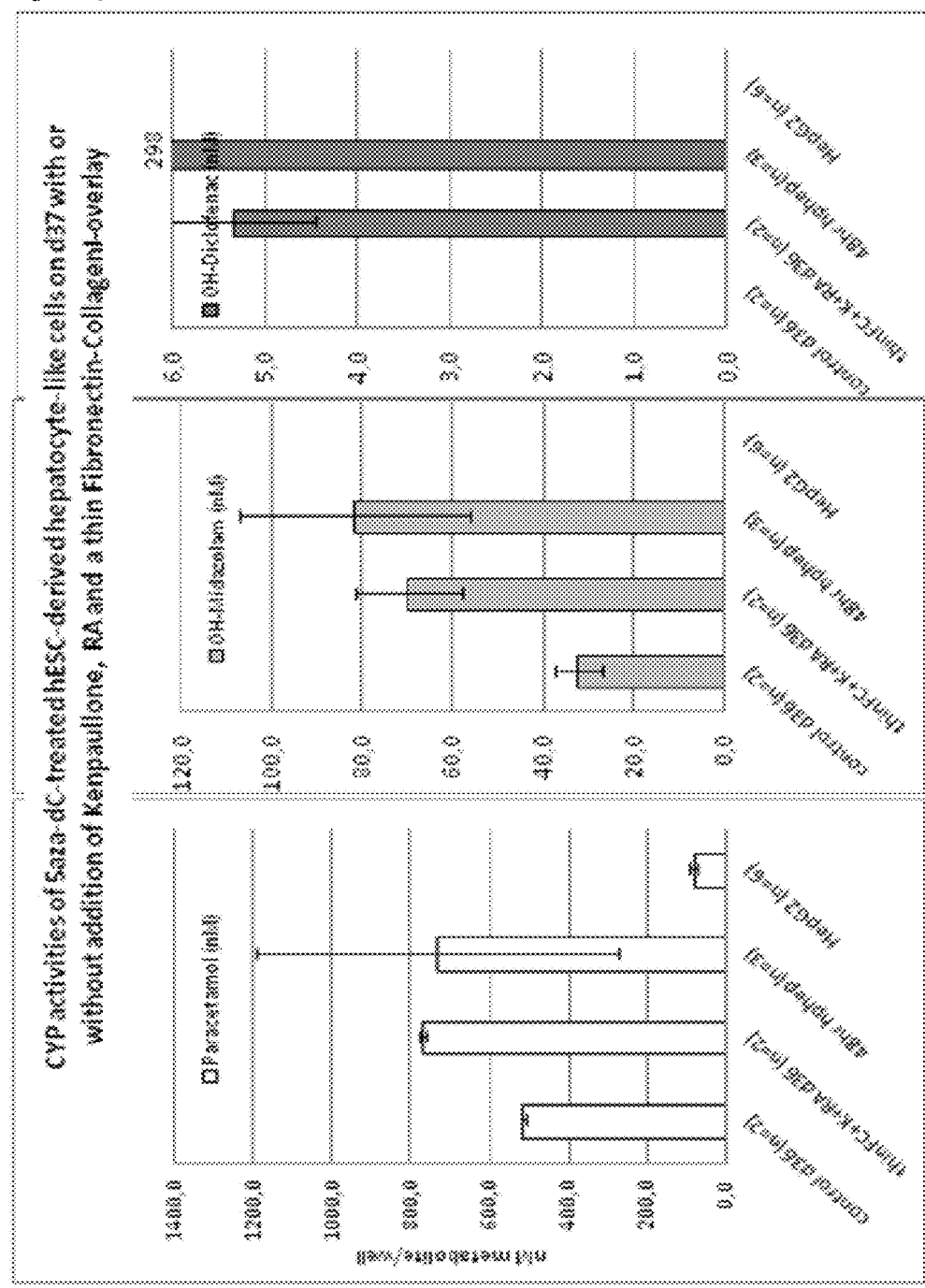
FIG. 10A. Functional expression of CYP enzymes in hESC-derived hepatocyte-like cells (derived with basic protocol) treated early with 5-aza-deoxycytidine and exposed late to retinoic acid, Kenpaullone and a matrix overlay.
Figure 10B:
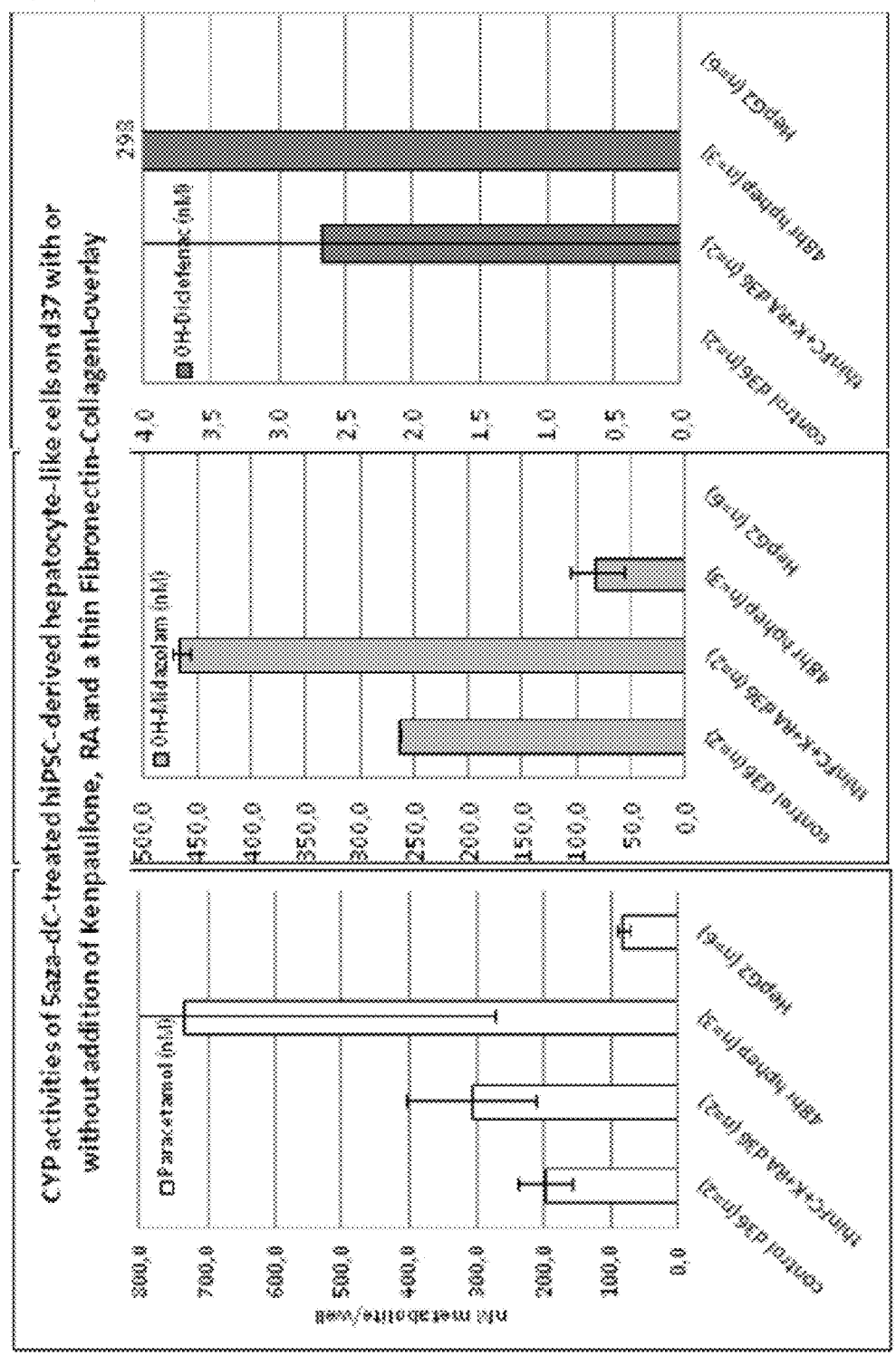
FIG. 10B. Functional expression of CYP enzymes in hiPSC-derived hepatocyte-like cells (derived with basic protocol D) treated early with 5-aza-deoxycytidine and exposed late to retinoic acid, Kenpaullone and a matrix overlay.

For analysing functional expression of CYP enzymes on day 36 (i.e. on day 22 of the maturation step; FIG. 10), the cell cultures are subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 26 µM Phenacetin (model substrate for CYP1A), 9 µM Diclofenac (model substrate for CYP2C9) and 3 µM Midazolam (model substrate for CYP3A), is added to the cells (e.g. 220 µl/24 well) and incubated for 16 hr at 37° C. Then supernatant is collected and centrifuged for 20 min at 10.000 rcf at 4° C. Subsequently, 120 µl of the supernatant is transferred into a 96 well plate which is sealed with a tight seal tape and stored at −20 or −80° C. until LC/MS-analysis of metabolite formation: Acetaminophen (Paracetamol) for CYP1A, OH-Diclofenac for CYP2C9 and OH-Midazolam for CYP3A, Results:

FIG. 9 A-G: Upon treatment with the demethylating agent 5-aza-2-deoxycytidine during the pre-endodermal phase and a combination of RA, Kenpaullone and matrix overlay during the differentiation and maturation phase, both hepatocyte-like cells derived from hESC and hiPSC showed similar increases of mRNA expression of the adult hepatic markers CYP2B6, CYP3A4, CYP3A5, CAR, GSTA1-1, NTCP and CYP1A2 on day 29 and 36 of the protocol (i.e. on day 15 and 22 of the differentiation and maturation phase).

FIG. 10 A,B: Treatment with a combination of RA, Kenpaullone and matrix overlay during the differentiation and maturation phase reproducibly increases CYP1A, 2C9 and 3A activity in hESC-derived and hiPSC-derived hepatocytes which were derived from hPS cells treated with the demethylating agent 5-aza-2-deoxycytidine during the pre-endodermal phase.

Figures 12, 12A:
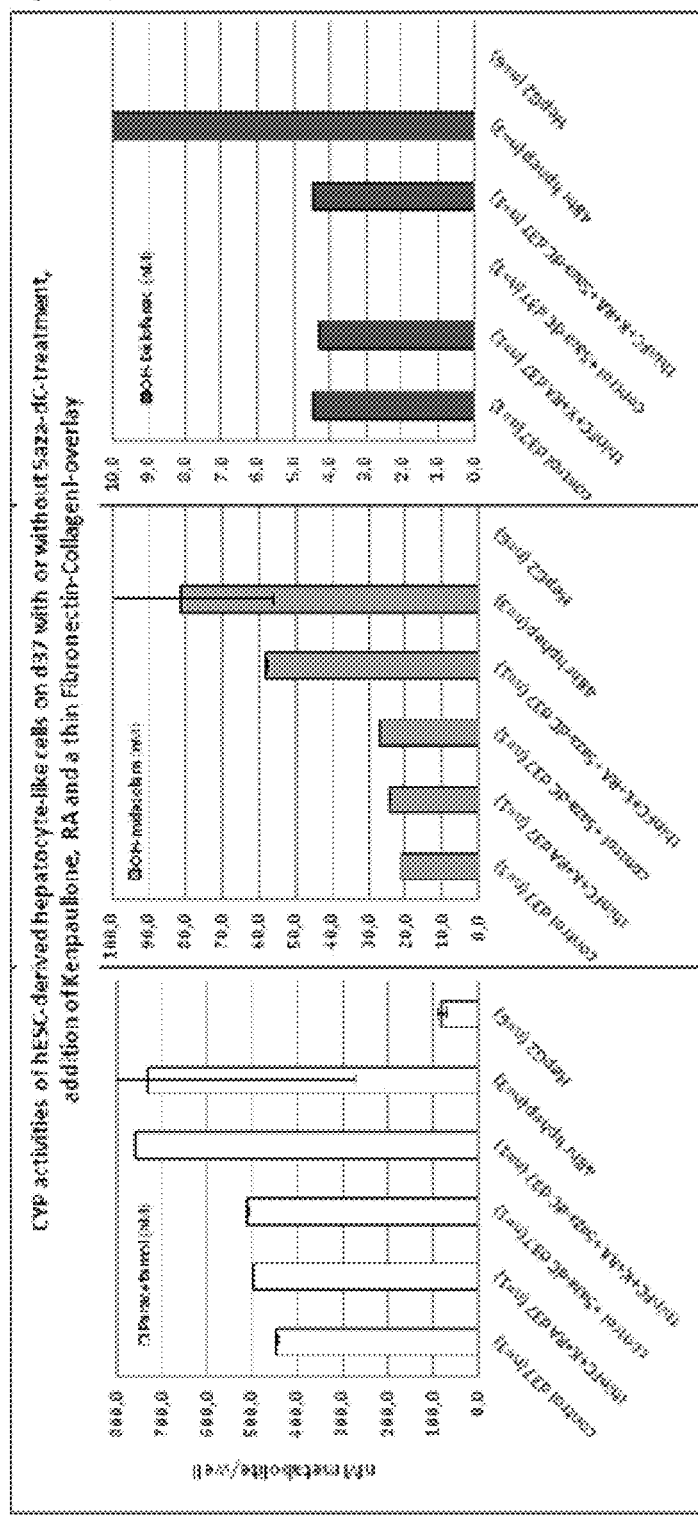
FIG. 12A. Comparison of functional expression of CYP enzymes in hESC -derived hepatocyte-like cells (derived with basic protocol C) with and without early treatment with 5-aza-deoxycytidine and with and without late exposure to retinoic acid, Kenpaullone and a matrix overlay.
Figure 12B:
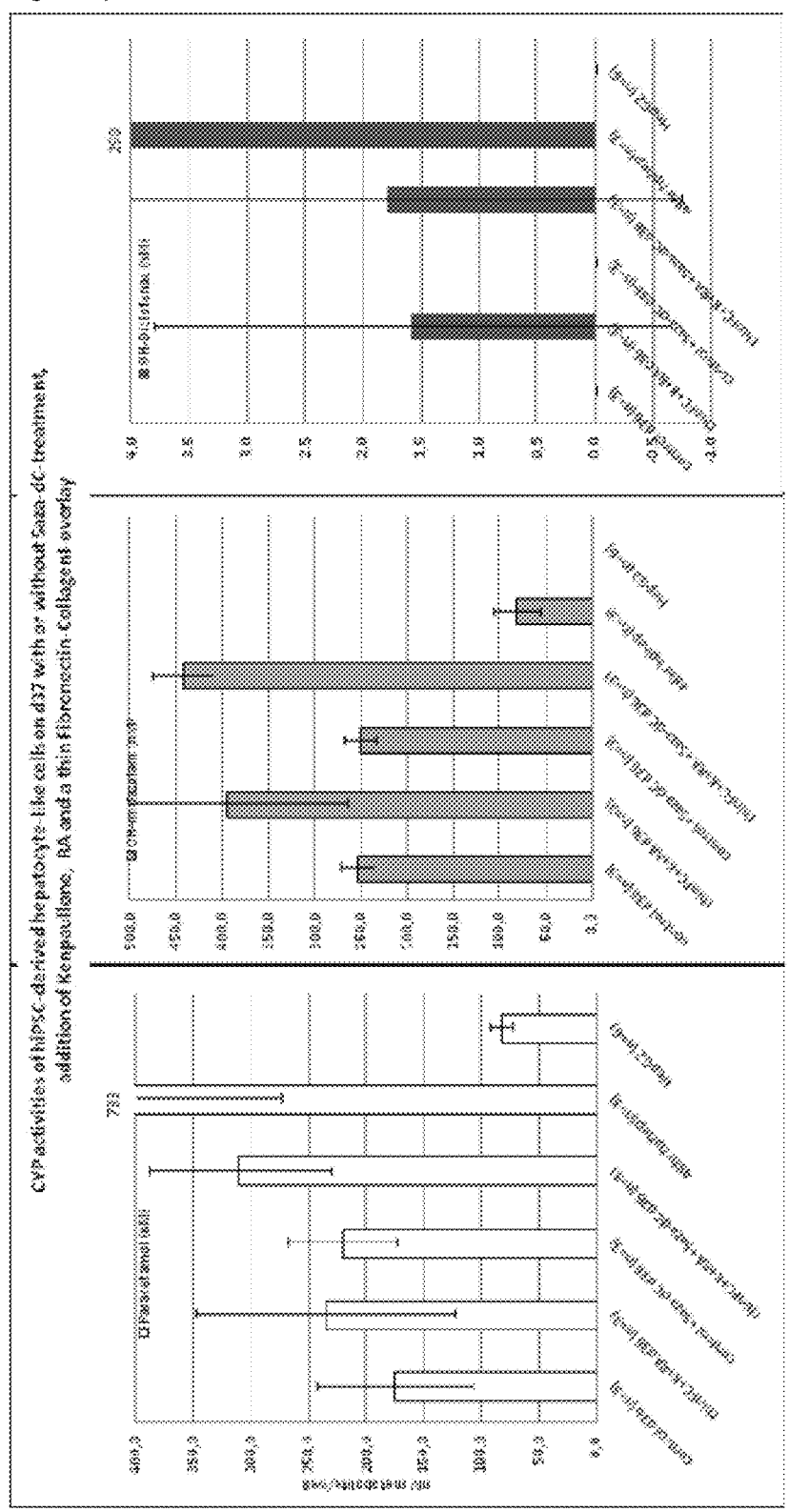
FIG. 12B. Comparison of functional expression of CYP enzymes in hiPSC-derived hepatocyte-like cells (derived with basic protocol D) with and without early treatment with 5-aza-deoxycytidine and with and without late exposure to retinoic acid, Kenpaullone and a matrix overlay.

FIG. 11: Corresponding morphology of cells can be seen in FIG. 11 which displays cell morphology of hESC- and hiPSC-derived hepatocyte-like cells where differentiating hPS cells were treated with DNA demethylation agent during pre-endodermal phase and obtained hepatocyte-like cells then exposed to matrix overlay in combination with Kenpaullone and RA. Images show that hepatic morphology is maintained for up to and beyond 42 days after initiation of hPS cell differentiation in the hepatocyte-like cells obtained by cell treatment with DNA demethylation agent, matrix overlay in combination with Kenpaullone and RA whereas untreated control cells start to die off or de-differentiate FIG. 12 A,B: Here a comparison of CYP activity in hESC- and hiPSC-derived hepatocytes obtained with or without treatment with the demethylating agent 5-aza-2-deoxycytidine on day 2-3 of the protocol and with or without continuous treatment with 0.2 µM 9cis-RA and 0.5 µM Kenpaullone during the differentiation and maturation phase is presented. For both CYP1A and 3A activity the highest values are obtained for hepatocyte-like cells treated with all 4 factors, 5-aza-2-deoxycytidine, matrix overlay, Kenpaullone and RA, suggesting a synergistic effect of those 4 factors on CYP1A and 3A activity and the induction of the most mature hepatic phenotype by combined treatment with all 4 factors. No additional increase on CYP2C9 activity could be observed due to treatment with a DNA demethylation agent.

The general trend seen here is that both hiPS and hESC-derived hepatocytes show increase in expression of mature markers; with treatment generating a small increase initially (d29) and a larger increase by d36. For example, FIG. 9A shows that the combination of DNA-demethylation treatment combined with later RA+matrix overlay +Kenpaullone gives an increase in expression of CYP2B6 in both hESC and iPS-derived hepatocyte-like cells, and that this increase is more marked at d36 than d29. The synergistic effect of combining early DNA-demethylation treatment with later RA+matrix overlay+Kenpaullone can be illustrated in, for example, the expression of NTCP (see FIG. 5A versus FIG. 9F) where higher fold NTCP expression is the result of this synergy. Once again, the skilled person may utilise the results exemplified in FIGS. 9 and 10 to improve overall hepatic phenotype of treated cells or to upregulate one or more selected gene markers.

Example 9

Stable CYP Expression in Hepatocyte-Like Cells Derived from hESC and hiPSC Treated with a Demethylating Agent, Retinoic Acid, Kenpaullone and a Matrix Overlay Procedure:

Following the basic protocols C (hESC-derived hepatocytes) or D (hiPSC-derived hepatocytes), cells in the DE-step were treated with 10 nM of the DNA demethylating agent 5-aza-2-deoxycytidine for 24 hr on day 2 to 3 of the protocol. Later in the protocol, hPS cell derived hepatic progenitor cells and hepatocyte-like cells cultured on a Fibronectin-based coating were treated with continuous/long term treatment with 0.2 μM 9cis-RA and 0.5 μM Kenpaullone starting on day 14 of the protocol (i.e. on day 1 of the maturation step) and received thin Fibronectin-Collagen I-overlays on day 14 and 16 of the protocol (i.e. on day 1 and 3 of the differentiation and maturation phase) and is refreshed thereafter once a week on day 23, 30, 37 and so on (i.e. on day 9, 16, 23 and so on of the differentiation and maturation phase).

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 μl of the 3 mg/ml Collagen I-solution per ml medium (=25 μg Collagen I/ml) and 50 μl of a 1 mg/ml Fibronectin solution per ml medium (=50 μg Fibronectin/ml). Remove the old medium from the cultures and add 0.5 ml of the Collagen I and Fibronectin-containing medium per $cm^2$ culture surface (=12.5 μg Collagen I/$cm^2$ and 25 μg Fibronectin/$cm^2$). For refreshing the overlay once a week, add 4 μl of the 3 mg/ml Collagen I-solution per ml medium (=6.25 μg/ml) and 10 μl of a 1 mg/ml Fibronectin solution per ml medium (=5 μg/ml).

For analysis of mRNA expression (FIG. 9), hESC- and hiPSC-derived hepatocytes were harvested on day 22, 29 and 36 of the protocol (i.e. on day 8, 15 and 22 of the maturation step) and human primary hepatocytes 4 and 48 hr after plating. Gene expression was analysed using qRT-PCR, normalised to the house-keeping gene CREBBP, and the results presented as relative quantification normalised to a calibrator.

For analysing CYP enzyme activity in hESC- and hiPSC-derived hepatocytes on day 22, 29 and 36 (i.e. on day 8, 15 and 22 of the maturation step) and human primary hepatocytes 4, 24, 48, 72 and 96 hr after plating, cell cultures were subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 26 μM Phenacetin (model substrate for CYP1A), 9 μM Diclofenac (model substrate for CYP2C9) and 3 μM Midazolam (model substrate for CYP3A), is added to the cells (e.g. 220 μl/24 well) and incubated for 16 hr at 37° C. Then supernatant is collected and centrifuged for 20 min at 10.000 rcf at 4° C. Subsequently, 120 μl of the supernatant is transferred into a 96 well plate which is sealed with a tight seal tape and stored at −20 or −80° C. until LC/MS-analysis of metabolite formation: Acetaminophen (Paracetamol) for CYP1A, OH-Diclofenac for CYP2C9 and OH-Midazolam for CYP3A, Results:

The inventors have further investigated the long-term effects of early DNA-demethylation treatment combined with late RA+matrix overlay+Kenpaullone to determine whether hepatic phenotype and expression of hepatic markers genes is maintained after long periods in culture.

FIG. 16 A,B: HESC and hiPSC-derived hepatocyte-like cells obtained by treatment with a DNA demethylating agent during early endodermal development and exposure to retinoic acid, Kenpaullone and matrix overlay during the differentiation and maturation phase show a surprisingly stable or increasing level of CYP1A, 2C9 and 3A activity (FIG. 16 A-2) as well as a stable or increasing mRNA expression of several CYPs (FIG. 16 B) in contrast to human primary hepatocytes which typically quickly lose CYP activity and mRNA expression in culture. HepG2 have very low or no expression of many adult hepatic genes. Thus the skilled person may employ this treatment technique and be assured that long-term maintenance of hepatic phenotype is possible; they may further tailor a treatment programme based on this and on previous examples should they wish to generate long-term expression of just one or more specific markers.

Example 10

Validation of Improved Definitive Endoderm Phenotype in hESC- and hiPSC-Derived DE Treated with a DNA Demethylation Agent Procedure:

Following the basic protocol C (both for hESC- and hiPSC-derived hepatocytes), cells were treated with 10 nM 5-aza-2-deoxycytidine at different time points and for different durations during the pre-endodermal phase, e.g. on day 2-3, 2-4, 3-4 and 4-6 of the protocol (hESC-DE: no 5azadC n=4, 5azadC d2-3 n=4, d3-4 n=1, d2-4 n=1, d4-6 n=1; hiPSC-DE: no 5azadC n=5, 5azadC d2-3 n=5, d3-4 n=2, d2-4 n=1, d4-6 n=1; with n being the number of individual experiments).

For analysis of mRNA expression, hESC- and hiPSC-derived DE-cells were harvested on day 7 of the protocol and gene expression was analysed using qRT-PCR, normalised to the house-keeping gene CREBBP, and the results presented as relative quantification normalised to a calibrator.

Results:

FIG. 13A:

DE derived from hESC treated with 10 nM 5-aza-2-deoxycytidine on day 2-3 (FIG. 13 A2) is more homogeneous and has more pronounced cell-cell contacts compared to untreated control DE (FIG. 13 A1). Note the presence of undifferentiated cells in the control DE (FIG. 13 A1) which is in accordance with higher expression of Oct4 and Nanog mRNA expression in control DE (compare FIG. 13 D). Similar results were obtained when treating cells on days 2-4, 3-4 and 4-6 and with 100 nM 5-aza-2-deoxycytidine. 1 nM 5-aza-2-deoxycytidine had less effect (data not shown).

FIG. 13B:

HiPSC-derived DE treated with 10 nM 5-aza-2-deoxycytidine on day 2-3 (FIG. 13 B2) is more confluent and has more pronounced cell-cell contacts than control DE (FIG. 13 B1). Similar results were obtained when treating cells days 2-4, 3-4 and 4-6 and with 100 nM 5-aza-2-deoxycytidine. 1 nM 5-aza-2-deoxycytidine had less effect (data not shown).

FIG. 13C:

HiPSC-derived DE treated with 10 nM 5-aza-2-deoxycytidine on day 2-3 has much less Oct4-immunopositive cells at day 7 compared to untreated controls, i.e. less undifferentiated cells are left and the DE is more homogeneous after treatment with a demethylating agent.

FIG. 13D:

Expression of the stem cell marker Oct4 is much lower in hESC- and hiPSC-derived DE treated with 10 nM 5azadC on day 2-3, 3-4, 2-4, and 4-6 than in untreated controls (FIG. 13 D1). In 5azadC-treated hESC-derived DE mRNA expression of the stem cell marker Nanog is strongly decreased whereas it remains mainly unaffected in hiPSC-derived DE (FIG. 13 D1). Expression of the DE markers Sox17, Cxcr4, FoxA2 and hHex is up-regulated in 5azadC-treated hESC- and hiPSC-derived DE compared to untreated controls while the effect is stronger in hESC-derived DE than in hiPSC-derived DE (FIG. 13 D3-6). Expression of the extraembryonic marker Sox7 is very low both in control and 5azadC-treated hESC- and hiPSC-derived DE with the exception of 5azadC-treatment on days 2-4 and 4-6 which increases Sox7 mRNA levels.

Taken together, the treatment of the cells with a DNA demethylation agent during the pre-endodermal phase led to improved DE morphology and DE cell yield in both hESC and hiPSC derived cells (FIG. 13 A-B). Furthermore it resulted in a stronger decrease of the stem cell marker Oct4 as detected by immunocytochemistry (FIG. 13 C), to an improved expression of well defined DE markers SOX17, CXCR4, HEX, Foxa2, as well as a decrease of the extraembryonic endoderm marker Sox7 and of the stem markers Oct4 and Nanog (FIG. 13 D). Therefore the skilled person wishing to produce a more homogeneous population of definitive endoderm cells can select from one or more DNA-demethylation agents and employ them e.g. at days 2-3 or 3-4 during differentiation of pluripotent stem cell types.

Example 11

Highly Homogeneous Definitive Endoderm Derived from a Panel of 27 hPSC Lines Upon Treatment with a DNA Demethylating Agent During DE Differentiation Procedure:

Following the basic protocols C or D, cells derived from 27 hPSC lines were treated with nM 5-aza-2-deoxycytidine on day 2-3 during the pre-endodermal phase (protocol C: ChiPSC14, ChiPSC19, ChiPSC22, P11015, SA167, SA181, SA461, and Va19; protocol D: ChiPSC4, ChiPSC6b, ChiPSC7, ChiPSC8, ChiPSC9, ChiPSC10, ChiPSC11, ChiPSC13, ChiPSC15, ChiPSC17, ChiPSC18, ChiPSC19, ChiPSC20, ChiPSC21, ChiPSC23, ChiPSC24, P11012, P11021, P11025, and SAl21). 23 out of 27 hPSC lines were tested with both protocols C and D. Out of these 23 lines, only 4 cell lines (ChiPSC14, ChiPSC23, P11015, and P11032) could only be differentiated with one of the two protocols. Four hPSC lines (ChiPSC8, ChiPSC9, ChiPSC10, and ChiPSC11) were only tested with protocol D.

For analysis of mRNA expression, hESC- and hiPSC-derived DE-cells were harvested on day 7 of the protocol and gene expression was analysed using qRT-PCR, normalised to the house-keeping gene CREBBP, and the results presented as relative quantification normalised to a calibrator.

Figure 14C:
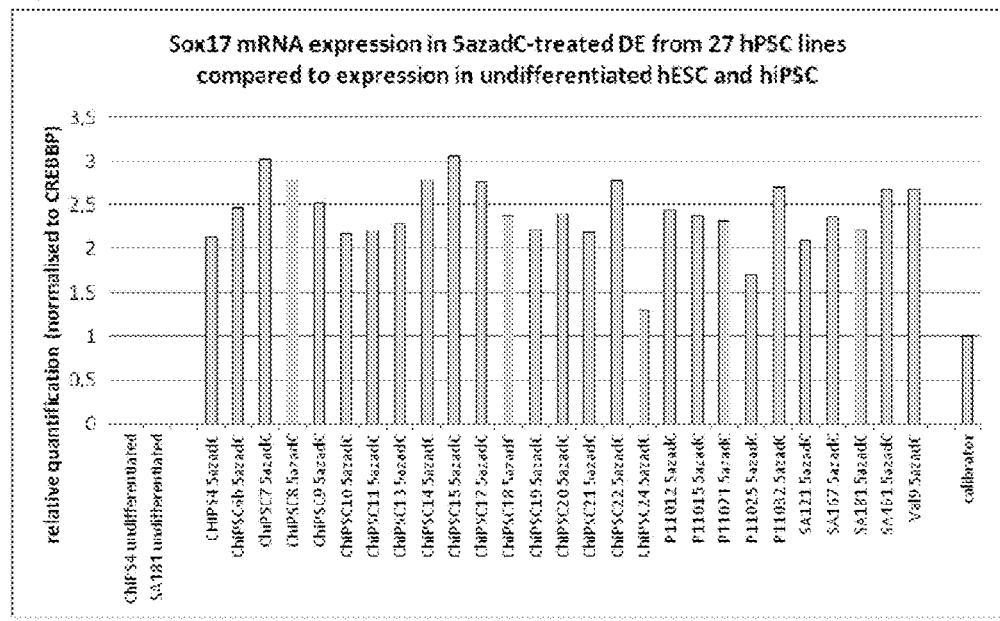
FIG. 14C. mRNA expression of DE marker Sox17 in definitive endodermal cells derived from 27 different hESC- and hiPSC lines (derived with basic protocols C and D, respectively) with a 5-deoxycytidine treatment during the pre-endodermal phase (day 0-7 of the protocol).
Figure 14D:
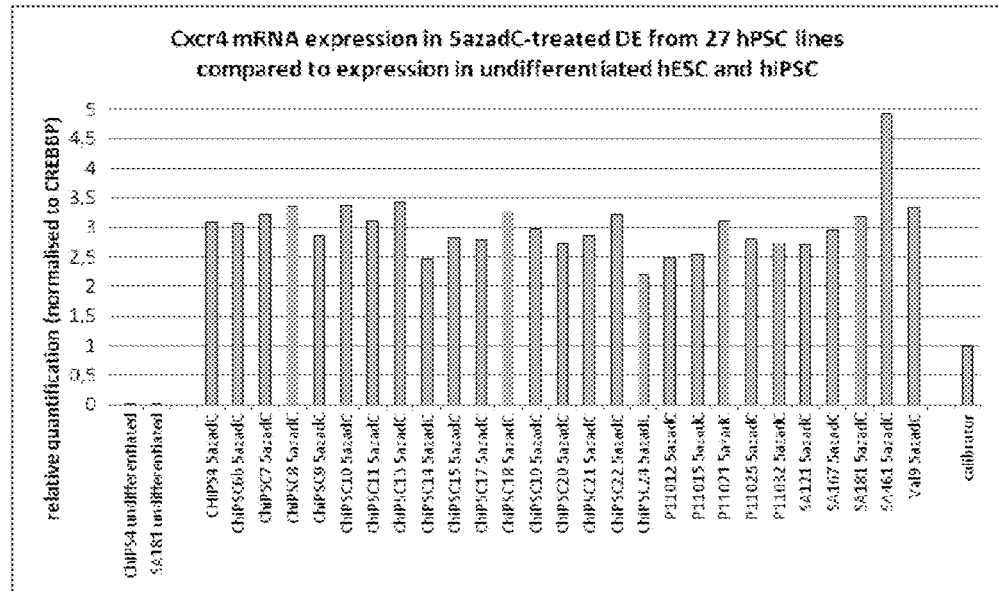
FIG. 14D. mRNA expression of DE marker Cxcr4 in definitive endodermal cells derived from 27 different hESC- and hiPSC lines (derived with basic protocols C and D, respectively) with a 5-deoxycytidine treatment during the pre-endodermal phase (day 0-7 of the protocol).

Results:

FIG. 14A-D:

Using the basic protocols C or D including a DNA demethylating treatment on day 2-3 during the pre-endodermal phase, undifferentiated stem cells from 27 different hPSC lines could be differentiated into highly homogeneous DE displaying low mRNA expression levels of the stem cell markers Oct-4 and Nanog (FIG. 14A, B) and high levels of the DE markers Sox17 and Cxcr4 (FIG. 14C, D) compared to undifferentiated hESC (SA181) and hiPSC (ChiPSC4).

Taken together, the treatment of the cells during the pre-endodermal phase with a DNA demethylating agent allows derivation of homogeneous DE with low expression levels of stem cell markers and high expression levels of DE markers from all hPSC lines tested. The derivation of homogeneous DE is crucial for derivation of homogeneous hepatocyte cultures which could be obtained from all lines tested (data not shown).

Therefore the skilled person wishing to produce a homogeneous population of definitive endoderm cells (and hepatocytes) from any given hPSC line can include a treatment with a DNA demethylating agent, for instance, on day 2-3 during the pre-endodermal phase.

Example 12

Both DNA Demethylating Agents 5-Aza-2-Deoxycytidine and 5-Azacytidine Improve the Definitive Endoderm Phenotype in hESC- and hiPSC-Derived DE Procedure:

Following the basic protocols C (P11032, SA181) or D (P11012), cells derived from 3 different hPSC lines were treated with either 10 nM 5-aza-2-deoxycytidine or 1 µM 5-azacytidine on day 2-3 during the pre-endodermal phase.

For analysis of mRNA expression, hESC- and hiPSC-derived DE-cells were harvested on day 7 of the protocol and gene expression was analysed using qRT-PCR, normalised to the house-keeping gene CREBBP, and the results presented as relative quantification normalised to a calibrator.

Figure 15C:
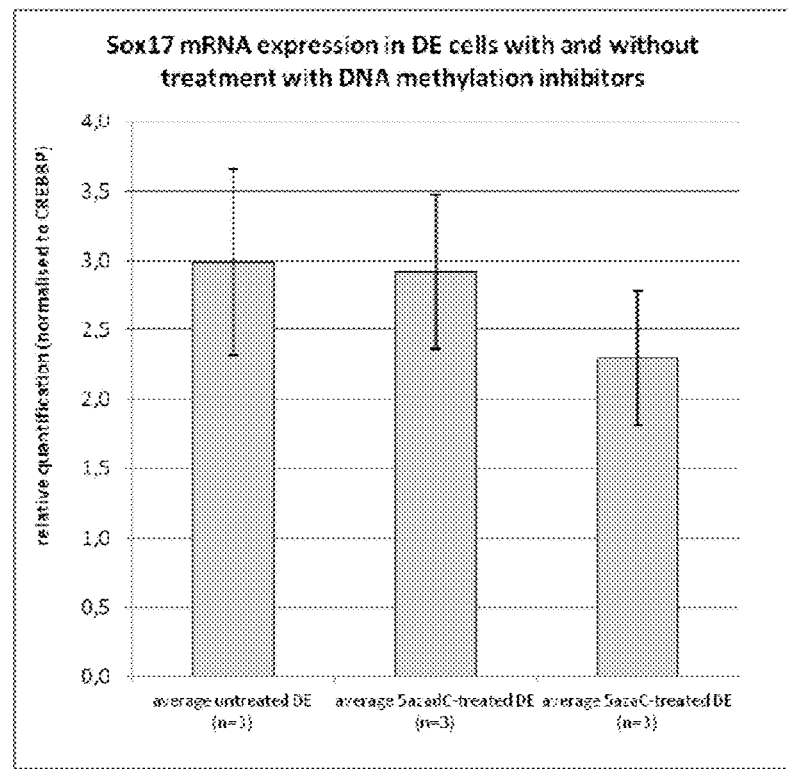
FIG. 15C. mRNA expression of DE marker Sox17 in definitive endodermal cells derived from 3 hESC- and hiPSC lines (derived with basic protocols C and D, respectively) with or without a treatment with 5-aza-deoxycytidine or 5cytidine during the pre-endodermal phase (day 0-7 of the protocol).

Results:

FIG. 15:

A, B) Without treatment with a demethylating agent, the three hPSC lines P11032, SA181 and P11012 produced heterogeneous DE with relatively high mRNA expression of stem cell markers Oct4 and Nanog (FIG. 15A, B). Treatment with the DNA demethylating agents 5-aza-2-deoxycytidine (5azadC) and 5-azacytidine (5azaC) significantly decreased Oct4 and Nanog mRNA (FIG. 15 A, B) and thus allowed derivation of a homogeneous DE population from these three hPSC lines.

Figure 15D:
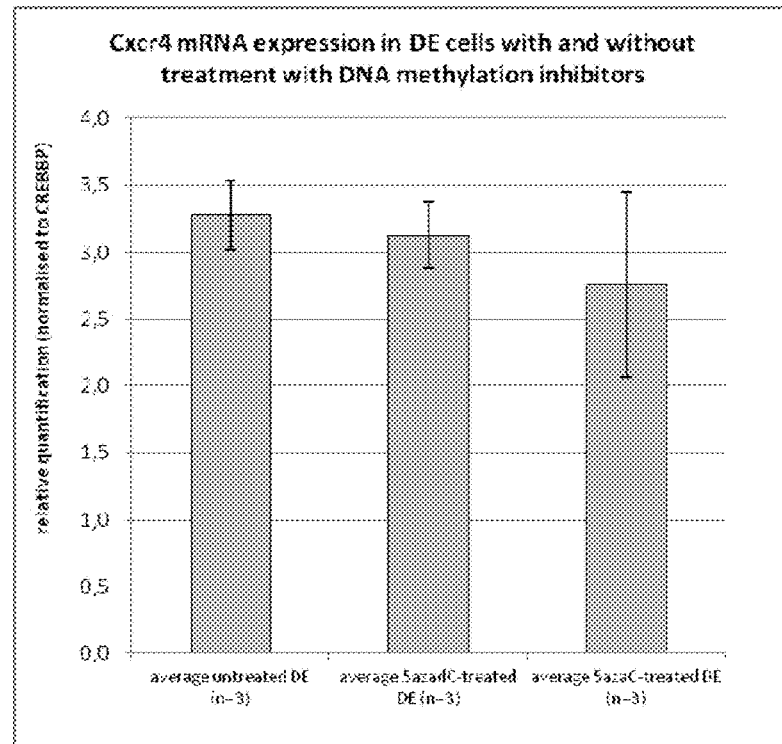
FIG. 15D. mRNA expression of DE marker Cxcr4 in definitive endodermal cells derived from 3 hESC- and hiPSC lines (derived with basic protocols C and D, respectively) with or without a treatment with 5-aza-deoxycytidine or 5cytidine during the pre-endodermal phase (day 0-7 of the protocol).

C, D) No significant changes in mRNA expression of the DE markers Sox17 and Cxcr4 could be observed upon treatment with 10 nM 5-aza-2-deoxycytidine or 1 µM 5-azacytidine (FIG. 15 C, D).

Taken together, treatment with both DNA demethylating agents 5-aza-2-deoxycytidine (5azadC) and 5-azacytidine (5azaC) allows derivation of homogeneous DE from hPSC lines, giving otherwise heterogeneous DE if untreated.

Therefore the skilled person wishing to produce a homogeneous population of definitive endoderm cells can select from one or more DNA-demethylation agents and employ them e.g. at days 2-3 during differentiation of pluripotent stem cell types.

Example 13

Further Improvement of Functionality in Hepatocyte-Like Cells Derived from hESC and hiPSC Treated with a Demethylating Agent, Two Activators of a Retinoic Acid Responsive Receptor, Kenpaullone and a Matrix Overlay Procedure:

Following the basic protocol D (hiPSC-derived hepatocytes), differentiating hPS cells in the pre-endodermal phase were treated with 10 nM of the DNA demethylating agent 5-aza-2-deoxycytidine for 24 hr on day 2 to 3 of the protocol. Later in the protocol, hPS cell derived hepatic progenitor cells and hepatocyte-like cells cultured on a Fibronectin-based coating were treated with continuous/long term treatment with 0.2 µM 9cis-RA and 0.5 µM Kenpaullone starting on day 14 of the protocol (i.e. on day 1 of the differentiation and maturation phase) and received thin Fibronectin-Collagen I-overlays on day 14 and 16 of the protocol (i.e. on day 1 and 3 of the differentiation and maturation phase) and which are refreshed thereafter once a week on day 23, 30, 37 and so on (i.e. on day 9, 16, 23 and so on of the differentiation and maturation phase). One group received in addition to the described treatment 0.2 µM 13cis-RA starting from day 21 of the protocol (i.e. on day 7 of the differentiation and maturation phase).

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 µl of the 3 mg/ml Collagen I-solution per ml medium (=25 µg Collagen I/ml) and 50 µl of a 1 mg/ml Fibronectin solution per ml medium (=50 µg Fibronectin/ml). Remove the old medium from the cultures and add 0.5 ml of the Collagen I and Fibronectin-containing medium per cm$^2$ culture surface (=12.5 µg Collagen I/cm$^2$ and 25 µg Fibronectin/cm$^2$). For refreshing the overlay once a week, add 4 µl of the 3 mg/ml Collagen I-solution per ml medium (=6.25 µg/ml) and 10 µl of a 1 mg/ml Fibronectin solution per ml medium (=5 µg/ml).

For analysis of mRNA expression, hESC- and hiPSC-derived hepatocytes were harvested on day 36 of the protocol (i.e. on day 22 of the differentiation and maturation phase) and human primary hepatocytes 48 hr after plating. Gene expression was analysed using qRT-PCR, normalised to the house-keeping gene CREBBP, and the results presented as relative quantification normalised to a calibrator.

For analysing CYP enzyme activity in hiPSC-derived hepatocytes on day 36 (i.e. on day 22 of the differentiation and maturation phase), HepG2 and human primary hepatocytes 48 hr after plating, cell cultures were subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 10 µM Phenacetin (model substrate for CYP1A), 10 µM Bupropion (model substrate for CYP2B6), 10 µM Diclofenac (model substrate for CYP2C9), 10 µM Bufuralol (model substrate for CYP2D6) and 5 µM Midazolam (model substrate for CYP3A), is added to the cells (e.g. 220 µl/24 well) and incubated for 16 hr at 37° C. Then supernatant is collected and centrifuged for 20 min at 10.000 rcf at 4° C. Subsequently, 120 µl of the supernatant is transferred into a 96 well plate which is sealed with a tight seal tape and stored at −20 or −80° C. until LC/MS-analysis of metabolite formation: Acetaminophen (Paracetamol) for CYP1A, OH-Bupropion for CYP2B6, OH-Diclofenac for CYP2C9, OH-Bufuralol for CYP2D6, and OH-Midazolam for CYP3A, Results:

The inventors have further investigated the effects of treatment with an additional activator of a retinoic acid responsive receptor in addition to early DNA-demethylation treatment and with late RA+matrix overlay+Kenpaullone treatment to determine if this further improved hepatocyte maturation.

FIG. 17 A-E:

HiPSC-derived hepatocyte-like cells obtained by treatment with a DNA demethylating agent during early endodermal development and exposure to 9cis RA, Kenpaullone and matrix overlay during the differentiation and maturation phase showed a further increase of CYP1A-, CYP2B6-, CYP2C9-, CYP2D6- and CYP3A-activity upon treatment with 13cis RA.

FIG. 18 A-E:

HiPSC-derived hepatocyte-like cells obtained by treatment with a DNA demethylating agent during early endodermal development and exposure to 9cis RA, Kenpaullone and matrix overlay together with the additional activator of a retinoic acid responsive receptor 13cis RA during the differentiation and maturation phase showed the highest mRNA expression levels of CYP2C9, CYP3A4, CYP3A5 and PXR.

Figures 17, 17A:
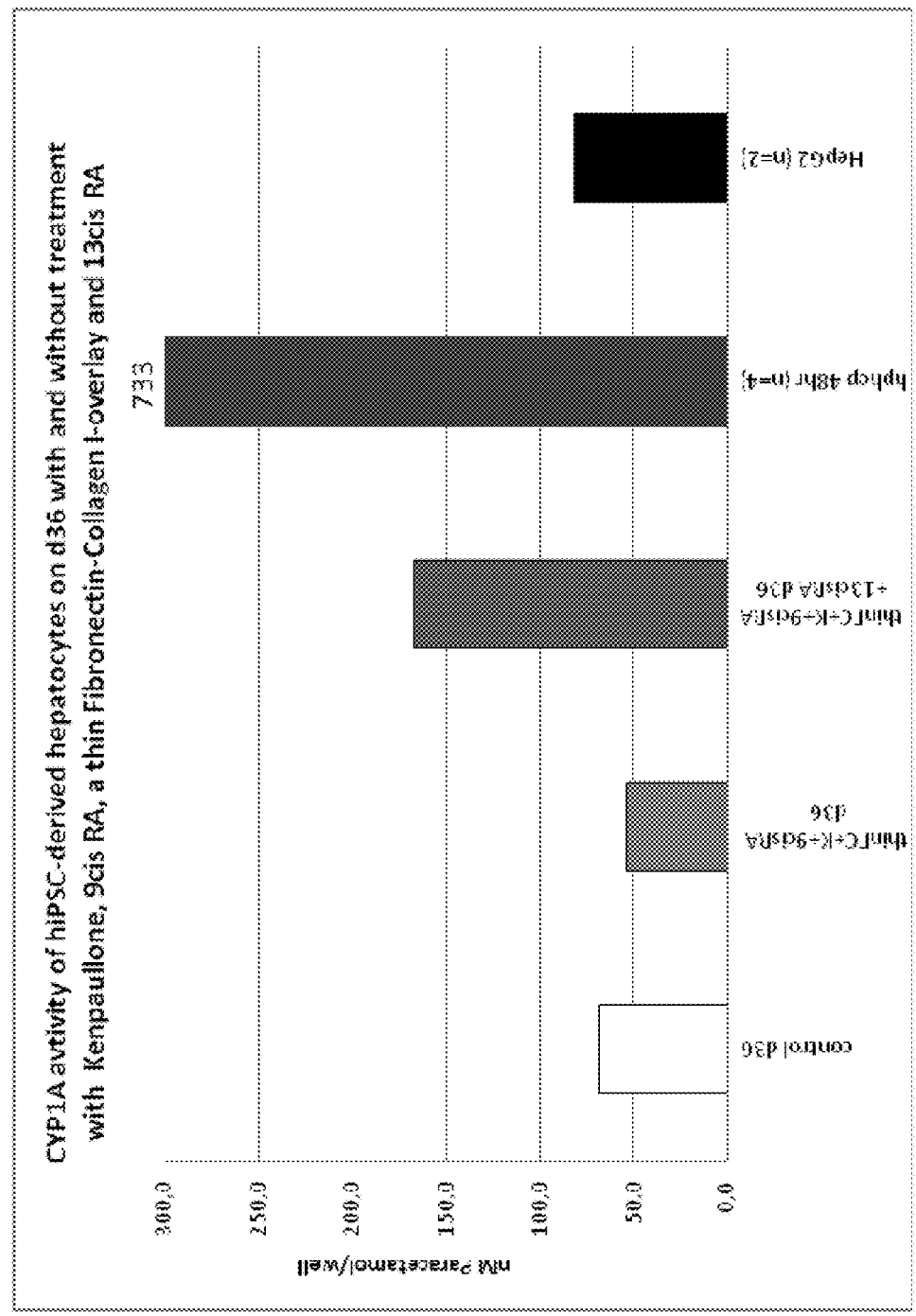
FIG. 17A. Functional expression of CYP1A in hiPSC-derived hepatocyte-like cells (derived with basic protocol C) with early treatment with 5-deoxycytidine and late exposure to one or two activators of a retinoic acid responsive receptor, Kenpaullone and a matrix overlay.
Figures 18, 18A:
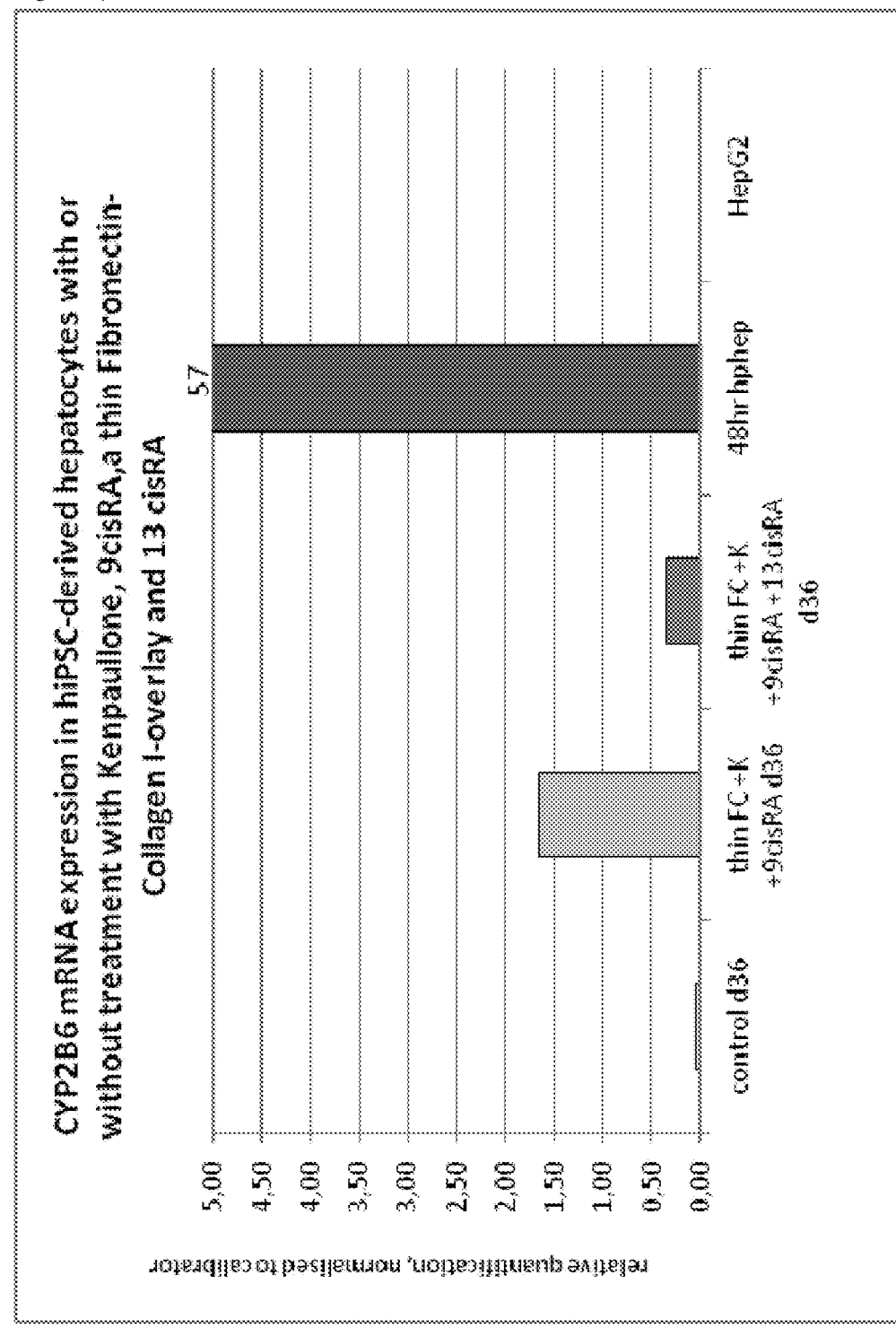
FIG. 18A. mRNA expression of CYP2B6 in hiPSC-derived hepatocyte-like cells (derived with basic protocol D) with early treatment with 5-deoxycytidine and late exposure to one or two activators of a retinoic acid responsive receptor, Kenpaullone and a matrix overlay.
Figure 19B:
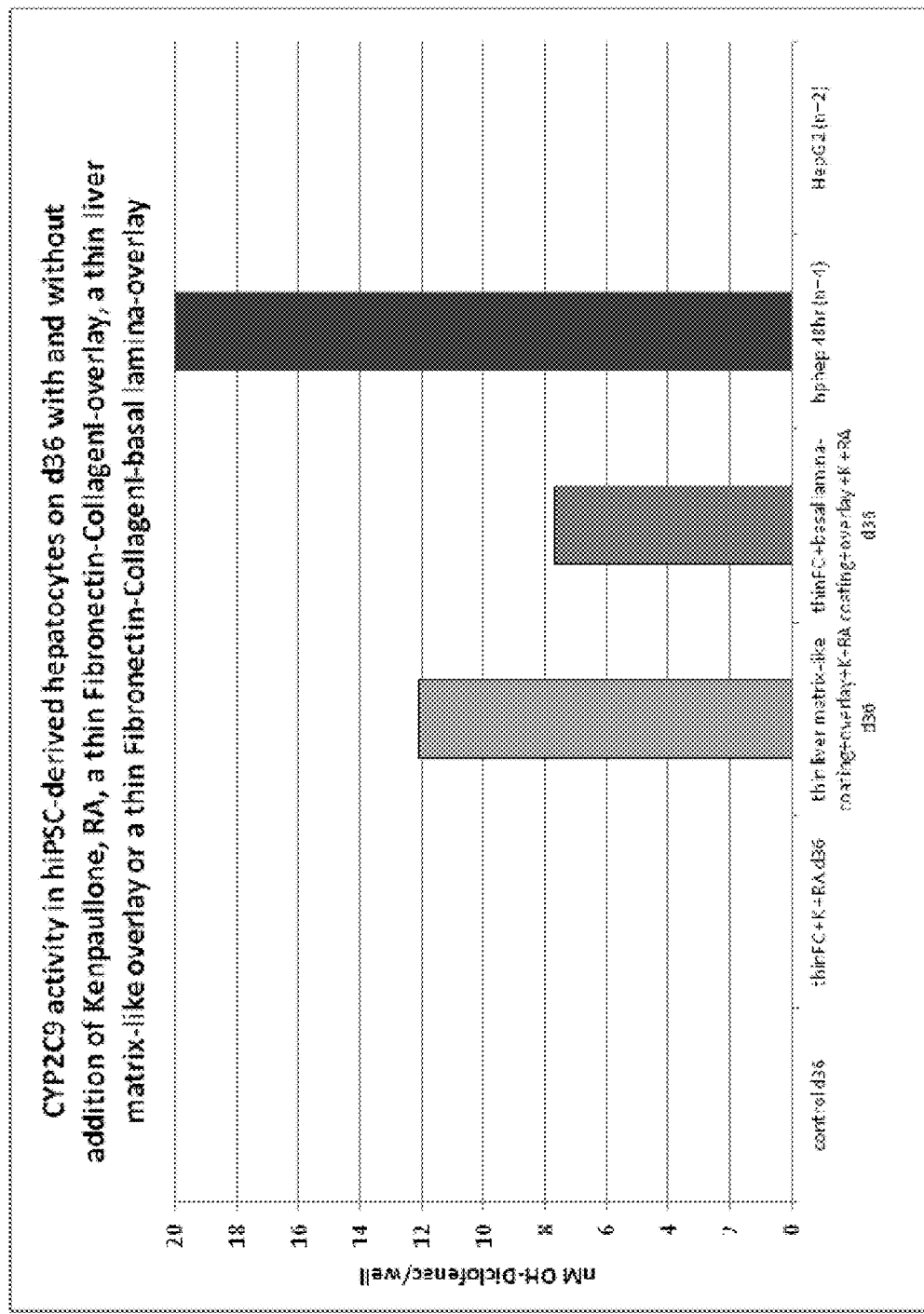
FIG. 19B. Functional expression of CYP2C9 in hiPSC-derived hepatocyte-like cells (derived with basic protocol D) treated early with 5-deoxycytidine and exposed late to retinoic acid, Kenpaullone and a simple or more complex matrix overlay.

In contrast to an increase of CYP2B6 activity (FIG. 17 B), a decrease of CYP2B6 mRNA expression can be found (FIG. 18 A) in the 13cis RA-treated group.

Thus the skilled person may employ treatment with more than one activator of a retinoic acid responsive receptor, e.g. with two, three, four or more activators, in order to obtain hepatocyte-like cells with the most mature characteristics.

Example 14

Further Improvement of Functionality in Hepatocyte-Like Cells Derived from hESC and hiPSC Treated with a Demethylating Agent, Retinoic Acid, Kenpaullone and More Complex Matrix Overlay Procedure:

Following the basic protocols C (hESC-derived hepatocytes) and D (hiPSC-derived hepatocytes), cells in the pre-endodermal phase were treated with 10 nM of the DNA demethylating agent 5-aza-2-deoxycytidine for 24 hr on day 2 to 3 of the protocol.

Later in the protocol, hPS cell derived hepatic progenitor cells and hepatocyte-like cells derived from hPS cells were treated with continuous/long term treatment with 0.2 µM 9cis-RA and 0.5 µM Kenpaullone starting on day 14 of the protocol (i.e. on day 1 of the differentiation and maturation phase) and received thin Fibronectin-Collagen I-overlays on day 14 and 16 of the protocol (i.e. on day 1 and 3 of the differentiation and maturation phase) and which are refreshed thereafter once a week on day 23, 30, 37 and so on (i.e. on day 9, 16, 23 and so on of the differentiation and maturation phase).

One experimental group was grown on a liver matrix like-coating, consisting of Fibronectin, Collagen I, Collagen IV, Laminin, Nidogen/Entactin and Biglycan, and received a thin liver matrix like-overlay consisting of Fibronectin, Collagen I, Collagen IV, Laminin, Nidogen/Entactin and Biglycan.

Another experimental group was cultured on a Fibronectin-Collagen I-basal lamina mix-coating, consisting of Fibronectin, Collagen I and a preparation of human extracellular matrix (including collagens, laminin, fibronectin, tenascin, elastin, proteoglycans and glycosaminoglycans), and received a thin Fibronectin-Collagen I-basal lamina mix-overlay, consisting of Fibronectin, Collagen I and a preparation of human extracellular matrix (including collagens, laminin, fibronectin, tenascin, elastin, proteoglycans and glycosaminoglycans).

The control group was grown on the standard Fibronectin-based coating and received thin Fibronectin-Collagen I-overlays on day 14 and 16 of the protocol (i.e. on day 1 and 3 of the differentiation and maturation phase) and which are refreshed thereafter once a week on day 23, 30, 37 and so on (i.e. on day 9, 16, 23 and so on of the differentiation and maturation phase).

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 µl of the 3 mg/ml Collagen I-solution per ml medium (=25 µg Collagen I/ml) and 50 µl of a 1 mg/ml Fibronectin solution per ml medium (=50 µg Fibronectin/ml). Remove the old medium from the cultures and add 0.5 ml of the Collagen I and Fibronectin-containing medium per cm$^2$ culture surface (=12.5 µg Collagen I/cm$^2$ and 25 µg Fibronectin/cm$^2$). For refreshing the overlay once a week, add 4 µl of the 3 mg/ml Collagen I-solution per ml medium (=6.25 µg/ml) and 10 µl of a 1 mg/ml Fibronectin solution per ml medium (=5 µg/ml).

For the thin liver matrix like-overlay, add 8 µl of the 3 mg/ml Collagen I-solution per ml medium (=25 µg Collagen I/ml), 50 µl of a 1 mg/ml Fibronectin solution per ml medium (=50 µg Fibronectin/ml), 1.2 µl of a 0.5 mg/ml Collagen IV-solution per ml medium (=0.6 µg/ml), 6 µl of a 100 µg/ml Nidogen/Entactin-solution per ml medium (=0.6 µg/ml), 6 µl of a 100 µg/ml Laminin1-solution per ml medium (=0.6 µg/ml), and 6 µl of a 200 µg/ml Biglycan-solution per ml medium (=1.2 µg/ml). For the thin Fibronectin-Collagen I-basal lamina-overlay, add 8 µl of the 3 mg/ml Collagen I-solution per ml medium (=25 µg Collagen I/ml), 50 µl of a 1 mg/ml Fibronectin solution per ml medium (=50 µg Fibronectin/ml), and 6 µl of a 1 mg/ml human extracellular matrix-preparation per ml medium (=6 µg/ml), An example for a suitable human extracellular matrix preparation is MaxGel™ from Sigma-Aldrich.

For analysing CYP enzyme activity in hESC- and hiPSC-derived hepatocytes on day 36 (i.e. on day 22 of the differentiation and maturation phase), HepG2 and human primary hepatocytes 48 hr after plating, cell cultures were subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 10 µM Phenacetin (model substrate for CYP1A), 10 µM Bupropion (model substrate for CYP2B6), 10 µM Diclofenac (model substrate for CYP2C9), 10 µM Bufuralol (model substrate for CYP2D6) and 5 µM Midazolam (model substrate for CYP3A), is added to the cells (e.g. 220 µl/24 well) and incubated for 16 hr at 37° C. Then supernatant is collected and centrifuged for 20 min at 10.000 rcf at 4° C. Subsequently, 120 µl of the supernatant is transferred into a 96 well plate which is sealed with a tight seal tape and stored at −20 or −80° C. until LC/MS-analysis of metabolite formation: Acetaminophen (Paracetamol) for CYP1A, OH-Bupropion for CYP2B6, OH-Diclofenac for CYP2C9, OH-Bufuralol for CYP2D6, and OH-Midazolam for CYP3A, Results:

The inventors have further investigated the effects of treatment with more complex, ECM-like coatings and overlays in addition to early DNA-demethylation treatment and late retinoic acid and Kenpaullone treatment to determine if this further improved hepatocyte maturation compared to the standard Fibronectin-based coating and the thin Fibronectin-Collagen I-overlay.

FIG. 19A-C:

HESC- and hiPSC-derived hepatocyte-like cells obtained by treatment with a DNA demethylating agent during early endodermal development and exposure to retinoic acid, Kenpaullone and a matrix overlay during the differentiation and maturation phase showed a higher CYP2C9-, and CYP3A-activity when both coating and overlay were more complex and ECM-like compared to the standard Fibronectin-based coating and the thin Fibronectin-Collagen I-overlay of the control group.

Thus the skilled person may employ treatment with more complex coatings and overlays resembling the liver matrix in order to obtain hepatocyte-like cells with the most mature characteristics.

Example 15

Improvement of Functionality in Hepatocyte-Like Cells Derived from hiPSC Treated with a Demethylating Agent, Kenpaullone and 9 Cis Retinoic Acid or Analogs of 9 Cis Retinoic Acid Procedure:

Following the basic protocol D, cells in the pre-endodermal phase were treated with 10 nM of the DNA demethylating agent 5-aza-2-deoxycytidine for 24 hr on day 2 to 3 of the protocol.

Later in the protocol, hPS cell derived hepatic progenitor cells and hepatocyte-like cells derived from hPS cells were treated with continuous/long term treatment with 0.2 µM 9cis-RA and 0.5 µM Kenpaullone starting on day 14 of the protocol (i.e. on day 1 of the differentiation and maturation phase) and received thin Fibronectin-Collagen I-overlays on day 14 and 16 of the protocol (i.e. on day 1 and 3 of the differentiation and maturation phase) and which are refreshed thereafter once a week on day 23, 30, 37 and so on (i.e. on day 9, 16, 23 and so on of the differentiation and maturation phase).

Some experimental groups were treated with 0.5 µM all trans-retinoic acid (ATRA), 5 µM AM580, 0.2 µM 13cis-RA, 5 µM LGD1069, 5 µM LG100268 or 5 µM SR11237 instead of 0.2 µM 9cis-RA.

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 µl of the 3 mg/ml Collagen I-solution per ml medium (=25 µg Collagen I/ml) and 50 µl of a 1 mg/ml Fibronectin solution per ml medium (=50 µg Fibronectin/ml). Remove the old medium from the cultures and add 0.5 ml of the Collagen I and Fibronectin-containing medium per cm$^2$ culture surface (=12.5 µg Collagen I/cm$^2$ and 25 µg Fibronectin/cm$^2$). For refreshing the overlay once a week, add 4 µl of the 3 mg/ml Collagen I-solution per ml medium (=6.25 µg/ml) and 10 µl of a 1 mg/ml Fibronectin solution per ml medium (=5 µg/ml).

For analysing CYP enzyme activity in hESC-derived hepatocytes on day 36 (i.e. on day 22 of the differentiation and maturation phase), cell cultures were subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, 25 mM HEPES, 10 µM Phenacetin (model substrate for CYP1A), 10 µM Bupropion (model substrate for CYP2B6), 10 µM Diclofenac (model substrate for CYP2C9), 10 µM Bufuralol (model substrate for CYP2D6) and 5 µM Midazolam (model substrate for CYP3A), is added to the cells (e.g. 220 µl/24 well) and incubated for 16 hr at 37° C. Then supernatant is collected and centrifuged for 20 min at 10.000 rcf at 4° C. Subsequently, 120 µl of the supernatant is transferred into a 96 well plate which is sealed with a tight seal tape and stored at −20 or −80° C. until LC/MS-analysis of metabolite formation: Acetaminophen (Paracetamol) for CYP1A, OH-Bupropion for CYP2B6, OH-Diclofenac for CYP2C9, OH-Bufuralol for CYP2D6, and OH-Midazolam for CYP3A, Results:

The inventors have investigated if other RXR- and RAR-agonist besides 9cis-RA can induce an improved functionality of hiPSC-derived hepatocytes.

Figure 20:
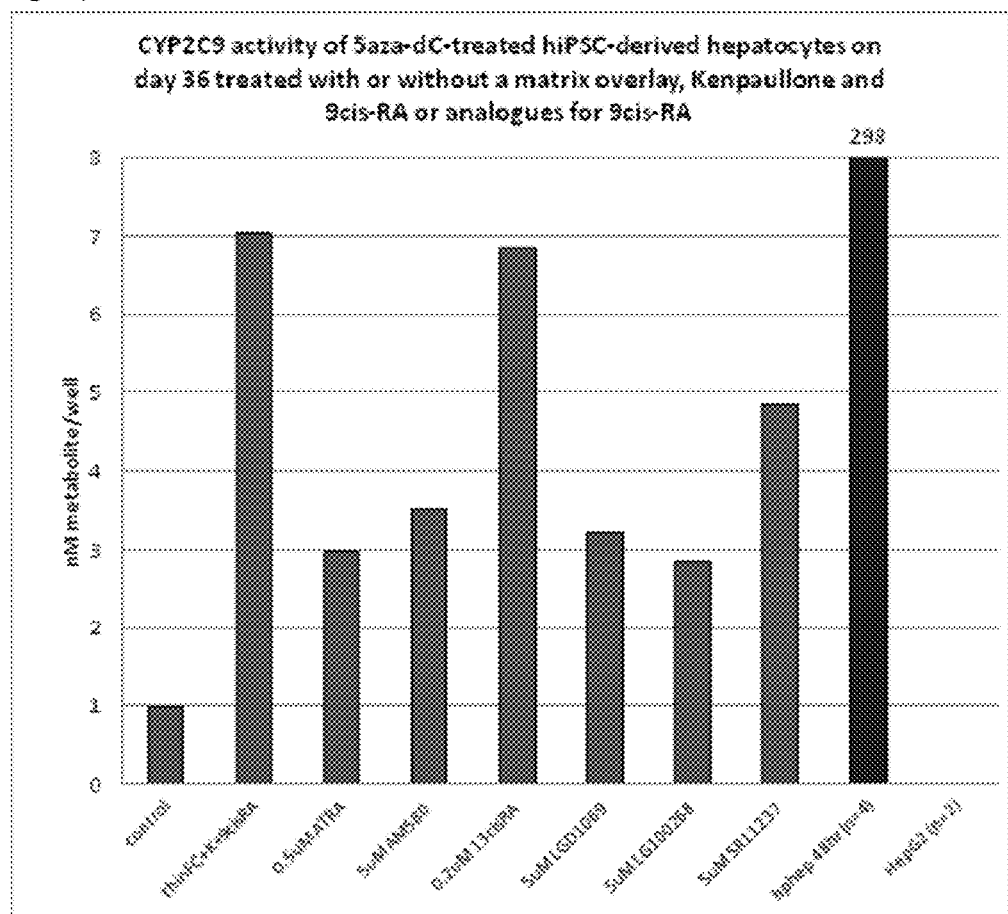
FIG. 20. Functional expression of CYP2C9 enzyme in hiPSC-derived hepatocyte-like cells (derived with basic protocol D) treated early with 5-deoxycytidine and exposed late to Kenpaullone, 9cis retinoic acid, or an analogue to 9cis retinoic acid.

FIG. 20:

Treatment with 13cis-RA increases CYP2C9 activity to similar levels as upon treatment with 9cis-RA whereas treatment with SR11237, ATRA, AM580, LGD1069 and LG100268 leads to a slightly smaller increase (FIG. 20).

Thus the skilled person may use other RXR- and RAR-agonist, e.g. 13cis-RA, ATRA, AM580, LGD1069, LG100268 and SR11237, besides 9cis-RA for obtaining more mature hepatocyte-like cells.

Example 16

Improvement of Functionality in Hepatocyte-Like Cells Derived from hESC and hiPSC Treated with a Demethylating Agent, 9 Cis Retinoic and Kenpaullone Acid or Analogs of Kenpaullone Procedure:

Following the basic protocols C (hESC-derived hepatocytes) and D (hiPSC-derived hepatocytes), cells in the pre-endodermal phase were treated with 10 nM of the DNA demethylating agent 5-aza-2-deoxycytidine for 24 hr on day 2 to 3 of the protocol. Later in the protocol, hPS cell derived hepatic progenitor cells and hepatocyte-like cells derived from hPS cells were treated with continuous/long term treatment with 0.2 µM 9cis-RA and 0.5 µM Kenpaullone starting on day 14 of the protocol (i.e. on day 1 of the differentiation and maturation phase) and received thin Fibronectin-Collagen I-overlays on day 14 and 16 of the protocol (i.e. on day 1 and 3 of the differentiation and maturation phase) and which are refreshed thereafter once a week on day 23, 30, 37 and so on (i.e. on day 9, 16, 23 and so on of the differentiation and maturation phase).

One experimental group was treated with 0.5 µM Indirubin-3-oxime instead of 0.5 µM Kenpaullone.

The thin Fibronectin-Collagen I-overlay is applied as following: Prepare a 3 mg/ml rat tail Collagen I-solution by diluting the Collagen I stock with 0.02M acetic acid. Pre-warm the cell culture medium to room temperature and add 8 µl of the 3 mg/ml Collagen I-solution per ml medium (=25 µg Collagen I/ml) and 50 µl of a 1 mg/ml Fibronectin solution per ml medium (=50 µg Fibronectin/ml). Remove the old medium from the cultures and add 0.5 ml of the Collagen I and Fibronectin-containing medium per cm$^2$ culture surface (=12.5 µg Collagen I/cm$^2$ and 25 µg Fibronectin/cm$^2$). For refreshing the overlay once a week, add 4 µl of the 3 mg/ml Collagen I-solution per ml medium (=6.25 µg/ml) and 10 µl of a 1 mg/ml Fibronectin solution per ml medium (=5 µg/ml).

For analysing CYP enzyme activity in hESC- and hiPSC-derived hepatocytes on day 36 (i.e. on day 22 of the differentiation and maturation phase), cell cultures were subjected to a CYP activity assay according to the following protocol: Cells are washed twice with warm Williams medium E w/o phenol red (+0.1% PEST). Then CYP activity assay, consisting of warm Williams medium E w/o phenol red (+0.1% PEST), 2 mM L-Glutamine, mM HEPES, 10 µM Phenacetin (model substrate for CYP1A), 10 µM Bupropion (model substrate for CYP2B6), 10 µM Diclofenac (model substrate for CYP2C9), 10 µM Bufuralol (model substrate for CYP2D6) and 5 µM Midazolam (model substrate for CYP3A), is added to the cells (e.g. 220 µl/24 well) and incubated for 16 hr at 37° C. Then supernatant is collected and centrifuged for 20 min at 10.000 rcf at 4° C. Subsequently, 120 µl of the supernatant is transferred into a 96 well plate which is sealed with a tight seal tape and stored at −20 or −80° C. until LC/MS-analysis of metabolite formation: Acetaminophen (Paracetamol) for CYP1A, OH-Bupropion for CYP2B6, OH-Diclofenac for CYP2C9, OH-Bufuralol for CYP2D6, and OH-Midazolam for CYP3A, Results:

The inventors have investigated if other CDK- and GSK3-inhibitors besides Kenpaullone can induce an improved functionality of hiPSC-derived hepatocytes.

Figure 21:
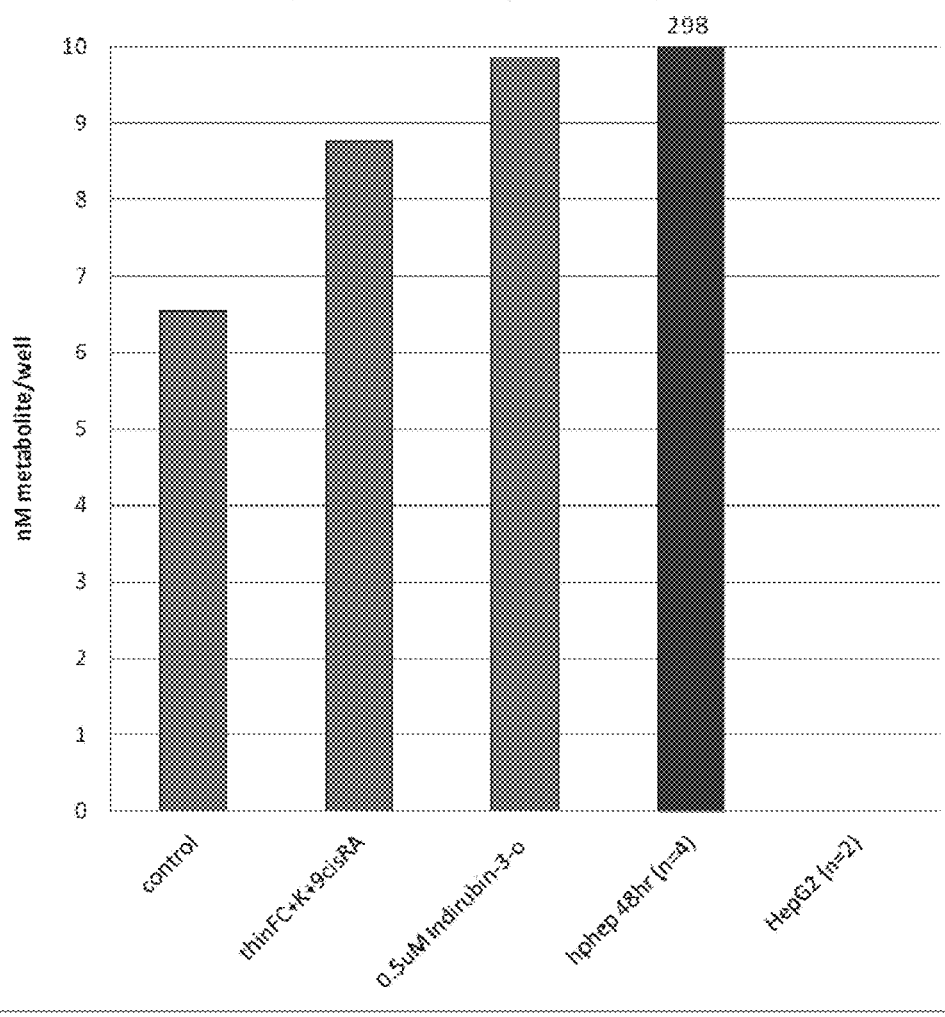

FIG. 21:

Treatment with Indirubin-3-oxime increases CYP2C9 and 3A activity to similar levels as upon treatment with Kenpaullone both in hiPSC-derived hepatocytes (FIG. 21 A1, A2) and in hESC-derived hepatocytes (FIG. 21 B1, B2).

Thus the skilled person may use other CDK- and GSK3-inhibitors besides Kenpaullone for obtaining more mature hepatocyte-like cells.

REFERENCES

Allenby, G. et al (1993) Retinoic acid receptors and retinoid X receptors: Interactions with endogenous retinoic acids. PNAS Biochemistry, 90:30-34

Brolen, G. et al. (2010) Hepatocyte-like cells derived from human embryonic stem cells specifically via definitive endoderm and a progenitor stage. J Biotechnol. 1; 145 (3):284-94

Chen, Y. F. et al. (2012) Rapid generation of mature hepatocyte-like cells from human induced pluripotent stem cells by an efficient three-step protocol. Hepatology. 2012 55(4):1193-203

Chung, Y. et al. (2008) Human Embryonic Stem Cell Lines Generated without Embryo Destruction. doi: 10.1016/j.stem.2007.12.013

Duan, Y. et al. Differentiation and characterization of metabolically functioning hepatocytes from human embryonic stem cells. Stem Cells. 28(4):674-86

Dunn, J et al. (1991) Long-term in Vitro function of adult hepatocytes in a collagen sandwich configuration. Biotechnol. Prog. 7:237-245

Funakoshi, N. et al. (2011) Comparison of hepatic-like cell production from human embryonic stem cells and adult liver progenitor cells: CAR transduction activates a battery of detoxification genes. Stem Cell Rev. 7(3):518-31

Hatzis, P. et al (2001) Regulatory Mechanisms Controlling Human Hepatocyte Nuclear Factor 4a Gene Expression. Mol. Cell. Biol. November 2001:7320-7330

Hay, D. et al (2007) Direct differentiation of human embryonic stem cells to hepatocyte-like cells exhibiting functional activities. Cloning Stem Cells. 2007 Spring; 9(1): 51-62. Erratum in: Cloning Stem Cells. 2009 March; 11(1):209.

Hay, D. et al (2008) Efficient differentiation of hepatocytes from human embryonic stem cells exhibiting markers recapitulating liver development in vivo. Stem Cells. April; 26(4):894-902.

Heins, N. et al (2004) Derivation, characterization, and differentiation of human embryonic stem cells. Stem Cells. 22(3):367-76.

Heyman, R A. et al. (1992) 9-cis retinoic acid is a high affinity ligand for the retinoid X receptor. Cell. 1992 68(2):397-406.

Idres, N. et al (2002) Activation of retinoic acid receptor-dependent transcription by all-trans-retinoic acid metabolites and isomers. J Biol Chem. 277(35):31491-8.

Klimanskaya, I. et al (2006) Human embryonic stem cell lines derived from single blastomeres. Nature, November 23; 444(7118):481-5. Epub 2006 Aug. 23. Erratum in: Nature. 2006 Nov. 23; 444(7118):512. Nature. 2007 Mar. 15; 446(7133):342.

Magee, T. et al (1998) Retinoic Acid Mediates Downregulation of the α-Fetoprotein Gene through Decreased Expression of Hepatocyte Nuclear Factors. J. Bio. Chem. 273, 45:30024-30032

Martin M. et al (2005) Human embryonic stem cells express an immunogenic nonhuman sialic acid. Nat Med. February; 11(2):228-32.

Mfopou, J. et al. (2010) Noggin, Retinoids, and Fibroblast Growth Factor Regulate Hepatic or Pancreatic Fate of Human Embryonic Stem Cells. Gastroenterology 138: 2233-2245.

Mercader, A. et al (2009) Human Embryo Culture. Essential Stem Cell Methods, Chapter 16, Academic Press, 1$^{st}$ Edition, Eds. Lanza, R. and Klimanskaya, I.

Page, J et al. (2007) Gene expression profiling of extracellular matrix as an effector of human hepatocyte phenotype in primary cell culture. Tox. Sci. 97(2):384-397

Qian, A. et al. (2000) Identification of Retinoic Acid-Responsive Elements on the HNF1a and HNF4α Genes. Biochem. Biophys. Res. Comm. 276:837-842

Si-Tayeb, K. et al. (2010) Highly efficient generation of human hepatocyte-like cells from induced pluripotent stem cells Hepatology. 51(1):297-305.

Song. Z. et al. (2009) Efficient generation of hepatocyte-like cells from human induced pluripotent stem cells. Cell Res. 19(11):1233-42

Sullivan, G. J. et al. (2010) Generation of functional human hepatic endoderm from human induced pluripotent stem cells. Hepatology. 51(1):329-35.

Takahashi, K. et al (2007) Induction of pluripotent stem cells from adult human fibroblasts by defined factors. Cell November 30; 131(5):861-72.

Thomson, J. et al. (1998) Embryonic stem cell lines derived from human blastocysts. Science. November 6; 282 (5391):1145-7. Erratum in: Science 1998 Dec. 4; 282 (5395):1827.

Touboul, T. et al. (2010) Generation of Functional Hepatocytes from Human Embryonic Stem Cells Under Chemically Defined Conditions that Recapitulate Liver Development. Hepatology 51:1754-1765

Turner, R. et al. (2011) Human hepatic stem cell and maturational liver lineage biology. Hepatology. 53(3): 1035-45

Wang, Y. et al. (2011) Lineage restriction of human hepatic stem cells to mature fates is made efficient by tissue-specific biomatrix scaffolds. Hepatology. 53(1):293-305.

Yu, J. and Thomson, J. (2009) Induced Puripotent Stem Cell Derivation. Essentials of Stem Cell Biology, Chapter 37, Academic Press, 2$^{nd}$ Edition (2009), Eds. Lanza, R. et al.

Zhou H. et al (2009). Generation of induced pluripotent stem cells using recombinant proteins. Cell Stem Cell. 4(5): 381-4.

The invention claimed is:

1. A method for promoting the maturation of in vitro derived human hepatocyte-like cells, the method comprising:
    exposing said human hepatocyte-like cells to an activator of a retinoic acid responsive receptor selected from the group consisting of 9-cis-retinoic acid, 13-cis-retinoic acid, SR11237, and combinations thereof, thereby promoting the maturation of said human hepatocyte-like cells by increasing the gene expression of one or more markers for mature hepatocytes selected from the group consisting of adult isoforms of HNF4α, CYP1A2, CYP2B6, CYP2C9, CYP3A4, CYP3A5, CAR, GSTA1-1, NTCP and PXR; wherein the human hepatocyte-like cells exposed to said activator of a retinoic acid responsive receptor do not exhibit gene and protein expression of Oct4.

2. The method according to claim 1, further comprising culturing human hepatic progenitor cells, which do not exhibit gene and protein expression of Oct4, under differentiation conditions to obtain said hepatocyte-like cells.

3. The method according to claim 2, further comprising initially culturing human pluripotent stem (hPS) cells under differentiation conditions to obtain said hepatic progenitor cells.

4. The method according to claim 3, wherein the initial culturing of hPS cells includes culturing the hPS cells under differentiation conditions to obtain cells of the definitive endoderm (DE cells) and further culturing the obtained cells under differentiation conditions to obtain said hepatic progenitor cells.

5. The method according to claim 4, wherein the differentiating hPS cells are exposed to a DNA demethylating agent, and wherein the exposure to said DNA demethylating agent takes place during the differentiation of the hPS cells into DE cells.

6. The method according to claim 3, wherein the differentiating hPS cells are exposed to a DNA demethylating agent.

7. The method according to claim 2, wherein the hepatic progenitor cells are derived from human pluripotent (hPS) stem cells.

8. The method according to claim 2, wherein said differentiation conditions for obtaining hepatocyte-like cells are characterized by culturing said human hepatic progenitor cells in a differentiation medium comprising one or more growth factors and/or one or more differentiation inducers.

9. The method according to claim 1, further comprising exposing said hepatocyte-like cells to a GSK-3 inhibitor.

10. The method according to claim 9, further comprising exposing said hepatocyte-like cells to a CDK inhibitor.

11. The method according to claim 9, wherein the GSK-3 inhibitor is selected from the group consisting of: 9-Bromo-7, 12-dihydro-indolo [3,2-d][1]benzazepin-6(5H)-one, also known as Kenpaullone or NSC 664704; 1-Aza-Ken-paullone (9-Bromo-7,12-dihydro-pyrido[3',2':2,3]azepino[4,5-b]indol-6(5H)-one); Alsterpaullone (9-Nitro-7,12-dihydroindolo-[3,2-d][1]benzazepin-6(5)-one); BIO (2'Z,3'E)-6-Bromoindirubin-3'-oxime (GSK-3 Inhibitor IX); BIO-Acetoxime (2'Z,3'E)-6-Bromoindirubin-3'-acetoxime (GSK-3 Inhibitor X); (5-Methyl-IH-pyrazol-3-yl)-(2-phenylquinazolin-4-yl)amine (GSK-3 Inhibitor XIII); Pyridocarbazole-cyclopenadienylruthenium complex (GSK-3 Inhibitor XV); TDZD-8 4-Benzyl-2-methyl-1,2,4-thiadiazolidine-3,5-dione (GSK-3beta Inhibitor I); 2-Thio(3-iodobenzyl)-5-(1-pyridyl)-[1,3,4]-oxadiazole (GSK-3beta Inhibitor II); OTDZT 2,4-Dibenzyl-5-oxothiadiazolidine-3-thione (GSK-3beta Inhibitor III); alpha-4-Dibromoacetophenone (GSK-3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWS119 pyrrolopyrimidine compound (GSK-3beta Inhibitor XII); L803 H-KEAPPAPPQSpP-NH$_2$ or its Myristoylated form (GSK-3beta Inhibitor XIII); 2-Chloro-1-(4,5-dibromo-thiophen-2-yl)-ethanone (GSK-3beta Inhibitor VI); Aminopyrimidine CHIR99021; 3-(2,4-Dichlorophenyl)-4-(1-methyl-1 H-indol-3-yl)-1 H-pyrrole-2,5-dione (SB216763); and Indirubin-3'-monoxime.

12. The method according to claim 9, wherein the GSK-3 inhibitor further exhibits inhibitory activity towards a cyclin dependent kinase (CDK).

13. The method according to claim 9, wherein the GSK-3 inhibitor further exhibits inhibitory activity towards cyclin dependent kinase 2 (CDK2).

14. The method according to claim 1, further comprising exposing said hepatocyte-like cells to an activator of Wnt signaling.

15. The method according to claim 14, wherein the activator of Wnt is a Wnt protein.

16. The method according to claim 1, further comprising exposing said hepatocyte-like cells to a CDK inhibitor.

17. The method according to claim 1, further comprising exposing said hepatocyte-like cells to a matrix overlay simultaneous to exposure to the activator of a retinoic acid responsive receptor.

18. The method according to claim 1, further comprising exposing said hepatocyte-like cells to a GSK-3 inhibitor and a matrix overlay simultaneous to exposure to the activator of a retinoic acid responsive receptor.

19. The method according to claim 1, further comprising exposing said hepatocyte-like cells to an activator of Wnt signaling and a matrix overlay simultaneous to exposure to the activator of a retinoic acid responsive receptor.

20. The method according to claim 1, further comprising exposing said hepatocyte-like cells to a CDK inhibitor and a matrix overlay simultaneous to exposure to the activator of a retinoic acid responsive receptor.

21. The method according to claim 1, wherein the activator of a retinoic acid responsive receptor is 9-cis-retinoic acid, 13-cis-retinoic acid, or a combination of 9-cis-retinoic acid and 13-cis-retinoic acid.

22. The method according to claim 1, wherein the activator of a retinoic acid responsive receptor is 9-cis-retinoic acid.

\* \* \* \* \*